US011396664B2

(12) United States Patent
Buerckstuemmer et al.

(10) Patent No.: US 11,396,664 B2
(45) Date of Patent: Jul. 26, 2022

(54) REPLICATIVE TRANSPOSON SYSTEM

(71) Applicants: Max-Delbrück-Centrum für Molekulare Medizin in der Helmholtz-Gemeinschaft, Berlin (DE); GENETIC INFORMATION RESEARCH INSTITUTE, Cupertino, CA (US)

(72) Inventors: Tilmann Buerckstuemmer, Cambridge (GB); Vladimir Vyacheslavovich Kapitonov, Mountain View, CA (US); Ivana Grabundzija, Berlin (DE); Zoltan Ivics, Berlin (DE)

(73) Assignees: MAX-DELBRÜCK-CENTRUM FÜR MOLEKULARE MEDIZIN IN DER HELMHOLTZ-GEMEINSCHAFT, Berlin (DE); GENETIC INFORMATION RESEARCH INSTITUTE, Cupertino, CA (US)

( * ) Notice: Subject to any disclaimer, the term of this patent is extended or adjusted under 35 U.S.C. 154(b) by 571 days.

(21) Appl. No.: 16/077,328

(22) PCT Filed: Feb. 10, 2017

(86) PCT No.: PCT/GB2017/050355
§ 371 (c)(1),
(2) Date: Aug. 10, 2018

(87) PCT Pub. No.: WO2017/137768
PCT Pub. Date: Aug. 17, 2017

(65) Prior Publication Data

US 2019/0323037 A1 Oct. 24, 2019

(30) Foreign Application Priority Data

Feb. 11, 2016 (GB) ..................................... 1602473

(51) Int. Cl.

| | |
|---|---|
| ***C12N 15/90*** | (2006.01) |
| ***A61K 35/545*** | (2015.01) |
| ***C12N 9/12*** | (2006.01) |
| ***C12N 15/85*** | (2006.01) |
| ***C12Q 1/686*** | (2018.01) |
| ***A61K 48/00*** | (2006.01) |

(52) U.S. Cl.
CPC ............ *C12N 15/90* (2013.01); *A61K 35/545* (2013.01); *A61K 48/00* (2013.01); *C12N 9/1241* (2013.01); *C12N 15/85* (2013.01); *C12Q 1/686* (2013.01)

(58) Field of Classification Search
CPC ......... C12N 15/85; C12N 15/86; C12N 15/90
See application file for complete search history.

(56) References Cited

U.S. PATENT DOCUMENTS 6,489,458 B2 12/2002 Hackett et al.

FOREIGN PATENT DOCUMENTS

CN 103923932 A 7/2014

OTHER PUBLICATIONS

Kapitonov and Jurka (Trends in Genetics 23(10):521-529, 2007). (Year: 2007).*
Grabundzija et al. Nature Communications DOI:10.1038/ncomms10716, pp. 1-12, Mar. 2016 (Year: 2016).*
Altschul, S.F. et al., "Basic Local Alignment Search Tool," *Journal of Molecular Biology*, vol. 215, pp. 403-410 (1990).
Andersson, R. et al., "An atlas of active enhancers across human cell types and tissues," *Nature*, vol. 507, pp. 455-461 (2014).
Ashburner, M. et al., "Gene Ontology: tool for the unification of biology," *Nature Genetics*, vol. 25, pp. 25-29 (2000).
Baykov, A. A. et al., "A Malachite Green Procedure for Orthophosphate Determination and Its Use In Alkaline Phosphatase-Based Enzyme Immunoassay," *Analytical Biochemistry*, vol. 171, pp. 266-270 (1988).
Bird, L.E. et al., "Helicases: a unifying structural theme?," *Current Opinion in Structural Biology*, vol. 8, pp. 14-18 (1998).
Brunner, S. et al., "Origins, genetic organization and transcription of a family of non-autonomous helitron elements in maize," *The Plant Journal*, vol. 43, pp. 799-810 (2005).
Bushman, F. et al., "Genome-Wide Analysis of Retroviral DNA Integration," *Nature Reviews Microbiology*, vol. 3, pp. 848-858 (2005).
Campbell, M. A. et al., "Comprehensive analysis of alternative splicing in rice and comparative analyses with Arabidopsis," *BMC Genomics*, vol. 7, No. 327, pp. 1-17 (2006).
Carette, J.E. et al., "Global gene disruption in human cells to assign genes to phenotypes by deep sequencing," *Nature Biotechnology*, vol. 29, pp. 542-546 (2011).

(Continued)

*Primary Examiner* — Marcia S Noble
(74) *Attorney, Agent, or Firm* — Bookoff McAndrews, PLLC

(57) ABSTRACT

The invention relates to a system and method for introducing DNA into cells. In particular, the invention relates to a method for introducing single or multiple copies of a DNA sequence or gene of interest into a cell comprising providing: a) a "copy and paste" transposase; and b) a construct comprising a DNA sequence or gene of interest flanked by a "copy and paste" transposon terminal sequence, such as an LTS or RTS. A novel "copy and paste" transposon of the Helitron family is described along with systems for using the corresponding transposase in methods for introducing DNA into cells, for example, to generate cell lines for use in protein production, cell and gene therapy or as reference standards.

12 Claims, 28 Drawing Sheets

Figure 1:
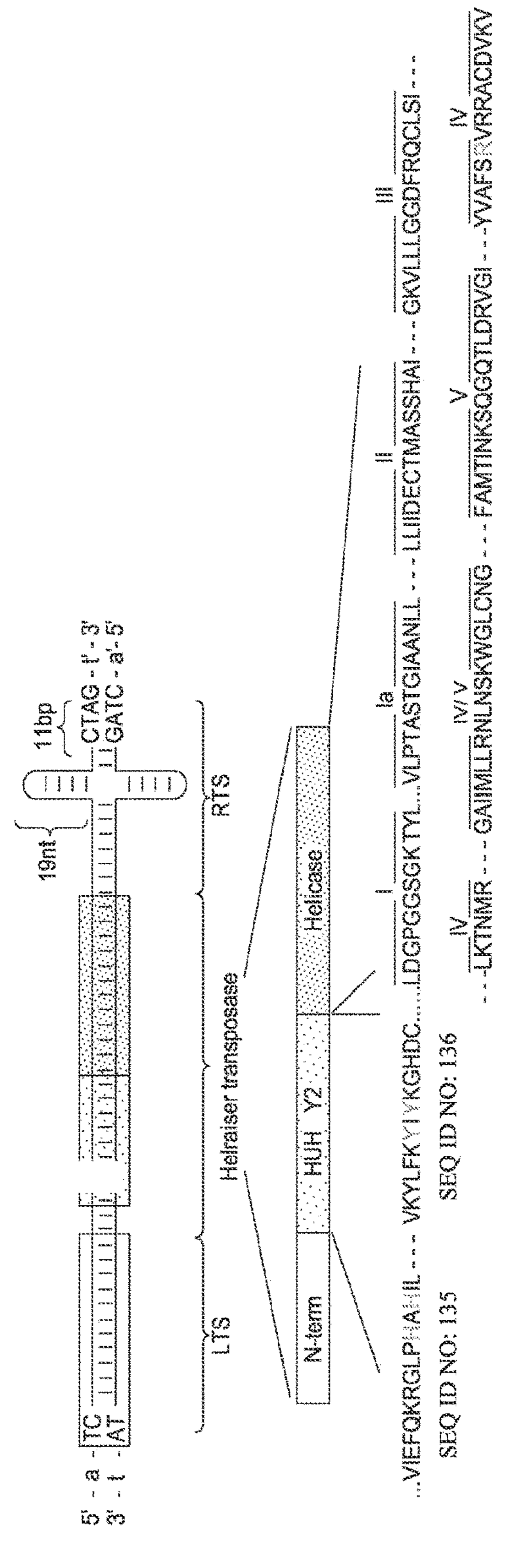

Specification includes a Sequence Listing.

(56) References Cited

OTHER PUBLICATIONS

Carette, J.E. et al., "Haploid Genetic Screens in Human Cells Identify Host Factors Used by Pathogens," *Science*, vol. 326, pp. 1231-1235 (2009).
Carette, J.E. et al., "Ebola virus entry requires the cholesterol transporter Niemann-Pick C1," *Nature*, vol. 477, pp. 340-343 (2011).
Carlson, C.M. et al., "Transposon Mutagenesis of the Mouse Germline," *Genetics*, vol. 165, pp. 243-256 (2003).
Chandler, M. et al., "Breaking and joining single-stranded DNA: the HUH endonuclease superfamily," *Nature Reviews Microbiology*, vol. 11, pp. 525-538 (2013).
Coates, B.S. et al., "Mobilizing the Genome of Lepidoptera through Novel Sequence Gains and End Creation by Non-autonomous *Lep1 Helitrons," DNA Research*, vol. 19, pp. 11-21 (2012).
Dayn, A. et al., "Transcriptionally driven cruciform formation in vivo," *Nucleic Acids Research*, vol. 20, pp. 5991-5997 (1992).
Dong, Y. et al. "Structural characterization of helitrons and their stepwise capturing of gene fragments in the maize genome," *BMC Genomics*, vol. 12, No. 609, pp. 1-11 (2011).
Du, C. et al., "The polychromatic Helitron landscape of the maize genome," *Proceedings of the National Academy of Sciences of the United States of America*, vol. 106, pp. 19916-19921 (2009).
Dyda, F. et al., "Crystal structure of the catalytic domain of HIV-1 integrase: similarity to other polynucleotidyl transferases," *Science*, vol. 266, pp. 1981-1986 (1994).
Edgar, R.C., "MUSCLE:multiple sequence alignment with high accuracy and high throughput," *Nucleic Acids Research*, vol. 32, pp. 1792-1797 (2004).
Ewing, A.D. et al., "High-throughput sequencing reveals extensive variation in human-specific L1 content in individual human genomes," *Genome Research*, vol. 20, pp. 1262-1270 (2010).
Faurez, F. et al., "Review: Replication of porcine circoviruses," *Virology Journal*, vol. 6, No. 60, pp. 1-8 (2009).
Feschotte, C. et al., "Treasures in the attic: rolling circle transposons discovered in eukaryotic genomes," *Proceedings of the National Academy of Sciences of the United States of America*, vol. 98, pp. 8923-8924 (2001).
Feschotte, C., "Transposable elements and the evolution of regulatory networks," *Nature Reviews Genetics*, vol. 9, pp. 397-405 (2008).
Fischer, S.E.J. et al., "Regulated transposition of a fish transposon in the mouse germ line," *Proceedings of the National Academy of Sciences of the United States of America*, vol. 98, pp. 6759-6764 (2001).
Floss, T. et al., "Conditional Gene Trapping Using the FLEx System," *Methods in Molecular Biology: Chromosomal Mutagenesis*, vol. 435, pp. 127-138, Humana Press Inc., Editors Davis, G. and Kayser, K.J. (2008).
Gaj, T. et al., "ZFN, TALEN, and CRISPR/Cas-based methods for genome engineering," *Trends in Biotechnology*, vol. 31, pp. 397-405 (2013).
Garcillan-Barcia, M.P. et al., "Single-stranded DNA intermediates in IS91 rolling-circle transposition," *Molecular Microbiology*, vol. 39, pp. 494-501 (2001).
Garcillan-Barcia, M.P. et al., "Distribution of IS91 family insertion sequences in bacterial genomes: evolutionary implications," *FEMS Microbiology Ecology*, vol. 42, pp. 303-313 (2002).
Grabherr, M.G. et al., "Full-length transcriptome assembly from RNA-Seq data without a reference genome," *Nature Biotechnology*, vol. 29, pp. 644-652 (2011).
Grabundzija, I. et al., "Comparative Analysis of Transposable Element Vector Systems in Human Cells," *Molecular Therapy*, vol. 18, pp. 1200-1209 (2010).
Guelen, L. et al., "Domain organization of human chromosomes revealed by mapping of nuclear lamina interactions," *Nature*, vol. 453, pp. 948-951 (2008).
Haas, B.J. et al., "De novo transcript sequence reconstruction from RNA-seq using the Trinity platform for reference generation and analysis," *Nature Protocols*, vol. 8, pp. 1494-1512 (2013).
Haas, B.J. et al., "Improving the *Arabidopsis* genome annotation using maximal transcript alignment assemblies," *Nucleic Acids Research*, vol. 31, pp. 5654-5666 (2003).
Han, M.J. et al., "Identification and Evolution of the Silkworm Helitrons and their Contribution to Transcripts," DNA *Research*, vol. 20, pp. 471-484 (2013).
Harrow, J. et al., "GENCODE: the reference human genome annotation for The ENCODE Project," *Genome Research*, vol. 22, pp. 1760-1774 (2012).
Ilyina, T.V. et al., "Conserved sequence motifs in the initiator proteins for rolling circle DNA replication encoded by diverse replicons from eubacteria, eucaryotes and archaebacterial," *Nucleic Acids Research*, vol. 20, pp. 3279-3285 (1992).
Ivics, Z. et al., "The expanding universe of transposon technologies for gene and cell engineering," *Mobile DNA*, vol. 1, No. 25, pp. 1-15 (2010).
Jiang, N. et al., "Pack-MULE transposable elements mediate gene evolution in plants," *Nature*, vol. 431, pp. 569-573 (2004).
Jurka, J. et al., "CENSOR—a program for identification and elimination of repetitive elements from DNA sequences," *Computers & Chemistry*, vol. 20, pp. 119-121 (1996).
Kacherovsky, N. et al., "Combination of Sleeping Beauty transposition and chemically induced dimerization selection for robust production of engineered cells," *Nucleic Acids Research*, vol. 40, No. 11, pp. 1-10 (2012).
Kapitonov, V.V. et al., "Helitrons on a roll: eukaryotic rolling-circle transposons," *Trends in Genetics*, vol. 23, pp. 521-529 (2007).
Kapitonov, V.V. et al., "Rolling-circle transposons in eukaryotes," *Proceedings of the National Academy of Sciences of the United States of America*, vol. 98, pp. 8714-8719 (2001).
Kapusta, A. et al., "Transposable Elements Are Major Contributors to the Origin, Diversification, and Regulation of Vertebrate Long Noncoding RNAs," *PLoS Genetics*, vol. 9, No. 4, pp. 1-20 (2013).
Koonin, E.V. et al., "Computer-assisted dissection of rolling circle DNA replication," *BioSystems* , vol. 30, pp. 241-268 (1993).
Kotecki, M. et al., "Isolation and Characterization of a Near-Haploid Human Cell Line," *Experimental Cell Research*, vol. 252, pp. 273-280 (1999).
Krasilnikov, A.S. et al., "Large-scale Effects of Transcriptional DNA Supercoiling in Vivo," *Journal of Molecular Biology*, vol. 292, pp. 1149-1160 (1999).
Lackner, D.H. et al., "A generic strategy for CRISPR-Cas9-mediated gene tagging," *Nature Communications*, vol. 6, No. 10237, pp. 1-7 (2015).
Lal, S.K. et al., "The Maize Genome Contains a Helitron Insertion," *The Plant Cell*, vol. 15, pp. 381-391 (2003).
Langmead, B. et al., "Ultrafast and memory-efficient alignment of short DNA sequences to the human genome," *Genome Biology*, vol. 10, No. 3, pp. R25.1-25.10 (2009).
Lee, T.Y. et al., "GPMiner: an integrated system for mining combinatorial cis-regulatory elements in mammalian gene group," *BMC Genomics*, vol. 13, Suppl. 1, pp. 1-12 (2012).
Li, B et al., "RSEM: accurate transcript quantification from RNA-Seq data with or without a reference genome," *BMC Bioinformatics*, vol. 12, No. 323, pp. 1-16 (2011).
Liang, Q. et al., "Chromosomal Mobilization and Reintegration of Sleeping Beauty and *PiggyBac* Transposons," *Genesis*, vol. 47, pp. 404-408 (2009).
Liu, L.F. et al., "Supercoiling of the DNA template during transcription," *Proceedings of the National Academy of Sciences of the United States of America*, vol. 84, pp. 7024-7027 (1987).
Liu, Z. et al., "Development of Expression Vectors for Transgenic Fish," *Bio/Technology*, vol. 8, pp. 1268-1272 (1990).
Lohse, M. et al., "RobiNA: a user-friendly, integrated software solution for RNA-Seq-based transcriptomics," *Nucleic Acids Research*, vol. 40, pp. W622-W627 (2012).
Luo, G. et al., "Chromosomal transposition of a Tc1/mariner-like element in mouse embryonic stem cells," *Proceedings of the National Academy of Sciences of the United States of America*, vol. 95, pp. 10769-10773 (1998).

(56) References Cited

OTHER PUBLICATIONS

Mates, L. et al., "Molecular evolution of a novel hyperactive Sleeping Beauty transposase enables robust stable gene transfer in vertebrates," *Nature Genetics*, vol. 41, pp. 753-761 (2009).
Mendiola, M.V. et al., "Differential roles of the transposon termini in IS97 transposition," *Proceedings of the National Academy of Sciences of the United States of America*, vol. 91, pp. 1 922-1926 (1994).
Mendiola, M.V. et al., "IS91 transposase is related to the rolling-circle-type replication proteins of the pUB110 family of plasmids," *Nucleic Acids Research*, vol. 20, p. 3521 (1992).
Ml, H. et al., "PANTHER in 2013: modeling the evolution of gene function, and other gene attributes, in the context of phylogenetic trees," *Nucleic Acids Research*, vol. 41, pp. D377-D386 (2013).
Morgante, M. et al., "Gene duplication and exon shuffling by helitron-like transposons generate intraspecies diversity in maize," *Nature Genetics*, vol. 37, pp. 997-1002 (2005).
Moriarity, B.S. et al., "A Sleeping Beauty forward genetic screen identifies new genes and pathways driving osteosarcoma development and metastasis," *Nature Genetics*, vol. 47, pp. 615-624 (2015).
Parsa, J.Y., et al., "Negative Supercoiling Creates Single-Stranded Patches of DNA That Are Substrates for AID-Mediated Mutagenesis," *PLoS Genetics*, vol. 8, No. 2, pp. 1-15 (2012).
Pritham, E.J., "Massive amplification of rolling-circle transposons in the lineage of the bat Myotis lucifugus," *Proceedings of the National Academy of Sciences of the United States of America*, vol. 104, pp. 1895-1900 (2007).
Quinlan, A.R. et al., "BEDTools: a flexible suite of utilities for comparing genomic features," *Bioinformatics*, vol. 26, pp. 841-842 (2010).
Rahmouni, A.R. et al., "Direct Evidence for the Effect of Transcription on Local DNA Supercoiling in Vivo," *Journal of Molecular Biology*, vol. 223, pp. 131-144 (1992).
Sabouri, N. et al., "DNA replication through hard-to-replicate sites, including both highly transcribed RNA Pol II and Pol III genes, requires the S. pombe Pfh1 helicase," *Genes & Development*, vol. 26, pp. 581-593 (2012).
Seim, I. et al., "Genome analysis reveals insights into physiology and longevity of the Brandt's bat *Myotis brandtii,*" *Nature Communications*, vol. 4, No. 2212, pp. 1-18 (2013).
Skarnes, W.C. et al., "A public gene trap resource for mouse functional genomics," *Nature Genetics*, vol. 36, pp. 543-544 (2004).
Steinacher, R. et al., "The DNA helicase Pfh1 promotes fork merging at replication termination sites to ensure genome stability," *Genes & Development*, vol. 26, pp. 594-602 (2012).
Strick, T.R. et al., "Behavior of Supercoiled DNA," *Biophysical Journal*, vol. 74, pp. 2016-2028 (1998).
Tchasovnikarova, I.A. et al., "Epigenetic silencing by the HUSH complex mediates position-effect variegation in human cells," *Science*, vol. 348, pp. 1481-1485 (2015).
Tempel, S. et al., "Model-based identification of Helitrons results in a new classification of their families in *Arabidopsis thaliana,*" *Gene*, vol. 403, pp. 18-28 (2007).
Thomas, J. et al., "Rolling-Circle Transposons Catalyze Genomic Innovation in a Mammalian Lineage," *Genome Biology and Evolution*, vol. 6, pp. 2595-2610 (2014).
Toleman, M.A., "ISCR Elements: Novel Gene-Capturing Systems of the 21st Century?," *Microbiology and Molecular Biology Reviews*, vol. 70, pp. 296-316 (2006).
Ton-Hoang, B. et al., "Single-Stranded DNA Transposition Is Coupled to Host Replication," *Cell*, vol. 142, pp. 398-408 (2010).
Ton-Hoang, B. et al., "Transposition of ISHp608, member of an unusual family of bacterial insertion sequences," *The EMBO Journal*, vol. 24, pp. 3325-3338 (2005).
Tower, J. et al., "Preferential Transposition of *Drosophila P* Elements to Nearby Chromosomal Sites," *Genetics*, vol. 133, pp. 347-359 (1993).
Van Mansfeld, A.D.M. et al., "Two juxtaposed tyrosyl-OH groups participate in $\phi$X174 gene A protein catalysed cleavage and ligation of DNA," *Nucleic Acids Research*, vol. 14, pp. 4229-4238 (1986).

Wilson, M.A. et al., "Pif1 helicase and Pol$\phi$ promote recombination-coupled DNA synthesis via bubble migration," *Nature*, vol. 502, pp. 393-396 (2013).
Xiong, W. et al., "HelitronScanner uncovers a large overlooked cache of Helitron transposons in many plant genomes, " *Proceedings of the National Academy of Sciences of the United States of America*, vol. 111, pp. 10263-10268 (2014).
Yang, L. et al., "Distribution, diversity, evolution, and survival of *Helitrons* in the maize genome," *Proceedings of the National Academy of Sciences of the United States of America*, vol. 106, pp. 19922-19927 (2009).
Yang, L. et al., "Structure-based discovery and description of plant and animal *Helitrons,*" *Proceedings of the National Academy of Sciences of the United States of America*, vol. 106, pp. 12832-12837 (2009).
Yassine, H. et al., "Experimental evidence for IS1294b-mediated transposition of the bla$_{CMY-2}$ cephalosporinase gene in Enterobacteriaceae," *The Journal of Antimicrobial Chemotherapy*, vol. 70, pp. 697-700 (2015).
"Myotis Lucifugus Clone CH235-147J18, Working Draft Sequence, 10 unordered pieces.", XP002769742, retrieved from EBI accession No. EM_HTG: AC200350 Database accession No. AC200350 Sequence, Mar. 29, 2007.
"Myotis Lucifugus Clone CH235-133P22, Working Draft Sequence, 7 unordered pieces.", XP002769743, retrieved from EBI accession No. EM_HTG: AC196304 Database accession No. AC196304 Sequence, Jan. 5, 2007.
"Myotis Lucifugus Clone CH235-106G8, Working Draft Sequence, 3 ordered pieces.", XP002769744, retrieved from EBI accession No. EM_HTG: AC198538 Database accession No. AC198538 Sequence, Feb. 27, 2007.
"Uncharacterized Protein LOC106448412 [Papilio Xuthus]" XP002769745, Database Accession No. XP_013168531.1, Aug. 5, 2015.
"Myotis Lucifugus Clone CH235-181B5, Working Draft Sequence, 9 ordered pieces.", XP00276946, retrieved from EBI accession No. EM_HTG: AC196306 Database accession No. AC196306 Sequence, Jan. 5, 2007.
"Nycticeius Humeralis Isolate Nhum2 Transposon Helibat, Partial Sequence.", retrieved from EBI accession No. EM_STD: HQ407504 Database accession No. HQ407504 Sequence & Database EMBL, Jan. 31, 2011.
"Lasiurus Seminolus Isolate Lsem1 Transposon Helibat, Partial Sequence.", retrieved from EBI accession No. EM_STD: HQ407507 Database accession No. HQ407507 Sequence & Database EMBL, Jan. 31, 2011.
"Pipistrellus Subflavus Isolate Psub2 Transposon Helibat, Partial Sequence", retrieved from EBI accession No. EM_STD: HQ407506 Database accession No. HQ407506 Sequence, Jan. 31, 2011.
Grabundzija, I. et al., "A Helitron Transposon Reconstructed From Bats Reveals a Novel Mechanism of Genome Shuffling in Eukaryotes," *Nature Comm.*, vol. 7, 10716, pp. 1-12, (2016).
Jainy, T. et al., "Helitrons, the Eukaryotic Rolling-Circle Transposable Elements," *Microbiology Spectrum*, pp. 1-32 (2015).
Jainy, T. et al., "The Limited Distribution Ofto Vesper Bats Supports Horizontal Transfer," *Gene Elsevier*, vol. 474, No. 1, pp. 52-58 (2010).
Yongbin, D. et al., "Structural Characterization of Helitrons and Their Stepwise Capturing of Gene Fragments in The Maize Genome," *BMC Genomics*, vol. 12, No. 1, p. 609 (2011).
International Search Report for PCT/GB2017/050355 dated May 22, 2017 (7 pages).
Castanera R. et al., "Highly expressed captured genes and cross-kingdom domains present in Helitrons create novel diversity in Pleurotus ostreatus and other fungi," BMC Genomics, vol. 15, article 1071 (2014).
Chellapan B. V. et al., "Non-canonical Helitrons in Fusarium oxysporum," Mobile DNA, vol. 7, article 27 (2016).

\* cited by examiner

Figure 1B

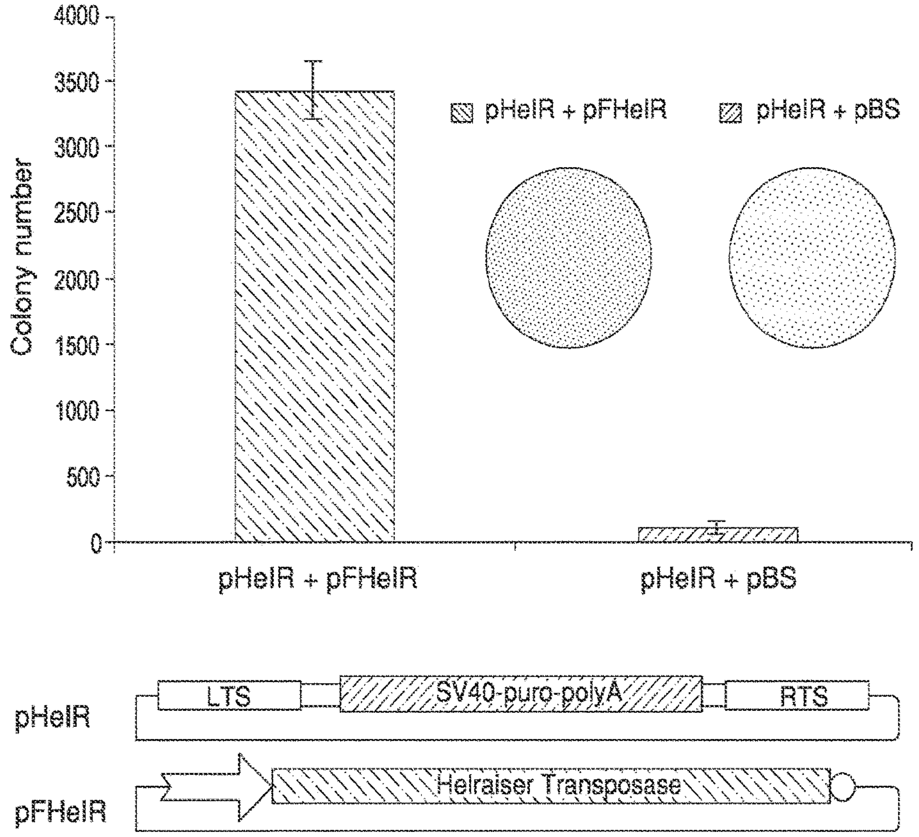

Figure 1C

SEQ ID NO:145 *caccatatga* TCCTATATAA... ...GGGCCACTAG *tatatatata* SEQ ID NO:146

SEQ ID NO: 147 *cctgtgcata* TCCTATATAA... ...GGGCCACTAG *taatatataa* SEQ ID NO: 148
SEQ ID NO: 149 *tgttctggca* TCCTATATAA... ...GGGCCACTAG *tgaatataat* SEQ ID NO: 150
SEQ ID NO: 151 *tactctatca* TCCTATATAA... ...GGGCCACTAG *tcaaatatat* SEQ ID NO: 152
SEQ ID NO: 153 *taagcaataa* TCCTATATAA... ...GGGCCACTAG *taattaataa* SEQ ID NO: 154
SEQ ID NO: 155 *cctatgtcta* TCCTATATAA... ...GGGCCACTAG *taaaaaataa* SEQ ID NO: 156

5' caccatatgaTCCTATATAATAAAAGAGAAACATGCAAATTGACCATCCC 3'

SEQ ID NO:157 pHe IR CCCTTTCAAT GTGCACGAATTTCGTGCAC CGGGCCACTAG SEQ ID NO:162
pHe IRΔHP CCCTTTCAAT — — — — — — — — — — — CGGGCCACTAG SEQ ID NO:163
pHe IRΔTH CCCTTTCAAT ACCTGTGGTGTACCGCAGGT CGGGCCACTAG SEQ ID NO: 164
pHe IRStemX CCCTTTCAAT ACCTGCGGAATTTCCGCAGGT CGGGCCACTAG SEQ ID NO: 165
pHe IRLoopX CCCTTTCAAT GTGCACGCCGGGCGTGCAC CGGGCCACTAG SEQ ID NO: 166

Figure 8

SEQ ID NO: 5

Helibat1 (Helraiser) complete consensus sequence

TGCTATATAATAAAAGAGAAACATGCAAATTGACCATCCCTCCGCTACGCTCAAGCCACGCCCACCAGCCAATCAGAAGTGACTATGCAAATTAACCCAACAAAGATGGCAGTTAAATTTGCATACGCA
GGTGTCAAGCGCCCCCAGGCAGGCAACGGCGGCCGCGGGCTCCCAGGACCTTCGCTGGCCCCGGGAGGCGAGCCGGCCGCGCCTAGCCACACCCGCGGGCTCCCGGGACCTTCGGCAGCAGAGAGCAGAG
CGGGAGAGCCGGCGGAGAGCGGGACGGTTTGGAGGACTTGGCAGAGCAGGAGGCCGCTGGACATAGAGCAGAGCGAGAGAGAGGGTGGCTTGGAGGGCGTGGCTCCCTCTGTCACCCCAGCTTCCTCATC
ACAGCTGTGGAAACTGACAGCAGGGAGGAGGAAGTCCCACCCCCACAGAATCAGCCAGAATCAGCCGTTGGTCAGACAGCTCTCAGCGGCCTGACAGCCAGGACTCTCATTCACCTGCATCTCAGACCG
TGACAGTAGAGAGGTGGGACTATGTCTAAAGAACAACTGTTGATACAACGTACCTCTGCACCCGAAACATGCCCCCGTTATCGACAGAAAATGTCTCGCAGCAGCAACGTGCGTCTGATCTTGAAACAACG
CGGCCCCTGCAACAGAATGTATCTGAAGAGCAGCTACTGGAAAAACGTCGCTCTGAAGCCGAAAAACAGCGGCGTCATCGACAGAAAATGTCTAAAGACCAACGTGCCTTTGAAGTTGAAAGAAGGCCG
TGGCGACGACAGAATATGTCTAGAGAACAGTCATCAACAAGTACTACCAATACCCGTACGAACTGCCTTCTCAGCAAAAATGGAGTACATGAGGATGCAATTCTGGAACATAGTTGTGGTGGAATGACT
GTTCGATGTGAATTTTGCCTATCACTAAATTTCTCTGATGAAAAACCATCCGATGGGAAATTTACTCGATGTTGTAGCAAAGGAAAGTCTGTCCAAATGATATACATTTTCCAGATTACCCGCATAT
TTAAAAAGATTAATGACAAACGAAGATTCTGACAGTAAAAATTTCATGGAAAATATTCGTTCCATAAATAGTTCTTTTGCTTTTGCTTCCATGGGTGCAAATATTGCATCGCCATCAGGATATGGGCCA
TACTGTTTTAGAATACACCGACAAGTTTATCACCGTACTGCAACTTTACATCCTTCGGATGGTGTTTCTCCGAAGTTGCTCAACTCTATATTTTCGATACACCGAACCTACAAGTAAAACATTACCA
ATGCCAGAAAACCAGGCCTGCTCAGAAAGACTCATGATCAACATCAACAACGTCATGCATGAAATAAATGAATTAACAAAATCGTACAAGATGCTACATGAGGTAGAAAAGGAAGCCCAATCTGAACCA
GCAGCAAAAGGTATTGCTCCCACAGAAGTAACAATGGCGATTAAATACGATCGTAACAGTGACCCAGGTAGATATAATTCTCCCCGTGTAACCGAGGTTGCTGTCATATTCAGAAACGAAGATGGAGAA
CCTCCTTTTGAAACGGACTTGCTCATTCATTGTAAACCAGATCCCAATAATCCAAATGCCACTAAAATGAAACAAATCAGTATCCTGTTTCCTACATTAGATGCAATGACATATCCTATTCTTTTTCCA
CATGGTGAAAAAGGCTGGGGAACAGATATTGCATTAAGACTCAGAGACAACAGTGTAATCGACAATAATACTAGACAAAATGTAAGCACACGAGTCACACAAATGCAGTATTATGCATTTCATCTCTCT
CTCCGCGACACGTTCAATCCTATTTTAAATGCAGGAAAATTAACTCAACAGTTTATTGTGGATTCATATTCAAAAATGGACGCCCAATCGCATAAATTTCATCAAAGCAAACCAATCTAAGTTCACAGTT
GAAAAATATAGTGGTTTGATGGATTATCTCAAATCTAGATCTGAAAATGACAATGTGCCGATTGGTAAAATGATAATACTTCCATCATCTTTTGAGGGTAGTCCCAGAAATATGCAGCAGCGATATCAG
GATGCTATGGCAATTGTAACGAAGTATGGCAAGCCCGATTTATTCATAACCATGACATGCAACCCCAAATGGGCAGATATTACAAACAATTTACAACCCTGGCAAAAAGTTGAAAACAGACCTGACTTG
GTAGCCAGAGTTTTTAATATTAAGCTGAATGCTCTTTTAAATGATATATGTAAATTCCATTTATTTGGCAAAGTAATAGCTAAAATTCATGTGCATTGAATTTCAGAAACGGGACTGCCTCACGCTCAC
ATATTATTGATATTAGATAGTGAGTCCAAATTACGTTCAGAAGATGACATTGACCGTATAGTTAAGGCAGAAATTCCAGATGAAGACCAGTGTCCTCGACTTTTTCAAATTGTAAAATCAAATATGGTA
CATGGACCATGTGGAATACAAAATCCAAATAGTCCATGTATGGAAAATGGAAAATGTTCAAAGGGATATCCAAAAGAATTTCAAAATGCGACCATTGGAAATATTGATGGATATCCAAATACAAACGA
AGATCTGGTAGCACCATGTCTATTGGAAATAAAGTTGTCGATAACACTTGGATTGTCCCTTATAACCCGTATTTGTGCCTTAAATATAACTGTCATATAAATGTTGAAGTCTGTGCATCAATTAAAAGT
GTCAAATATTTATTTAAATACATCTATAAAGGGCACGATTGTGCAAATATTCAAATTTCTGAAAAAAATATTATCAATCATGACGAAGTACAGGACTTCATTGACTCCAGGTATGTGAGCGCTCCTGAG
GCTGTTTGGAGACTTTTTGCAATGCGAATGCATGACCAATCTCATGCAATCACAAGATTAGCTATTCATTTGCCAAATGATCAGAATTTGTATTTTCATACCGATGATTTTGCTGAAGTTTTAGATAGG
GCTAAAAGGCATAACTCGACTTTGATGGCTTGGTTCTTATTGAATAGAGAAGATTCTGATGCACGTAATTATTATTATTGGGAGATTCCACAGCATTATGTGTTTAATAATTCTTTGTGGACAAAACGC
CGAAAGGGTGGGAATAAAGTATTAGGTAGACTGTTCACTGTCACCTTTAGAGAACCAGAACGATATTACCTTAGACTTTTGCTTCTGCATGTAAAAGGTGCGATAAGTTTTGAGGATCTGCGAACTGTA
GGAGGTGTAACTTATGATACATTTCATGAAGCTGCTAAACACCGAGGATTATTACTTGATGACACTATCTGGAAAGATACGATTGACGATGCAATCATCCTTAATATGCCCAAACAACTACGGCAACTT
TTTGCATATATATGTGTGTTTGGATGTCCTTCTGCTGCAGACAAATTATGGGATGAGAATAAATCTCATTTTATTGAAGATTTCTGTTGGAAATTACACCGAAGAGAAGGTGCCTGTGTGAACTGTGAA
ATGCATGCCCTTAACGAAATTCAGGAGGTATTCACATTGCATGGAATGAAATGTTCACATTTCAAACTTCCGGACTATCCTTTATTAATGAATGCAAATACATGTGATCAATTGTACGAGCAACAACAG
GCAGAGGTTTTGATAAATTCTCTGAATGATGAACAGTTGGCAGCCTTTCAGACTATAACTTCAGCCATCGAAGATCAAACTGTACACCCCAAATGCTTTTTCTTGGATGGTCCAGGTGGTAGTGGAAAA
ACATATCTGTATAAAGTTTTAACACATTATATTAGAGGTCGTGGTGGTACTGTTTTACCCACAGCATCTACAGCAATTGCTGCAAATTTACTTCTTGGTGGAAGAACCTTTCATTCCCAATATAAATTA
CCAATTCCATTAAATGAAACTTCAATTTCTAGACTCGATATAAAGAGTGAAGTTGCTAAAACCATTAAAAAGGCCCAACTTCTCATTATTGATGAATGCACCATGGCATCCAGTCATGCTATAAACGCC
ATAGATAGATTACTAAGAGAAATTATGAATTTGAATGTTGCATTTGGTGGAAAGTTCTCCTTCTCGGAGGGGATTTTCGACAATGTCTCAGTATTGTACCACATGCTATGGCATCGGCCATAGTACAA
ACGAGTTTAAAGTACTGTAATGTTTGGGGATGTTTCAGAAAGTTGTCTCTTAAAACAAATATGACATCAGAGGATTCTGCTTATAGTGAATGGTTAGTAAAACTTGGACATGGCAAACTTGATAGCAGT
TTTCATTTAGGAATGGATATTATTGAAATCCCCCATGAAATGATTTGTAACGGATCTATTATTGAAGCTACCTTTGGAAATAGTATATCTATAGATAATATTAAAAATATATCTAAACGTGCAATTCTT
TGTCCAAAAAATGACCATGTTCAAAAATTAAATGAACAAATTTTGGATATACTTGATGGAGATTTTCACACATATTTGAGTGATCATTCCATTGATTCAACACATGATCCTGAAAACGAAAATTTCCC
ATCGAATTTCTTAATAGTATTACTCCTTCCCGAATGCCGTGTCATAAATTAAAATTGAAAGTCGGTGCAATCATCATCCTATTGAGAAATCTTAATAGTAAATCGGGTCTTTGTAATGGTACTAGATTT
ATTATCAAAAGATTACGACCTAACATTATCGAAGCTGAAGTATTAACAGGATCTGCAGAGGGAGAGGTTGTTCTCATTCCAAGAATTGATTTGTCCCCATCTGACACTGGCTCCCATTTAAATTAATT
CGAAGACAGTTTCCCGTGATGCCAGCATTTGCGATGACTATTAATAAATCACAAGGACAAACTCTAGACAGAGTAGGAATATTCCTACCTGAACCCGTTTTCGCACATGGTCAGTTATATGTTGCTTTC
TCTCGAGTTCGAAGAGCATGTGACGTTAAAGTTAAAGTTGTAAATACTTCATCACAAGGAAATTAGTCAAGCACTCTGAAAGTGTTTTTACTCTTAATGTGGTATACAGGGAGATATTAGAATAAGTT
TAATCACTTTATCAGTCATTGTTTGCATCAATGTTGTTTTTATATCATGTTTTTGTTGTTTTTATATCATGTCTTTGTTGTTGTTATATCATGTTGTTATTGTTTATTTATTAATAAATTTATGTATTA
TTTCATATACATTTTACTCATTTCCTTTCATCTCTCACACTTCTATTATAGAGAAAGGGCAAATAGCAATATTAAAATATTTCCTCTAATTAATTCCCTTTCAATGTGCACGAATTTCGTGCACCGCG
CCACTAG

Helibat1

Figure 8 continued

SEQ ID NO:204

TCCTATATAATAAAAGAGAAACATGCAAATTGACCATCCCTCCGCTACGCTCAAGCCACGCCCACCAGCCAATCAGAAGTGACTATGCAAATTAACCCAACAAAGATGGCAGTTAAATTTGCATACGCA
GGTGTCAAGCGCCCCAGGAGGAAATTTATGTATTATTTTCATATACATTTTACTCATTTTCCTTTCATCTCTCACACTTCTATTATACAGAAAGGGCAAATACCAATATTAAAATATTTCCTCTAATTAA
TTCCCTTTCAATGTGCACGAATTTCGTGCACCGGGCCACTAG

Hel i bat N1 SEQ ID NO:205

TCCTATATAATAAAAGAGAAACATGCAAATTAGCCGTCCCTCTGCTACGCTCAAGCCACGCCCACAAGCCACGCCCACCAGCCAATCAGAGTGACTATGCAAATTAACCTGACAAAGATGGCGGTTAAT
TTGCATACGCAGGTGTCAAGCAAAGTAATAGCTAAAATTCATGTCATTGAATTTCAGAAACGCCGACTGGCTCACGCTCACATATTATTGATATTAGATAGTGAGTCCAAATTACGTTCCTCTAATTAA
TTCCCTTTCAATGTGCACGAATTTCGTGCACCAGCCTACTAG

Hel i bat N2 SEQ ID NO:206

TCTACTTATATAAAAACCCTCGGTGTAACATCACGTCCAGAAGCGCCGACCAACCCGAAGGAAGTCAGTCCTGCAGGGGTCGTCTTGGAAACGGCTGCGCCCTCCCCCACCTGTTTCCCCGGAGGCCGAG
GTTTCAGGCACGAACCCGGCCCAAATTTATATATTATTTTCATATACATTTTACTAATTTCCTTTCATCTCTCACACTTCTATTATACAGAAAGGGCAAATACCAATATTAAAATATCTCCCCTAATTAA
TTCCCTTTTAATGTGCACGAATTTCGTGCACCGCCTACTAG

Hel i bat N3 SEQ ID NO:207

TCTATATATATAAAAGGCTAAGTGTCCATCCAACCCGGTAGCTATGATGCACACTGACCACCAGGGGGCAGATGCTCAATGCAGGACCTGCCCATGATGTGCACTGGCCATTTAAAAATAAACGTGGGCTG

GAAAAAGTTTAGCTAAATCAGAAAGCAGGTCTAATTAAGCAAGTTTATTCTATATCTATAAAAGGCTAAGTTGACTCGTGCATGCGCGATACATATAAAGCTCTCGGCTGGCGCCAATCGCACACGTGTG

TTTCCATCTGTCATTCTCCATCATCAATTTCGTTCACACTTCTATTATACACAAAGCCCAAATACCCATATTAAAATATTTCTTCTAATTAATTCCTTTCAATGTGCACCAATCTGTGCACCCGCCCAC

TAG

Transposase coding sequences

Left terminal sequences (LTS)

Right terminal sequences (RTS)

Hairpin

Left end

1

SEQ ID NO:182 5'CACCATATGATCCTATATAATAAAAGAGAAACATGCAAATTGACCATCCC 3'

SEQ ID NO:183 3'GTGGTATACTAGGATATATTATTTTGTGTTTCATGGTTTAACTGGTAGGG 5'

2

Right end

3

SEQ ID NO:184 5'CCCTTTCAATGTGCACGAATTTCGTGCACCGGGCCACTAGTATATATATA 3'

SEQ ID NO:185 3'GGGAAAGTTACACGTGCTTAAAGCACGTGGCCCGGTGATCATATATATAT 5'

4

Figure 11D

```
i)
SEQ ID NO:186          7788                         HelibatN580.5                                   3438
ANKR01301689.1:-TAATATTGTATACCAACTA|TCTACACTAA...AGGCCTCTAG|TACTTAAATAAAAAAAATAA
ALEH01119295.1:ATAATATTGTATACCAACTA-------SEQ ID NO:188-----------TACTTAAATAAAAAAAATAA
SEQ ID NO:187          28384                                                                        28345

ii)
SEQ ID NO:189          11222                        HelibatN541                                     10286
AAPE02036247.1:CATATTCTCATACATACACA|TCTACACTAA...AGGCCTCTAG|TCTATATATAAAAGCCAAGC
ANKR01171035.1:CATATTCTTATACACACACA-------SEQ ID NO:191-----------TCTATATATAAAAGCCAAGC
SEQ ID NO:190          14668                                                                        14629

iii)
SEQ ID NO:192          26485                        HelibatN580.4                                   28277
ANKR02284387.1:TCCAGCATATA-TATATATA|TCTACACTAA...CCCATCTATA|TATTTGGTAATAAA-GGTTA
ALWT01028103.1:TCCAGCATATACTATATATA-------SEQ ID NO:194-----------TATTTGGTAATGAACGGTTA
SEQ ID NO:193          730                                                                          690
```

Figure 11E

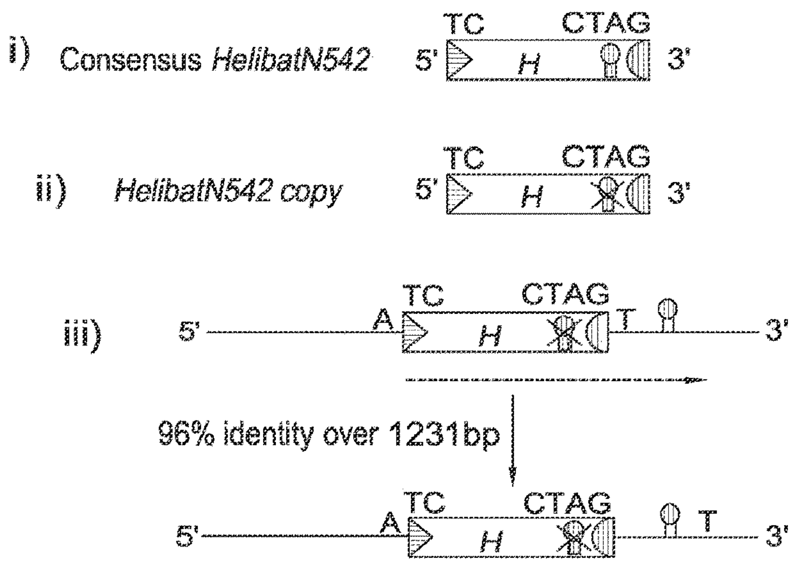

SEQ ID NO:195
5' CCCCCGAGTGCACAAATTTTTGTGCACCGGGCCTCTAG 3'

SEQ ID NO:196
5' AGGGCACAGGCCGGGCTGAGGGACCCCCGACCCTCTAG 3'

SEQ ID NO:197
5' TCAAATTGAGTTTCAACTAGCAGAATAATTATTTAAGA 3' iv)

SEQ ID NO:198 3776 SEQ ID NO:200 2493

AAPE02057204.1: GCACTAGTCTAATGCTAACA | TCCTCCTATCTAA...TTATTTAAGA | AAAAATAAACAATGACGAGG

AAPE02006537.1: GTAGGGAAACTTAATACTTA | ---TCCTATCTAA...TTATTTAAGA | TGCTCAATGCAGGAGCTGCC

SEQ ID NO:199 10322 SEQ ID NO:201 11597

SEQUENCE LISTING

<160> NUMBER OF SEQ ID NOS: 207

<210> SEQ ID NO 1
<211> LENGTH: 1496
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 1

Met Ser Lys Glu Gln Leu Leu Ile Gln Arg Ser Ser Ala Ala Glu Arg
1 5 10 15

Cys Arg Arg Tyr Arg Gln Lys Met Ser Ala Glu Gln Arg Ala Ser Asp
20 25 30

Leu Glu Arg Arg Arg Arg Leu Gln Gln Asn Val Ser Glu Glu Gln Leu
35 40 45

Leu Glu Lys Arg Arg Ser Glu Ala Glu Lys Gln Arg Arg His Arg Gln
50 55 60

Lys Met Ser Lys Asp Gln Arg Ala Phe Glu Val Glu Arg Arg Arg Trp
65 70 75 80

Arg Arg Gln Asn Met Ser Arg Glu Gln Ser Ser Thr Ser Thr Thr Asn
85 90 95

Thr Gly Arg Asn Cys Leu Leu Ser Lys Asn Gly Val His Glu Asp Ala
100 105 110

Ile Leu Glu His Ser Cys Gly Gly Met Thr Val Arg Cys Glu Phe Cys
115 120 125

Leu Ser Leu Asn Phe Ser Asp Glu Lys Pro Ser Asp Gly Lys Phe Thr
130 135 140

Arg Cys Cys Ser Lys Gly Lys Val Cys Pro Asn Asp Ile His Phe Pro
145 150 155 160

Asp Tyr Pro Ala Tyr Leu Lys Arg Leu Met Thr Asn Glu Asp Ser Asp
165 170 175

Ser Lys Asn Phe Met Glu Asn Ile Arg Ser Ile Asn Ser Ser Phe Ala
180 185 190

Phe Ala Ser Met Gly Ala Asn Ile Ala Ser Pro Ser Gly Tyr Gly Pro
195 200 205

Tyr Cys Phe Arg Ile His Gly Gln Val Tyr His Arg Thr Gly Thr Leu
210 215 220

His Pro Ser Asp Gly Val Ser Arg Lys Phe Ala Gln Leu Tyr Ile Leu
225 230 235 240

Asp Thr Ala Glu Ala Thr Ser Lys Arg Leu Ala Met Pro Glu Asn Gln
245 250 255

Gly Cys Ser Glu Arg Leu Met Ile Asn Ile Asn Asn Leu Met His Glu
260 265 270

Ile Asn Glu Leu Thr Lys Ser Tyr Lys Met Leu His Glu Val Glu Lys
275 280 285

Glu Ala Gln Ser Glu Ala Ala Ala Lys Gly Ile Ala Pro Thr Glu Val
290 295 300

Thr Met Ala Ile Lys Tyr Asp Arg Asn Ser Asp Pro Gly Arg Tyr Asn
305 310 315 320

Ser Pro Arg Val Thr Glu Val Ala Val Ile Phe Arg Asn Glu Asp Gly
325 330 335

Glu Pro Pro Phe Glu Arg Asp Leu Leu Ile His Cys Lys Pro Asp Pro
340 345 350

-continued

```
Asn Asn Pro Asn Ala Thr Lys Met Lys Gln Ile Ser Ile Leu Phe Pro
        355                 360                 365

Thr Leu Asp Ala Met Thr Tyr Pro Ile Leu Phe Pro His Gly Glu Lys
    370                 375                 380

Gly Trp Gly Thr Asp Ile Ala Leu Arg Leu Arg Asp Asn Ser Val Ile
385                 390                 395                 400

Asp Asn Asn Thr Arg Gln Asn Val Arg Thr Arg Val Thr Gln Met Gln
                405                 410                 415

Tyr Tyr Gly Phe His Leu Ser Val Arg Asp Thr Phe Asn Pro Ile Leu
            420                 425                 430

Asn Ala Gly Lys Leu Thr Gln Gln Phe Ile Val Asp Ser Tyr Ser Lys
        435                 440                 445

Met Glu Ala Asn Arg Ile Asn Phe Ile Lys Ala Asn Gln Ser Lys Leu
    450                 455                 460

Arg Val Glu Lys Tyr Ser Gly Leu Met Asp Tyr Leu Lys Ser Arg Ser
465                 470                 475                 480

Glu Asn Asp Asn Val Pro Ile Gly Lys Met Ile Ile Leu Pro Ser Ser
                485                 490                 495

Phe Glu Gly Ser Pro Arg Asn Met Gln Gln Arg Tyr Gln Asp Ala Met
            500                 505                 510

Ala Ile Val Thr Lys Tyr Gly Lys Pro Asp Leu Phe Ile Thr Met Thr
        515                 520                 525

Cys Asn Pro Lys Trp Ala Asp Ile Thr Asn Asn Leu Gln Arg Trp Gln
    530                 535                 540

Lys Val Glu Asn Arg Pro Asp Leu Val Ala Arg Val Phe Asn Ile Lys
545                 550                 555                 560

Leu Asn Ala Leu Leu Asn Asp Ile Cys Lys Phe His Leu Phe Gly Lys
                565                 570                 575

Val Ile Ala Lys Ile His Val Ile Glu Phe Gln Lys Arg Gly Leu Pro
            580                 585                 590

His Ala His Ile Leu Leu Ile Leu Asp Ser Glu Ser Lys Leu Arg Ser
        595                 600                 605

Glu Asp Asp Ile Asp Arg Ile Val Lys Ala Glu Ile Pro Asp Glu Asp
    610                 615                 620

Gln Cys Pro Arg Leu Phe Gln Ile Val Lys Ser Asn Met Val His Gly
625                 630                 635                 640

Pro Cys Gly Ile Gln Asn Pro Asn Ser Pro Cys Met Glu Asn Gly Lys
                645                 650                 655

Cys Ser Lys Gly Tyr Pro Lys Glu Phe Gln Asn Ala Thr Ile Gly Asn
            660                 665                 670

Ile Asp Gly Tyr Pro Lys Tyr Lys Arg Arg Ser Gly Ser Thr Met Ser
        675                 680                 685

Ile Gly Asn Lys Val Val Asp Asn Thr Trp Ile Val Pro Tyr Asn Pro
    690                 695                 700

Tyr Leu Cys Leu Lys Tyr Asn Cys His Ile Asn Val Glu Val Cys Ala
705                 710                 715                 720

Ser Ile Lys Ser Val Lys Tyr Leu Phe Lys Tyr Ile Tyr Lys Gly His
                725                 730                 735

Asp Cys Ala Asn Ile Gln Ile Ser Glu Lys Asn Ile Ile Asn His Asp
            740                 745                 750

Glu Val Gln Asp Phe Ile Asp Ser Arg Tyr Val Ser Ala Pro Glu Ala
        755                 760                 765
```

-continued

```
Val Trp Arg Leu Phe Ala Met Arg Met His Asp Gln Ser His Ala Ile
    770                 775                 780

Thr Arg Leu Ala Ile His Leu Pro Asn Asp Gln Asn Leu Tyr Phe His
785                 790                 795                 800

Thr Asp Asp Phe Ala Glu Val Leu Asp Arg Ala Lys Arg His Asn Ser
                805                 810                 815

Thr Leu Met Ala Trp Phe Leu Leu Asn Arg Glu Asp Ser Asp Ala Arg
            820                 825                 830

Asn Tyr Tyr Tyr Trp Glu Ile Pro Gln His Tyr Val Phe Asn Asn Ser
        835                 840                 845

Leu Trp Thr Lys Arg Arg Lys Gly Gly Asn Lys Val Leu Gly Arg Leu
    850                 855                 860

Phe Thr Val Ser Phe Arg Glu Pro Glu Arg Tyr Tyr Leu Arg Leu Leu
865                 870                 875                 880

Leu Leu His Val Lys Gly Ala Ile Ser Phe Glu Asp Leu Arg Thr Val
                885                 890                 895

Gly Gly Val Thr Tyr Asp Thr Phe His Glu Ala Ala Lys His Arg Gly
            900                 905                 910

Leu Leu Leu Asp Asp Thr Ile Trp Lys Asp Thr Ile Asp Asp Ala Ile
        915                 920                 925

Ile Leu Asn Met Pro Lys Gln Leu Arg Gln Leu Phe Ala Tyr Ile Cys
    930                 935                 940

Val Phe Gly Cys Pro Ser Ala Ala Asp Lys Leu Trp Asp Glu Asn Lys
945                 950                 955                 960

Ser His Phe Ile Glu Asp Phe Cys Trp Lys Leu His Arg Arg Glu Gly
                965                 970                 975

Ala Cys Val Asn Cys Glu Met His Ala Leu Asn Glu Ile Gln Glu Val
            980                 985                 990

Phe Thr Leu His Gly Met Lys Cys  Ser His Phe Lys Leu  Pro Asp Tyr
        995                 1000                1005

Pro Leu  Leu Met Asn Ala Asn  Thr Cys Asp Gln Leu  Tyr Glu Gln
    1010                1015                1020

Gln Gln  Ala Glu Val Leu Ile  Asn Ser Leu Asn Asp  Glu Gln Leu
    1025                1030                1035

Ala Ala  Phe Gln Thr Ile Thr  Ser Ala Ile Glu Asp  Gln Thr Val
    1040                1045                1050

His Pro  Lys Cys Phe Phe Leu  Asp Gly Pro Gly Gly  Ser Gly Lys
    1055                1060                1065

Thr Tyr  Leu Tyr Lys Val Leu  Thr His Tyr Ile Arg  Gly Arg Gly
    1070                1075                1080

Gly Thr  Val Leu Pro Thr Ala  Ser Thr Gly Ile Ala  Ala Asn Leu
    1085                1090                1095

Leu Leu  Gly Gly Arg Thr Phe  His Ser Gln Tyr Lys  Leu Pro Ile
    1100                1105                1110

Pro Leu  Asn Glu Thr Ser Ile  Ser Arg Leu Asp Ile  Lys Ser Glu
    1115                1120                1125

Val Ala  Lys Thr Ile Lys Lys  Ala Gln Leu Leu Ile  Ile Asp Glu
    1130                1135                1140

Cys Thr  Met Ala Ser Ser His  Ala Ile Asn Ala Ile  Asp Arg Leu
    1145                1150                1155

Leu Arg  Glu Ile Met Asn Leu  Asn Val Ala Phe Gly  Gly Lys Val
    1160                1165                1170

Leu Leu  Leu Gly Gly Asp Phe  Arg Gln Cys Leu Ser  Ile Val Pro
```

```
    1175                1180                1185

His Ala  Met Arg Ser Ala Ile  Val Gln Thr Ser Leu  Lys Tyr Cys
    1190                1195                1200

Asn Val  Trp Gly Cys Phe Arg  Lys Leu Ser Leu Lys  Thr Asn Met
    1205                1210                1215

Arg Ser  Glu Asp Ser Ala Tyr  Ser Glu Trp Leu Val  Lys Leu Gly
    1220                1225                1230

Asp Gly  Lys Leu Asp Ser Ser  Phe His Leu Gly Met  Asp Ile Ile
    1235                1240                1245

Glu Ile  Pro His Glu Met Ile  Cys Asn Gly Ser Ile  Ile Glu Ala
    1250                1255                1260

Thr Phe  Gly Asn Ser Ile Ser  Ile Asp Asn Ile Lys  Asn Ile Ser
    1265                1270                1275

Lys Arg  Ala Ile Leu Cys Pro  Lys Asn Glu His Val  Gln Lys Leu
    1280                1285                1290

Asn Glu  Glu Ile Leu Asp Ile  Leu Asp Gly Asp Phe  His Thr Tyr
    1295                1300                1305

Leu Ser  Asp Asp Ser Ile Asp  Ser Thr Asp Asp Ala  Glu Lys Glu
    1310                1315                1320

Asn Phe  Pro Ile Glu Phe Leu  Asn Ser Ile Thr Pro  Ser Gly Met
    1325                1330                1335

Pro Cys  His Lys Leu Lys Leu  Lys Val Gly Ala Ile  Ile Met Leu
    1340                1345                1350

Leu Arg  Asn Leu Asn Ser Lys  Trp Gly Leu Cys Asn  Gly Thr Arg
    1355                1360                1365

Phe Ile  Ile Lys Arg Leu Arg  Pro Asn Ile Ile Glu  Ala Glu Val
    1370                1375                1380

Leu Thr  Gly Ser Ala Glu Gly  Glu Val Val Leu Ile  Pro Arg Ile
    1385                1390                1395

Asp Leu  Ser Pro Ser Asp Thr  Gly Leu Pro Phe Lys  Leu Ile Arg
    1400                1405                1410

Arg Gln  Phe Pro Val Met Pro  Ala Phe Ala Met Thr  Ile Asn Lys
    1415                1420                1425

Ser Gln  Gly Gln Thr Leu Asp  Arg Val Gly Ile Phe  Leu Pro Glu
    1430                1435                1440

Pro Val  Phe Ala His Gly Gln  Leu Tyr Val Ala Phe  Ser Arg Val
    1445                1450                1455

Arg Arg  Ala Cys Asp Val Lys  Val Lys Val Val Asn  Thr Ser Ser
    1460                1465                1470

Gln Gly  Lys Leu Val Lys His  Ser Glu Ser Val Phe  Thr Leu Asn
    1475                1480                1485

Val Val  Tyr Arg Glu Ile Leu  Glu
    1490                1495


<210> SEQ ID NO 2
<211> LENGTH: 4491
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 2

atgtctaaag aacaactgtt gatacaacgt agctctgcag ccgaaagatg ccggcgttat     60
```

-continued

```
cgacagaaaa tgtctgcaga gcaacgtgcg tctgatcttg aaagaaggcg gcgcctgcaa    120
cagaatgtat ctgaagagca gctactggaa aaacgtcgct ctgaagccga aaaacagcgg    180
cgtcatcgac agaaaatgtc taaagaccaa cgtgcctttg aagttgaaag aaggcggtgg    240
cgacgacaga atatgtctag agaacagtca tcaacaagta ctaccaatac cggtaggaac    300
tgccttctca gcaaaaatgg agtacatgag gatgcaattc tcgaacatag ttgtggtgga    360
atgactgttc gatgtgaatt ttgcctatca ctaaatttct ctgatgaaaa accatccgat    420
gggaaattta ctcgatgttg tagcaaaggg aaagtctgtc caaatgatat acattttcca    480
gattacccgg catatttaaa aagattaatg acaaacgaag attctgacag taaaaatttc    540
atggaaaata ttcgttccat aaatagttct tttgcttttg cttccatggg tgcaaatatt    600
gcatcgccat caggatatgg gccatactgt tttagaatac acggacaagt ttatcaccgt    660
actggaactt tacatccttc ggatggtgtt tctcggaagt ttgctcaact ctatattttg    720
gatacagccg aagctacaag taaaagatta gcaatgccag aaaaccaggg ctgctcagaa    780
agactcatga tcaacatcaa caacctcatg catgaaataa atgaattaac aaaatcgtac    840
aagatgctac atgaggtaga aaaggaagcc caatctgaag cagcagcaaa aggtattgct    900
cccacagaag taacaatggc gattaaatac gatcgtaaca gtgacccagg tagatataat    960
tctccccgtg taaccgaggt tgctgtcata ttcagaaacg aagatggaga acctcctttt   1020
gaaagggact tgctcattca ttgtaaacca gatcccaata atccaaatgc cactaaaatg   1080
aaacaaatca gtatcctgtt tcctacatta gatgcaatga catatcctat tctttttcca   1140
catggtgaaa aaggctgggg aacagatatt gcattaagac tcagagacaa cagtgtaatc   1200
gacaataata ctagacaaaa tgtaaggaca cgagtcacac aaatgcagta ttatggattt   1260
catctctctg tgcgggacac gttcaatcct attttaaatg caggaaaatt aactcaacag   1320
tttattgtgg attcatattc aaaaatggag gccaatcgga taaatttcat caaagcaaac   1380
caatctaagt tgagagttga aaaatatagt ggtttgatgg attatctcaa atctagatct   1440
gaaaatgaca atgtgccgat tggtaaaatg ataatacttc catcatcttt tgagggtagt   1500
cccagaaata tgcagcagcg atatcaggat gctatggcaa ttgtaacgaa gtatggcaag   1560
cccgatttat tcataaccat gacatgcaac cccaaatggg cagatattac aaacaattta   1620
caacgctggc aaaaagttga aaacagacct gacttggtag ccagagtttt taatattaag   1680
ctgaatgctc ttttaaatga tatatgtaaa ttccatttat ttggcaaagt aatagctaaa   1740
attcatgtca ttgaatttca gaaacgcgga ctgcctcacg ctcacatatt attgatatta   1800
gatagtgagt ccaaattacg ttcagaagat gacattgacc gtatagttaa ggcagaaatt   1860
ccagatgaag accagtgtcc tcgacttttt caaattgtaa aatcaaatat ggtacatgga   1920
ccatgtggaa tacaaaatcc aaatagtcca tgtatggaaa atggaaaatg ttcaaaggga   1980
tatccaaaag aatttcaaaa tgcgaccatt ggaaatattg atggatatcc caaatacaaa   2040
cgaagatctg gtagcaccat gtctattgga aataaagttg tcgataacac ttggattgtc   2100
ccttataacc cgtatttgtg ccttaaatat aactgtcata taaatgttga agtctgtgca   2160
tcaattaaaa gtgtcaaata tttatttaaa tacatctata aagggcacga ttgtgcaaat   2220
attcaaattt ctgaaaaaaa tattatcaat catgacgaag tacaggactt cattgactcc   2280
aggtatgtga gcgctcctga ggctgtttgg agactttttg caatgcgaat gcatgaccaa   2340
tctcatgcaa tcacaagatt agctattcat ttgccaaatg atcagaattt gtattttcat   2400
accgatgatt ttgctgaagt tttagatagg gctaaaaggc ataactcgac tttgatggct   2460
```

```
tggttcttat tgaatagaga agattctgat gcacgtaatt attattattg ggagattcca   2520

cagcattatg tgtttaataa ttctttgtgg acaaaacgcc gaaagggtgg gaataaagta   2580

ttaggtagac tgttcactgt gagctttaga gaaccagaac gatattacct tagacttttg   2640

cttctgcatg taaaaggtgc gataagtttt gaggatctgc gaactgtagg aggtgtaact   2700

tatgatacat ttcatgaagc tgctaaacac cgaggattat tacttgatga cactatctgg   2760

aaagatacga ttgacgatgc aatcatcctt aatatgccca aacaactacg gcaacttttt   2820

gcatatatat gtgtgtttgg atgtccttct gctgcagaca aattatggga tgagaataaa   2880

tctcatttta ttgaagattt ctgttggaaa ttacaccgaa gagaaggtgc ctgtgtgaac   2940

tgtgaaatgc atgcccttaa cgaaattcag gaggtattca cattgcatgg aatgaaatgt   3000

tcacatttca aacttccgga ctatccttta ttaatgaatg caaatacatg tgatcaattg   3060

tacgagcaac aacaggcaga ggttttgata aattctctga atgatgaaca gttggcagcc   3120

tttcagacta taacttcagc catcgaagat caaactgtac accccaaatg ctttttcttg   3180

gatggtccag gtggtagtgg aaaaacatat ctgtataaag ttttaacaca ttatattaga   3240

ggtcgtggtg gtactgtttt acccacagca tctacaggaa ttgctgcaaa tttacttctt   3300

ggtggaagaa cctttcattc ccaatataaa ttaccaattc cattaaatga aacttcaatt   3360

tctagactcg atataaagag tgaagttgct aaaaccatta aaaaggccca acttctcatt   3420

attgatgaat gcaccatggc atccagtcat gctataaacg ccatagatag attactaaga   3480

gaaattatga atttgaatgt tgcatttggt gggaaagttc tccttctcgg aggggatttt   3540

cgacaatgtc tcagtattgt accacatgct atgcgatcgg ccatagtaca aacgagttta   3600

aagtactgta atgtttgggg atgtttcaga aagttgtctc ttaaaacaaa tatgagatca   3660

gaggattctg cttatagtga atggttagta aaacttggag atggcaaact tgatagcagt   3720

tttcatttag gaatggatat tattgaaatc ccccatgaaa tgatttgtaa cggatctatt   3780

attgaagcta cctttggaaa tagtatatct atagataata ttaaaaatat atctaaacgt   3840

gcaattcttt gtccaaaaaa tgagcatgtt caaaaattaa atgaagaaat tttggatata   3900

cttgatggag attttcacac atatttgagt gatgattcca ttgattcaac agatgatgct   3960

gaaaaggaaa attttcccat cgaatttctt aatagtatta ctccttcggg aatgccgtgt   4020

cataaattaa aattgaaagt gggtgcaatc atcatgctat tgagaaatct taatagtaaa   4080

tggggtcttt gtaatggtac tagatttatt atcaaaagat tacgacctaa cattatcgaa   4140

gctgaagtat taacaggatc tgcagaggga gaggttgttc tgattccaag aattgatttg   4200

tccccatctg acactggcct cccatttaaa ttaattcgaa gacagtttcc cgtgatgcca   4260

gcatttgcga tgactattaa taaatcacaa ggacaaactc tagacagagt aggaatattc   4320

ctacctgaac ccgttttcgc acatggtcag ttatatgttg ctttctctcg agttcgaaga   4380

gcatgtgacg ttaaagttaa agttgtaaat acttcatcac aagggaaatt agtcaagcac   4440

tctgaaagtg tttttactct taatgtggta tacagggaga tattagaata a            4491
```

<210> SEQ ID NO 3
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

-continued

<400> SEQUENCE: 3
tcctatataa taaaagagaa acatgcaaat tgaccatccc tccgctacgc tcaagccacg 60
cccaccagcc aatcagaagt gactatgcaa attaacccaa caaagatggc agttaaattt 120
gcatacgcag gtgtcaagcg ccccaggagg 150

<210> SEQ ID NO 4
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 4
aaatttatgt attattttca tatacatttt actcatttcc tttcatctct cacacttcta 60
ttatagagaa agggcaaata gcaatattaa aatatttcct ctaattaatt ccctttcaat 120
gtgcacgaat ttcgtgcacc gggccactag 150

<210> SEQ ID NO 5
<211> LENGTH: 5296
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 5
tcctatataa taaaagagaa acatgcaaat tgaccatccc tccgctacgc tcaagccacg 60
cccaccagcc aatcagaagt gactatgcaa attaacccaa caaagatggc agttaaattt 120
gcatacgcag gtgtcaagcg ccccaggagg caacggcggc cgcgggctcc caggaccttc 180
gctggccccg ggaggcgagg ccggccgcgc ctagccacac ccgcgggctc ccgggacctt 240
cgccagcaga gagcagagcg ggagagcggg cggagagcgg gaggtttgga ggacttggca 300
gagcaggagg ccgctggaca tagagcagag cgagagagag ggtggcttgg agggcgtggc 360
tccctctgtc accccagctt cctcatcaca gctgtggaaa ctgacagcag ggaggaggaa 420
gtcccacccc cacagaatca gccagaatca gccgttggtc agacagctct cagcggcctg 480
acagccagga ctctcattca cctgcatctc agaccgtgac agtagagagg tgggactatg 540
tctaaagaac aactgttgat acaacgtagc tctgcagccg aaagatgccg gcgttatcga 600
cagaaaatgt ctgcagagca acgtgcgtct gatcttgaaa gaaggcggcg cctgcaacag 660
aatgtatctg aagagcagct actggaaaaa cgtcgctctg aagccgaaaa acagcggcgt 720
catcgacaga aaatgtctaa agaccaacgt gcctttgaag ttgaaagaag gcggtggcga 780
cgacagaata tgtctagaga acagtcatca acaagtacta ccaataccgg taggaactgc 840
cttctcagca aaaatggagt acatgaggat gcaattctcg aacatagttg tggtggaatg 900
actgttcgat gtgaattttg cctatcacta aatttctctg atgaaaaacc atccgatggg 960
aaatttactc gatgttgtag caaagggaaa gtctgtccaa atgatataca ttttccagat 1020
tacccggcat atttaaaaag attaatgaca aacgaagatt ctgacagtaa aaatttcatg 1080
gaaaatattc gttccataaa tagttctttt gcttttgctt ccatgggtgc aaatattgca 1140
tcgccatcag gatatgggcc atactgtttt agaatacacg gacaagttta tcaccgtact 1200
ggaactttac atccttcgga tggtgtttct cggaagtttg ctcaactcta tattttggat 1260

```
acagccgaag ctacaagtaa aagattagca atgccagaaa accagggctg ctcagaaaga   1320
ctcatgatca acatcaacaa cctcatgcat gaaataaatg aattaacaaa atcgtacaag   1380
atgctacatg aggtagaaaa ggaagcccaa tctgaagcag cagcaaaagg tattgctccc   1440
acagaagtaa caatggcgat taaatacgat cgtaacagtg acccaggtag atataattct   1500
ccccgtgtaa ccgaggttgc tgtcatattc agaaacgaag atggagaacc tccttttgaa   1560
agggacttgc tcattcattg taaaccagat cccaataatc caaatgccac taaaatgaaa   1620
caaatcagta tcctgtttcc tacattagat gcaatgacat atcctattct tttccacat   1680
ggtgaaaaag gctggggaac agatattgca ttaagactca gagacaacag tgtaatcgac   1740
aataatacta gacaaaatgt aaggacacga gtcacacaaa tgcagtatta tggatttcat   1800
ctctctgtgc gggacacgtt caatcctatt ttaaatgcag gaaaattaac tcaacagttt   1860
attgtggatt catattcaaa aatggaggcc aatcggataa atttcatcaa agcaaaccaa   1920
tctaagttga gagttgaaaa atatagtggt ttgatggatt atctcaaatc tagatctgaa   1980
aatgacaatg tgccgattgg taaaatgata atacttccat catcttttga gggtagtccc   2040
agaaatatgc agcagcgata tcaggatgct atggcaattg taacgaagta tggcaagccc   2100
gatttattca taaccatgac atgcaacccc aaatgggcag atattacaaa caatttacaa   2160
cgctggcaaa aagttgaaaa cagacctgac ttggtagcca gagtttttaa tattaagctg   2220
aatgctcttt taaatgatat atgtaaattc catttatttg gcaaagtaat agctaaaatt   2280
catgtcattg aatttcagaa acgcggactg cctcacgctc acatattatt gatattagat   2340
agtgagtcca aattacgttc agaagatgac attgaccgta tagttaaggc agaaattcca   2400
gatgaagacc agtgtcctcg actttttcaa attgtaaaat caaatatggt acatggacca   2460
tgtggaatac aaaatccaaa tagtccatgt atggaaaatg gaaaatgttc aaagggatat   2520
ccaaaagaat ttcaaaatgc gaccattgga aatattgatg gatatcccaa atacaaacga   2580
agatctggta gcaccatgtc tattggaaat aaagttgtcg ataacacttg gattgtccct   2640
tataacccgt atttgtgcct taaatataac tgtcatataa atgttgaagt ctgtgcatca   2700
attaaaagtg tcaaatattt atttaaatac atctataaag ggcacgattg tgcaaatatt   2760
caaatttctg aaaaaaatat tatcaatcat gacgaagtac aggacttcat tgactccagg   2820
tatgtgagcg ctcctgaggc tgtttggaga ctttttgcaa tgcgaatgca tgaccaatct   2880
catgcaatca caagattagc tattcatttg ccaaatgatc agaatttgta ttttcatacc   2940
gatgattttg ctgaagtttt agatagggct aaaaggcata actcgacttt gatggcttgg   3000
ttcttattga atagagaaga ttctgatgca cgtaattatt attattggga gattccacag   3060
cattatgtgt ttaataattc tttgtggaca aaacgccgaa agggtgggaa taaagtatta   3120
ggtagactgt tcactgtgag ctttagagaa ccagaacgat attaccttag acttttgctt   3180
ctgcatgtaa aggtgcgat aagttttgag gatctgcgaa ctgtaggagg tgtaacttat   3240
gatacatttc atgaagctgc taaacaccga ggattattac ttgatgacac tatctggaaa   3300
gatacgattg acgatgcaat catccttaat atgcccaaac aactacggca actttttgca   3360
tatatatgtg tgtttggatg tccttctgct gcagacaaat tatgggatga gaataaatct   3420
cattttattg aagatttctg ttggaaatta caccgaagag aaggtgcctg tgtgaactgt   3480
gaaatgcatg cccttaacga aattcaggag gtattcacat tgcatggaat gaaatgttca   3540
catttcaaac ttccggacta tcctttatta atgaatgcaa atacatgtga tcaattgtac   3600
```

-continued

```
gagcaacaac aggcagaggt tttgataaat tctctgaatg atgaacagtt ggcagccttt   3660

cagactataa cttcagccat cgaagatcaa actgtacacc ccaaatgctt tttcttggat   3720

ggtccaggtg gtagtggaaa aacatatctg tataaagttt taacacatta tattagaggt   3780

cgtggtggta ctgttttacc cacagcatct acaggaattg ctgcaaattt acttcttggt   3840

ggaagaacct ttcattccca atataaatta ccaattccat taaatgaaac ttcaatttct   3900

agactcgata taaagagtga agttgctaaa accattaaaa aggcccaact tctcattatt   3960

gatgaatgca ccatggcatc cagtcatgct ataaacgcca tagatagatt actaagagaa   4020

attatgaatt tgaatgttgc atttggtggg aaagttctcc ttctcggagg ggattttcga   4080

caatgtctca gtattgtacc acatgctatg cgatcggcca tagtacaaac gagtttaaag   4140

tactgtaatg tttggggatg tttcagaaag ttgtctctta aacaaatat gagatcagag   4200

gattctgctt atagtgaatg gttagtaaaa cttggagatg gcaaacttga tagcagtttt   4260

catttaggaa tggatattat tgaaatcccc catgaaatga tttgtaacgg atctattatt   4320

gaagctacct ttggaaatag tatatctata gataatatta aaaatatatc taaacgtgca   4380

attctttgtc caaaaaatga gcatgttcaa aaattaaatg aagaaatttt ggatatactt   4440

gatggagatt ttcacacata tttgagtgat gattccattg attcaacaga tgatgctgaa   4500

aaggaaaatt ttcccatcga atttcttaat agtattactc cttcgggaat gccgtgtcat   4560

aaattaaaat tgaaagtggg tgcaatcatc atgctattga gaaatcttaa tagtaaatgg   4620

ggtctttgta atggtactag atttattatc aaaagattac gacctaacat tatcgaagct   4680

gaagtattaa caggatctgc agagggagag gttgttctga ttccaagaat tgatttgtcc   4740

ccatctgaca ctggcctccc atttaaatta attcgaagac agtttcccgt gatgccagca   4800

tttgcgatga ctattaataa atcacaagga caaactctag acagagtagg aatattccta   4860

cctgaacccg ttttcgcaca tggtcagtta tatgttgctt tctctcgagt tcgaagagca   4920

tgtgacgtta aagttaaagt tgtaaatact tcatcacaag ggaaattagt caagcactct   4980

gaaagtgttt ttactcttaa tgtggtatac agggagatat tagaataagt ttaatcactt   5040

tatcagtcat tgtttgcatc aatgttgttt ttatatcatg tttttgttgt ttttatatca   5100

tgtctttgtt gttgttatat catgttgtta ttgtttattt attaataaat ttatgtatta   5160

ttttcatata cattttactc atttcctttc atctctcaca cttctattat agagaaaggg   5220

caaatagcaa tattaaaata tttcctctaa ttaattccct ttcaatgtgc acgaatttcg   5280

tgcaccgggc cactag                                                     5296
```

```
<210> SEQ ID NO 6
<211> LENGTH: 4491
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6

atgtccaagg aacagctgct gattcagcgg agctccgccg ccgagagatg ccgccgctat     60

cgccagaaaa tgtctgccga gcagagggcc tccgatctgg agcgccggcg gagactgcag    120

cagaacgtga gcgaagagca gctgctggag aagcggcggt ctgaagccga gaagcagaga    180

agacaccggc agaaaatgtc caaagatcag agggccttcg aggtggagcg gcggaggtgg    240

agaagacaga atatgagcag agaacagtct tctaccagca caaccaatac cgggagaaac    300
```

-continued

```
tgtctgctgt ccaagaacgg cgtgcacgaa gatgccatcc tggagcacag ctgtggcggc    360
atgaccgtga gatgcgagtt ttgtctgagc ctgaattttt ccgacgagaa gccatctgat    420
ggcaagttta ccagatgttg ttccaaaggg aaagtgtgcc caaatgatat ccacttcccc    480
gactacccag cctatctgaa gaggctgatg accaacgagg atagcgattc caagaacttc    540
atggaaaata tcaggagcat caactcctct ttcgcctttg cctctatggg cgccaacatt    600
gcctccccct ctgggtacgg cccttactgt ttccggattc acggacaggt gtaccaccgc    660
accggcaccc tgcacccctc tgacggcgtg tctcggaagt tcgcccagct gtatatcctg    720
gacaccgccg aggccacctc caagaggctg gccatgcctg agaatcaggg ctgcagcgaa    780
aggctgatga tcaacattaa caacctgatg cacgagatca acgagctgac caagagctac    840
aagatgctgc acgaggtgga gaaagaagcc cagtctgagg ccgccgccaa ggggatcgcc    900
cccaccgagg tgaccatggc catcaaatat gatcggaatt ccgatcctgg ccggtacaat    960
agcccaagag tgacagaggt ggccgtgatt ttcaggaacg aggacggaga gcccccccttc   1020
gagagggatc tgctgattca ctgtaagcct gaccctaata accctaatgc caccaagatg   1080
aagcagattt ctatcctgtt cccaaccctg gacgccatga cctatcctat tctgttcccc   1140
cacggcgaaa agggatgggg gacagatatc gccctgcggc tgagggacaa ttccgtgatt   1200
gacaataata ccagacagaa cgtgcggaca agggtgacac agatgcagta ttacggcttc   1260
cacctgtctg tgagagacac ctttaatcca atcctgaatg ccggaaagct gacccagcag   1320
tttatcgtgg actcctactc caagatggaa gccaacagaa ttaatttcat caaggccaat   1380
cagtctaagc tgcgggtgga gaaatactct gggctgatgg attacctgaa gtctaggtct   1440
gagaatgaca acgtgcctat tggaaagatg atcattctgc ccagctcttt tgaagggagc   1500
ccacggaata tgcagcagcg gtaccaggat gccatggcca ttgtgacaaa gtatgggaag   1560
cctgatctgt tcatcacaat gacatgtaac cccaagtggg ccgatattac caacaacctg   1620
cagaggtggc agaaggtgga gaacagaccc gacctggtgg ccagggtgtt caacatcaag   1680
ctgaacgccc tgctgaacga catttgcaag tttcacctgt ttgggaaggt gattgccaaa   1740
attcacgtga ttgagtttca gaaacggggc ctgccacacg cccacatcct gctgatcctg   1800
gactccgaaa gcaagctgag atctgaggac gatatcgaca ggattgtgaa ggccgagatc   1860
cccgacgagg atcagtgtcc acgcctgttc cagattgtga aatccaacat ggtgcacggc   1920
ccttgtggga tccagaatcc caactcccca tgcatggaaa acgggaagtg cagcaagggc   1980
tatcccaagg agttccagaa cgccaccatc ggcaacatcg acggctatcc aaaatataag   2040
aggaggtccg gctctaccat gagcattggc aataaggtgg tggataacac ctggatcgtg   2100
ccttataacc cctatctgtg cctgaagtac aactgtcaca tcaatgtgga ggtgtgcgcc   2160
tccatcaaat ccgtgaagta cctgttcaaa tacatctaca aaggccacga ctgcgccaat   2220
atccagatct ctgagaagaa cattattaac cacgatgagg tgcaggactt tattgattct   2280
agatacgtga gcgcccccga ggccgtgtgg agactgttcg ccatgaggat gcacgaccag   2340
agccacgcca tcacccggct ggccatccac ctgcccaatg atcagaatct gtactttcac   2400
accgatgatt tcgccgaggt gctggatagg gccaagagac acaacagcac cctgatggcc   2460
tggttcctgc tgaacaggga ggattccgac gccaggaact attattattg ggaaatccca   2520
cagcactacg tgtttaacaa cagcctgtgg accaagagaa gaaaagggggg caacaaggtg   2580
ctgggccgcc tgttcaccgt gtcttttaga gagcctgaaa ggtactacct gaggctgctg   2640
```

-continued

```
ctgctgcacg tgaaggggc catctctttc gaagacctgc gcaccgtggg gggagtgacc   2700

tacgatacct tccacgaagc cgccaaacac aggggcctgc tgctggacga cacaatctgg   2760

aaagacacca tcgatgatgc cattattctg aacatgccaa agcagctgag acagctgttc   2820

gcctacatct gcgtgtttgg atgcccctcc gccgccgaca agctgtggga tgagaataag   2880

tcccacttta ttgaggattt ctgttggaag ctgcacagaa gggagggggc ctgtgtgaac   2940

tgcgaaatgc acgccctgaa tgagatccag gaagtgttta cactgcacgg catgaagtgt   3000

tctcacttca aactgcctga ctatcctctg ctgatgaatg ccaacacctg tgatcagctg   3060

tacgagcagc agcaggccga ggtgctgatc aattccctga atgacgagca gctggccgcc   3120

ttccagacca ttacatctgc cattgaggac cagaccgtgc accccaagtg cttcttcctg   3180

gacggacccg gagggtctgg caagacctac ctgtataaag tgctgacaca ctatatcaga   3240

ggaagggggg ggaccgtgct gcctaccgcc agcacaggca ttgccgccaa cctgctgctg   3300

gggggcagga ccttccactc tcagtacaag ctgcccatcc ctctgaacga gacatctatc   3360

tctagactgg acatcaaatc cgaggtggcc aagaccatta aaaaggccca gctgctgatt   3420

atcgacgagt gtaccatggc cagctcccac gccatcaacg ccatcgacag actgctgagg   3480

gaaatcatga acctgaacgt ggccttcgga ggcaaggtgc tgctgctggg cggcgatttt   3540

aggcagtgcc tgagcattgt gccccacgcc atgcggtccg ccatcgtgca gacctccctg   3600

aagtattgta atgtgtgggg ctgcttccgg aagctgagcc tgaaaaccaa tatgaggagc   3660

gaggacagcg cctacagcga gtggctggtg aagctgggcg atggaaaact ggattcctcc   3720

ttccacctgg ggatggacat tatcgagatc cccccacgaga tgatttgtaa cgggagcatt   3780

atcgaggcca ccttcgggaa ctccatcagc atcgataaca tcaagaatat ttctaagaga   3840

gccattctgt gcccaaagaa cgaacacgtg cagaagctga atgaggagat cctggatatt   3900

ctggacggag atttccacac ctacctgtct gacgatagca tcgattccac cgacgacgcc   3960

gagaaggaaa acttcccaat tgaattcctg aatagcatca cccccagcgg catgccctgt   4020

cacaagctga agctgaaggt gggcgccatc atcatgctgc tgcggaacct gaactctaag   4080

tggggcctgt gtaacggcac ccgctttatc attaaaaggc tgaggccaaa catcattgaa   4140

gccgaggtgc tgaccggcag cgccgaaggc gaagtggtgc tgatcccacg cattgacctg   4200

tctccaagcg acaccggcct gcccttcaaa ctgatccgcc gccagtttcc tgtgatgccc   4260

gccttcgcca tgacaattaa caagtcccag ggccagacac tggaccgcgt gggcattttt   4320

ctgcccgaac cagtgttcgc ccacgggcag ctgtatgtgg cctttagcag agtgcgccgg   4380

gcctgcgatg tgaaggtgaa agtggtgaac acctcttccc agggcaagct ggtgaagcac   4440

agcgaatctg tgttcacact gaacgtggtg tatagagaga tcctggaata a            4491
```

```
<210> SEQ ID NO 7
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Met Tyr Pro Tyr Asp Val Pro Asp Tyr Ala Tyr Pro Tyr Asp Val Pro
1               5                   10                  15

Asp Tyr Ala
```

<210> SEQ ID NO 8
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 8
caaggatctt accgctgttg agatccagtt cgatgtaacc cactcgtgca cccaactgat 60
cttcagcatc ttttacttaa gcttccagcg 90

<210> SEQ ID NO 9
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 9
ggtatgtcgg gaacctctcc 20

<210> SEQ ID NO 10
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 10
ggtatgtcgg gaacctctcc agg 23

<210> SEQ ID NO 11
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 11
gtcaccaatc ctgtccctag 20

<210> SEQ ID NO 12
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 12
tatattccca gggccggtta 20

<210> SEQ ID NO 13
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 13
tctccacctc agtgatgacg 20

<210> SEQ ID NO 14
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 14
aggaggatca cagcaacacc 20

<210> SEQ ID NO 15
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 15
acaggaggtg ggggttagac 20

<210> SEQ ID NO 16
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 16
ctgcacgtga gcttcagcta 20

<210> SEQ ID NO 17
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 17
aagccggtgc ccatca 16

<210> SEQ ID NO 18
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 18
ccgcgtgatc ggcgactt 18

<210> SEQ ID NO 19

<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
gtggctctaa gggtaaatca 20

<210> SEQ ID NO 20
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
taatcataga accttcctac 20

<210> SEQ ID NO 21
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
ggcctgacat ctgattgcgg 20

<210> SEQ ID NO 22
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
caggggaatc tgacatcggt 20

<210> SEQ ID NO 23
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 23
ggttgttttc tccttggccc 20

<210> SEQ ID NO 24
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 24
atcctagagc caaccccagt 20

<210> SEQ ID NO 25
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 25
aagtgctaag aaagcggcac 20

<210> SEQ ID NO 26
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 26
tccaacaggc tcagtgacaa g 21

<210> SEQ ID NO 27
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 27
cacttctggg tgcgtactgt 20

<210> SEQ ID NO 28
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 28
gcttgctaga gggtcacagg 20

<210> SEQ ID NO 29
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 29
taacacgtcg ccttcaactg 20

<210> SEQ ID NO 30
<211> LENGTH: 20
<212> TYPE: DNA
<213> ORGANISM: Artificial Sequence
<220> FEATURE:

-continued

<221> NAME/KEY: source
<223> OTHER INFORMATION: /note="Description of Artificial Sequence:
      Synthetic primer"

<400> SEQUENCE: 30
ttacaatctg gcggcttcat 20

<210> SEQ ID NO 31
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31
caccagggca agggtctg 18

<210> SEQ ID NO 32
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 32
gctcgtagaa ggggaggttg 20

<210> SEQ ID NO 33
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 33
gccttcctgg agacct 16

<210> SEQ ID NO 34
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 34
ggcgcttgac acctgcgtat 20

<210> SEQ ID NO 35
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 35
gtggcttgag cgtagcggag 20

<210> SEQ ID NO 36
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 36
acactctttc cctacacgac gctcttccga tct 33

<210> SEQ ID NO 37
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 37
tttgcatgtt tctcttttat tatatag 27

<210> SEQ ID NO 38
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 38
attaattccc tttcaatgtg cacgaa 26

<210> SEQ ID NO 39
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 39
ttccctttca atgtgcacga attt 24

<210> SEQ ID NO 40
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 40
acactctttc cctacacgac gctcttccga tct 33

<210> SEQ ID NO 41
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 41
aatttcgtgc accgggccac t 21

<210> SEQ ID NO 42
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 42
ccttctatga acggctgggc tt 22

<210> SEQ ID NO 43
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 43
gggctttact gtgaccgcag at 22

<210> SEQ ID NO 44
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 44
acactctttc cctacacgac gctcttccga tct 33

<210> SEQ ID NO 45
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 45
gaaaaccctg gaccaatggt ttgt 24

<210> SEQ ID NO 46
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 46
gtgactggag ttcagacgtg 20

<210> SEQ ID NO 47
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 47
caagcagaag acggcatacg agat 24

<210> SEQ ID NO 48
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 48
gtgactggag ttcagacgtg tgctcttccg atct 34

<210> SEQ ID NO 49
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 49
aatgatacgg cgaccaccga gatctacact ctttccctac acgacgctct tccgatct 58

<210> SEQ ID NO 50
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"
<220> FEATURE:
<221> NAME/KEY: modified_base
<222> LOCATION: (38)..(40)
<223> OTHER INFORMATION: a, c, t, g, unknown or other

<400> SEQUENCE: 50
gtgactggag ttcagacgtg tgctcttccg atctdddnnn aacg 44

<210> SEQ ID NO 51
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"
<220> FEATURE:
<221> NAME/KEY: modified_base
<222> LOCATION: (38)..(40)
<223> OTHER INFORMATION: a, c, t, g, unknown or other

<400> SEQUENCE: 51
gtgactggag ttcagacgtg tgctcttccg atcthhhnnn ctac 44

<210> SEQ ID NO 52
<211> LENGTH: 44
<212> TYPE: DNA
<213> ORGANISM: Artificial Sequence
<220> FEATURE:

-continued

<221> NAME/KEY: source
<223> OTHER INFORMATION: /note="Description of Artificial Sequence:
      Synthetic primer"
<220> FEATURE:
<221> NAME/KEY: modified_base
<222> LOCATION: (38)..(40)
<223> OTHER INFORMATION: a, c, t, g, unknown or other

<400> SEQUENCE: 52
gtgactggag ttcagacgtg tgctcttccg atcthhhnnn ggac 44

<210> SEQ ID NO 53
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (35)..(35)
<223> OTHER INFORMATION: a, c, t, g, unknown or other
<220> FEATURE:
<221> NAME/KEY: modified_base
<222> LOCATION: (37)..(38)
<223> OTHER INFORMATION: a, c, t, g, unknown or other

<400> SEQUENCE: 53
gtgactggag ttcagacgtg tgctcttccg atctnbnnbh cgtt 44

<210> SEQ ID NO 54
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (36)..(36)
<223> OTHER INFORMATION: a, c, t, g, unknown or other
<220> FEATURE:
<221> NAME/KEY: modified_base
<222> LOCATION: (38)..(38)
<223> OTHER INFORMATION: a, c, t, g, unknown or other
<220> FEATURE:
<221> NAME/KEY: modified_base
<222> LOCATION: (40)..(40)
<223> OTHER INFORMATION: a, c, t, g, unknown or other

<400> SEQUENCE: 54
gtgactggag ttcagacgtg tgctcttccg atctvnvnvn gcaa 44

<210> SEQ ID NO 55
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (36)..(36)
<223> OTHER INFORMATION: a, c, t, g, unknown or other
<220> FEATURE:
<221> NAME/KEY: modified_base
<222> LOCATION: (38)..(40)
<223> OTHER INFORMATION: a, c, t, g, unknown or other

<400> SEQUENCE: 55
gtgactggag ttcagacgtg tgctcttccg atcthnhnnn gtcc 44

<210> SEQ ID NO 56
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"
<220> FEATURE:
<221> NAME/KEY: modified_base
<222> LOCATION: (38)..(38)
<223> OTHER INFORMATION: a, c, t, g, unknown or other
<220> FEATURE:
<221> NAME/KEY: modified_base
<222> LOCATION: (40)..(40)
<223> OTHER INFORMATION: a, c, t, g, unknown or other

<400> SEQUENCE: 56
gtgactggag ttcagacgtg tgctcttccg atcthhhnhn attc 44

<210> SEQ ID NO 57
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"
<220> FEATURE:
<221> NAME/KEY: modified_base
<222> LOCATION: (38)..(40)
<223> OTHER INFORMATION: a, c, t, g, unknown or other

<400> SEQUENCE: 57
gtgactggag ttcagacgtg tgctcttccg atctbbbnnn gaat 44

<210> SEQ ID NO 58
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"
<220> FEATURE:
<221> NAME/KEY: modified_base
<222> LOCATION: (38)..(40)
<223> OTHER INFORMATION: a, c, t, g, unknown or other

<400> SEQUENCE: 58
gtgactggag ttcagacgtg tgctcttccg atcthhhnnn gaac 44

<210> SEQ ID NO 59
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"
<220> FEATURE:
<221> NAME/KEY: modified_base
<222> LOCATION: (36)..(36)
<223> OTHER INFORMATION: a, c, t, g, unknown or other
<220> FEATURE:
<221> NAME/KEY: modified_base
<222> LOCATION: (38)..(40)
<223> OTHER INFORMATION: a, c, t, g, unknown or other

<400> SEQUENCE: 59
gtgactggag ttcagacgtg tgctcttccg atctvnvnnn gtaa 44

<210> SEQ ID NO 60
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"
<220> FEATURE:
<221> NAME/KEY: modified_base
<222> LOCATION: (36)..(36)
<223> OTHER INFORMATION: a, c, t, g, unknown or other
<220> FEATURE:
<221> NAME/KEY: modified_base
<222> LOCATION: (38)..(40)
<223> OTHER INFORMATION: a, c, t, g, unknown or other

<400> SEQUENCE: 60
gtgactggag ttcagacgtg tgctcttccg atcthnhnnn gtcc 44

<210> SEQ ID NO 61
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"
<220> FEATURE:
<221> NAME/KEY: modified_base
<222> LOCATION: (38)..(40)
<223> OTHER INFORMATION: a, c, t, g, unknown or other

<400> SEQUENCE: 61
gtgactggag ttcagacgtg tgctcttccg atcthhhnnn ttac 44

<210> SEQ ID NO 62
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"
<220> FEATURE:
<221> NAME/KEY: modified_base
<222> LOCATION: (35)..(35)
<223> OTHER INFORMATION: a, c, t, g, unknown or other
<220> FEATURE:
<221> NAME/KEY: modified_base
<222> LOCATION: (38)..(40)
<223> OTHER INFORMATION: a, c, t, g, unknown or other

<400> SEQUENCE: 62
gtgactggag ttcagacgtg tgctcttccg atctnddnnn agtg 44

<210> SEQ ID NO 63
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"
<220> FEATURE:
<221> NAME/KEY: modified_base
<222> LOCATION: (38)..(40)
<223> OTHER INFORMATION: a, c, t, g, unknown or other

<400> SEQUENCE: 63
gtgactggag ttcagacgtg tgctcttccg atctbbbnnn cact 44

<210> SEQ ID NO 64
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"
<220> FEATURE:
<221> NAME/KEY: modified_base
<222> LOCATION: (36)..(36)
<223> OTHER INFORMATION: a, c, t, g, unknown or other
<220> FEATURE:
<221> NAME/KEY: modified_base
<222> LOCATION: (38)..(40)
<223> OTHER INFORMATION: a, c, t, g, unknown or other

<400> SEQUENCE: 64
gtgactggag ttcagacgtg tgctcttccg atctvnvnnn tcaa 44

<210> SEQ ID NO 65
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"
<220> FEATURE:
<221> NAME/KEY: modified_base
<222> LOCATION: (38)..(40)
<223> OTHER INFORMATION: a, c, t, g, unknown or other

<400> SEQUENCE: 65
gtgactggag ttcagacgtg tgctcttccg atctdvvnnn ttga 44

<210> SEQ ID NO 66
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"
<220> FEATURE:
<221> NAME/KEY: modified_base
<222> LOCATION: (38)..(38)
<223> OTHER INFORMATION: a, c, t, g, unknown or other
<220> FEATURE:
<221> NAME/KEY: modified_base
<222> LOCATION: (40)..(40)
<223> OTHER INFORMATION: a, c, t, g, unknown or other

<400> SEQUENCE: 66
gtgactggag ttcagacgtg tgctcttccg atcthvvnvn taca 44

<210> SEQ ID NO 67
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"
<220> FEATURE:
<221> NAME/KEY: modified_base
<222> LOCATION: (38)..(40)

<223> OTHER INFORMATION: a, c, t, g, unknown or other

<400> SEQUENCE: 67
gtgactggag ttcagacgtg tgctcttccg atctsvvnnn tgta 44

<210> SEQ ID NO 68
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 68
gcctccatca aatccgtgaa gttcctgttc aaatacatct acaaaggc 48

<210> SEQ ID NO 69
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 69
gtgaagtacc tgttcaaatt tatctacaaa ggccacgact gc 42

<210> SEQ ID NO 70
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 70
cagaaacggg gcctgccagc agccgcaatc ctgctgatcc tgg 43

<210> SEQ ID NO 71
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 71
cagaaacggg gcctgccaca agcccaaatc ctgctgatcc tgg 43

<210> SEQ ID NO 72
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 72
gcctccatca aatccgtgaa gttcctgttc aaatttatct acaaaggc 48

<210> SEQ ID NO 73
<211> LENGTH: 39

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 73

ggacccggag ggtctggcca aacctacctg tataaagtg                          39


<210> SEQ ID NO 74
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 74

ctgtatgtgg cctttagcca agtgcgccgg gcctgcgat                          39


<210> SEQ ID NO 75
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 75

gataatgtgc cgattggcac catggttatt ctgccgagca gttttg                  46


<210> SEQ ID NO 76
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 76

cagattagcg aaaaaaactg aatcaaccac gatgaggtg                          39


<210> SEQ ID NO 77
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 77

gccagcatta aaagcgtgaa attcctgttc aaatatatct ataaaggc                48


<210> SEQ ID NO 78
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 78
```

gtgaaatacc tgttcaaatt tatctataaa ggccacgatt gc 42

<210> SEQ ID NO 79
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 79
cagaaacggg gcctgccagc agccgcaatc ctgctgatcc tgg 43

<210> SEQ ID NO 80
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 80
cagaaacgtg gtctgccgca agcccaaatt ctgctgattc tgg 43

<210> SEQ ID NO 81
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 81
gccagcatta aaagcgtgaa attcctgttc aaatttatct ataaaggc 48

<210> SEQ ID NO 82
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 82
ggtccgggtg gcagcggtaa cacctatctg tataaagtg 39

<210> SEQ ID NO 83
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 83
ctgtacgttg cctttagcaa cgttcgtcgt gcatgtgat 39

<210> SEQ ID NO 84
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 84
caccatatga tcctatataa taaaagagaa acatgcaaat tgaccatccc 50

<210> SEQ ID NO 85
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 85
ccctttcaat gtgcacgaat ttcgtgcacc gggccactag tatatatata 50

<210> SEQ ID NO 86
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 86
ccctttcaat gtgcacgaac gggccactag tatatatata aagc 44

<210> SEQ ID NO 87
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 87
ctaattaatt ccctttcaat cgggccacta gtatatatat aaagc 45

<210> SEQ ID NO 88
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 88
ttatatatat actagtggcc cgacctgcgg tacaccgcag gtattg 46

<210> SEQ ID NO 89
<211> LENGTH: 74
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 89
gctatttgcc ctttctctat aatagaagtg tgagagatga aaggaaatga gtaaaatgta 60
tatgaaaata atac 74

<210> SEQ ID NO 90
<211> LENGTH: 71
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 90
gagaaagggc aaatagcaat attaaaatat ttcctctaat taattccctt tcaatacctg 60
cggtgtaccg c 71

<210> SEQ ID NO 91
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 91
tatcatgtct ggatccaaat ttatgtatta ttttcatata c 41

<210> SEQ ID NO 92
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 92
ttatatatat actagtgg 18

<210> SEQ ID NO 93
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 93
tatcatgtct ggatcc 16

<210> SEQ ID NO 94
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 94
ttatatatat actagtggcc cggtgcacga cggacgtgca cattg 45

<210> SEQ ID NO 95
<211> LENGTH: 74
<212> TYPE: DNA
<213> ORGANISM: Artificial Sequence
<220> FEATURE:
<221> NAME/KEY: source -continued
<223> OTHER INFORMATION: /note="Description of Artificial Sequence:
      Synthetic primer"

<400> SEQUENCE: 95
gctatttgcc ctttctctat aatagaagtg tgagagatga aaggaaatga gtaaaatgta     60
tatgaaaata atac                                                       74

<210> SEQ ID NO 96
<211> LENGTH: 80
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 96
gagaaagggc aaatagcaat attaaaatat ttcctctaat taattccctt tcaatgtgca     60
cgacggacgt gcaccgggcc                                                 80

<210> SEQ ID NO 97
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 97
tatcatgtct ggatccaaat ttatgtatta ttttcatata c                         41

<210> SEQ ID NO 98
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 98
ttatatatat actagtgg                                                   18

<210> SEQ ID NO 99
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 99
tatcatgtct ggatcc                                                     16

<210> SEQ ID NO 100
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 100

-continued

```
aatttccgca ggtcgggcca c                                              21


<210> SEQ ID NO 101
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 101

ccgcaggtat tgaaaggg                                                  18


<210> SEQ ID NO 102
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 102

cctcctgggg cgcttgacac ctgcg                                          25


<210> SEQ ID NO 103
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 103

tggctggtgg gcgtggcttg                                                20


<210> SEQ ID NO 104
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 104

tcatctctca cacttctatt atagag                                         26


<210> SEQ ID NO 105
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 105

gtaatacgac tcactatagg gc                                             22


<210> SEQ ID NO 106
<211> LENGTH: 19
<212> TYPE: DNA
<213> ORGANISM: Artificial Sequence
<220> FEATURE:
<221> NAME/KEY: source
```

<223> OTHER INFORMATION: /note="Description of Artificial Sequence:
      Synthetic primer"

<400> SEQUENCE: 106
agggctccgc ttaagggac 19

<210> SEQ ID NO 107
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 107
ggcagttaaa tttgcatacg cag 23

<210> SEQ ID NO 108
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 108
cagttaccta gaaggaaaca gag 23

<210> SEQ ID NO 109
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 109
gtcacagccc atgatatgcc c 21

<210> SEQ ID NO 110
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 110
cttgctgttt gaatatgaaa ttatgttatt c 31

<210> SEQ ID NO 111
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 111
cattatgcca atttcacaga tgagg 25

<210> SEQ ID NO 112

-continued

<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 112
gaaggtaatt tagaagtgaa agaacac 27

<210> SEQ ID NO 113
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 113
gtatctatca cctcacctag ttaac 25

<210> SEQ ID NO 114
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 114
gctggaacgt taattatgat gcg 23

<210> SEQ ID NO 115
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 115
gttgatatgg aagatgagaa tgaaac 26

<210> SEQ ID NO 116
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 116
ctgacaggat tttggagaat acg 23

<210> SEQ ID NO 117
<211> LENGTH: 87
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 117
gactctacta gtgccaccat gtacccttac gacgtaccgg attacgccta cccttacgac    60
gtaccggatt acgccactag tgactct    87

<210> SEQ ID NO 118
<211> LENGTH: 87
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 118
agagtcacta gtggcgtaat ccggtacgtc gtaagggtag gcgtaatccg gtacgtcgta    60
agggtacatg gtggcactag tagagtc    87

<210> SEQ ID NO 119
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 119
cgctggaagc ttaag    15

<210> SEQ ID NO 120
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 120
gcgcgggaat tccaccatat g    21

<210> SEQ ID NO 121
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 121
gcgcgggaat tcgggatggt caatttgc    28

<210> SEQ ID NO 122
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 122
gcgcgggaat tcccctttca atgtgcacg    29

<210> SEQ ID NO 123

<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 123
gcgcgggaat tctatatata ta 22

<210> SEQ ID NO 124
<211> LENGTH: 2928
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 124
cctggagagg ttcccgacat acctcctata taataaaaga gaaacatgca aattgaccat 60
ccctccgcta cgctcaagcc acgcccacca gccaatcaga agtgactatg caaattaacc 120
caacaaagat ggcagttaaa tttgcatacg caggtgtcaa gcgccccagg aggatcgatg 180
agtaattcat acaaaaggac tcgcccctgc cttggggaat cccagggacc gtcgttaaac 240
tcccactaac gtagaaccca gagatcgctg cgttcccgcc ccctcacccg cccgctctcg 300
tcatcactga ggtggagaag agcatgcgtg aggctccggt gcccgtcagt gggcagagcg 360
cacatcgccc acagtccccg agaagttggg gggaggggtc ggcaattgaa ccggtgccta 420
gagaaggtgg cgcggggtaa actgggaaag tgatgtcgtg tactggctcc gcctttttcc 480
cgagggtggg ggagaaccgt atataagtgc agtagtcgcc gtgaacgttc tttttcgcaa 540
cgggtttgcc gccagaacac aggtaagtgc cgtgtgtggt tcccgcgggc ctggcctctt 600
tacgggttat ggcccttgcg tgccttgaat tacttccacg cccctggctg cagtacgtga 660
ttcttgatcc cgagcttcgg gttggaagtg ggtgggagag ttcgaggcct tgcgcttaag 720
gagccccttc gcctcgtgct tgagttgagg cctggcttgg gcgctggggc cgccgcgtgc 780
gaatctggtg gcaccttcgc gcctgtctcg ctgctttcga taagtctcta gccatttaaa 840
atttttgatg acctgctgcg acgctttttt tctggcaaga tagtcttgta aatgcgggcc 900
aagatctgca cactggtatt tcggtttttg gggccgcggg cggcgacggg gcccgtgcgt 960
cccagcgcac atgttcggcg aggcggggcc tgcgagcgcg gccaccgaga atcggacggg 1020
ggtagtctca agctggccgg cctgctctgg tgcctggcct cgcgccgccg tgtatcgccc 1080
cgccctgggc ggcaaggctg gcccggtcgg caccagttgc gtgagcggaa agatggccgc 1140
ttcccggccc tgctgcaggg agctcaaaat ggaggacgcg gcgctcggga gagcgggcgg 1200
gtgagtcacc cacacaaagg aaaagggcct ttccgtcctc agccgtcgct tcatgtgact 1260
ccacggagta ccgggcgccg tccaggcacc tcgattagtt ctcgagcttt tggagtacgt 1320
cgtctttagg ttggggggag gggttttatg cgatggagtt tccccacact gagtgggtgg 1380
agactgaagt taggccagct tggcacttga tgtaattctc cttggaattt gccctttttg 1440
agtttggatc ttggttcatt ctcaagcctc agacagtggt tcaaagtttt tttcttccat 1500
ttcaggtgtc gtgagccacc atgggatccg agagcgacga gagcggcctg cccgccatgg 1560
agatcgagtg ccgcatcacc ggcaccctga acggcgtgga gttcgagctg gtgggcggcg 1620
gagagggcac ccccgagcag ggccgcatga ccaacaagat gaagagcacc aaaggcgccc 1680

```
tgaccttcag cccctacctg ctgagccacg tgatgggcta cggcttctac cacttcggca   1740

cctaccccag cggctacgag aaccccttcc tgcacgccat caacaacggc ggctacacca   1800

acacccgcat cgagaagtac gaggacggcg gcgtgctgca cgtgagcttc agctaccgct   1860

acgaggccgg ccgcgtgatc ggcgacttca aggtgatggg caccggcttc cccgaggaca   1920

gcgtgatctt caccgacaag atcatccgca gcaacgccac cgtggagcac ctgcacccca   1980

tgggcgataa cgatctggat ggcagcttca cccgcacctt cagcctgcgc gacggcggct   2040

actacagctc cgtggtggac agccacatgc acttcaagag cgccatccac cccagcatcc   2100

tgcagaacgg gggccccatg ttcgccttcc gccgcgtgga ggaggatcac agcaacaccg   2160

agctgggcat cgtggagtac cagcacgcct tcaagacccc ggatgcagat gccggtgaag   2220

aaggatccta gacgcgtgga tccaataaaa gatccttatt ttcattggat ctgtgtgttg   2280

gtttttgtg tggctagcaa atttatgtat tattttcata tacattttac tcatttcctt   2340

tcatctctca cacttctatt atagagaaag ggcaaatagc aatattaaaa tatttcctct   2400

aattaattcc ctttcaatgt gcacgaattt cgtgcaccgg gccactagta tatatataaa   2460

gcttggtatg tcgggaacct ctccaggcag cggccgccca aggtcgggca ggaagagggc   2520

ctatttccca tgattccttc atatttgcat atacgataca aggctgttag agagataatt   2580

agaattaatt tgactgtaaa cacaaagata ttagtacaaa atacgtgacg tagaaagtaa   2640

taatttcttg ggtagtttgc agttttaaaa ttatgtttta aaatggacta tcatatgctt   2700

accgtaactt gaaagtattt cgatttcttg gctttatata tcttgtggaa aggacgaaac   2760

accggtatgt cgggaacctc tccgttttag agctagaaat agcaagttaa aataaggcta   2820

gtccgttatc aacttgaaaa agtggcaccg agtcggtgct ttttttatcg gatcccgggc   2880

ccgtcgactg cagaggcctg catgcaagct tggcgtaatc atggtcat                2928
```

<210> SEQ ID NO 125
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 125

```
cctggagagg ttcccgacat acc                                             23
```

<210> SEQ ID NO 126
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 126

```
ggtatgtcgg gaacctctcc agg                                             23
```

<210> SEQ ID NO 127
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 127
tcctatataa taaaagagaa acatgcaaat tgaccatccc tccgctacgc tcaagccacg 60
cccaccagcc aatcagaagt gactatgcaa attaacccaa caaagatggc agttaaattt 120
gcatacgcag gtgtcaagcg ccccaggagg 150

<210> SEQ ID NO 128
<211> LENGTH: 1335
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 128
gagtaattca tacaaaagga ctcgcccctg ccttggggaa tcccagggac cgtcgttaaa 60
ctcccactaa cgtagaaccc agagatcgct gcgttcccgc cccctcaccc gcccgctctc 120
gtcatcactg aggtggagaa gagcatgcgt gaggctccgg tgcccgtcag tgggcagagc 180
gcacatcgcc cacagtcccc gagaagttgg ggggaggggt cggcaattga accggtgcct 240
agagaaggtg gcgcggggta aactgggaaa gtgatgtcgt gtactggctc cgcctttttc 300
ccgagggtgg gggagaaccg tatataagtg cagtagtcgc cgtgaacgtt ctttttcgca 360
acgggtttgc cgccagaaca caggtaagtg ccgtgtgtgg ttcccgcggg cctggcctct 420
ttacgggtta tggcccttgc gtgccttgaa ttacttccac gcccctggct gcagtacgtg 480
attcttgatc ccgagcttcg ggttggaagt gggtgggaga gttcgaggcc ttgcgcttaa 540
ggagcccctt cgcctcgtgc ttgagttgag gcctggcttg ggcgctgggg ccgccgcgtg 600
cgaatctggt ggcaccttcg cgcctgtctc gctgctttcg ataagtctct agccatttaa 660
aatttttgat gacctgctgc gacgcttttt ttctggcaag atagtcttgt aaatgcgggc 720
caagatctgc acactggtat ttcggttttt ggggccgcgg gcggcgacgg ggcccgtgcg 780
tcccagcgca catgttcggc gaggcggggc ctgcgagcgc ggccaccgag aatcggacgg 840
gggtagtctc aagctggccg gcctgctctg gtgcctggcc tcgcgccgcc gtgtatcgcc 900
ccgccctggg cggcaaggct ggcccggtcg gcaccagttg cgtgagcgga aagatggccg 960
cttcccggcc ctgctgcagg gagctcaaaa tggaggacgc ggcgctcggg agagcgggcg 1020
ggtgagtcac ccacacaaag gaaaagggcc tttccgtcct cagccgtcgc ttcatgtgac 1080
tccacggagt accgggcgcc gtccaggcac ctcgattagt tctcgagctt ttggagtacg 1140
tcgtctttag gttgggggga ggggttttat gcgatggagt ttccccacac tgagtgggtg 1200
gagactgaag ttaggccagc ttggcacttg atgtaattct ccttggaatt tgcccttttt 1260
gagtttggat cttggttcat tctcaagcct cagacagtgg ttcaaagttt ttttcttcca 1320
tttcaggtgt cgtga 1335

<210> SEQ ID NO 129
<211> LENGTH: 711
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 129

```
atgggatccg agagcgacga gagcggcctg cccgccatgg agatcgagtg ccgcatcacc     60

ggcaccctga acggcgtgga gttcgagctg gtgggcggcg gagagggcac ccccgagcag    120

ggccgcatga ccaacaagat gaagagcacc aaaggcgccc tgaccttcag cccctacctg    180

ctgagccacg tgatgggcta cggcttctac cacttcggca cctaccccag cggctacgag    240

aacccctttcc tgcacgccat caacaacggc ggctacacca acacccgcat cgagaagtac   300

gaggacggcg gcgtgctgca cgtgagcttc agctaccgct acgaggccgg ccgcgtgatc    360

ggcgacttca aggtgatggg caccggcttc cccgaggaca gcgtgatctt caccgacaag    420

atcatccgca gcaacgccac cgtggagcac ctgcaccccca tgggcgataa cgatctggat   480

ggcagcttca cccgcacctt cagcctgcgc gacggcggct actacagctc cgtggtggac    540

agccacatgc acttcaagag cgccatccac cccagcatcc tgcagaacgg gggccccatg    600

ttcgccttcc gccgcgtgga ggaggatcac agcaacaccg agctgggcat cgtggagtac    660

cagcacgcct tcaagacccc ggatgcagat gccggtgaag aaggatccta g             711
```

<210> SEQ ID NO 130
<211> LENGTH: 49
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 130

```
aataaaagat ccttatttc attggatctg tgtgttggtt ttttgtgtg                 49
```

<210> SEQ ID NO 131
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 131

```
aaatttatgt attattttca tatacatttt actcatttcc tttcatctct cacacttcta     60

ttatagagaa agggcaaata gcaatattaa aatatttcct ctaattaatt ccctttcaat    120

gtgcacgaat ttcgtgcacc gggccactag                                     150
```

<210> SEQ ID NO 132
<211> LENGTH: 266
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 132

```
ccaaggtcgg gcaggaagag ggcctatttc ccatgattcc ttcatatttg catatacgat     60

acaaggctgt tagagagata attagaatta atttgactgt aaacacaaag atattagtac    120

aaaatacgtg acgtagaaag taataatttc ttgggtagtt tgcagtttta aaattatgtt    180

ttaaaatgga ctatcatatg cttaccgtaa cttgaaagta tttcgatttc ttggctttat    240

atatcttgtg gaaaggacga aacacc                                         266
```

<210> SEQ ID NO 133
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 133
ggtatgtcgg gaacctctcc 20

<210> SEQ ID NO 134
<211> LENGTH: 145
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 134
gttttagagc tagaaatagc aagttaaaat aaggctagtc cgttatcaac ttgaaaaagt 60
ggcaccgagt cggtgctttt tttatcggat cccgggcccg tcgactgcag aggcctgcat 120
gcaagcttgg cgtaatcatg gtcat 145

<210> SEQ ID NO 135
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 135

Val Ile Glu Phe Gln Lys Arg Gly Leu Pro His Ala His Ile Leu
1 5 10 15

<210> SEQ ID NO 136
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 136

Val Lys Tyr Leu Phe Lys Tyr Ile Tyr Lys Gly His Asp Cys
1 5 10

<210> SEQ ID NO 137
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 137

Leu Asp Gly Pro Gly Gly Ser Gly Lys Thr Tyr Leu
1 5 10

<210> SEQ ID NO 138

<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 138

Val Leu Pro Thr Ala Ser Thr Gly Ile Ala Ala Asn Leu Leu
1 5 10

<210> SEQ ID NO 139
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 139

Leu Leu Ile Ile Asp Glu Cys Thr Met Ala Ser Ser His Ala Ile
1 5 10 15

<210> SEQ ID NO 140
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 140

Gly Lys Val Leu Leu Leu Gly Gly Asp Phe Arg Gln Cys Leu Ser Ile
1 5 10 15

<210> SEQ ID NO 141
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 141

Leu Lys Thr Asn Met Arg
1 5

<210> SEQ ID NO 142
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 142

Gly Ala Ile Ile Met Leu Leu Arg Asn Leu Asn Ser Lys Trp Gly Leu
1 5 10 15

Cys Asn Gly

<210> SEQ ID NO 143
<211> LENGTH: 18
<212> TYPE: PRT

<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 143

Phe Ala Met Thr Ile Asn Lys Ser Gln Gly Gln Thr Leu Asp Arg Val
1 5 10 15

Gly Ile

<210> SEQ ID NO 144
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 144

Tyr Val Ala Phe Ser Arg Val Arg Arg Ala Cys Asp Val Lys Val
1 5 10 15

<210> SEQ ID NO 145
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 145
caccatatga tcctatataa 20

<210> SEQ ID NO 146
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 146
gggccactag tatatatata 20

<210> SEQ ID NO 147
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 147
cctgtgcata tcctatataa 20

<210> SEQ ID NO 148
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

-continued

<400> SEQUENCE: 148
gggccactag taatatataa 20

<210> SEQ ID NO 149
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 149
tgttctggca tcctatataa 20

<210> SEQ ID NO 150
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 150
gggccactag tgaatataat 20

<210> SEQ ID NO 151
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 151
tactctatca tcctatataa 20

<210> SEQ ID NO 152
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 152
gggccactag tcaaatatat 20

<210> SEQ ID NO 153
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 153
taagcaataa tcctatataa 20

<210> SEQ ID NO 154
<211> LENGTH: 20
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154

gggccactag taattaataa                                              20


<210> SEQ ID NO 155
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155

cctatgtcta tcctatataa                                              20


<210> SEQ ID NO 156
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156

gggccactag taaaaaataa                                              20


<210> SEQ ID NO 157
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157

caccatatga tcctatataa taaaagagaa acatgcaaat tgaccatccc             50


<210> SEQ ID NO 158
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158

gtgcacgaat ttcgtgcac                                               19


<210> SEQ ID NO 159
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159

acctgtggta caccgcaggt                                              20
```

<210> SEQ ID NO 160
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 160
acctgcggaa tttccgcagg t 21

<210> SEQ ID NO 161
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 161
gtgcacgccg gacgtgcac 19

<210> SEQ ID NO 162
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 162
ccctttcaat gtgcacgaat ttcgtgcacc gggccactag 40

<210> SEQ ID NO 163
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 163
ccctttcaat cgggccacta g 21

<210> SEQ ID NO 164
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 164
ccctttcaat acctgtggtg taccgcaggt cgggccacta g 41

<210> SEQ ID NO 165
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 165
ccctttcaat acctgcggaa tttccgcagg tcgggccact ag 42

<210> SEQ ID NO 166
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 166
ccctttcaat gtgcacgccg ggcgtgcacc gggccactag 40

<210> SEQ ID NO 167
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 167
atcctatata a 11

<210> SEQ ID NO 168
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 168
gggccactag t 11

<210> SEQ ID NO 169
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 169
gggccactag tcctatataa 20

<210> SEQ ID NO 170
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 170
ttcgtgcacc gggccactag 20

<210> SEQ ID NO 171
<211> LENGTH: 36

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 171

tcaaatatat tagaaggtgg taagtgctat ggaaaa                              36


<210> SEQ ID NO 172
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172

attgaccatc cctccgctac                                                20


<210> SEQ ID NO 173
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173

tagactcatt ctacaaacaa tgaaaccaag agtgttagac attaaggtca t             51


<210> SEQ ID NO 174
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174

tcttcgccca ccccaacttg                                                20


<210> SEQ ID NO 175
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (9)..(9)
<223> OTHER INFORMATION: a, c, t, g, unknown or other

<400> SEQUENCE: 175

tgtaaaatna aaataaataa catattgtaa acttgaaat                           39


<210> SEQ ID NO 176
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"

<400> SEQUENCE: 176
tcttcgccca ccccaacttg 20

<210> SEQ ID NO 177
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 177
ttaaatatat tattcaatgt agccttgatt gttggaaa 38

<210> SEQ ID NO 178
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 178
tcttcgccca ccccaacttg 20

<210> SEQ ID NO 179
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 179
tatgactata ataagagaaa ggcagcctgg gaagag 36

<210> SEQ ID NO 180
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 180
ataagggcga cacggaaatg 20

<210> SEQ ID NO 181
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 181
ctaagaatat cattgtataa tctctttgtt tatatgt 37

<210> SEQ ID NO 182
<211> LENGTH: 50

-continued

<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 182
caccatatga tcctatataa taaaagagaa acatgcaaat tgaccatccc 50

<210> SEQ ID NO 183
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 183
gggatggtca atttggtact ttgtgtttta ttatatagga tcatatggtg 50

<210> SEQ ID NO 184
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 184
ccctttcaat gtgcacgaat ttcgtgcacc gggccactag tatatatata 50

<210> SEQ ID NO 185
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 185
tatatatata ctagtggccc ggtgcacgaa attcgtgcac attgaaaggg 50

<210> SEQ ID NO 186
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 186
taatattgta taccaactat ctacactaaa ggcctctagt acttaaataa aaaaaataa 59

<210> SEQ ID NO 187
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 187

```
ataatattgt ataccaacta tacttaaata aaaaaaataa                           40


<210> SEQ ID NO 188
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 188

tctacactaa aggcctctag                                                 20


<210> SEQ ID NO 189
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189

catattctca tacatacaca tctacactaa aggcctctag tctatatata aaagccaagc     60


<210> SEQ ID NO 190
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190

catattctta tacacacaca tctatatata aaagccaagc                           40


<210> SEQ ID NO 191
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191

tctacactaa aggcctctag                                                 20


<210> SEQ ID NO 192
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192

tccagcatat atatatatat ctacactaac ccatctatat atttggtaat aaaggtta       58


<210> SEQ ID NO 193
<211> LENGTH: 40
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 193

tccagcatat actatatata tatttggtaa tgaacggtta                      40


<210> SEQ ID NO 194
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194

tctacactaa cccatctata                                            20


<210> SEQ ID NO 195
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195

cccccgagtg cacaaatttt tgtgcaccgg gcctctag                        38


<210> SEQ ID NO 196
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196

agggcacagg ccgggctgag ggacccccga ccctctag                        38


<210> SEQ ID NO 197
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197

tcaaattgag tttcaactag cagaataatt atttaaga                        38


<210> SEQ ID NO 198
<211> LENGTH: 63
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198

gcactagtct aatgctaaca tcctcctatc taattattta agaaaaaata aacaatgacg 60

agg                                                              63
```

<210> SEQ ID NO 199
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 199
gtagggaaac ttaatactta tcctatctaa ttatttaaga tgctcaatgc aggagctgcc 60

<210> SEQ ID NO 200
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 200
tcctcctatc taattattta aga 23

<210> SEQ ID NO 201
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 201
tcctatctaa ttatttaaga 20

<210> SEQ ID NO 202
<211> LENGTH: 91
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 202
ccctttcaat gtgcacgaat ttcgtgcacc gggccactag tatatatata aagcttggta 60
tgtcgggaac ctcgggacag gattggtgac a 91

<210> SEQ ID NO 203
<211> LENGTH: 91
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 203
ccctttcaat gtgcacgaat ttcgtgcacc gggccactag tatatatata aagcttggta 60
tgtcgggaac ctcgggacag gattggtgac a 91

<210> SEQ ID NO 204
<211> LENGTH: 300
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 204
tcctatataa taaaagagaa acatgcaaat tgaccatccc tccgctacgc tcaagccacg 60
cccaccagcc aatcagaagt gactatgcaa attaacccaa caaagatggc agttaaattt 120
gcatacgcag gtgtcaagcg ccccaggagg aaatttatgt attattttca tatacatttt 180
actcatttcc tttcatctct cacacttcta ttatagagaa agggcaaata gcaatattaa 240
aatatttcct ctaattaatt ccctttcaat gtgcacgaat ttcgtgcacc gggccactag 300

<210> SEQ ID NO 205
<211> LENGTH: 300
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 205
tcctatataa taaaagagaa acatgcaaat tagccgtccc tctgctacgc tcaagccacg 60
cccacaagcc acgcccacca gccaatcaga gtgactatgc aaattaacct gacaaagatg 120
gcggttaatt tgcatacgca ggtgtcaagc aaagtaatag ctaaaattca tgtcattgaa 180
tttcagaaac gcggactgcc tcacgctcac atattattga tattagatag tgagtccaaa 240
ttacgttcct ctaattaatt ccctttcaat gtgcacgaat ttcgtgcacc aggctactag 300

<210> SEQ ID NO 206
<211> LENGTH: 300
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 206
tctacttata taaaaaccct gggtgtaaca tcacgtccag aagcgcgacc aaccggaagg 60
aagtcagtcc tgcaggggtc gtcttggaaa cggctgcgcc ctcccccagc tgtttccccg 120
gagggcgagg tttcaggcag gaacccgccc aaatttatat attattttca tatacatttt 180
actaatttcc tttcatctct cacacttcta ttatagagaa agggcaaata gcaatattaa 240
aatatctccg ctaattaatt cccttttaat gtgcacgaat ttcgtgcacc gggctactag 300

<210> SEQ ID NO 207
<211> LENGTH: 390
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 207
tctatatata taaaaggcta agtgtccatc caaccggtag ctatgatgca cactgaccac 60
cagggggcag atgctcaatg caggagctgc catgatgtgc actggccatt taaaaataaa 120
cgtgggctgg aaaaagttta gctaaatcag aaagcaggtc taattaagca agtttattct 180

-continued

| | |
|---|---|
| atatctataa aaggctaagt tgactcgtgc atgcgcgata catataaagc tctcgctggc | 240 |
| gccaatcgca cacgtgtgtt tcgatctgtc attgtcgatc atgaatttgg ttgacacttc | 300 |
| tattatagag aaagggcaaa tagcgatatt aaaatatttc ttctaattaa ttcctttcaa | 360 |
| tgtgcacgaa tctgtgcacc gggccactag | 390 |

REPLICATIVE TRANSPOSON SYSTEM

CROSS-REFERENCE TO RELATED APPLICATIONS

This application is a U.S. national stage filing under 35 U.S.C. § 371 of International Application No. PCT/GB2017/050355, filed on Feb. 10, 2017, which claims benefit of priority to GB Application No. 1602473.9, filed on Feb. 11, 2016.

SEQUENCE LISTING

This application contains a sequence listing, submitted electronically in ASCII format under the filename Sequence_Listing.txt, which is incorporated by reference herein in its entirety. The ASCII copy of the sequence listing was created on Aug. 9, 2018, and is 96,583 bytes in size.

FIELD OF THE INVENTION

The invention relates to a system and method for introducing DNA into cells. This invention relates to a system for generating single or multiple copies of a DNA sequence in a cell. The system includes the use of a Helitron transposase and a DNA sequence which has RTS and LTS sequences which are recognised by the transposase.

Background of the Invention

Use of transposon systems for gene and cell engineering have been described (reviewed, for example in Ivics and Izsvák, Mobile DNA 2010, 1:25 doi:10.1186/1759-8753-1-25). These systems use transposons, such as sleeping beauty (SB) (see U.S. Pat. No. 6,489,459, for example) and PiggyBac, which use a cut/paste mechanism for gene duplication and expression. A disadvantage of these systems is that, once inserted into the host genome, they cannot amplify the copy number of the cargo they delivered.

Accordingly, there is a need for new transposon-based systems.

A novel group of DNA transposons widespread throughout the eukaryotic kingdom and termed Helitrons was discovered by in silico genome sequence analysis (reviewed in Kapitonov V V, Jurka J. Helitrons on a roll: eukaryotic rolling-circle transposons. *Trends Genet* 23, 521-529 (2007) and Thomas J, Pritham E J. Helitrons, the Eukaryotic Rolling-circle Transposable Elements. *Microbiology spectrum* 3, (2015))

Helitron transposition displays a number of features unusual for DNA transposons, such as the lack of target site duplications (TSDs) (reviewed in Kapitonov et al. (2007) and Thomas et al. (2015) Furthermore, putative Helitron transposases do not contain an RNase-H like catalytic domain (Dyda F, Hickman A B, Jenkins T M, Engelman A, Craigie R, Davies D R. Crystal structure of the catalytic domain of HIV-1 integrase: similarity to other polynucleotidyl transferases. *Science* 266, 1981-1986 (1994)) but encode a "RepHel" motif made up by a replication initiator (Rep) and a DNA helicase (Hel) domain (Kapitonov et al. (2007); Thomas et al. (2015) and Kapitonov V V, Jurka J. Rolling-circle transposons in eukaryotes. *Proceedings of the National Academy of Sciences of the United States of America* 98, 8714-8719 (2001). Rep is a nuclease domain belonging to the HUH superfamily of nucleases that are involved in catalytic reactions for endonucleolytic cleavage, DNA transfer and ligation (Ilyina T V, Koonin E V. Conserved sequence motifs in the initiator proteins for rolling circle DNA replication encoded by diverse replicons from eubacteria, eucaryotes and archaebacteria. *Nucleic Acids Res* 20, 3279-3285 (1992) and Koonin E V, Ilyina T V. Computer-assisted dissection of rolling circle DNA replication. *Biosystems* 30, 241-268 (1993)). HUH nucleases cleave exclusively ssDNA, and have a key role in the initiation of "rolling circle replication" (RCR) of certain bacteriophages such as ϕX174 (van Mansfeld A D, van Teeffelen H A, Baas P D, Jansz H S. Two juxtaposed tyrosyl-OH groups participate in phi X174 gene A protein catalysed cleavage and ligation of DNA. *Nucleic Acids Res* 14, 4229-4238 (1986)), ssDNA viruses, and bacterial plasmids (reviewed in Chandler M, de la Cruz F, Dyda F, Hickman A B, Moncalian G, Ton-Hoang B. Breaking and joining single-stranded DNA: the HUH endonuclease superfamily. *Nature reviews Microbiology* 11, 525-538 (2013)), as well as in "rolling circle" (RC) transposition of IS91 family bacterial transposons (del Pilar Garcillan-Barcia M, Bernales I, Mendiola M V, de la Cruz F. Single-stranded DNA intermediates in IS91 rolling-circle transposition. *Molecular microbiology* 39, 494-501 (2001); Garcillan-Barcia M P, de la Cruz F. Distribution of IS91 family insertion sequences in bacterial genomes: evolutionary implications. *FEMS microbiology ecology* 42, 303-313 (2002) and Mendiola M V, Bernales I, de la Cruz F. Differential roles of the transposon termini in IS91 transposition. *Proceedings of the National Academy of Sciences of the United States of America* 91, 1922-1926 (1994)).

The key elements of the proposed RC transposition mechanism (Mendiola M V, de la Cruz F. IS91 transposase is related to the rolling-circle-type replication proteins of the pUB110 family of plasmids. *Nucleic Acids Res* 20, 3521 (1992)) involve two tyrosine (Tyr) residues in the active site of IS91's HUH transposase (del Pilar Garcillan-Barcia et al. (2001)). Briefly, the model proposes a site-specific nick at the transposon 5'-end, with the transposase forming a 5'-phosphotyrosine intermediate. The 3'-OH at the nick serves to initiate DNA synthesis while one transposon DNA strand peels off. The nick generated in the target DNA possibly by the second active site Tyr leads to the resolution of the 5'-phosphotyrosine. Once the entire transposon has been replicated, transposase catalyzes a second strand transfer event by nicking the 3'-end of the transposon and joining it to the 5'-end of the target site (Kapitonov et al. (2007); Chandler et al. (2013) and (Mendiola et al. (1994)).

It has been suggested that Helitrons are the first eukaryotic RC transposons (Kapitonov et al. (2001)) and, while Helitron transposons can capture and mobilize gene fragments in eukaryotes, definite information involving their transposition mechanism remains elusive due to the lack of an active element isolated from any species i.e. no one has previously been able to isolate a Helitron transposon that can actively replicate in cells. Instead, all of our knowledge on Helitron transposition stems from bioinformatic analysis of genomic sequence remnants of dysfunctional Helitron transposons or transposon fragments.

The only Helitron transposons found in the sequenced mammalian genomes are from vespertilionid bats (Pritham E J, Feschotte C. Massive amplification of rolling-circle transposons in the lineage of the bat *Myotis lucifugus*. *Proceedings of the National Academy of Sciences of the United States of America* 104, 1895-1900 (2007); Thomas J, Phillips C D, Baker R J, Pritham E J. Rolling-circle transposons catalyze genomic innovation in a Mammalian lineage. *Genome biology and evolution* 6, 2595-2610 (2014) and Thomas J, Sorourian M, Ray D, Baker R J, Pritham E J. The limited distribution of Helitrons to vesper bats supports horizontal transfer. *Gene* 474, 52-58 (2011)). The predicted transposase encoded by bat Helitrons contains the typical "RepHel" motif, the elements are characterized by 5'-TC and CTRR-3' termini that do not contain inverted repeats but have a short palindromic motif located upstream of the 3'-terminus, and insertions occurred precisely between 5'-A and T-3' nucleotides at host AT target sites (Pritham et al. (2007)). Although the vast majority of Helitron families harbor short palindromic sequences in their 3'-termini (Kapitonov et al. (2001); Coates B S, Hellmich R L, Grant D M, Abel C A. Mobilizing the genome of Lepidoptera through novel sequence gains and end creation by non-autonomous Lep1 *Helitrons. DNA research: an international journal for rapid publication of reports on genes and genomes* 19, 11-21 (2012); Du C, Fefelova N, Caronna J, He L, Dooner H K. The polychromatic Helitron landscape of the maize genome. *Proceedings of the National Academy of Sciences of the United States of America* 106, 19916-19921 (2009); Lal S K, Giroux M J, Brendel V, Vallejos C E, Hannah L C. The maize genome contains a helitron insertion. *The Plant cell* 15, 381-391 (2003); Xiong W, He L, Lai J, Dooner H K, Du C. HelitronScanner uncovers a large overlooked cache of Helitron transposons in many plant genomes. *Proceedings of the National Academy of Sciences of the United States of America* 111, 10263-10268 (2014)) the role of these sequences in Helitron transposition is unclear.

Genomic data suggest that Helitron transposition is often associated with the capture and mobilization of host genomic fragments, resulting in the dissemination of genomic regulatory elements (Pritham et al. (2007) and Thomas et al. (2014)), gene fragment duplications (Morgante M, Brunner S, Pea G, Fengler K, Zuccolo A, Rafalski A. Gene duplication and exon shuffling by helitron-like transposons generate intraspecies diversity in maize *Nature genetics* 37, 997-1002 (2005)), the generation of chimeric transcripts (Thomas et al. (2014) and Morgante et al. (2005)) and the creation of putative regulatory RNAs (Thomas et al. (2014) and Morgante et al. (2005)). Several mechanisms have been proposed to explain Helitron gene capture (Kapitonov et al. (2007); Thomas et al. (2015); Coates et al. (2012); Dong Y, et al. Structural characterization of helitrons and their stepwise capturing of gene fragments in the maize genome. *BMC genomics* 12, 609 (2011); Toleman M A, Bennett P M, Walsh T R. ISCR elements: novel gene-capturing systems of the 21st century? *Microbiol Mol Biol Rev* 70, 296-316 (2006); Yassine H, et al. Experimental evidence for IS1294b-mediated transposition of the blaCMY-2 cephalosporinase gene in Enterobacteriaceae. *The Journal of antimicrobial chemotherapy* 70, 697-700 (2015); Brunner S, Pea G, Rafalski A. Origins, genetic organization and transcription of a family of non-autonomous helitron elements in maize *The Plant journal: for cell and molecular biology* 43, 799-810 (2005); Feschotte C, Wessler S R. Treasures in the attic: rolling circle transposons discovered in eukaryotic genomes. *Proceedings of the National Academy of Sciences of the United States of America* 98, 8923-8924 (2001) and Tempel S, Nicolas J, El Amrani A, Couee I. Model-based identification of Helitrons results in a new classification of their families in *Arabidopsis thaliana. Gene* 403, 18-28 (2007)) but due to the lack of an active Helitron transposon that can replicate in cells, both the process and regulation of Helitron transposition has remained enigmatic. Everything that is known to date about Helitron biology derives from in silico or genetic analysis, because no active Helitron transposon, as defined by the active transposase enzyme in conjunction with functional terminal sequences enabling the replication of the intervening genomic content, has previously been isolated.

SUMMARY OF THE INVENTION

As described herein, the present invention relates to the resurrection of an active copy of the autonomous Helibat1 transposon, herein designated "Helraiser", and characterization of its transposition in vitro and in human cells ex vivo.

Helraiser, an ancient element from the bat genome, has been used as an experimental tool to unravel the mechanism of Helitron transposition. A hairpin close to the 3'-end of the transposon functions as a transposition terminator. However, the 3'-end can be bypassed by the transposase, resulting in transduction of flanking sequences to new genomic locations. Helraiser transposition generates covalently closed circular intermediates, suggestive of a replicative transposition mechanism, which provides a powerful means to disseminate captured transcriptional regulatory signals across the genome. The generation of novel transcripts by Helitron promoter capture, both experimentally and by transcriptome analysis in bats, is described. These results provide mechanistic insight into Helitron transposition, and its impact on diversification of gene function by genome shuffling as well as provide experimental insight into the molecular requirements of transposition, target site selection properties, and gene capture in cell culture and in bats in vivo.

Importantly, the Helraiser transposase is capable of catalyzing DNA transposition in trans when used in conjunction with donor DNA flanked by appropriate sequences.

This system can be used to introduce single or multiple copies of the donor DNA into the genome of a cell. What sets Helraiser apart from other transposon systems (eg., Sleeping Beauty, PiggyBac) is that it uses a copy/paste mechanism for duplication rather than a cut/paste mechanism characteristic of these other systems, meaning that a multiplicative effect of duplication/replication can be achieved using as little as a single copy of the mobilizable element present to start. This has applications in engineering cell lines to carry multiple copies of preferred regions. It also allows the stepwise amplification of the DNA cargo in the recipient cell by additional rounds of transposition.

Accordingly, in one aspect, there is provided a system for generating single or multiple copies of a DNA sequence in an isolated or cultured cell comprising a copy/paste transposase and a donor DNA recognized by the transposase. Suitably the "DNA sequence" is a DNA sequence of interest which may be a "gene of interest" (i.e. encoding a protein of interest) wherein said term also includes a genomic region (e.g. a region of the genome comprising an enhancer, repressor, CpG island, etc.). The term "donor DNA" as used herein refers to a gene of interest, or genomic region, provided in a construct, e.g. an expression vector, optionally arranged with suitable upstream and/or downstream terminal sequences which enable a transposase-mediated transposition event to occur.

In another aspect, there is provided a method for introducing a single or multiple copies of a DNA sequence or gene of interest into a cell comprising providing: a) a Helitron transposase; and b) a contruct comprising a Helitron tranposase LTS sequence. In one embodiment, the construct in b) further comprises a DNA sequence or gene of interest flanked by a Helraiser LTS sequence. Suitably, the cell may be prokaryotic or eukaryotic.

In another aspect, there is provided a method for introducing single or multiple copies of a DNA sequence or gene of interest into a eukaryotic cell comprising providing: a) a "copy and paste" transposase; and b) a construct comprising a DNA sequence or gene of interest flanked by a "copy and paste" transposon terminal sequence, such as an LTS or RTS. Suitable "copy and paste" transposases include transposases of the Helitron family including the Helraiser transposase as described herein. Suitable Helitron family transposases are described, for example in Kapitonov and Jurka (2007) and Thomas et al. (2015)). Suitable LTS and RTS are those identified to complement a particular copy and paste transposon such as a Helitron, In one embodiment of any aspect of the invention, the "copy and paste" transposase is a Helitron transposase and the LTS is derived from a Helitron transposon. Suitably, the DNA sequence or gene of interest is introduced into the genome of the cell.

Advantageously, the "copy/paste" transposase is an active element capable of transposition. In one embodiment, the "copy/paste" transposase is not a prokaryotic, such as a bacterial, "copy/paste" transposon. Suitably the "copy/paste" transposase has been resurrected from a eukaryotic genome.

In one embodiment of any aspect of the invention, the transposon terminal sequence is a Helraiser LTS sequence comprising a nucleic acid sequence as set out in SEQ ID NO: 3 or a sequence having at least 80% identity thereto.

Advantageously, inserting an LTS sequence alone allows the simple generation of a transposon donor sequence where the downstream genomic content can be subjected to transposition, as initiated by the addition of the transposase. This is of particular advantage where the sequential introduction of LTS and RTS is cumbersome, e.g. when one aims to amplify genomic content in eukaryotic cells and LTS and/or RTS have to be introduced by conventional genome engineering technologies, such those based on CRISPR/Cas, TALENs, Zn finger nucleases or Meganucleases.

In another embodiment, the gene of interest is also flanked by an RTS sequence comprising a nucleic acid sequence as set out in SEQ ID NO: 4 or a sequence having at least 80% identity thereto. As described herein, (see FIG. 3A, for example) a single LTS sequence may be sufficient to trigger transposition of downstream DNA cargo by Helraiser transposase, but transposition rates are higher if the desired gene or genomic region is flanked with both LTS and RTS sequences. Advantageously, the addition of the RTS helps define where transposase activity should terminate thus providing more controlled transposition. In one embodiment, a mutated RTS may be used preferably such that a gene of interest may be copied and integrated but not mobilised by the transposase.

Suitably a donor DNA comprises a DNA sequence, such as a DNA sequence for a target gene e.g. wherein a target gene encodes a protein of interest, positioned between right and left terminal sequences (RTS and LTS sequences). In one embodiment, the RTS has a nucleic acid sequence comprising CTAG at the 3' end while the LTS has a nucleic acid sequence comprising TC at the 5' end. Suitably the LTS comprises or has a nucleic acid sequence as set out in SEQ ID NO: 3 or a sequence with at least 80% identity thereto, while the RTS has a nucleic acid sequence as set out in SEQ ID NO: 4, or a sequence with at least 80% identity thereto.

In one aspect there is provided an in vitro system for generating single or multiple copies of a DNA sequence in an isolated or cultured mammalian cell comprising a copy/paste transposase of eukaryotic e g mammalian origin and a donor DNA recognized by the transposase.

Suitably a "copy/paste" transposase is a Helitron transposase. Helitron (or rolling-circle) transposons and transposases are described, for example in Kapitonov et al. (2007). In one embodiment of any aspect of the invention the transposase is a Helitron transposase having an amino acid sequence with at least 80% sequence identity with the amino acid sequence set out in Seq ID NO: 1 (see Table 6: Table of SEQ ID NOS; SEQ ID NO: 1 is the amino acid sequence of Helraiser transposase). In another embodiment, the Helitron transposase is one having at least 80, 85, 90, 95 or 95% identity with the amino acid sequence set out in SEQ ID NO: 1. The Helitron transposase may be provided in DNA, RNA or protein form. In one embodiment, the transposase is Helraiser transposase. Suitably, the transposase is derived from or has the amino acid sequence as set out in SEQ ID NO: 1. In one embodiment, the Helraiser transposase is encoded by the nucleic acid sequence set out in SEQ ID NO: 2 (see Table 6: Table of SEQ ID NOS; SEQ ID NO: 2 is a nucleic acid sequence encoding the Helraiser transposase, see also FIG. 8) or a codon-optimised version thereof such as, for example, the nucleic acid sequence set out in SEQ ID NO: 6.

In one embodiment, the transposase and the construct comprising the gene of interest are provided as two separate entities. Suitably entities may be DNA constructs such as expression vectors or plasmids although it is also envisaged that the transposase may be provided as a naked DNA, mRNA or as a protein. In one embodiment, the construct comprising the gene or genomic region of interest flanked by the Helraiser terminal sequence(s) may be created or present within a cell line which is subsequently transfected with a construct encoding a transposase. In another embodiment, the construct comprising the gene of interest flanked by the Helraiser terminal sequence(s) may be part of a separate plasmid for co-transfection with the construct encoding a transposase. In another embodiment, the transposase, gene of interest and LTS are provided as a transposon in a single construct.

In one embodiment of any aspect of the invention, the transposase may be encoded by a Helitron transposon. For example, the transposase may be encoded by a transposon nucleic acid sequence such as the Helraiser transposon nucleic acid sequence as set out in SEQ ID NO: 5 (See Table 6: TABLE OF SEQ ID NOS; See also FIG. 8). In accordance with one aspect of the invention, there is provided a Helitron transposon. Accordingly, the invention provides an isolated nucleic acid sequence as set out in SEQ ID NO: 5 or a sequence with at least 80% identity thereto. Suitably, there is provided a nucleic acid sequence at least 80, 85, 90, 95 or 95% identity to SEQ ID NO: 5, or a codon-optimised version thereof. In one embodiment, there is provided an isolated nucleic acid having the sequence set out in SEQ ID NO: 5.

In one embodiment, the target gene/DNA sequence of interest may be an endogenous gene. In another embodiment, the target DNA sequence may be a genomic region of interest, such as an enhancer, a repressor, a CpG island or any non-coding element of interest. In both of these embodiment, the method of the present invention may be used to generate multiple copies of the endogenous gene so as to generate a cell line which may be used as a reference cell line. In another embodiment, a gene of interest may be provided as a cDNA sequence.

The DNA sequence positioned between the LTS and RTS is preferably one which provides a DNA sequence of interest such as a DNA sequence encoding a protein of interest for expression in the cell system.

Advantageously, using a Helitron transposase system such as Helraiser as described herein facilitates the replication of donor DNA and its introduction into a multiplicity of sites within the genome. As such, the methods or system in accordance with the invention may be used to introduce single or multiple copies of a target gene of interest.

In one embodiment, the cell or the isolated or cultured cell for use in the method of the invention is a prokaryotic cell such as bacteria. In another embodiment, the cell may be a eukaryotic cell such as insect, yeast, plant or mammalian cell. Suitable cultured cells are familiar to those skilled in the art. In one embodiment, the cell is a mammalian cell such as a mouse, rat or human cell, such as a CHO cell, a 293T cell, a HEK293 cell, a human induced pluripotent stem cell, a human or murine embryonic stem cell, a hematopoietic stem cell, a T cell or a B cell. Where the cell is a mammalian or human cell, it may be a cell for use in therapy. In another embodiment, the cell may be a cell type which can be used to generate a reference cell line, such as a tumour cell line, a HAP1 or eHAP cell, an HCT116 cell, a DLD-1 cell, a HEK293 cells and so forth. In another embodiment, the cell may be suitable for protein production. For example, the cell may be a HeLa, 293T cell, CHO cell or other suitable mammalian cell system. Suitable cell lines for mammalian protein production will be known to those skilled in the art and include CHO cells, HEK293 and 293T cells, for example.

In one embodiment, the method of the present invention may be used to generate a cell line. Such a cell line may be transient or stable.

One suitable system for Helraiser transposition is described herein in the Examples and with reference to FIG. 1B.

In another embodiment, the nucleic acid encoding the transposase is integrated into the genome of the cell. In another embodiment, the donor DNA is part of a plasmid or a recombinant viral vector. In a further embodiment, the donor DNA comprises at least a portion of an open reading frame. In a yet further embodiment, the donor DNA comprises at least a regulatory region of a gene, such as a transcriptional regulatory region which may be selected from the group consisting of a promoter, an enhancer, a silencer, a locus-control region, and a border element. Suitably, the donor DNA comprises a promoter operably linked to at least a portion of an open reading frame.

The donor DNA and/or the construct comprising the transposase sequence may be introduced into the cell using a method selected from the group consisting of: particle bombardment; electroporation; microinjection; combining the nucleic acid fragment with lipid containing vesicles or DNA condensing reagents; and incorporating the nucleic acid fragment into a viral vector and contacting the viral vector with the cell. In one embodiment of any aspect of the invention, the transposase may be introduced as an mRNA molecule.

In another aspect there is provided a method for introducing multiple copies of a DNA sequence into a genome whereby a Helitron transposase and donor DNA are introduced into a cell. In one embodiment, the transposase and donor DNA are supplied separately. In another embodiment, the transposase and donor DNA are supplied on the same DNA construct. Advantageously, where the transposase is supplied in a separate construct it may only be expressed and effective as long as it is present in the cell. This may enable transposition events to be limited, if desirable. In another embodiment, the transposase is introduced in RNA or protein form.

In another aspect there is provided a method for introducing multiple copies of a DNA sequence into a genome whereby a donor DNA is first introduced into the genome of a cell followed by introduction of a Helitron transposase.

In another aspect there is provided a method for introducing multiple copies of a DNA sequence into a genome whereby the RTS and LTS sequences flank an endogenous gene. The invention also provides a method for introducing single or multiple copies of a DNA sequence or gene of interest into a cell by providing a construct comprising a DNA sequence flanked by a Helraiser LTS sequence. In one embodiment, the RTS has a nucleic acid sequence comprising CTAG at the 3' end while the LTS has a nucleic acid sequence comprising TC at the 5' end. Suitably the LTS has a nucleic acid sequence as set out in SEQ ID NO: 3 or a sequence with at least 80% identity thereto, while the RTS has a nucleic acid sequence as set out in SEQ ID NO: 4, or a sequence with at least 80% identity thereto. Suitably, the method comprises modifying the cell genome in order to introduce the RTS and LTS in such a way that they lie either side of the endogenous cell gene of interest such that the endogenous cell gene is targeted for multiplication by the transposase. In one embodiment, the RTS and/or LTS sequences are introduced using a genome targeting or engineering method. In one embodiment a genome editing method such as CRISPR, Zinc-finger nucleases (ZFNs), meganucleases, transcription activator-like effector nucleases (TALENs) (reviewed, for example by Gaj et al. in Trends in Biotechnology, Volume 31, Issue 7, p 397-405, July 2013), other programmable nuclease technology, or rAAV technology may be used to introduce the RTS and/or LTS.

In one embodiment of any aspect of the invention, the method comprises the steps of:

a) providing a first construct which comprises a nucleic acid sequence encoding a gene of interest flanked by at least one Helraiser terminal sequence
b) introducing said first construct into a cell;
c) providing a second construct which comprises a nucleic acid sequence encoding Helraiser transposase;
d) introducing said second construct into said cell obtained in b);
e) incubating the cell obtained in d) under conditions for transposase activity; and
f) detecting multiple copies of said gene of interest.

In another aspect there is provided a method for introducing multiple copies of a DNA sequence into a genome whereby the DNA sequence is inserted randomly into the genome flanked by an RTS and LTS and a Helitron transposase is subsequently introduced. In one embodiment of any aspect of the invention, the Helitron transposase is a Helraiser transposase as described herein. In one embodiment of any aspect of the invention, the copy number of the target gene can be modulated by multiple rounds of transposase transduction.

In one embodiment of any aspect of the invention, the genome consists of a mammalian genome, suitably a CHO genome. In another embodiment of any aspect, the genome is a haploid human genome. Suitable haploid genomes are those observed in KBM-7 cells (as described, for example, by Kotecki et al. 1999 Nov. 1; 252(2):273-80) or HAP1 cells (as described, for example, Carette J E et al. Nature. 2011 Aug. 24; 477(7364): 340-343).

In another aspect, there is provided a cell containing multiple copies of a DNA sequence introduced by the system in any aspect or embodiment as described herein. Suitably, the cell is a mammalian cell.

In another aspect, there is provided a cell line produced by a method in accordance with the invention. Advantageously a cell line produced using a Helitron transposition event (or events) in accordance with the invention can be readily detected by analysing a cell line for the presence of the Helraiser LTS and/or RTS DNA sequence within its genome. Suitable methods for detection include PCR. In one embodiment, the cell line is a CHO cell line.

In one embodiment, such a cell line is for use as a reference standard. Suitably, a mammalian cell in accordance with the invention may be used to extract DNA which serves as a DNA molecular reference standard. Suitably, the mammalian cell in accordance with the invention may also be used for immunohistochemistry to provide reference materials with various expression levels of the target gene/protein, such as ERBB2/Her2 and CD274/PD-L1. Descriptions of uses of reference standards can be found, for example, in Horizon Discovery Product Catalogue (www.horizondiscovery.com). Here, examples of the gene sequences which may be useful in such applications are also described.

A cell line in accordance with the invention may also be for use in production of a protein of interest. Thus in another embodiment, a mammalian cell may be used for the production of a protein encoded by the DNA sequence i.e. the protein of interest encoded by the gene of interest. Thus, in one embodiment, there is provided a mammalian cell in accordance with the invention which is a stable host cell producing a recombinant protein, e.g. monoclonal antibody candidate, as a biotherapeutic molecule. Suitably, multiple constructs comprising genes of interest may be introduced into the same cell to generate a biotherapeutic such as an antibody or composition comprising an antibody or fragment thereof. Suitable methods for generating such biotherapeutic molecules are described herein.

In another embodiment, the invention provides a cell line produced in accordance with the methods of the invention for use in therapy. Suitably said cell line may be for use in gene therapy, cell therapy, tissue therapy or immunotherapy.

In another aspect, there is provided a nucleic acid isolated from a cell in accordance with the invention.

Also provided is a nucleic acid comprising a nucleic acid sequence positioned between a RTS and LTS, wherein the RTS and LTS can bind to a Helraiser transposase protein, wherein the Helraiser transposase protein comprises an amino acid sequence having at least 80% identity to SEQ ID NO: 1, binds to the RTS and LTS and catalyses the integration of the nucleic acid into DNA in an isolated cell. Suitably, the nucleic acid in accordance with any aspect of the invention is part of a plasmid.

In addition, the invention provides a nucleic acid encoding a Helraiser protein wherein the Helraiser protein comprises an amino acid sequence having at least 80% identity to SEQ ID NO: 1. In one embodiment, the Helraiser transposase protein has the amino acid sequence set out in SEQ ID NO: 1. Suitably the Helraiser transposase protein binds to the RTS and or LTS and catalyses integration of nucleic acid into DNA in an isolated cell. Suitably the RTS has a nucleic acid sequence as set out in SEQ ID NO: 4 and the LTS has a nucleic acid sequence as set out in SEQ ID NO: 3. The invention further provides a vector comprising a nucleic acid and a cell comprising the nucleic acid or vector.

Accordingly, in one aspect, the invention provides an isolated amino acid sequence comprising an amino acid sequence with 80% identity to the amino acid sequence set out in SEQ ID NO: 1 wherein said isolated amino acid sequence encodes a Helitron transposase described herein as "Helraiser" transposase. In one embodiment, the Helraiser transposase is one having at least 80, 85, 90, 95 or 95% identity with the amino acid sequence set out in SEQ ID NO: 1. In another embodiment, the amino acid sequence comprises a N-terminal nuclear localisation sequence, a zinc-finger-like motif and a RepHel enzymatic core, which in turn comprises a Rep nuclease domain having an HUH motif and a helicase domain, as described herein. In another embodiment, the amino acid sequence comprises the amino acid sequence set out in SEQ ID NO:1.

Suitably, the transposase is derived from or has the amino acid sequence as set out in SEQ ID NO: 1.

In another aspect there is provided an isolated nucleic acid sequence comprising a nucleic acid encoding the amino acid sequence in accordance with the invention. Suitably said isolated nucleic acid sequence encodes a Helraiser transposase in accordance with the invention. In one embodiment the nucleic acid sequence shows a level of homology with the sequence set out in SEQ ID NO: 2. For example, the sequence set out in SEQ ID NO: 2 may be codon-optimised so as to encode the same amino acid sequence as that set out in SEQ ID NO: 1. In one embodiment, the Helraiser transposase is encoded by the nucleic acid sequence set out in SEQ ID NO: 2 (see Table 6: TABLE OF SEQ ID NOS; SEQ ID NO: 2 is a nucleic acid sequence encoding the Helraiser transposase, see also FIG. 8). In another embodiment, the Helraiser transposase is encoded by the nucleic acid sequence set out in SEQ ID NO: 6 which is an example of a codon-optimised sequence.

Importantly, the Helraiser transposase is capable of catalyzing DNA transposition in trans when used in conjunction with donor DNA flanked by appropriate sequences. Suitable methods for determining this functional activity are described herein in Example 1, for example In another aspect, the invention provides isolated nucleic acid molecules comprising the appropriate sequences for catalysing DNA transposition with a Helraiser transposon. Accordingly, the invention provides an isolated nucleic acid sequence comprising a Helraiser left terminal sequence (LTS). In one embodiment, the LTS comprises a nucleic acid sequence having the nucleotides TC at the 5' end. Suitably there is provided a nucleic acid comprising a nucleic acid sequence as set out in SEQ ID NO: 3 or a sequence with at least 80% identity thereto. In another embodiment, the invention provides an isolated nucleic acid sequence comprising a Helraiser right terminal sequence (RTS). In one embodiment, the RTS has a nucleic acid sequence comprising CTAG at the 3' end. Suitably there is provided a nucleic acid comprising a nucleic acid sequence as set out in SEQ ID NO: 4, or a sequence with at least 80% identity thereto. In one embodiment, the LTS or RTS sequence in accordance with the invention is one having at least 80, 85, 90, 95 or 95% identity with the amino acid sequence set out in SEQ ID NO: 3 or SEQ ID NO: 4 and which retains the functional activity of being capable of interacting with a Helraiser transposon in accordance with the invention, when flanking a gene of interest, such that DNA transposition of the gene of interest is catalysed.

In another aspect of the invention, there is provided an isolated nucleic acid comprising a nucleic acid sequence of a gene of interest flanked by at least an LTS Helraiser terminal sequence comprising the sequence set out in SEQ ID NO: 3 or a sequence having 80% identity thereto. In one embodiment, the isolated nucleic acid further comprises an RTS Helraiser terminal sequence comprising the sequence set out in SEQ ID NO: 4 or a sequence having 80% identity thereto. Such a nucleic acid may also be referred to as a donor DNA.

In another aspect, there is provided an expression vector comprising a nucleic acid sequence in accordance with the invention. Thus, in one embodiment the invention provides an expression vector comprising an LTS or/and RTS sequence (as set out in SEQ ID NO: 3 or 4) respectively as well as an expression vector comprising a sequence encoding a transposase in accordance with the invention.

In one embodiment, an expression vector may further comprising at least one of:

a) a generic gRNA recognition site, preferably TialL, flanking the LTS and RTS;

b) a promoter sequence arranged such that the gene of interest is under the control of said promoter;

c) a polyadenylation cassette following said gene of interest.

In another aspect, the invention provides a recombinant host cell comprising a nucleic acid sequence or an expression vector in accordance with the invention. Suitable host cells are described herein and include, for example, CHO cells.

In another aspect, the invention provides a method of production of a protein of interest comprising culturing a cell produced in accordance with a method of the invention or a recombinant host cell in accordance with the invention in a suitable medium and harvesting the protein of interest from the cell or suitable medium.

In another aspect, there is provided a method for treating a disease by providing a gene of interest to a subject in need thereof comprising:

a) isolating a cell line suitable for using in said subject;

b) introducing an isolated nucleic acid or an expression vector in accordance with the invention, into said cell line wherein said nucleic acid or expression vector comprises a gene of interest corresponding to said protein of interest;

c) introducing an amino acid sequence, a nucleic acid sequence or an expression vector in accordance with the invention such that a Helraiser transposition event occurs to generate an engineered cell line comprising said gene of interest;

d) expanding said engineered cell line in cell culture to provide a population of engineered cells; and e) introducing said engineered cells into said subject.

Suitably, there is therefore provided an ex vivo method of treating a disease in a subject. In this embodiment, the gene of interest may encode a protein of interest which is expressed in the engineered cells to provide that protein to the subject or patient. The cell line may be, for example, a T cell, macrophage cell, B cell, dendritic cell, NK cell, haematopoietic stem cell, myeloid-erythroid progenitor (CMEP) cell or common lymphoid progenitor (CLP) cell.

In another aspect, the invention provides a method for treating a disease in a subject in need thereof comprising:

a) providing a first expression vector comprising an isolated nucleic acid providing a gene of interest in accordance with the invention;

b) providing a second expression vector comprising a nucleic acid sequence encoding a transposase in accordance with the invention;

c) introducing said first and second expression vectors into said subject.

Suitably, there is therefore provided an in vivo method of treating a disease in a subject.

In a further aspect, the invention provides a pharmaceutical composition comprising a first expression vector comprising an isolated nucleic acid providing a gene of interest in accordance with the invention and a transposase. In one embodiment, the transposase may be provided within a second expression vector comprising a nucleic acid sequence encoding a transposase in accordance with the invention. In another embodiment, the transposase may be provided as a mRNA or protein.

The invention provides a cell line in accordance with any aspect of the invention for use in therapy. Further aspects include use of a cell line in accordance with the invention in the manufacture of a medicament for use in treatment of disease.

In another aspect the invention provides the use of a transposon or transposase or a method in accordance with any aspect or embodiment of the invention in random mutagenesis. Suitable methods are described herein. See Example 8, for example. In particular, there is provided use of a transposon, transposase or method in accordance with the invention in a method for insertional mutagenesis in a haploid cell background. The use of libraries obtained by such techniques are described, for example in Carette et al. Nature Biotechnology, pages 542-546; Vol. 29 (6), 2011 and Moriarity et al. *Nature Genetics* 2015, doi:10.1038/ng.3293.

Thus, the invention also provides a use of a Helitron transposase together with a donor encoding a reporter gene, flanked by LTS and/or RTS, to generate a library of cell lines containing various genomic integration events of the reporter.

In another aspect, there is provided a method for detecting a cell line derived from a Helitron transposition method comprising analysing said cell line for the presence of an LTS and/or RTS sequence in accordance with the invention.

In yet another aspect, the invention provides, a method for generating a cell line comprising:

a) providing a construct comprising a Helitron LTS sequence; and b) introducing said construct into a cell line.

Suitably, said construct in part a) further comprises a Helitron RTS sequence. In one embodiment, said LTS and/or RTS are targeted to a DNA sequence of interest. The invention also provides a cell line produced by a method in accordance with this aspect.

In another aspect there is provided a method for producing a cell line comprising multiple copies of a DNA sequence of interest comprising:

a) taking a cell line comprising a Helitron LTS sequence in accordance with the invention;

b) introducing a Helitron transposase under conditions for transposase activity;

c) isolating clonal cell lines bearing multiple copies of said DNA sequence.

The invention further provides an isolated clonal cell line produced by a method in accordance with this aspect. Such a cell line may be a CHO cell line, HAP1 or eHAP cell line. In another aspect of the invention, there is provided a use of a copy and paste transposon in a eukaryotic cell to generate a cell having single or multiple copies of a DNA sequence. In a yet further aspect of the invention, there is provided a use of a Helitron transposon in a prokaryotic or a eukaryotic cell to generate a cell having single or multiple copies of a DNA sequence.

FIGURES

FIG. 1. Features of Helraiser transposition in human HeLa cells. A) Schematic representation of the Helraiser transposon. LTS and RTS terminal sequences are in uppercase, flanking A and T host target site sequences are in lowercase. Conserved amino acid motifs within Helraiser transposase are shown, where motif I refers to SEQ ID NO: 137, motif Ia refers to SEQ ID NO: 138, motif II refers to SEQ ID NO: 139, motif III refers to SEQ ID NO: 140, motif IV refers to SEQ ID NO: 141, motif IV/V refers to SEQ ID NO: 142, motif V refers to SEQ ID NO: 143, and motif IV refers to SEQ ID NO: 144. B) Helraiser colony-forming efficiency. Shown are tissue culture plates containing stained puro-resistant HeLa cell colonies. Helraiser donor (pHelR) and helper (pFHelR) plasmids. pHelR: White rectangle inside RTS: represents the hairpin; pFHelR: black arrow: represents the promoter driving transposase expression, black circle: represents the polyA signal; these annotations are used consistently in all the figures. Data are represented as mean±SEM. C) Helraiser transposition generates canonical insertions. Helraiser LTS- or RTS-to-genome junctions are shown for ten independent transposon insertions. Helraiser sequences are shown in uppercase with the conserved 5'- and 3'-terminal sequences in a black background, flanking host genomic sequence is in lowercase. The flanking pHelR plasmid sequence (upper line) is in italic. D) Relative transposition efficiencies of Helraiser and Sleeping Beauty (SB100X) measured by colony formation in HeLa cells. Data are represented as mean±SEM. E) Relative transposition efficiencies of Helibat1 and the non-autonomous subfamilies HelibatN1, HelibatN2 and HelibatN3. Data are represented as mean±SEM.

FIG. 2. Functional analysis of the HUH nuclease and SF1B helicase domains. A) Transposition activity of Helraiser transposase mutants in HeLa cells, relative to HelR (WT) set to 100%. Data are represented as mean±SEM. B) Cleavage of single-stranded DNA oligonucleotides by the Helraiser transposase in vitro. C) DNA binding assay with the Helraiser transposase and its point mutant and truncated derivatives. D) Colorimetric ATPase assay with the wildtype (WT) and K1068Q mutant transposase protein. Data are represented as mean±SD. For each treatment (ATP+dsDNA, ATP+ssDNA or ATP alone), the leftmost bar shows the data for 0.02 uM WT, the central bar shows the data for 0.08 uM WT, and the rightmost bar shows the data for 0.3 uM K1068Q.

FIG. 3. Role of the 3'-terminal sequences and hairpin structure in Helraiser transposition. A) Colony forming efficiencies of the pHelR, pHelRΔLTS, pHelRΔRTS and pHelRΔHP donor plasmids. Data are represented as mean±SD. For each donor plasmid, data are presented for 'donor+ helper' (left-hand bar), and 'donor+control' (right-hand bar). B) Average transposon copy numbers per clone and transposition efficiencies of HelR, HelRΔRTS and HelRΔHP transposons normalized by the average colony numbers (inset). The difference in transposition efficiencies of HelRΔRTS and HelRΔHP transposons is not statistically significant, *p>0.05, unpaired t-test. Data are represented as mean±SEM. C) M-fold (Zuker, 2003) predicted structures of the HelR, HelRATH, HelRStemX and HelRLoopX hairpins. D) Relative colony-forming activities of hairpin mutants. Bars (left to right) represent HelR, DHP, ATH, StemX and LoopX respectively. Data are represented as mean±SEM.

FIG. 4. Helitron circles. A) Helitron circle donor plasmid (pHelRCD) and Helraiser transposase-generated Helitron circle (pHelRC). White arrow represents the Amp/SV40 promoter; white circle represents the polyA signal. B) Transposition of Helitron circles generated from pHelRCD (left hand side of graph) or pHelRC (right hand side of graph), measured by numbers of colonies formed. For each donor plasmid, data are presented for donor+ helper (left hand bar) and donor+control (right hand bar). C) PCR detection of Helitron circles generated with HelR, HelRMut and HelRΔHP transposons. HelRMut, transposon deletion version where the last 9 nt of the palindrome is deleted; $H_2O$, no template control. D) Relative transposition efficiencies of pHelRCpuro (left hand side of graph) and pHelRCΔHPpuro (right hand side of graph). For each donor plasmid, data are presented for donor+ helper (left hand bar) and donor+ control (right hand bar). Data are represented as mean±SEM. Schematics of the pHelRCpuro and pHelRCΔHPpuro plasmids are presented under the graph.

FIG. 5. Genome-wide analysis of de novo Helraiser insertions in the human genome. A) The sequence logo was created with WebLogo (http://weblogo.berkeley.edu). Transposon integrations are between the positions −1 and 1. The lower panel shows the distribution of dinucleotides at the integration sites. B) Fold enrichment of relative integration frequencies compared to random genomic sites (front bar of each pair) and control sites imitating the base composition characteristics of Helraiser integration sites (rear bar of each pair). Top genes are the 500 genes with highest expression level. Integration frequencies into promoter regions of silent genes and H3K9me3 regions were not significantly different from controls; all other differences were statistically significant (Fisher's exact test p-value <=0.05). C) Fold enrichment of relative integration frequencies per chromosome compared to random genomic sites (front bar of each pair) and control sites imitating the base composition characteristics of Helraiser integration sites (rear bar of each pair). D) Chromosomal distribution of 133 Helraiser re-transposition events (arrows above the chromosomes). The arrows underneath chromosomes 8, 20 and 21 represent the positions of the original chromosomal donor sites.

FIG. 6. Mechanism of Helraiser gene capture. A) Identification of novel 3'-terminal sequences generated by pHelRΔRTS and pHelRΔHP transposition. Relative positions of canonical and de novo 3'-ends generated in pHelR, pHelRΔHP and pHelRΔRTS transposition are indicated thus: arrow at end of pHelR RTS (canonical RTS), arrows between puro$^r$ and polyA signal on pHelRΔHP and pHelRΔRTS (truncations) and arrows upstream of the LTS on pHelRΔHP and pHelRΔRTS (read-throughs). Sequences representing new transposon 3'-terminus-to-genome junctions are shown on the right: for Vector pHelR, insertion H1-2, the transposition RTS refers to SEQ ID NO: 170 and the genome sequence refers to SEQ ID NO: 171; for Vector pHelRΔHP, insertion 2, the transposition RTS refers to SEQ ID NO: 172 and the genome sequence refers to SEQ ID NO: 173; for Vector pHelRΔHP, insertion 14, the transposition RTS refers to SEQ ID NO: 174 and the genome sequence refers to SEQ ID NO: 175; for Vector pHelRΔHP, insertion 19, the transposition RTS refers to SEQ ID NO: 176 and the genome sequence refers to SEQ ID NO: 177; for Vector pHelRΔRTS, insertion 2, the transposition RTS refers to SEQ ID NO: 178 and the genome sequence refers to SEQ ID NO: 179; and for Vector pHelRΔRTS, insertion 15, the transposition RTS refers to SEQ ID NO: 180 and the genome sequence refers to SEQ ID NO: 181. B) Gene capture efficiency of HelR and HelRΔHP transposons as measured by transduction of a neomycin resistance cassette. For each plasmid, the left hand bar shows data produced using puromycin only, the right hand bar shows data produced using puromycin and neomycin. Data are represented as mean±SEM. C) De novo formation of novel transcripts by HelibatN3 transposition. [i] The HelibatN3 transposon contains a fragment of the NUBPL gene containing the promoter and a small piece of the coding region followed by a splice donor (SD) between the left and right terminal sequences (LTS and RTS) of the transposon. [ii] HelibatN3 transposon tagged with a puromycin resistance selectable marker. The T2A self-cleaving peptide sequence allows processing of the primary fusion protein to allow more reliable puro expression. The two examples show exonization of non-coding RNA and truncation of mRNAs by imposed splicing. MED27, mediator complex subunit 27 gene; GREB1L, growth regulation by estrogen in breast cancer-like gene.

Figures 7A, 7B, 7C:
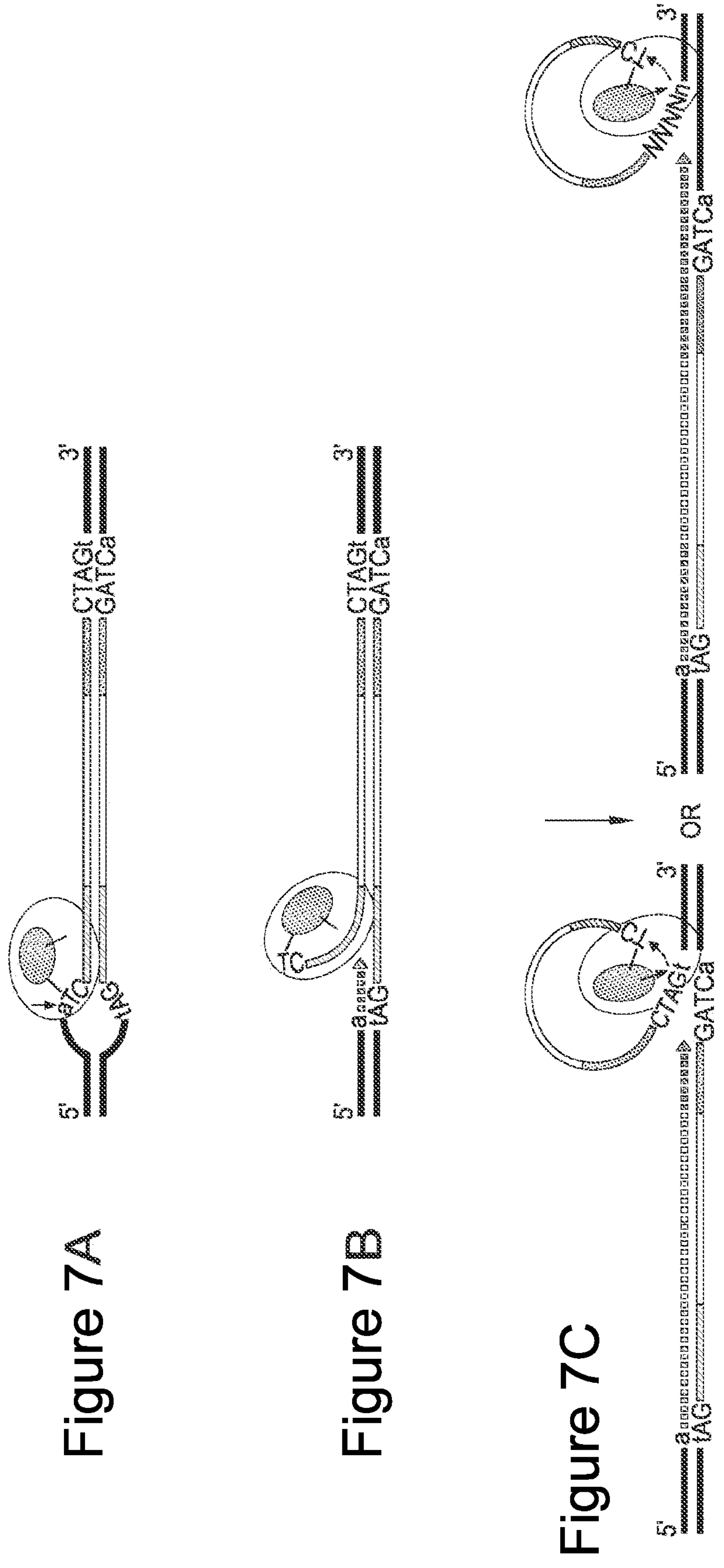
Figure 7D:
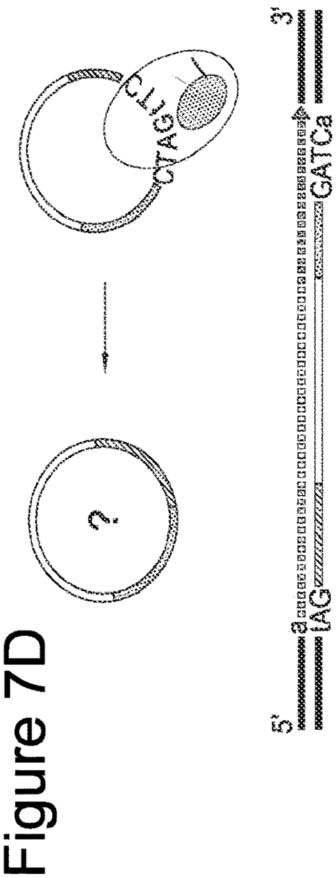
Figure 7E:
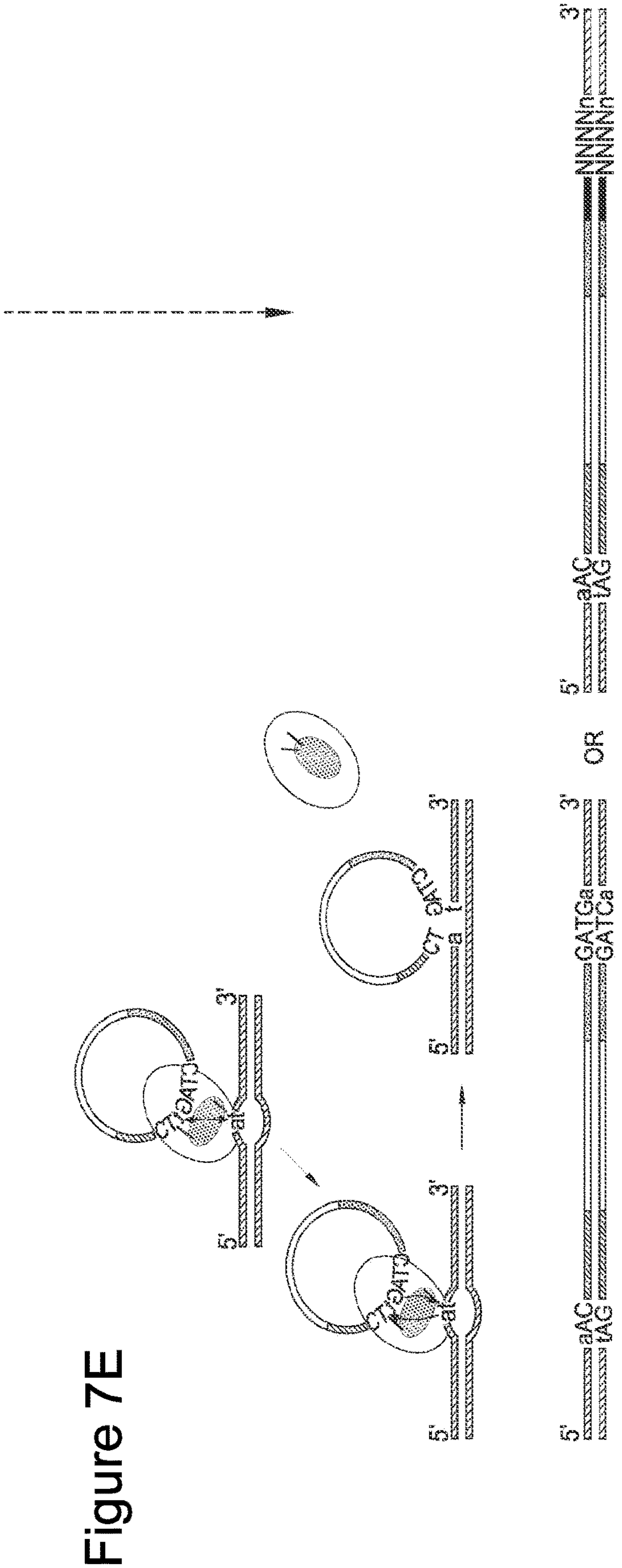

FIG. 7. Proposed model of Helraiser transposition. A) Helraiser transposase (oval) binds the LTS and nicks ssDNA donor site generating a 5'-phosphotyrosine intermediate between the tyrosine residue in the HUH nuclease active site and transposon end. B) A free 3'—OH group at the donor site primes some type of unscheduled DNA synthesis, while the helicase domain unwinds the dsDNA helix in a 5' to 3' direction. C) [left half of figure] The hairpin structure in the RTS induces pausing of the helicase required for the recognition and nicking of the CTAG-3' tetrad at the RTS by the second tyrosine of the HUH domain. This generates a free 3'—OH group at the transposon RTS that attacks the first 5'-phosphotyrosine linkage generating a free ssDNA circle. The ssDNA circle is possibly converted into dsDNA circle used for further rounds of transposition. [right half of figure] Alternatively, the transposase reads through the RTS and mobilizes the host flanking sequence, thereby generating an alternative, de novo 3'-end. Further steps in transposition of the canonical transposon and the transposon containing the captured host sequence are identical. D) Two tyrosine residues in the nuclease active site catalyze cleavage of the ss target DNA and the Helitron circle, mediating the strand transfer reaction. E) [left half of figure] The ss transposon DNA covalently bound to the target is passively replicated and converted into the ds form during the DNA synthesis phase of the cell cycle, leading to the amplification of the transposon number in the host genome and transduction of host genomic sequence. [right half of figure] The alternative outcome of the transposition if a de novo 3' end had been generated (see FIG. 7D, right half)

FIG. 8. DNA sequences. The complete DNA sequence of the consensus Helibat1 (Helraiser) transposon, and the consensus left terminal and right terminal sequences of autonomous and non-autonomous transposons that were used in the transposon donor constructs. The 5'-TC and CTAG-3' terminal sequences are typed in bold.

Figure 9:
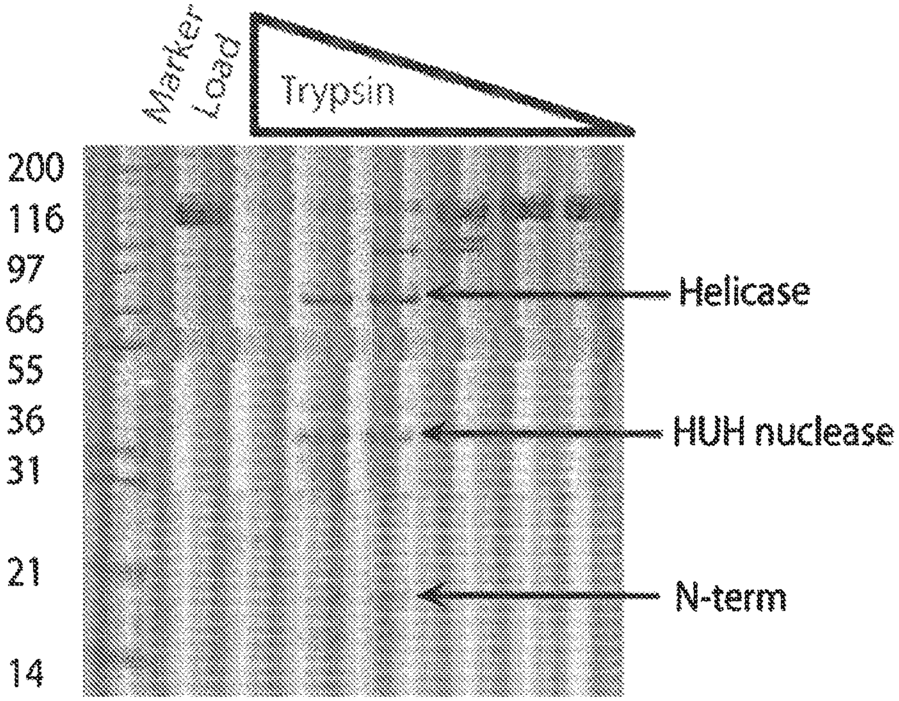

FIG. 9. Protein sequence alignment and domain mapping. SDS-PAGE analysis of the purified Helraiser digest by increasing amounts of trypsin. N-terminal sequencing identified the helicase fragment encompassing the amino acids 811-1496, HUH nuclease fragment containing amino acids 491-745 and N-terminal fragment spanning the amino acids 251 to 481.

Figure 10:
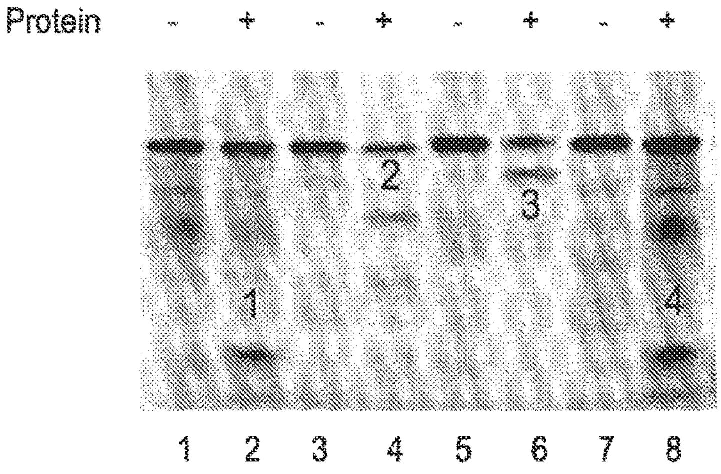

FIG. 10. Structural and functional properties of Helraiser transposase domains. In vitro cleavage ssDNA of 5'- or 3'-terminus top and bottom strand. 15% TBE-UREA gel of 5' FAM-labeled oligonucleotides cleavage by Helraiser transposase. Schematic of DNA on the right depicts the four ssDNA substrates, 5'- and 3'-terminus sequence is in bold, flanking sequence in regular script, and 3'-hairpin is underlined. The arrows show the cleavage sites, and numbers show the ssDNA fragments sequenced.

FIG. 11. Examples of diversification of 3'-ends of Helitrons in *Myotis* genomes. A) Acquisition of a novel Helitron end. Insertion of a Helitron copy adjacent to a Helitron with truncated 5'-end can lead to acquisition of a novel 3'-end. B) Insertion of Helitron right next to each other. Insertion of a Helitron between 5'-A of the host and T-3' of a Helitron can result in insertions, where a 3'-end of one Helitron abuts the 5'-end of another Helitron. C) Generation of a de novo end, possibly by the truncation of the 3'-end. D) Comparison of host sequences with Helitron insertions (described from A-C) and the orthologous empty (insertion-free) sites. The first line is the host sequence flanking the Helitron insertion. The second line is the orthologous empty site. The sequences on the left and right hand ends represent the host sequence whereas the sequence between the vertical lines represents the Helitron sequences. The accession number and coordinates are shown. E) Generation of de novo termini by end-bypass [i] The top cartoon shows the structure of the HelibatN542 consensus. The terminal sequence of the consensus is shown adjacent to the cartoon. The palindrome within the terminus is shown in grey and sequences that comprise the stem of the palindrome are underlined. [ii] Cartoon representation of the structure of a HelibatN542 copy lacking the palindromic sequence, resulting in a different 3'-end. The sequence of the novel 3'-end is shown next to the cartoon. [iii] Location of the two HelibatN542 copies in the genome. The transposition of one copy (shown as dashed lines) resulted in end-bypass of the CTAG-3' terminus and terminated at a random sequence followed by a short palindrome. The copy was then inserted to a different position ( ) in the genome. The novel terminal sequence including the palindrome is shown next to the cartoon. [iv] The first line is the host sequence with the Helitron insertion and the novel terminus. The second line is the paralogous copy with the Helitron and the novel terminus. The sequences on the left and right hand ends represent the flanking host sequence whereas the sequence between the vertical lines represents the Helitron and the captured host sequences. The accession number and coordinates are shown.

Figure 12A:
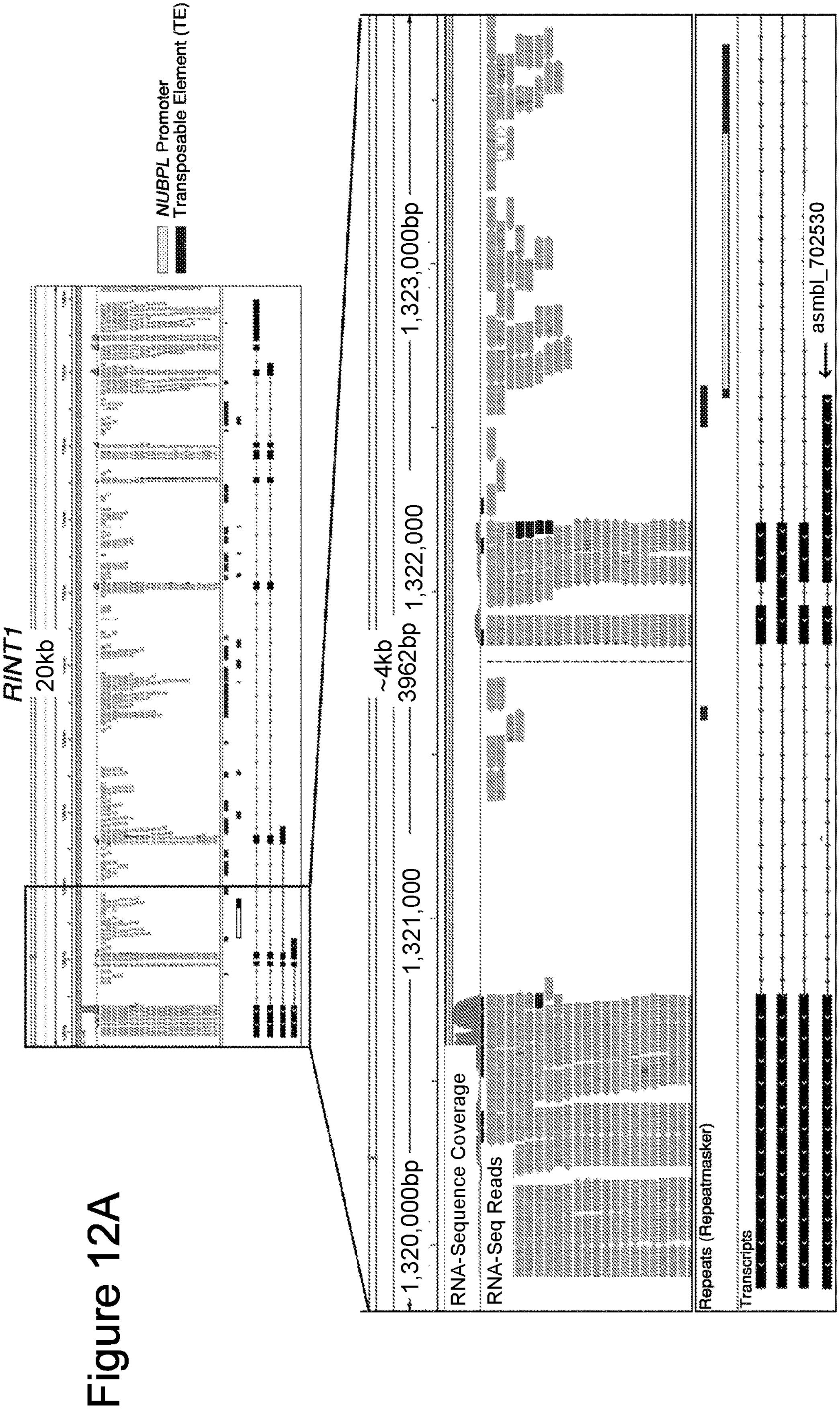
Figure 12B:
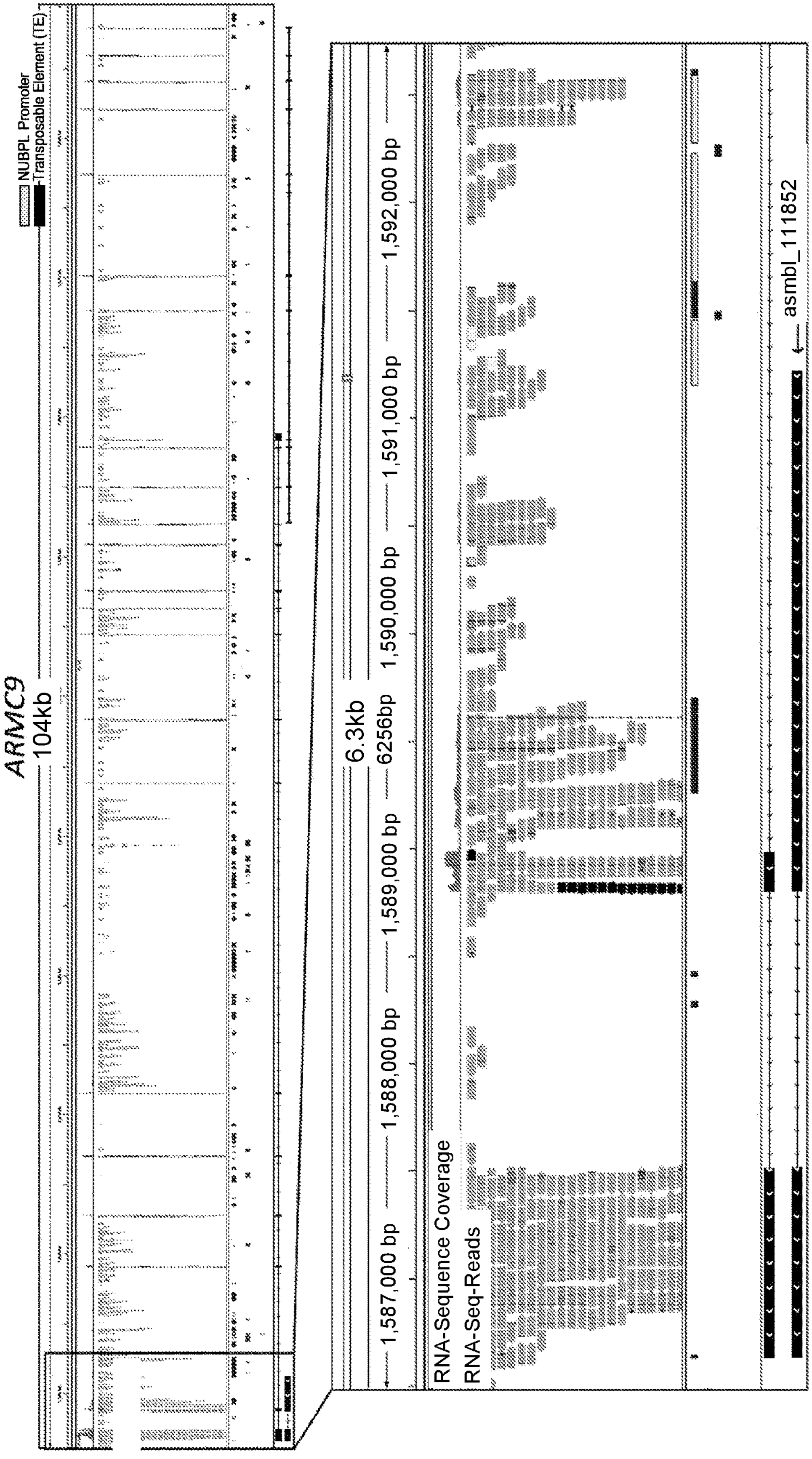

FIG. 12. RINT1, ARMC9 and RNF10 loci (*M. brandtii*). A) RIND locus. B) ARMC9 locus. C) RNF10 locus. Shown at the top of each panel is an IGV genome browser snapshot of the full gene models determined by our transcriptome assembly (only transcript assemblies with FPKM>0.5 shown). The expanded versions represent the regions of the gene models that contain the NUBPL-driven transcripts. In the expanded versions, the top tracks represent the total coverage of the RNA-seq reads for the gene models, the tracks below show a subset of the reads aligning to the regions. The third tracks indicate the locations of repeats and transposable elements (dark grey bars), as well as the locations of the NUBPL fragments (light grey bars). The bottom tracks contain the transcript assemblies (FPKM>0.5), including the transcripts of interest (asmbl_702530 for RINT1, asmbl_111852 for ARMC9 and asmbl_680940 for RNF10).

FIG. 13. Integration of the Turbo GFP donor by HelRaiser transposition into the AAVS1 locus of HEK293 cells: (A) Schematic depiction of the Turbo GFP donor and CRISPR-mediated insertion at the AAVS1 locus. HelRaiser LTS and RTS sequences flank the TurboGFP cassette which also contains an EF1A promoter and a polyadenylation signal. To enable CRISPR/Cas9-mediated integration at the AAVS1 locus, the donor sequence was also flanked with tia1L recognition sites that trigger integration upon co-expression of the tia1L-specific gRNA (B) DNA Sequencing of the insertion site in a representative targeted clone demonstrating correct insertion of the TurboGFP donor into the AAVS1 locus at the predicted gRNA cut site.

FIG. 14. HelRaiser transposase increases the copy number of the integrated TurboGFP donor. (A) HEK293 cells containing a single copy of TurboGFP tagging cassette described in FIG. 13 were subjected to Helraiser transposition. Individual clones were isolated by limiting dilution and analyzed by digital droplet PCR (ddPCR) analysis to quantify the TurboGFP copy number before (−) and after (+) transfection with the Transposase plasmid. (B) Flow cytometric analysis of TurboGFP expression in HEK293 clones harbouring the HelRaiser TurboGFP donor, before (filled histogram) and after (open histogram) transfection with the HelRaiser Transposase expression plasmid.

Figure 15:
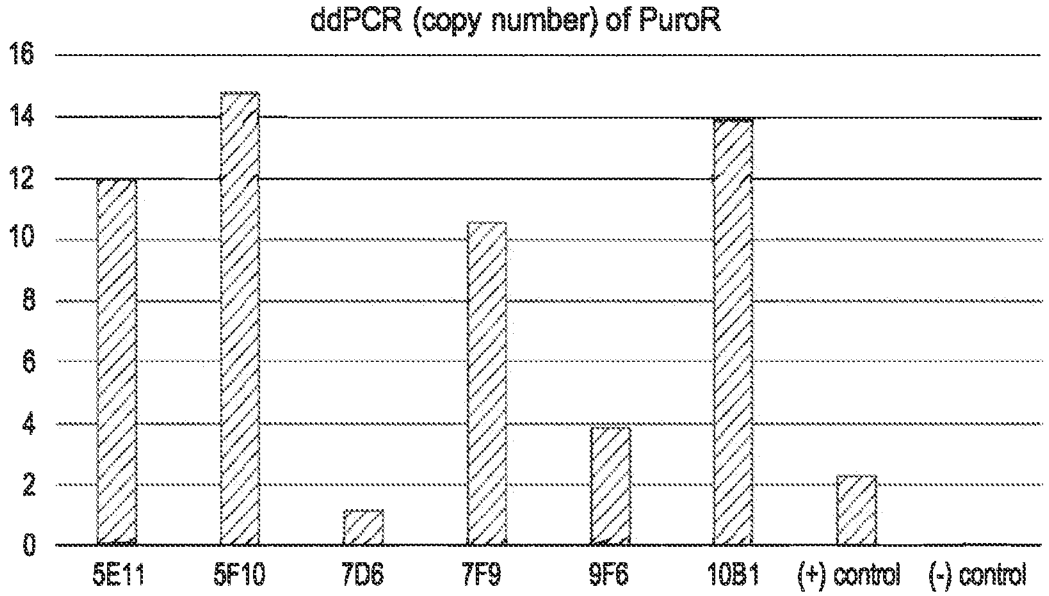

FIG. 15: Use of HelRaiser transposase to produce cell lines bearing multiple stably integrated copies of a gene of interest. HEK293 cells were transfected with HelRaiser transposase and a donor plasmid containing transposon terminal sequences (LTS and RTS) encompassing a Puromycin resistance (PuroR) genes. Following transfection and integration of the PuroR gene into the HEK293, cells were selected by applying 1 μg/ml Puromycin for a week. Single clones were obtained by limiting dilution and expanded. Genomic DNA from selected clones was analysed by digital droplet PCR (ddPCR), quantifying the copy number of the PuroR gene. As positive control ((+) control), a reference cell line was included that bears two copies of the PuroR gene. As negative control ((−) control), parental HEK293 cells were included.

TABLES

Table 1. Contingency Count Table for Helitron enrichment analyses in +1-1 kb regions around TSSs in *M. brandtii.*

* # of times Helarons overlap with +/−1 kb regions around TSSs

ł # of +/−1 kb regions around TSSs that do not overlap with Helarons x # of Helitrons that do not overlap with +/−1 kb regions around TSSs + # of regions (estimated) that do not overlap with either Helarons or +/−1 kb regions around TSSs ° Left p-values indicate probability of Helitrons being depleted in +/−1 kb regions around TSSs. Right p-values indicate the probability of enrichment, and Two-Tailed the probability of Helitrons being different than what is expected by chance.

Table 2. Analysis of 3'-ends of recently active Helitrons in *Myotis* genomes.

Table 3. Candidate NUBPL-driven transcripts. This table lists the information for each candidate NUBPL-driven transcript including its ID, the name of the gene it belongs to, the scaffold and coordinates of the transcript, and its tissue-specific expression, if any. The information about the specific NUBPL promoter insertion is listed on the right side of the table, and includes the donor Helitron element, the distance of the element from the TSS (annotated based on our transcriptome assembly; positive number indicates that it overlaps the TSS), and its approximate age, determined as described in Methods. Transcripts labeled in green are those whose TSS is donated by the NUBPL-promoter containing insertion. The numbers 1 and 2 indicate the orientation of the transcript. Transcripts denoted with a 1 are driven in the canonical direction by the NUBPL promoter, whereas transcripts denoted with a 2 are driven in the reverse direction. Many (11) of these insertions are present in the genomes of the other three sequenced vespertilionid bats (*M. lucifugus, M. davidii, Eptesicus fuscus*), but there are several (12) lineage-specific insertions, including those in the FOXJ2 and STX10 genes that are specific to *M. brandtii*, consistent with Helibat activity throughout the diversification of vesper bats (Thomas et al. (2014)) Nine insertions appear to drive their transcripts in the canonical direction, whereas eight insertions drive transcripts in the reverse direction, suggesting that the captured NUBPL promoter is bi-directional. This is further supported by the presence of many characteristic promoter sequence features (TATA, CAAT, and GC boxes as well as predicted TF binding sites/overrepresented sites) on both strands of the captured promoter sequence (data not shown). In spite of the small set, these genes are enriched for several GO Terms: protein ubiquitination (GO: 0016567; p=1.295e-02), regulation of signal transduction involved in mitotic G2 DNA damage checkpoint (GO: 1902504; p=1.481e-02), protein modification by small protein conjugation (GO: 0032446; p=1.66e-02), protein modification by small protein conjugation or removal (GO: 0070647; p=3.104e-02), organelle organization (GO: 0006996; p=3.312e-02), cell cycle (GO: 0007049; p=4.082e-02), and actin polymerization-dependent cell motility (GO: 0070358; p=4.439e-02).

Table 4. List of primers. For primer pairs where reverse primer is reverse complement of the forward primer sequence, only forward primer sequence is shown.

Table 5 shows the sequence of the Tagging Cassette bearing Tia1L-LTS-EF1A-TurboGFP-RTS-Tia1L described in Example 2.

Table 6 shows a list of sequences and their corresponding SEQ ID NOs:

DETAILED DESCRIPTION OF INVENTION

As described herein, the invention provides methods, systems and molecules for the introduction of single or multiple copies of a DNA sequence into a cell. The DNA sequence may comprise a gene of interest or may be genomic sequence or a shorter nucleic acid sequence which is desired. The gene of interest may encode a protein or interest.

Transposon-based systems for the introduction of a nucleic acid into DNA of a cell are described, for example, in U.S. Pat. No. 6,489,458.

The term “construct” as referred to herein includes expression constructs such as expression vectors which may be plasmids or may be sequences for packaging into viral vectors (retroviral, adenoviral, such as rAAV, for example). Suitable constructs for use in the methods of the present invention will be familiar to those skilled in the art and include those exemplified herein. The skilled person will also recognise that additional components such as promoter sequences may be incorporated. Suitable promoters may enable constitutive expression or may enable inducible expression.

DNA molecules, constructs, expression vectors, plasmids etc. in accordance with the invention may be introduced into cells by any number of means including, for example, by electroporation, microinjection, combining with cationic lipid vesicles, DNA condensing reagents, DNA nanoparticles or precipitation techniques and incorporating into a viral vector.

Suitably, the transposase, as a transposase-expressing helper plasmid, and the corresponding construct comprising the tagged transposon (comprising the gene of interest flanked by LTS and RTS) are provided in a bi-component transposition system comprising a tagged transposon and a transposase-expressing helper plasmid. Alternatively, a one-component system, e.g. a transposase present on the LTS/RTS flanked transposon, may be provided. While a one component system may be easier to deliver, a two component system may be preferable from a safety point of view because the transposase enzyme and transposase substrate are spatially separated. As a consequence, with the two component system, the transposition reaction comes to an end once the transposase plasmid has vanished and the transposon is no longer present in the cell. This may prevent continued transposition which may otherwise occur in an uncontrolled manner Uses of the Helraiser Transposon In one embodiment a plasmid encoding a Helitron transposase is introduced into a mammalian cell leading to expression of the transposase protein. A donor DNA is either also added or already present which comprises a DNA sequence which encodes a region of DNA, for which single or multiple copies of the DNA are desired within the genome, flanked by RTS and LTS sequences. Following introduction of the transposase, the donor DNA is replicated and introduced into a multiplicity of sites within the genome. Accordingly, in one aspect, the invention provides a donor DNA comprising a region of DNA, for which single or multiple copies are required, wherein said donor DNA is flanked by an LTS sequence. In one embodiment the donor DNA is flanked by an LTS and an RTS sequence.

Reference Standards

The donor DNA may be used to generate a cell line which can be used to generate reference standards. Thus the invention provides a method to generate a cell line comprising multiple copies of a gene of interest wherein first a cell line with a single copy of a gene of interest is generated in which the gene of interest is flanked by at least the LTS Helraiser terminal sequence (and, optionally, also the RTS). In one embodiment, the gene of interest may be an endogenous gene into which the flanking LTS and RTS have been introduced by a gene editing technique. In another embodiment, the gene of interest may be an introduced or non-endogenous gene. Suitably the "gene of interest" may be a gene or a part thereof which is found to duplicate itself. Thus, in another embodiment the donor DNA represents a region of DNA which is found to duplicate itself in certain diseases like cancer and the presence of which can be used to help provide a diagnosis for a disease. Examples of genes that may be useful as reference standards include ERBB2/Her2, MET, CDK4 or CD274/PD-L1.

For generating reference standards, a method in accordance with the invention may preferably comprise selecting clones with known copy numbers and/or generating a cell in such a way that a defined copy number is obtained. Cell lines which may be used for generating reference standards include CHO cells, HAP1 or eHAP cell lines, for example.

Protein Production

Biopharmaceutical drug discovery is reliant on the expression of recombinant protein in mammalian cell-based manufacturing platforms. The generation of these stably expressing host cells is complex and requires a laborious screening methodology. Previous technologies rely on the random insertion of a recombinant transgene cassette into the genome of the target mammalian cell. The cells constructed have a wide range of expression, growth and stability characteristics. In order to obtain a commercially viable production host cell, hundreds of clones are screened. In addition, a process of amplification of the transgene can be employed by increasing the selection pressure of the associated resistance genes, e.g. glutamine synthase, dihydrofolate reductase. This process is prone to inaccuracy during the amplification of the transgene cassette causing instability in the transgene expression. Chinese hamster ovary (CHO) cells remain the default expression host for manufacture of therapeutic biologics, although a number of other suitable cell lines will be familiar to those skilled in the art and include NS0 murine myeloma, PER.C6®, Baby Hamster kidney, Human embryonic kidney (HEK293), Chicken embryo fibroblast, Madin Darby bovine kidney, Madin Darby canine kidney and VERO cells.

The Helraiser transposase protein provides an advantage over previous systems to efficiently generate a reduced panel of cells for screening. In a single step, multiple copies of the transgene flanked by RTS and/or LTS can be incorporated into the genome of a target cell at high frequencies. The incorporations may be targeted to known hot spots within the genome of the target cell. The copy and paste activity of Helraiser transposase protein can be utilised to further amplify sequences previously incorporated into the genome. This can be from a single integration site or multiple sites without the need for chemical treatment, e.g. methionine sulfoximine or methotrexate. The removal of the laborious screening step allows higher-producing cells with desirable growth and stability characteristics to be identified more quickly. In one example, this system may be used to amplify an existing transgene in an established bioproduction line.

Thus, in another embodiment the donor DNA may encode a therapeutic protein, like an antibody which is produced by a cell carrying multiple copies of the protein integrated by the transposase. By flanking an expression cassette comprising the antibody with RTS and LTS sequences and introducing it into a suitable cell type (e.g, CHO) with the transposase, a large number of copies of the cassette are inserted into the genome resulting in higher levels of expression compared to a single insertion event.

Cell and Gene Therapy

In one embodiment, the invention provides a system of introducing a nucleic acid or gene of interest into a subject in need of that nucleic acid. Suitably a subject may be any eukaryotic cell such as a plant, mammalian, human cell etc.

Where a subject such as a human patient has a pathology associated with a loss of function mutation, gene therapy has the potential to restore health. Gene therapy involves introducing an expression construct into the cells of a patient. This can be performed ex vivo or in vivo, with ex vivo applications being safer and more straightforward.

In the presence of the appropriate transposase, sequences flanked by the LTS and RTS sequences from the Helraiser transposon are efficiently integrated into chromosomal DNA (as shown in FIG. 1). The copy and paste properties of the Helraiser transposon result in a high proportion of the transduced cells having multiple copies of the introduced gene sequences (as shown in FIGS. 3 and 15).

Accordingly, the present invention describes a system and methods that can be used to generate engineered cells which, once re-introduced into the patient, can achieve restoration of the missing function for the pathology being treated with a lower proportion of edited cells than required in existing techniques. Thus the present invention may be used to generate engineered cells which can treat pathologies driven by a missing secreted protein, whether this be an enzyme, hormone, growth factor, cytokine or clotting factor.

In addition, the introduction of a therapeutic antibody may be beneficial in situations where cellular signalling is disrupted. Engineered cells can be used to secrete a therapeutic antibody at appropriate locations in a patient and the tendency of the Helitron system for multiple copy integration affords higher levels of expression than previously reported systems.

Suitable cells for use in methods in accordance with the invention depend on the type of cell which it is advantageous to target (i.e. the target cell) which may in turn depend on the disease to be treated. Suitable human target cells include liver cells, pancreatic cells, skeletal muscle cells, fibroblasts, retinal cells, synovial joint cells, cells involved in hearing processes, lung cells, T cells, B cells, macrophages, NK cells, neurons, glial cells, stem cells, endothelial cells and cancer cells. Thus, reference to isolating a cell line suitable for using in a subject may refer to choosing a suitable cell line available from external sources or generating a cell line from the subject in need of treatment.

In one embodiment, the methods of the invention may be applicable to generating therapeutic cells such as CAR T cells.

Suitable stem cells include mammalian such as human stem cells, including hematopoietic, neural, embryonic, induced pluripotent stem cells (iPS), mesenchymal, mesodermal, liver, pancreatic, muscle, retinal etc. stem cells. Also included are suitable mammalian stem cells such as mouse stem cells, including mouse embryonic stem cells.

The invention also provides a system enabling introduction of a gene of interest to a subject such as a human patient and therefore provides methods for treating disease and pharmaceutical compositions. Advantageously, a Helitron system can replace viruses, being cheaper to manufacture, less immunogenic and less prone to epigenetic silencing Other Uses A transposon system or method comprising a copy and paste transposon as described herein may also be used as a tool for mutagenesis techniques.

Aspects and embodiments of the invention are also set out in the following clauses:

1. A system for generating multiple copies of a DNA sequence in an isolated or cultured cell comprising a copy/paste transposase and a donor DNA recognized by the transposase.
2. A system as claimed in clause1 wherein the transposase is encoded by a Helitron transposon.
3. A system as claimed in clause1 or clause2 wherein the transposase is a Helitron transposase with at least 80% sequence identity with Seq ID NO: 1.
4. A system as claimed in any preceding clause wherein the donor DNA is flanked by an LTS nucleic acid sequence as set out in SEQ ID NO: 3 and a RTS nucleic acid sequence as set out in SEQ ID NO: 4.
5. A system as claimed in any preceding clause wherein the transposase is Helraiser transposase having an amino acid sequence as set out in SEQ ID NO: 1.
6. A method for introducing multiple copies of a DNA sequence into a genome whereby a Helitron transposase and donor DNA are introduced into a cell.
7. A method as claimed in clause 6 wherein the transposase and donor DNA are supplied separately.
8. A method as claimed in clause 6 wherein the transposase and donor DNA are supplied on the same DNA construct.
9. A method as claimed in clause 6 wherein the transposase is introduced in RNA or protein form.
10. A method for introducing multiple copies of a DNA sequence into a genome whereby a donor DNA is first introduced into the genome of a cell followed by introduction of a Helitron transposase.
11. A method for introducing multiple copies of a DNA sequence into a genome whereby the RTS and LTS sequences flank an endogenous gene.
12. A method as claimed in clause 11 whereby the RTS sequence is introduced using a genome targeting method.
13. A method as claimed in clause 11 wherein the method uses CRISPR, ZFN, TALEN, or rAAV technology to introduce the RTS.
14. A method as claimed in clause 11 whereby the LTS sequence is introduced using a genome targeting method
15. A method as claimed in clause 14 wherein the method uses CRISPR, ZFN, TALEN, or rAAV technology to introduce the LTS.
16. A method for introducing multiple copies of a preferred DNA into a genome whereby the preferred DNA is inserted randomly into the genome flanked by an RTS and LTS and a Helitron transposase is subsequently introduced.
17. A method as claimed in any of clauses 6 to 16 whereby the genome consists of a mammalian genome.
18. A method as claimed in clause 17 whereby the genome is a CHO genome.
19. A method as claimed in any of clauses 6 to 16 wherein the genome is a haploid genome.
20. A mammalian cell containing multiple copies of a preferred DNA introduced by the system of any of clauses 1 to 5 or the method of any of clauses 6 to 19.
21. A mammalian cell of Clause 20 used as a DNA or RNA molecular reference standard.
22. A mammalian cell of Clause 20 used as an IHC reference standard.
23. A mammalian cell of Clause 20 used for the production of a protein encoded by the preferred DNA.
24. A nucleic acid isolated from the cell of Clause 20.

Various further aspects and embodiments of the present invention will be apparent to those skilled in the art in view of the present disclosure.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above and tables described below.

EXAMPLES

Example 1—Helraiser Characterisation

Methods

Constructs and PCRs

Detailed cloning procedures of transposon and transposase expression vectors as well as primer sequences for PCRs are provided as follows:

Transposase vectors. The coding region of the Helraiser transposase was synthesized by GenScript following human codon optimization, and cloned by SpeI/XhoI into the expression vector FV4a (Liu Z J, Moav B, Faras A J, Guise K S, Kapuscinski A R, Hackett P B. Development of expression vectors for transgenic fish. Bio/technology 8, 1268-1272 (1990)) to yield the transposase helper plasmid pFHelR.)) to yield the transposase helper plasmid pFHelR. An N-terminal 2XHA-tag was inserted as a synthetic double-stranded oligonucleotide encoding MYPYDVPDYAYPYDVPDYA (SEQ ID NO: 7) into the SpeI site of pFHelR to yield pF-HA-HelR. The CMV promoter-driven transposase expression plasmid pCHelR was generated by inserting the SpeI/XhoI fragment of pFHelR into the NheI/XhoI sites of pcDNA3.1(−) (Invitrogen). To create the pCHelRGFP plasmid, the XhoI/NotI fragment of pMSCV20Ires-GFP (from B. Schroeder, MDC) was inserted into the XhoI/NotI sites of pCHelR. Transposase catalytic mutant expression plasmids were generated by mutagenic PCR using pCHelR as a template. The transposase vector used for Helraiser protein expression in insect cells was generated by subcloning the Helraiser transposase coding sequence synthesized by GENEART (Invitrogen) into pFastBac HT-A (Invitrogen) using NcoI and XhoI restriction sites.

Transposon Vectors.

An SV40-puro or SV40-neo selection cassette was cloned between the consensus LTS and RTS sequences of Helibat1 (pHelR), HelibatN1, HelibatN2 and HelibatN3 that were synthesized by GeneScript (FIG. 8). Transposon donor vectors pHelRΔHP, pHelRMut, pHelRATH, pHelRStemX and pHelRLoopX were generated by deletion or replacement of the palindromic sequence in the transposon 3'-end. pHelRMut and pHelRΔHP vectors were created by deletion PCR using primer pairs: Hel-Mut fwd/Hel-Mut rev, and HelRDelH fwd and HelRDelH rev, respectively. To generate pHelRATH and pHelRLoopX donor plasmids four oligonucleotides ATH1, ATH2, ATH3, ATH4 and LX1, LX2, LX3, LX4, respectively, were annealed in equimolar ratios (0.8 µM each oligo, 0.2 mM dNTP mix and 1 µl PfuUltra II Fusion HotStart DNA Polymerase (Agilent technologies)/50 µl reaction). The temperature profile for the oligo annealing reaction was 10 cycles at 95° C. for 20 s, 72° C. for 10 s. 1 µl of the annealing reaction was used for the PCR amplification of the ATH or LX fragments using the ATH5/ATH6 and LX5/LX6 primer pairs, respectively. In the final step, ATH and LX PCR fragments were digested by SpeI and BamHI and cloned into the SpeI/BamHI sites of pHelR. To generate the pHelRStemX transposon donor plasmid, pHelRATH was used as a template in mutagenesis PCR together with the primers SX fwd and SX rev. After the PCR reaction the ends of the linear fragment were ligated together, thereby generating pHelRStemX. To create pHelRΔRTS, pHelR was digested with SpeI/BamHI restriction enzymes. The restriction sites were blunted with Klenow (Fermentas) and re-ligated. The pHelRΔLTS donor plasmid was generated through NdeI and EcoRI digestion of the Hel1C backbone followed by Klenow treatment of the restriction sites and vector backbone re-ligation. The pHelRPN and pHelRΔHPN donor plasmids were generated by inserting the SpeI fragment from the pUC19SBneo (Grabundzija I, et al. Comparative analysis of transposable element vector systems in human cells. *Mol Ther* 18, 1200-1209 (2010)) vector into the SpeI site of the pHelR and pHelRΔHP vectors, respectively *Mol Ther* 18, 1200-1209 (2010)) vector into the SpeI site of the pHelR and pHelRΔHP vectors, respectively. To generate the Helitron circle donor plasmid pHelRCD, first pIRES-EGFP-N1 vector was constructed by cloning the NotI/BamHI fragment of pWAS-EGFP into the NotI/BamHI sites of the pGFP-N1 plasmid (Clontech). The EcoRI/BamHI fragment of the pIRES-EGFP-N1 plasmid was then cloned into the EcoRI/BamHI sites of the pHelR plasmid, thereby creating pHelRCD. The pHelRCneo vector was created by inserting the BamHI/EcoRI fragment from pHC plasmid (generated through Helraiser transposition from the pHelRCD donor plasmid in HeLa cells) into the BamHI/MfeI sites of pcDNA3.1(−). In the next step, the neo coding sequence in pHelRCneo was exchanged with the puro coding sequence from the pHel1C plasmid using the AvrII/BamHI restriction sites, thereby generating the pHelRCpuro vector. The Helitron circle vector with the deletion of the palindromic sequence in the transposon 3'-terminus, pHelRCΔHPpuro, was generated via site directed mutagenesis PCR using pHelRCpuro as a template and Hel-Mut fwd/Hel-Mut rev primer pair. The integrity of all coding regions and transposon constructs generated by PCR was verified by DNA sequencing.

Cells and Transfection $2 \times 10^5$ HeLa cells were seeded onto 6-well plates one day prior to transfection. Two of jetPRIME transfection reagent (Polyplus Transfection) and 200 µl of jetPRIME buffer were used to transfect 1 µg of DNA (each transfection reaction contained 500 ng transposon donor and 500 ng transposase helper or pBluescript vector (Stratagene)). Forty-eight hours after transfection, a fraction of the transfected cells (10 or 20%) was replated on 100 mm dishes and selected for transposon integration (2 µg/ml puro or 2 µg/ml puro and 1.4 mg/ml G418). After 2-3 weeks of selection, colonies were either picked or fixed in 4% paraformaldehyde (PFA) in phosphate-buffered saline (PBS) and stained with methylene blue in PBS for colony counting and analysis.

Insertion Site- and Copy Number Analysis by Splinkerette PCR

Transposon copy numbers were determined by splinkerette PCR as follows: HeLa cell clones were grown until confluency on 6-well plates, washed with PBS and incubated overnight at 55° C. with shaking in lysis buffer (100 mM Tris pH 8.0, 5 mM EDTA, 0.2% SDS, 200 mM NaCl and 100 µg/µl proteinase K). HeLa genomic DNA (gDNA) was isolated from lysed cells with standard phenol/chloroform extraction. Five µg of gDNA was digested with FspBI for four hours followed by ethanol precipitation. In the next step, samples were ligated (300 ng) to BfaI splinkerette adapters (100 pmol) in 20 µl reactions. Three microliters of the ligation reaction were used for the first PCR with primers Linker primer and Hel1. The temperature profile for the first PCR round was: one cycle of 94° C. for 3 min, followed by 15 cycles of 94° C. for 30 s, 70° C. for 30 s and 72° C. for 30 s; 5 cycles of 94° C. for 30 s, 63° C. for 30 s and 72° C. for 2 s with an increase of 2 s per cycle; 5 cycles of 94° C. for 30 s, 62° C. for 30 s and 72° C. for 12 s with an increase of 2 s per cycle; 5 cycles of 94° C. for 30 s, 61° C. for 30 s and 72° C. for 22 s with an increase of 2 s per cycle and 5 cycles of 94° C. for 30 s, 60° C. for 30 s and 72° C. for 30 s. Nested PCR was performed with primers Nested and -Hel2, and 1 µl of a 1:100 dilution of the first PCR was used per 50 µl reaction. The temperature profile for the nested PCR started with a cycle of 3 min at 94° C. followed by 10 cycles of 94° C. for 30 s, 65° C. for 30 s and 72° C. for 30 s and 20 cycles of 94° C. for 30 s, 55° C. for 30 s and 72° C. for 2 min. The final elongation was performed for 5 min at 72° C.

In order to analyze transposon-genome junction sites at the 3'-terminus of the Helraiser insertions generated with the pHelR, pHelRΔHP and pHelRΔRTS transposons, first left-end splinkerette PCR was performed with the gDNA isolated from HeLa clones to determine genomic locations of the transposon insertions. In the next step, specific primers complementary to the genomic sequence located between 50 and 100 bp downstream from each transposon insertion were designed (WT6a, WT6b, WT6c, WT6d, DelH2, DelH14, DelH19, DelRTS2, DelRTS15a), and used in genomic PCR together with the HelCD1 primer complementary to the sequence at the 5'-terminus of the Helraiser transposon. The temperature profile for PCR was: 95° C. 2 min, followed by 40 cycles of 95° C. 20 s, 57° C. 20 s, 72° C. 90 s. The final elongation step was performed at 72° C. 5 min. PCR products obtained in the genomic PCR were sequenced and analyzed.

Circle Detection Assay

Low molecular weight DNA was isolated from transfected HeLa cells and used in a modified inverse PCR protocol to detect Helitron circles.

Helraiser circle formation in HeLa cells was confirmed by circle detection PCR. First, $2\times10^5$ HeLa cells were seeded onto six well plates one day prior to transfection. 48 hours post-transfection, plasmids were isolated from the cells using a modified Qiagen QIAprep Spin Miniprep protocol using 300 μl 1.2% SDS supplemented with 50 μg of Proteinase K in the cell lysis step instead of the P2 buffer. The rest of the plasmid isolation procedure was performed according to the manufacturer's protocol. 150 ng of isolated plasmid was used for PCR with the primers Hel1 and Hel5. The temperature profile for PCR was: 98° C. for 2 min, followed by 34 cycles of 98° C. for 10 s, 59° C. for 15 s, 72° C. for 10 s. The final elongation was performed at 72° C. for 5 min.

Helraiser Re-Transposition in HeLa Cells

Cells expressing the Helraiser transposase were enriched by repeatedly transfecting the HeLa-derived transposon donor H1 cell line containing four mapped Helraiser insertions with the pCHelRGFP helper plasmid and sorting GFP+ cells. We then subjected the pooled DNA of the enriched cell population to high-throughput sequencing of transposon insertion sites.

For re-transposition assays, H1 cells were grown on a 100-mm plate (2 μg/ml puromycin) until confluency. One day prior to transfection, $2\times10^6$ cells were seeded onto a new 100-mm plate. Twenty μl of jetPRIME transfection reagent and 500 μl of jetPRIME buffer were used to transfect 3.5 μg of pCHelRGFP plasmid to the cells. Forty-eight hours after transfection, cells were FACS-sorted for GFP expression and $5\times10^5$ GFP-positive cells were plated on a 150-mm plate (2 μg/ml puromycin) and left to grow for one week. The procedure was repeated two more times with seven days between the cycles, each time using those cells for transfection that were FACS-sorted the week before. After the cells were transfected and FACS-sorted for the third time, they were grown on a 150-mm plate (2 μg/ml puromycin) until confluency and pooled for genomic DNA isolation and insertion site analysis.

Genome-Wide Insertion Site Analysis

HeLa cells were transfected as previously described with pCHelR and pHelR. Three weeks post-transfection, puro-resistant colonies were pooled and gDNA isolated. DNA sequences flanking the transposon ends were mapped against the human genome (hg19) with Bowtie (Langmead B, Trapnell C, Pop M, Salzberg S L. Ultrafast and memory-efficient alignment of short DNA sequences to the human genome. *Genome biology* 10, R25 (2009) allowing up to one mismatch. Only uniquely mapped reads matching to the genome without error were kept. Redundant reads mapping to the same genomic location were merged together. We discarded all integrations into genomic locations matching to the last four bases of the transposon end, because these sites could also be mispriming artifacts. Further details are provided belowbelow.

Integration Site and Fusion-Transcript Library Construction

The generation of the insertion site and fusion-transcript libraries was based on a computation-assisted hemi-specific PCR scheme. The PCR assays relied on the use of hemi-specific primers (Ewing A D, Kazazian H H, Jr. High-throughput sequencing reveals extensive variation in human-specific L1 content in individual human genomes. *Genome research* 20, 1262-1270 (2010) *Genome research* 20, 1262-1270 (2010)) carrying only 4 specific nucleotides (4-mers) at their 3'-ends followed by random sequences and a specific overhang. These primers are to anneal to the neighborhood of the transposon-genome or transposon-genomic transcript junctions of the template genomic DNA, or cDNA, respectively, in order to tag these loci for nested PCR amplifications. The 4-mers of the hemi-specific primers were designed computationally. Possible 4-mers were ranked by their representation in the human genome or transcriptome, excluding those which could give rise to unwanted amplicons on the transposon sequences or on primer overhangs. Similarly, an algorithm was implemented to predict the combination of those six 4-mers, which result in the most comprehensive library for the human genome, or transcriptome, and the transposon vectors used. Next, multi-step PCR schemes were performed to obtain indexed, Illumina-flow cell compatible fusion transcriptome, or integrome libraries.

Insertion-Library Preparation and High-Throughput Sequencing of Integration Sites of Helitron Transposons in the Human Genome 300 ng of gDNA isolated from pools of puromycin-resistant HeLa colonies were used as template for the initial 6 parallel PCR reactions, containing 6 different hemi-specific primers, with the following conditions: for the 5' Helitron transposon end: 95° C. 1 min, 40 cycles of (94° C. 30 s, 65° C. 30 s, 72° C. 30 s), 2 cycles of (94° C. 30 s, 25° C. 1 min, ramp to 72° C. at 0.2° C./s, 72° C. 1 min) with 5 pmol of Hel_Lft_1 specific for the 5'-Helitron sequence or 5 pmol of Hel_3P_1 for the 3'-transposon end with the same program but with 62° C. annealing temperature. The first PCR reactions were supplemented with 25 μls of PCR master mix containing 15 pmol of Hel_Lft_2 for the 5'- and Hel_3P_2 for the 3'-transposon end, respectively. The PCR program for the 5'-end was: 15 super-cycles of [3 cycles of (94° C. 30 s, 65° C. 30 s, 72° C. 40 s) 1 cycle of (94° C. 30 s, 60° C. 30 s, 72° C. 40 s)]. For the 3'-end 62° C. annealing temperature was used for the 3 cycles. The PCR products were column-purified and 2 μls of the 30 μl elutes were used for the exponential PCRs, with the primer PE_first and Hel_L_bc for the 5'- and Hel_3P_bc for the 3'-transposon ends, respectively, using the following cycling conditions: 95° C. 30 s, 20 cycles of 94° C. 30 s, 65° C. 30 s, 72° C. 1 min. For the 3'-transposon end the annealing temperature was 58° C. 1 μl 10× diluted $1^{st}$ exponential PCR products were used to add Illumina adaptors to the amplicons using Pfx polymerase (Life Technologies) with these cycling conditions: 95° C. 30 s, 20 cycles of 94° C. 15 s, 68° C. 1 min. The final PCR products were run on agarose gels and amplicons between 200 and 500 bp were excised and column-purified (Zymoclean Gel DNA Recovery Kit, Zymo Research). The sequencing of the resulting libraries was carried out on Illumina HiSeq 2500 instruments at the Beckman Coulter Genomics Danvers Mass. USA sequencing facility.

The raw reads were processed for mapping as follows. Primer-, transposon-, and right Illumina adapter-related sequences were trimmed. The resulting reads were quality filtered by omitting reads containing 'N' bases and by trimming reads as soon as 2 of 5 bases has quality encoding less than phred score 20. All trimmed reads shorter than 24 bases were dropped. The remaining sequences were mapped against the h19 human genome assembly with Bowtie (Langmead et al. (2009)). (2009)).

Protein Expression and Purification

Point mutations were made using the QuikChange site-directed mutagenesis method (Agilent). Baculovirus production and protein expression were performed by the Protein Expression Laboratory at the National Cancer Institute as follows:

Cell pellets were resuspended in Nickel affinity column binding buffer (20 mM $NaH_2PO_4$ pH 7.4, 500 mM NaCl, 50 mM imidazole, 1 mM TCEP). All subsequent steps were performed at 4° C. Lysis was done by incubating the cells on ice for 30 minutes, then sonication with a Misonix Sonicator 3000 (5×20-sec pulses with 3 minute pause at 82 Watts). The soluble fraction was isolated by centrifugation at 20,000×g, loaded onto a HiTrap CHeLating column (GE Healthcare) equilibrated in Nickel affinity column binding buffer, and eluted using a linear gradient with elution buffer (20 mM $NaH_2PO_4$ pH 7.4, 500 mM NaCl, 250 mM imidazole, 1 mM TCEP). The eluted protein was dialyzed overnight in 20 mM $NaH_2PO_4$ pH 7.0, 250 mM NaCl, 1 mM DTT and 1 mg/ml TEV protease added at 1:100 protease to protein volume ratio. The product was loaded onto a HiTrap Heparin HP column (GE Healthcare) pre-equilibrated with Heparin column binding buffer (20 mM $NaH_2PO_4$ pH 7.0, 250 mM NaCl, 1 mM TCEP), and eluted using a linear gradient with elution buffer (20 mM $NaH_2PO_4$ pH 7.0, 2 M NaCl, 1 mM TCEP). The Helraiser transposase was loaded on a HiLoad 16/60 Superdex 200 sizing column (GE Healthcare) equilibrated with 50 mM HEPES pH 7.5, 150 mM NaCl, 0.5 mM EDTA, 1 mM TCEP, and fractions containing the purified protein were concentrated to 10 mg/ml. All point mutants were purified in the same manner, and exhibited no changes in either expression or purification behavior (>90% homogeneity) from that of the wild-type transposase. The same procedure was also used to purify truncated versions of the transposase.

Cleavage Assay and Sequencing of Cleavage Products

DNA cleavage was measured using 6-FAM labeled oligonucleotides (BioTeZ Berlin-Buch GMBH). Reactions generally consisted of 500 nM DNA substrate and 500 nM protein in buffer (50 mM Tris pH 7.5, 100 mM NaCl, 0.5 mM ETDA, 1 mM TCEP) with or without 5 mM $MnCl_2$. Further details are provided as follows:

Cleavage was done at 37° C. for 1 hr, and quenched by addition of 2 μl Proteinase K (New England BioLabs) and 2 μl of 0.5 M EDTA. For reactions with 5 mM $MgCl_2$, reaction was done overnight at 37° C. Proteinase K digestion was at 45° C. for 30 min, after which an equal volume of loading dye (80% formamide, 1 mg/ml xylene cyanol, 1 mg/ml bromophenol blue, 10 mM EDTA) was added and reactions incubated at 22° C. for 15 min, and then five min at 95° C. prior to gel loading on 15% Tris/Borate/EDTA/Urea gels (Invitrogen). The results were visualized using a Typhoon Trio (GE Healthcare).

Gels were stained with SYBR Safe DNA gel stain (Invitrogen), visualized by blue light, and each band cut out. ssDNA extraction was done by crushing the gel and shaking overnight at 37° C. in Extraction Buffer (0.5 N NH4Ac, 10 mM MgAc, 1 mM EDTA, 0.1% SDS). To remove any remaining contaminants, the solution was centrifuged at 14,000×g for 2 min at 4° C., and the supernatant further cleaned of salts using an Illustra MicroSpin G-25 Columns (GE Healthcare). ssDNA was ligated using ssDNA ligase kit (New England Biolabs) to the following oligonucleotide: 5'/5rApp/CAAGGATCTTACCGCTGTTGAGATCCAG-TTCGATGTAACCCACTCGTGCAC CCAACT-GATCTTCAGCATCTTTTACTTAAGCTTCCAGCG/3SpC3/-3' (SEQ ID NO:8). Then using PCR and primers designed for the known part of the sequence of the 5' end and reverse primer to the above oligonucleotide, the fragment was amplified. The resulting dsDNA was cloned into pUC19 using EcoRI and HindIII restriction sites, and sequenced at the FDA-FBR facility.

Protease Digest and N-Terminal Sequencing

Helraiser transposase was diluted at 1 mg/ml in 20 ml of digestion buffer (50 mM Hepes pH 7.5, 150 mM NaCl, 5 mM $MgCl_2$, 1 mM TCEP), and a series of trypsin dilutions were added to final concentrations ranging from 0.1-1 mg/ml. Samples were incubated at 37° C. for 1 hr, and reactions quenched with NuPAGE loading dye (Novex) and boiling at 95° C. for 5 min. Samples were then immediately loaded onto a 4-12% NuPAGE bis Tris gel (Novex). Bands were transferred to blot paper using Invitrogen's iBlot kit, and the sequence of each N-terminal sequence was determined by the FDA-FBR facility.

EMSA

Binding of the Helraiser transposase to various DNA oligonucleotides was measured by EMSA using 6% TBE gels (Invitrogen). Purified protein at 15 nM-150 nM was incubated for 30 min at room temperature in binding buffer (50 mM Tris pH 7.5, 100 mM NaCl, 10 mM $MgCl_2$, 0.5 mM ETDA, 1 mM TCEP) with 50 nM 6-FAM labeled oligonucleotides. After addition of DNA gel loading solution (Quality Biological, INC), samples were run on 6% TBE gels and visualized.

Results

Structural Hallmarks of the Resurrected Helraiser Transposon

To build a model of an autonomous Helibat element, the *M. lucifugus* genome was subjected to bioinformatic analysis (see below). below The resulting 5296-bp Helraiser consensus sequence (FIG. 8) contains all of the known hallmarks of an autonomous Helitron as identified by sequence analysis (reviewed in Kapitonov et al. (2007) and Thomas et al. (2015)). The 1496 amino acid (aa) long coding sequence of the Helraiser transposase is flanked by left and right terminal sequences of the transposon, designated LTS and RTS, respectively (FIG. 1A and FIG. 8), that terminate with the conserved 5'-TC/CTAG-3' motifs characteristic of the Helibat1 family (Pritham et al. (2007)). (2007)) A 19-bp-long palindromic sequence with the potential to form a hairpin structure when single-stranded is located 11 nucleotides upstream of the RTS end (FIG. 1A and FIG. 8).

The Helraiser transposase contains a putative, N-terminal nuclear localization signal (NLS) and a zinc finger-like motif, followed by a RepHel enzymatic core (Kapitonov et al. (2001) and Pritham et al. (2007)) RepHel consists of a ~300-aa-long Rep nuclease domain, characterized by the conserved HUH motif and two active site Tyr residues, and a ~600-aa helicase domain containing the eight conserved motifs characteristic of the SF1 superfamily of DNA helicases (FIG. 1A).

Molecular Reconstruction of the Helraiser Transposon

Using a set of ~300-aa protein sequences corresponding to the conserved rolling-circle replication initiator domain (Rep) present in the RepHel proteins encoded by diverse known Helitrons in plants and metazoans, we identified all bat sequences coding for this domain by using them as queries in a Censor (Jurka J, Klonowski P, Dagman V, Pelton P. CENSOR—a program for identification and elimination of repetitive elements from DNA sequences. *Computers & chemistry* 20, 119-121 (1996)) search against the GenBank *Myotis lucifugus* assembly. To check if the identified DNA sequences might have been composed from different families, we performed their clustering by BLASTCLUST (standalone Blast, NCBI). Based on the clustering results, we concluded that the bat genome contained only one major family of autonomous-like Helitrons. All these sequences, even those contaminated by premature stop codons and short indels, have been used to derive a ~900-bp Rep consensus sequence coding for the catalytic domain. At the next step, genomic sequences >90% identical to the 200-bp 5'- and 3'-terminal parts of the Rep consensus have been expanded up to 2 kb upstream and downstream of the termini, respectively. For the two sets of multiple alignments of the expanded sequences two consensus sequences were derived. These two terminal consensuses and the Rep consensus have been assembled together into one long expanded consensus. This procedure has been iteratively repeated till both ends of the bat autonomous-like Helitron have been identified, and the first version of the autonomous bat consensus sequence (Helitron-1_ML) was built.

Next, by using Censor, we collected all copies in the *M. lucifugus* genome >90% identical to the Helitron-1_ML. Based on the pairwise alignment of the collected sequences expanded 1 kb in both directions, we removed all copies that were generated by long segmental duplications (>90% identical to each other) unrelated directly to the multiplication of Helitrons by their transposition. As a result we collected a final set composed of 500 copies of Helitron-1_ML. After multiple alignment of all these sequences and Helitron-1_ML, we derived a second version of the consensus, a 5301-bp Helitron-1a_ML coding for a 1458-aa RepHel protein and ~95% identical to the collected 500 copies.

The consecutive analysis of the Helitron-1a_ML copies revealed that the genome contains only a small number of autonomous-like copies, when the majority of the copies are in fact copies of two non-autonomous Helitron-1N1_ML and Helitron-2N2_ML transposons. The 2437-bp Helitron-1N1_ML and 2144-bp Helitron-1N2_ML consensus sequences encoded the 610-aa N-terminal and 390-aa C-terminal portions of the Helitron-1a_ML RepHel protein, respectively. Presumably, these non-autonomous transposons were transposed by the RepHel transposase expressed by some autonomous Helitrons. Therefore, we concluded that the regions in the non-autonomous transposons coding for remnants of RepHel may contain mutations that can destroy or damage proper functions of the protein reconstructed from copies of the non-autonomous elements. To avoid this problem, copies of the non-autonomous transposons were excluded from the "500-fragments" set. As a result, only 46 sequences, supposedly fragments of the real autonomous Helitron, have remained in the modified set. Based on re-alignment of the Helitron-1a_ML consensus sequence with these 46 sequences, a new 5295-bp Helitron-1b_ML consensus sequence encoding the 1494-aa RepHel protein was derived (~95% identity between the consensus and 46 sequences).

At this point Helitron-1b_ML and Helitron-1a_ML consensus sequences were 98.81% identical and the RepHel proteins encoded by these consensus sequences differed from each other by 13 aa replacements and by a 36-aa C-tail added to the Helitron-1b_ML coding sequence.

Since the sequences in the original "500-fragments" set have not contained short fragment of long autonomous Helitrons generated by insertions of other transposable elements and by internal deletions, for each of the 46 coding sequences the Helitron-1b_ML was derived from, all terminal and additional internal fragments were manually added creating thereby a set of 177 fragments. Based on re-alignment of the Helitron-1b_ML consensus with all these fragments, the final version of the 5296-bp autonomous consensus sequence that we named Helraiser was derived (FIG. 8).

Helraiser Transposition in Human Cells

We synthesized the functional components of the transposon (i.e., the transposase as well as the LTS and RTS sequences), and generated a bi-component transposition system consisting of a puromycin gene (puro)-tagged transposon (designated pHelR) and a transposase-expressing helper plasmid (designated pFHelR, FIG. 1B). As shown in FIG. 1B, transfection of the Helraiser system into human HeLa cells generated, on average, 3400 puro-resistant colonies per plate versus ~100 colonies per plate in the absence of transposase. Thus, the Helraiser transposon system appears to contain all of the determinants required for transposition activity in human cells.

Sequence analysis of ten independent Helraiser insertions recovered by splinkerette-PCR (see Methods "Insertion site- and copy number analysis by splinkerette PCR") revealed that, in all cases, there were direct canonical junctions of the transposon LTS 5'-TC motif to an A nucleotide, and of the RTS CTAG-3' motif to a T nucleotide (FIG. 1C). Thus, Helitron transposition into an AT dinucleotide target site was faithfully recapitulated by Helraiser.

To evaluate the relative transposition efficiency of Helraiser, we directly compared it with a hyperactive variant of Sleeping Beauty (SB100X), one of the most active vertebrate cut-and-paste transposons (Mates L, et al. Molecular evolution of a novel hyperactive Sleeping Beauty transposase enables robust stable gene transfer in vertebrates. *Nature genetics* 41, 753-761 (2009)) Helraiser demonstrated only about two-fold lower colony forming activity than SB100X in human HeLa cells (FIG. 1D), indicating a relatively high transposition activity even without optimization.

In order to test the ability of the Helraiser transposase to cross-mobilize the non-autonomous transposons HelibatN1, HelibatN2 and HelibatN3, their consensus LTS and RTS sequences were synthesized and tagged with neomycin (neo) or puro antibiotic resistance genes, and their transposition activities assayed as described above. HelibatN1 was the most active (~28% of the activity of the wild-type Helraiser transposon); HelibatN3 displayed detectable activity (~2%), whereas HelibatN2 was apparently inactive under these experimental conditions (FIG. 1E). These data indicate that Helraiser represents an ancient Helibat1 transposase that was probably responsible for mobilizing and propagating at least some of the most abundant non-autonomous Helitron subfamilies in the *M. lucifugus* genome.

Functional Analysis of the HUH Nuclease and SF1B Helicase Domains

Figure 2A:
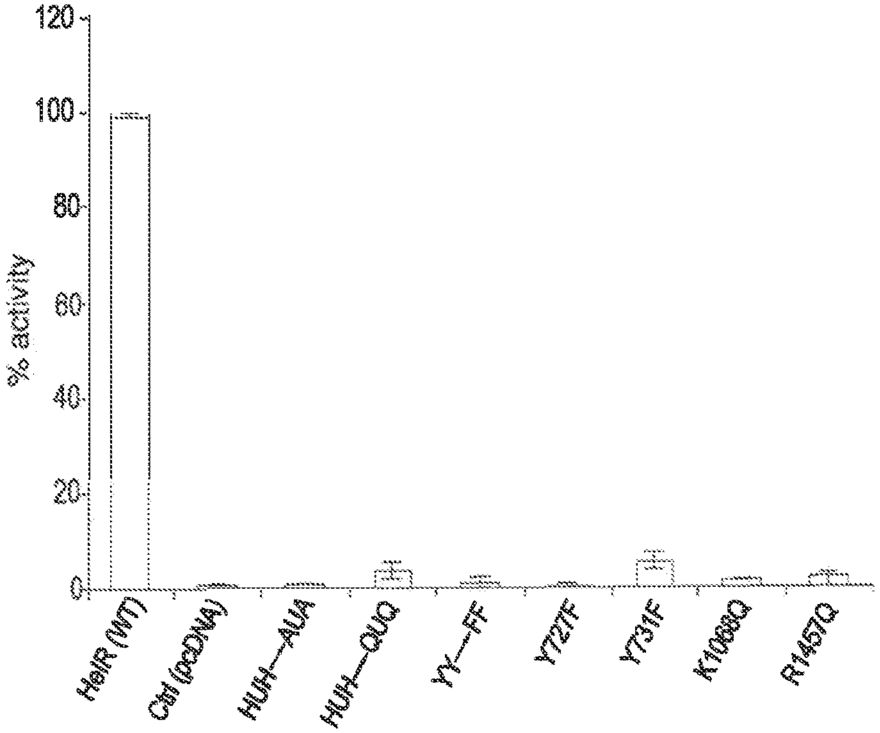
Figure 2B:
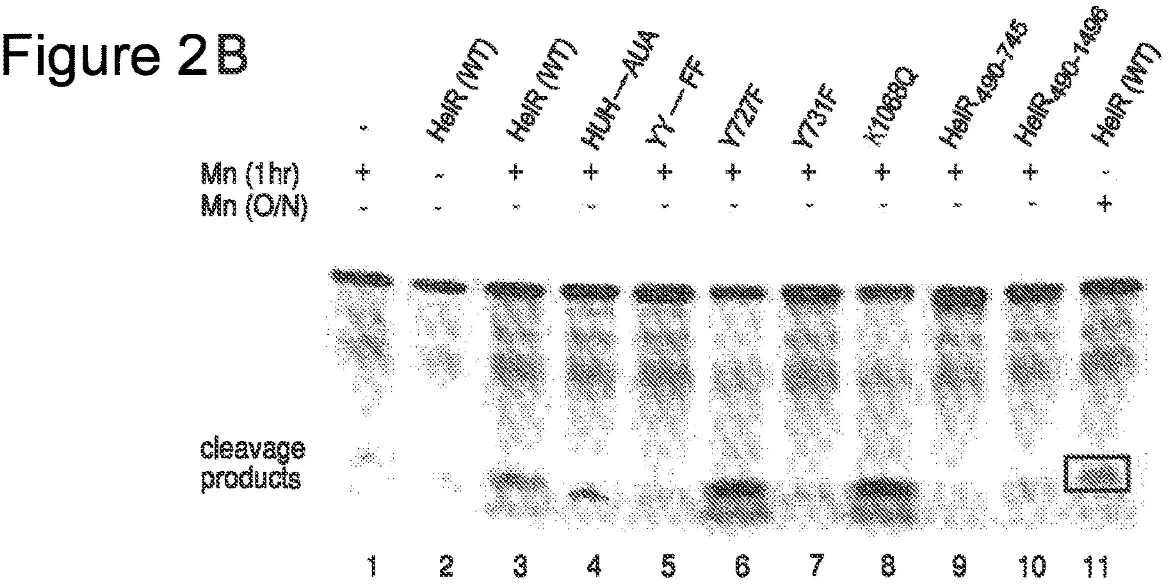

To determine the functional significance of some of the conserved amino acids of the Helraiser transposase, we mutated both H593 and H595 and the putative catalytic Y727 and Y731 residues (both individually and together) in the HUH nuclease domain, as well as K1068 of the Walker A motif and the arginine finger R1457 residue located in motif VI of the helicase domain (FIG. 2A). Each of these mutations resulted in loss of transposition activity in HeLa cells (FIG. 2A), suggesting that both nuclease and helicase activities are required for transposition.

In vitro assays using purified Helraiser transposase demonstrated cleavage of ssDNA (representing 40 bases of the Helraiser LTS and RTS plus 10 bases of flanking DNA) (FIG. 2B), but not dsDNA (data not shown). Sequencing of the most prominent cleavage products (labelled 1-4, FIG. 10) revealed cleavage between flanking DNA and the Helraiser 5'-TC dinucleotide on the top LTS strand (lane 2), between an internal AT dinucleotide on the bottom strand of the LTS (lane 4) and precisely at the transposon end on both strands of the RTS (lanes 6 and 8). These results indicate that the transposon sequence determinants for precise cleavage of the transposon ends are located within the terminal 40 bps on each end.

As expected from an HUH nuclease, cleavage activity required a divalent metal ion (compare lanes 2 and 3, FIG. 2B), and was more efficient with $Mn^{2+}$ than with $Mg^{2+}$ [compare lanes 3 (1 hr at 37° C.) and 11 (overnight at 37° C.)]. We did not detect ssDNA cleavage on the LTS top strand with either the His->Ala mutant of the HUH motif (lane 4) or when both Tyr residues were simultaneously mutated (lane 5). We observed a marked difference when the two Tyr residues were individually mutated: mutation of the first Tyr (Y727F) had no effect on cleavage (lane 6), whereas mutation of the second Tyr (Y731F) led to loss of cleavage activity (lane 7). The K1068Q mutation in the helicase domain had no effect on ssDNA cleavage (lane 8). Collectively, these results show that conserved residues of the HUH domain are important for cleavage of ssDNA, and that the two Tyr residues of the active site have distinct roles in Helitron transposition.

Figure 2C:
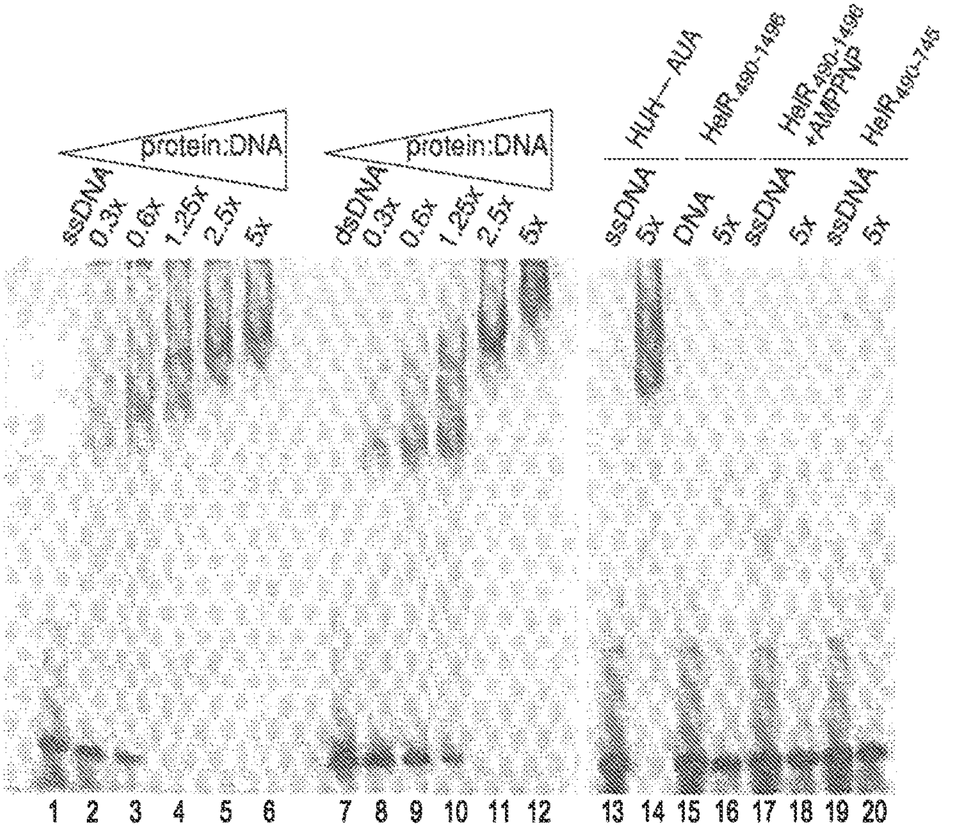

Limited proteolysis on purified Helraiser transposase resulted in three stable fragments corresponding to the N-terminal-, the nuclease- and the helicase domains (FIG. 9). We used these experimentally determined domain boundaries to design truncated transposases lacking the N-terminal domain and encompassing the nuclease ($HelR_{490-745}$) or nuclease-helicase ($HelR_{490-1486}$) domains Neither of the purified truncated transposase fragments could cleave DNA (FIG. 2B, lanes 9 and 10), suggesting that the N-terminal domain might be involved in DNA-binding. Indeed, as shown in FIG. 2C, although both the wild-type Helraiser transposase (lanes 1-12) and the full-length His->Ala mutant (lanes 13-14) can bind the oligonucleotides used in the cleavage assays, the truncated versions lacking the N-terminal 489 amino acids did not bind DNA (lanes 15-20). These data indicate that the N-terminus of the Helraiser transposase, containing a predicted zinc finger-like motif (Pritham et al. (2007)) encodes a DNA binding domain that is crucial for its ability to bind and cleave ssDNA.

Figure 2D:
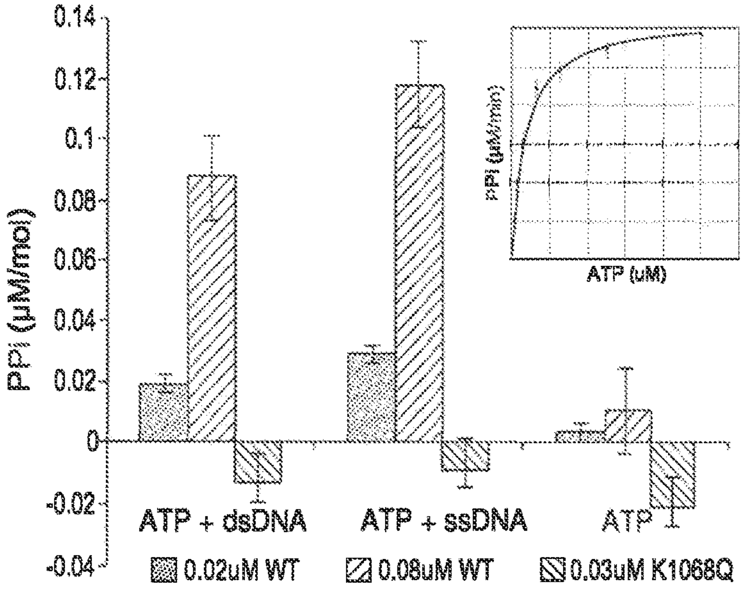

Consistent with helicase activity, the purified transposase hydrolyzes ATP with a $K_m$ of 46+/−3.3 μM and $k_{cat}$ of 6.8+/−0.11 $s^{-1}$ (inset in FIG. 2D). Importantly, the ATP hydrolysis rate is dramatically stimulated by the addition of either dsDNA or ssDNA (FIG. 2D), an effect seen with other SF1 helicases (Bird L E, Subramanya H S, Wigley D B. Helicases: a unifying structural theme? *Curr Opin Struct Biol* 8, 14-18 (1998)).*Curr Opin Struct Biol* 8, 14-18 (1998)) Mutation of the Walker A motif K1068 abolished ATP hydrolysis (FIG. 2D).

Colorimetric ATPase Assay

ATP hydrolysis was analyzed by measuring the formation of free phosphate (Pi) as a function of time using procedures adapted from Baykov et al. (Baykov A A, Evtushenko O A, Avaeva S M. A malachite green procedure for orthophosphate determination and its use in alkaline phosphatase-based enzyme immunoassay. *Anal Biochem* 171, 266-270 (1988)). Helraiser transposase or mutant proteins were diluted to final concentrations between 0.3-1 μM in buffer containing 50 mM HEPES pH 7.5, 100 mM NaCl, 1 mM DTT and 2 mM $MgCl_2$ and then heated to 37° C. for 10 min. Reactions were initiated by the addition of ATP (Jena biosciences) to either a final concentration of 1 mM or a concentration range between 0.0078 and 1 mM in a total volume of 180 μl. Samples (20 μl) were removed at various time points and immediately quenched in wells of a 96-well plate, each containing 5 μl of 0.5 M EDTA. An aliquot (150 μl) of a 1 mM malachite green stock solution was added to each well, and the absorbance at 650 nm was measured using a Molecular Devices Spectramax M5 microplate reader. The amount of phosphate released was calculated by comparison to a standard curve generated using $KH_2PO_4$. DNA stimulation of ATP hydrolysis was measured using the same buffer and protein concentration range (0.3, 0.08, 0.02 □M), and ATP (1 mM), but with the addition of 1 μM of either a 50-base-long ssDNA or 50-bp-long dsDNA prior to the addition of ATP. Calculations of $K_m$ and $k_{cat}$ were done in EXCEL (Microsoft) and KaleidaGraph 4.0.

Figure 3A:
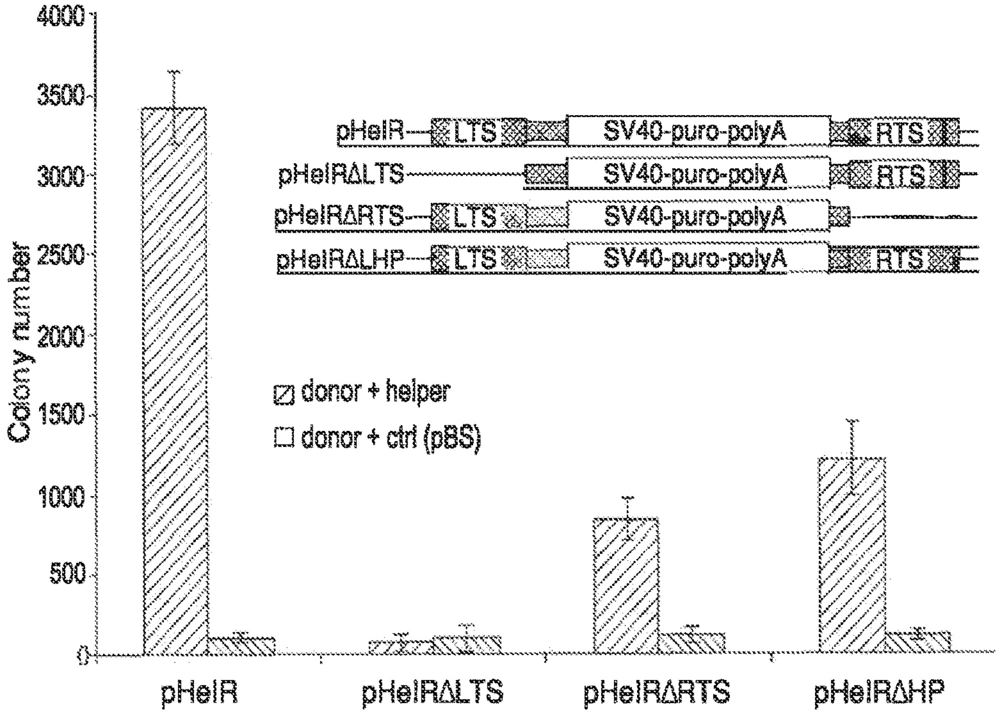

Role of the Terminal Sequences and 3'-Hairpin Structure in Helraiser Transposition To examine the importance of Helraiser's terminal sequences on transposition, we created mutants of the transposon vector, pHelRΔLTS and pHelRΔRTS, by deleting either the LTS or the RTS sequences. The presence of the LTS was essential as its deletion abolished Helraiser transposition (as judged by indistinguishable colony numbers in the presence and absence of transposase in HeLa cells). Surprisingly, the presence of the RTS was not essential, although its removal resulted in a decrease of colony-forming activity to ~24% of the intact transposon (FIG. 3A).

Figure 3B:
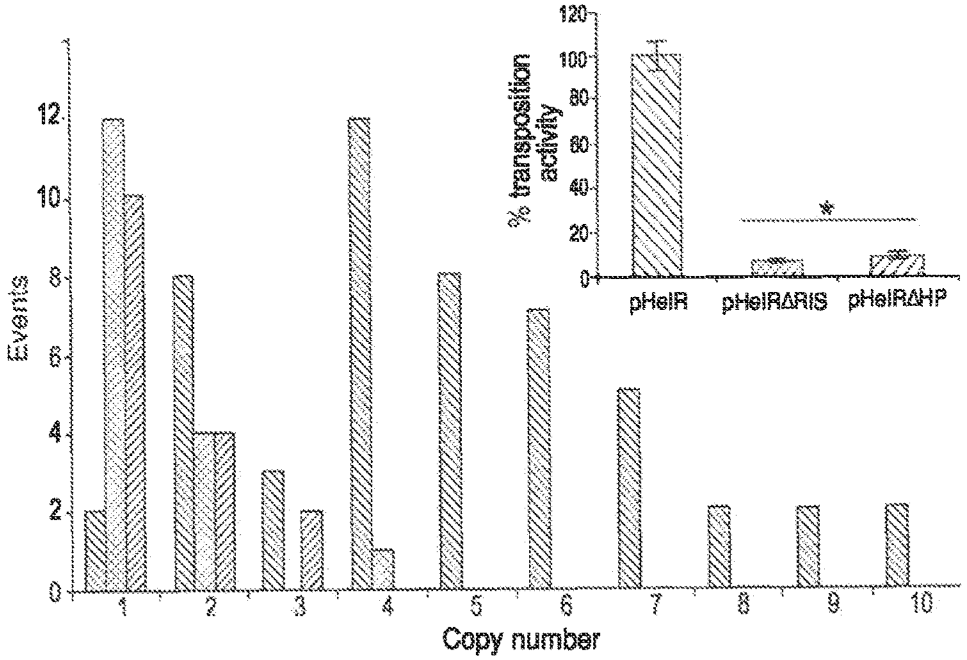

To investigate the role of the RTS further, we created a transposon vector, pHelRΔHP, where the 19-bp palindromic sequence predicted to form a hairpin ("HP") structure was deleted. As shown in FIG. 3A, pHelRΔHP yielded ~35% of the transposon colony-forming activity of the intact transposon. Notably, this is comparable to the number of colonies generated with pHelRΔRTS, in which the entire RTS was deleted. Splinkerette PCR analysis of transposon insertion sites from 51 HeLa clones obtained with the wild-type Helraiser transposon indicated an average copy number of four, with a range between one and ten transposon insertions per clone (inset, FIG. 3B). The same analysis of 16 clones generated with pHelRΔHP, and 15 generated with pHelRΔRTS revealed that both mutant transposons generated, on average, a single insertion per clone (FIG. 3B). Hence, the corrected transposition efficiency of the HelRΔHP and HelRΔRTS transposon mutants are 8.8% and 6% of the transposition efficiency obtained with the wild-type transposon, respectively (inset, FIG. 3B).

Figure 3C:
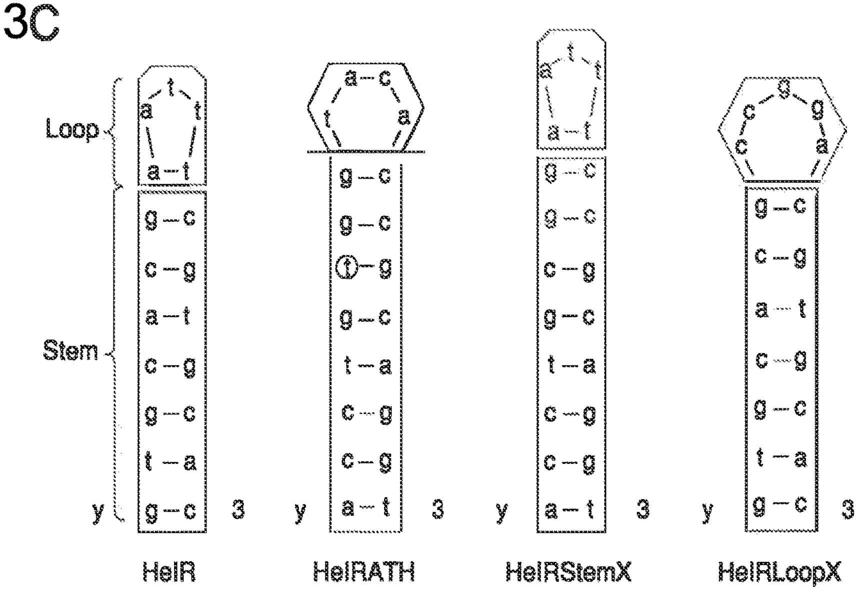

To investigate the role of Helraiser's RTS hairpin in more depth, we generated three modified transposon donor vectors (pHelRATH, pHelRStemX, pHelRLoopX), in which the hairpin sequence was mutated in different ways (FIG. 3C). In pHelRATH, the Helraiser hairpin sequence was replaced with that of the Helitron1 transposon family in *Arabidopsis thaliana* (Kapitonov et al. (2001). pHelRStemX retained the Helraiser hairpin loop, whereas the stem sequence was exchanged with that of the *A. thaliana* hairpin. In pHelR-LoopX, the stem sequence of the Helraiser hairpin was retained but the ATT nucleotides in the loop were replaced with CGG, and the Helraiser A-T bp at the base of the loop was changed to A-A.

Figure 3D:
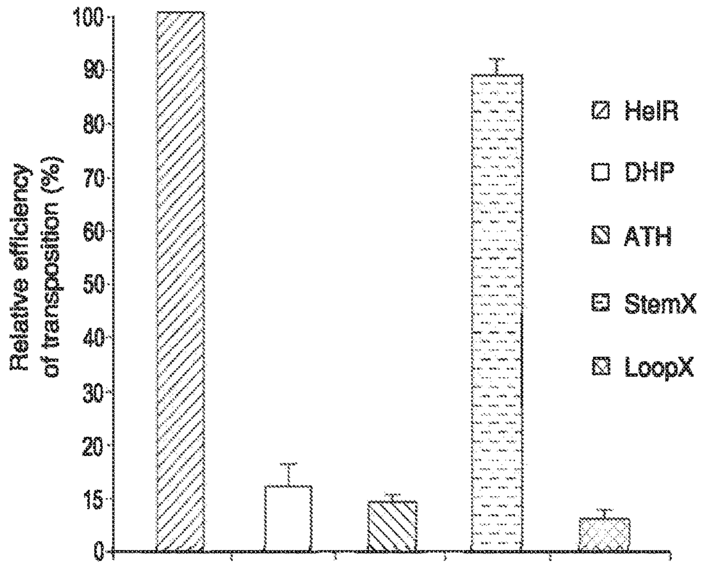

Both pHelRATH and pHelRLoopX showed transposition activities similar to pHelRΔHP where the complete palindrome was deleted (FIG. 3D). In contrast, pHelRStemX demonstrated ~90% of the wild-type transposition activity. These results suggested that, even though the RTS palindrome is not absolutely required for Helraiser transposition, the palindromic sequence is important for transposition regulation.

Helitron Transposition Generates Transposon Circles

Figure 4A:
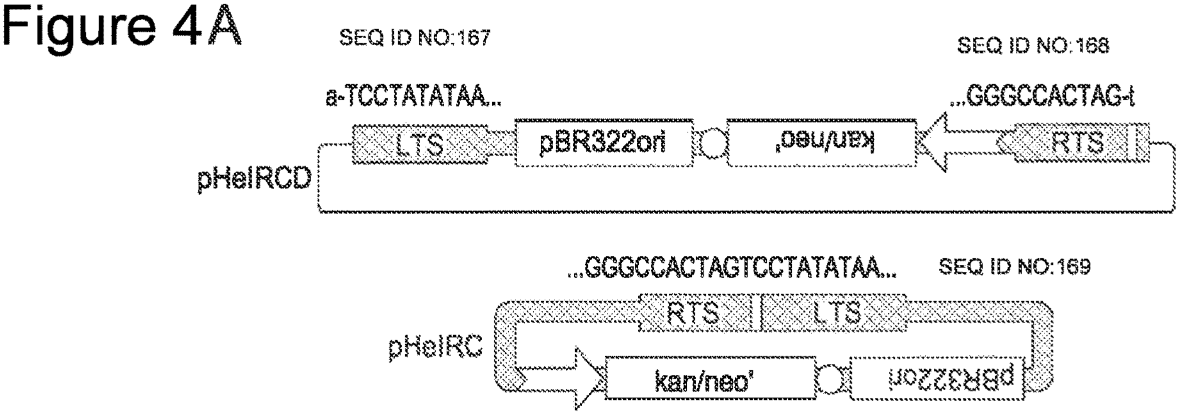

During Helraiser insertion site analysis using inverse PCR, we often observed prominent, ~150-bp PCR products (data not shown). DNA sequencing of these PCR amplicons revealed precise head-to-tail junctions of the Helraiser transposon ends (the 5'-TC dinucleotide of the LTS is directly and precisely joined to the CTAG-3' tetranucleotide of the RTS) (FIG. 4A). These data suggested the formation of circular intermediates in Helraiser transposition.

Figure 4B:
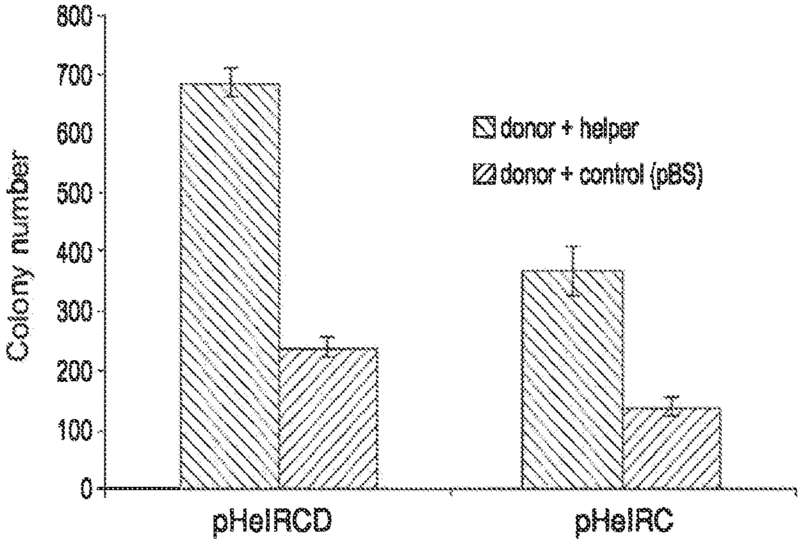

To confirm that transposon circles were generated during transposition, we constructed a plasmid-rescue Helraiser donor vector, pHelRCD ("CD": circle donor), in which the transposon LTS and RTS sequences flanked a plasmid replication origin and a kan/neo selection cassette (FIG. 4A). After co-transfection of HeLa cells with pHelRCD and transposase helper plasmids, low molecular weight DNA was isolated and electroporated into *E. coli* cells that were subjected to kan selection. One of the fifty *E. coli* colonies contained a Helraiser-derived Helitron circle (designated "pHelRC") consisting of the complete transposon sequence and a perfect head-to-tail-junction of the Helraiser LTS and RTS (FIG. 4A). Helitron circles are transpositionally active; transposition of pHelRC generated, on average ~360 colonies per plate, which constitutes ~51% of the colony-forming efficiency of the plasmid-based pHelRCD Helitron circle donor vector (FIG. 4B).

Figure 4C:
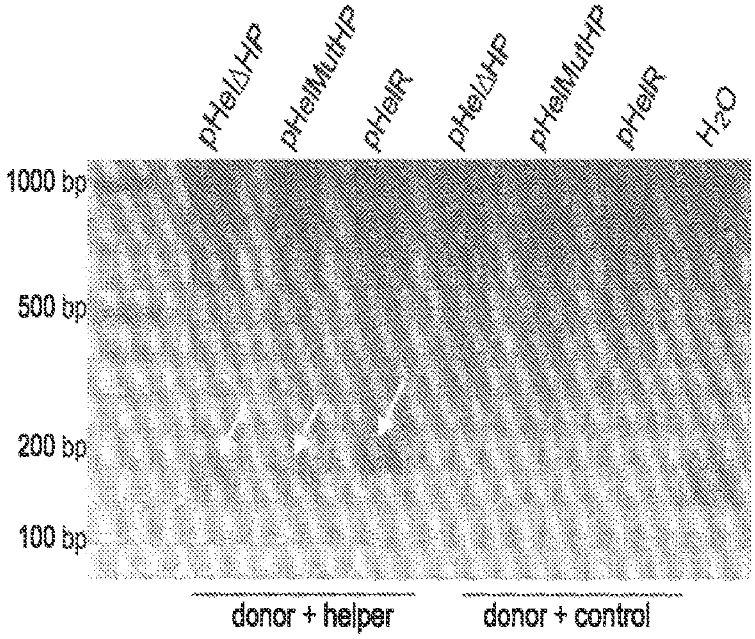
Figure 4D:
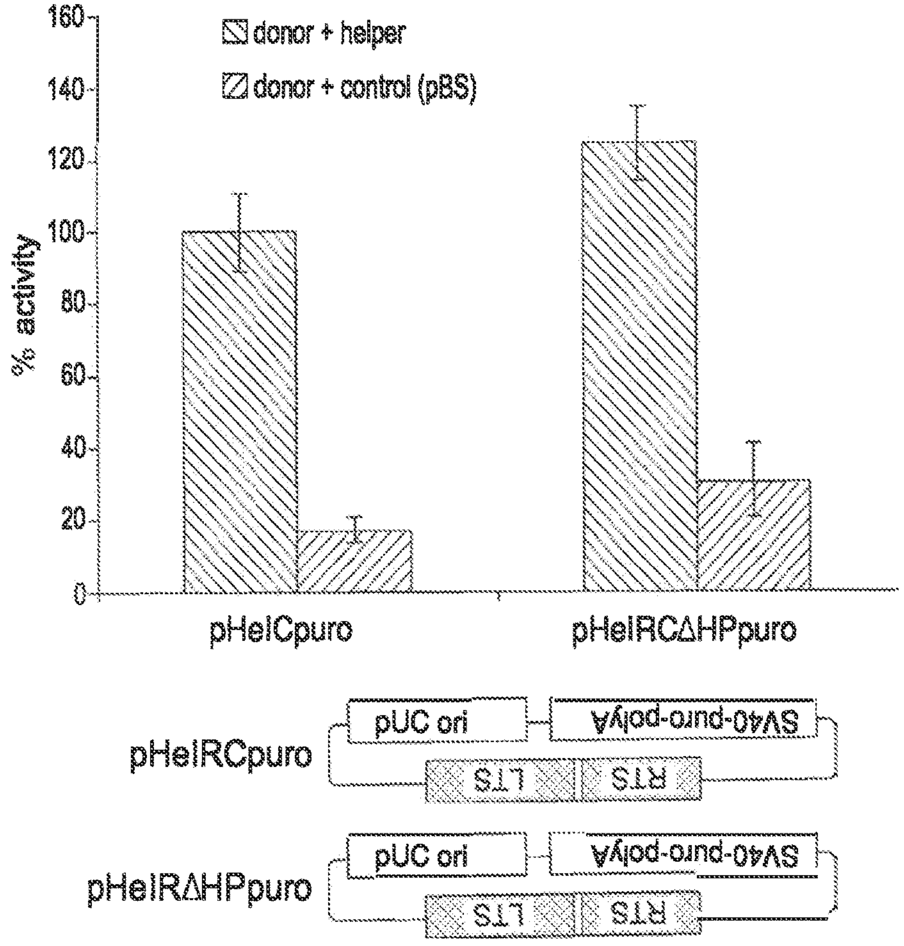

The palindrome in the Helraiser RTS is not required for Helitron circle formation, because the pHelRΔHP and pHelRMutH vectors, where the palindrome has been completely or partially deleted, were proficient in generating circles in the presence of Helraiser transposase (FIG. 4C). Interestingly, deletion of the palindrome did not have the same detrimental effect on transposition of Helitron circles as with plasmid donors, as evidenced by similar colony numbers obtained with pHelRCpuro and pHelRCDΔHPpuro in the presence of transposase (FIG. 4D). This results suggests that in the context of transposon circles with joined ends only one nick in the donor DNA has to be made, and thus there is no need to signal the 3'-end of the transposon. In sum, the results indicate the generation of transposon circles as intermediates of Helraiser transposition.

Genome-Wide Analysis of Helraiser Insertions

Figure 5A:
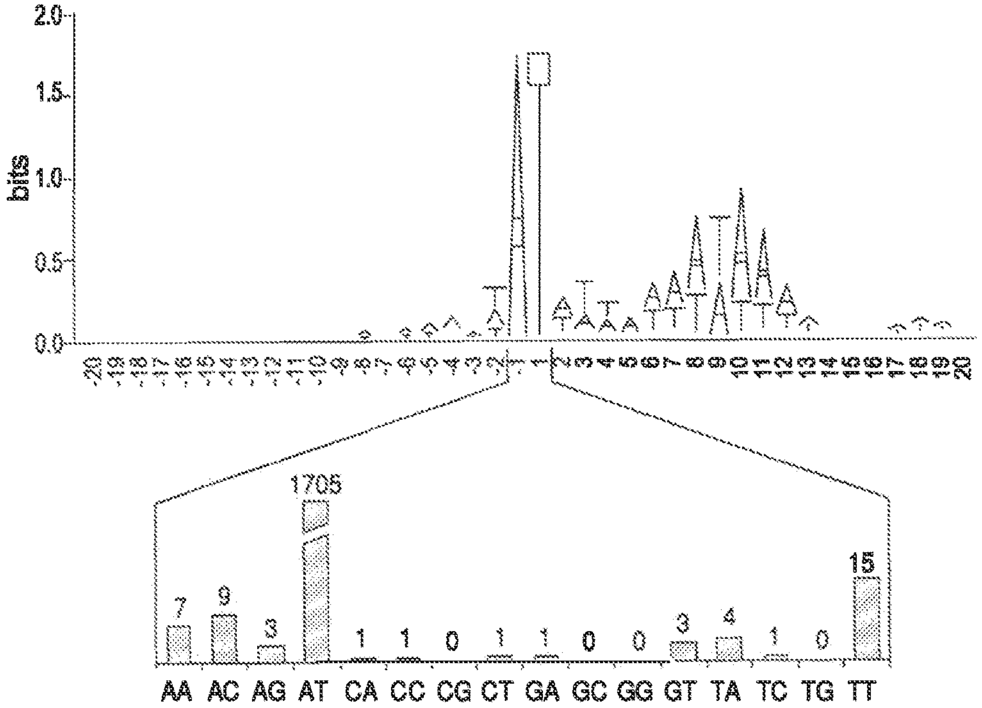

Although patterns of Helitron insertions have been extensively analyzed in the genomes of many eukaryotic species (Pritham et al. (2007); Thomas et al. (2014); Coates et al. (2012); Du et al. (2009); Morgante et al. (2005); Dong Y, et al. Structural characterization of helitrons and their stepwise capturing of gene fragments in the maize genome. *BMC genomics* 12, 609 (2011); Han M J, Shen Y H, Xu M S, Liang H Y, Zhang H H, Zhang Z. Identification and evolution of the silkworm helitrons and their contribution to transcripts. *DNA research: an international journal for rapid publication of reports on genes and genomes* 20, 471-484 (2013); Yang L, Bennetzen J L. Structure-based discovery and description of plant and animal Helitrons. *Proceedings of the National Academy of Sciences of the United States of America* 106, 12832-12837 (2009) and Yang L, Bennetzen J L. Distribution, diversity, evolution, and survival of Helitrons in the maize genome. *Proceedings of the National Academy of Sciences of the United States of America* 106, 19922-19927 (2009)) these patterns are shaped at least in part by natural selection and genetic drift at the level of the host species. By contrast, de novo transposition events recovered in cultured cells are subject to hardly any selection or drift, and thus more directly reflect the transposon's integration preferences. In order to characterize de novo Helraiser transposition events in the human genome, we generated, mapped and bioinformatically annotated 1751 Helraiser insertions recovered in HeLa cells. Sequence logo analysis of the targeted sites confirmed AT target dinucleotides as highly preferred sites for integration (FIG. 5A), as previously observed for endogenous Helitron transposons in bats and other eukaryotic genomes (Kapitonov et al. (2007); Thomas et al. (2015); Kapitonov et al. (2001) and Pritham et al. (2007)) However, targeting of AT dinucleotides for insertions was not absolute: 46 insertions occurred into other sequences, with TT, AC and AA being the most prominent alternative dinucleotides (FIG. 5A). In addition to the central AT dinucleotide, we observe a strong preference for an AT-rich DNA sequence within ~20 bps around the actual integration site; this preference is the most pronounced towards sequences flanking the 3'-end of the integrated transposon (FIG. 5A).

Figure 5B:
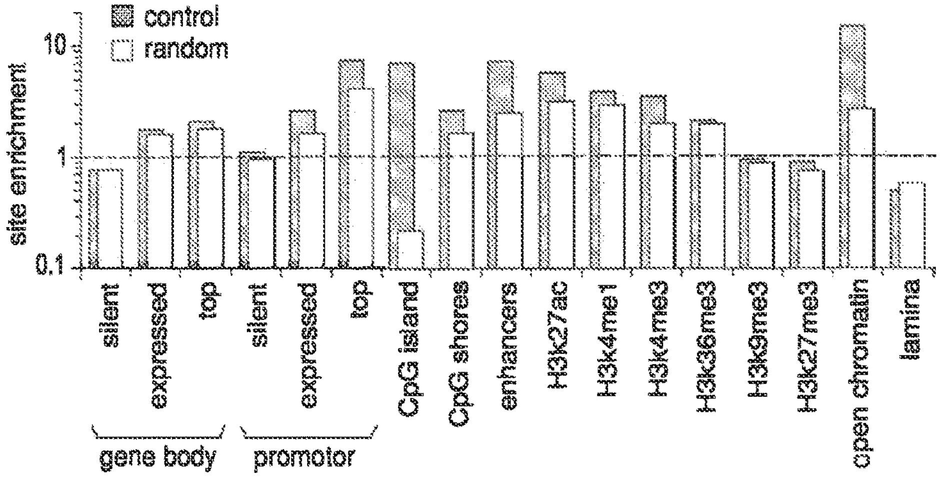
Figure 5C:
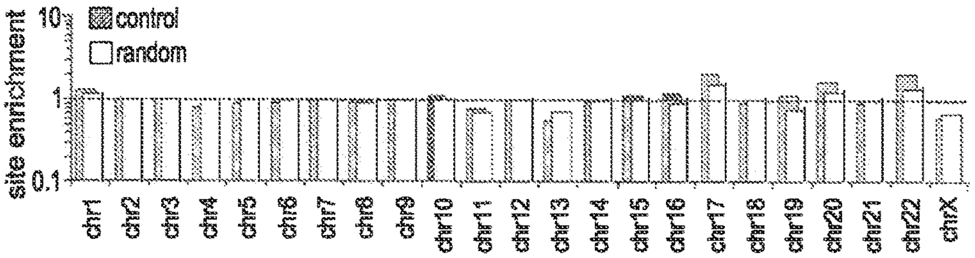

We next analyzed relative frequencies of Helraiser insertions into different genomic features against computer-generated control datasets of genomic sites that were either picked randomly or modeled by taking into account the base composition observed at transposon insertions (see below). below FIG. 5B shows a significant, 2.5-fold and 1.8-fold enrichment of Helraiser integrations compared to control sites into promoter regions (i.e. between 5 kb upstream and 2 kb downstream of transcriptional start sites) and gene bodies (transcription units without their promoter regions), respectively, as defined by the GENCODE catalogue (Harrow J, et al. GENCODE: the reference human genome annotation for The ENCODE Project. *Genome research* 22, 1760-1774 (2012)) For both, transcriptional activity appears to positively correlate with integration events because highly expressed genes in HeLa cells are more frequently targeted by Helraiser insertions, as evidenced by a 7.3-fold enrichment in promoters and a 2.1-fold enrichment in bodies of the 500 most highly expressed genes (FIG. 5B). In addition, Helraiser shows a strong, 6.9-fold enrichment for integration into CpG islands (by using base composition-corrected control sites), CpG shores (2.6-fold enrichment over control sites in 5-kb windows flanking CpG islands), enhancer regions (derived from CAGE peaks (Andersson R, et al. An atlas of active enhancers across human cell types and tissues. *Nature* 507, 455-461 (2014)) 7.1-fold enrichment), chromosomal regions enriched for the histone modifications H3K27ac (enhancer, 5.6-fold), H3K4me1 (enhancer, 3.8-fold), H3K4me3 (active promoter, 3.4-fold), H3K36me3 (transcribed gene body, 2.1-fold) and open chromatin regions as defined by DNaseI footprinting, FAIRE and ChIP-Seq experiments (regions taken from the UCSC Open Chrom Synth track, 14.2-fold). On the other hand, we detected a clear lack of preference for transposition into chromosomal regions characterized by the heterochromatin marks H3K9me3 or H3K27me3 and a significant, 2.2-fold underrepresentation of insertions into lamina-associated domains (Guelen L, et al. Domain organization of human chromosomes revealed by mapping of nuclear lamina interactions. *Nature* 453, 948-951 (2008)) (FIG. 5B). Finally, there was no correlation between transposon insertion site enrichment and gene density (FIG. 5C).

To test whether Helraiser exhibits preference for mobilization into cis-linked loci when transposition is initiated from genomic donor sites (often seen with many 'cut-and-paste' transposons and termed 'local hopping' (Carlson C M, Dupuy A J, Fritz S, Roberg-Perez K J, Fletcher C F, Largaespada D A. Transposon mutagenesis of the mouse germline. Genetics 165, 243-256 (2003); Fischer S E, Wienholds E, Plasterk R H. Regulated transposition of a fish transposon in the mouse germ line. *Proceedings of the*

Figure 5D:
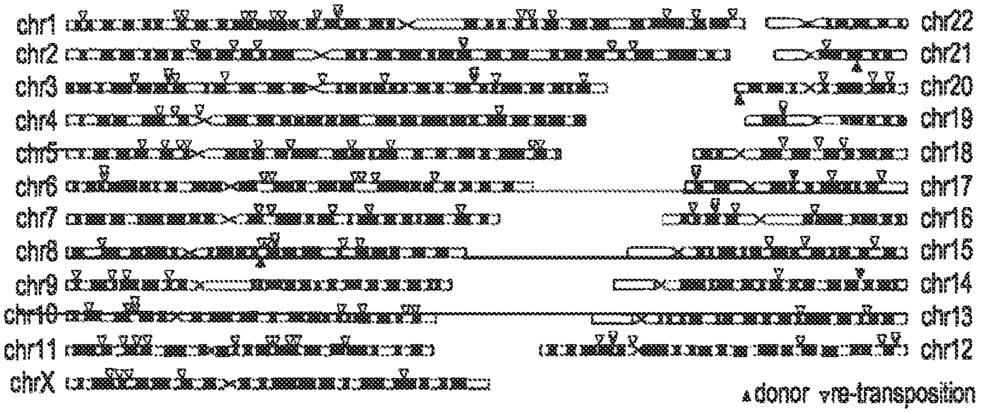

*National Academy of Sciences of the United States of America* 98, 6759-6764 (2001); Luo G, Ivics Z, Izsvak Z, Bradley A. Chromosomal transposition of a Tcl/mariner-like element in mouse embryonic stem cells. *Proceedings of the National Academy of Sciences of the United States of America* 95, 10769-10773 (1998) and Tower J, Karpen G H, Craig N, Spradling A C. Preferential transposition of *Drosophila* P elements to nearby chromosomal sites. *Genetics* 133, 347-359 (1993)) we employed a transposon donor cell line containing four identified chromosomal Helraiser donor sites, and re-transfected these cells with a transposase helper plasmid to drive secondary transposition events to new chromosomal sites. Analysis of the re-transposition insertion sites revealed no clustering of the new transposon insertions around the original donor sites (FIG. 5D).

Helraiser Insertion Site Analysis

We identified 1751 independent integration events. For statistical analysis, we created sets of randomly chosen genomic sites according to two different background models. The model ('random') is normalized relative the abnormal karyotype of HeLa cells. The second model ('control') also accounts for the mappability of sequencing reads and imitates the base composition at integration sites. To determine the karyotype of HeLa cells, we used ChIP-Seq input data sets generated by the Broad/MGH ENCODE group. Since these data sets were generated without the application of specifically binding antibodies, the read densities can be used as estimates for the relative copy numbers of the underlying genomic regions. Mapped sequencing reads of two biological replicates for HeLa cells as well as for 12 other cell types with normal karyotype were downloaded from the UCSC Genome Bioinformatics web site. We computed for each data set pair of HeLa cells and normal cells the fold changes of the read counts in sliding windows each covering 1000 consecutive reads from the normal cell data set. The resulting fold changes were multiplied by the assumed average ploidy of HeLa cells (i.e. 3) and divided by ploidy of the normal cells (i.e. 2 for non-sex chromosomes, and chrX and chrY depending on the gender of the control cell data set), then smoothed with a running median filter of window size 30000, and finally rounded to the closest integer value. The results from all pairs of HeLa cell and normal cell data sets were then joined by computing medians. Tested on data originating from normal cells, the method correctly predicted normal karyotypes (data not shown). For the 'random' background model we sampled 500000 random positions in the genome in a way that the probability for choosing a genomic position is proportional to the ploidy of its chromosomal fragment. The 'control' background model was generated as follows. First we sampled 100 million random genomic positions in a way that the probability for choosing a genomic position is proportional to the ploidy of its chromosomal fragment. From these positions we sampled mock sequencing reads having the same length distribution as the real sequencing reads mapped at transposon integration sites. The mock reads were then processed as the sequencing reads described before. The resulting mock sites were scored using a position specific weight matrix (PWM) derived from base composition at integration sites (FIG. 5A). From the mock sites we sampled 100,000 control sites in a way that their PWM score distribution resembled the PWM score distribution of the real integration sites. The information about gene expression levels, histone modifications and chromatin accessibility, and the genomic locations of CpG islands and lamina associated domains was downloaded from UCSC. Open chromatin regions are derived from DNaseI HS data, FAIRE data and ChIP data, validated regions taken from the UCSC Open Chrom Synth track, release 2 (February 2012).

Gene Capture by Helraiser

Our results presented in FIG. 3A demonstrated that some transposition could take place even if the entire RTS was missing. This raises the question of what sequence determinants define the 3'-end of the mobilized DNA segment.

Figure 6A:
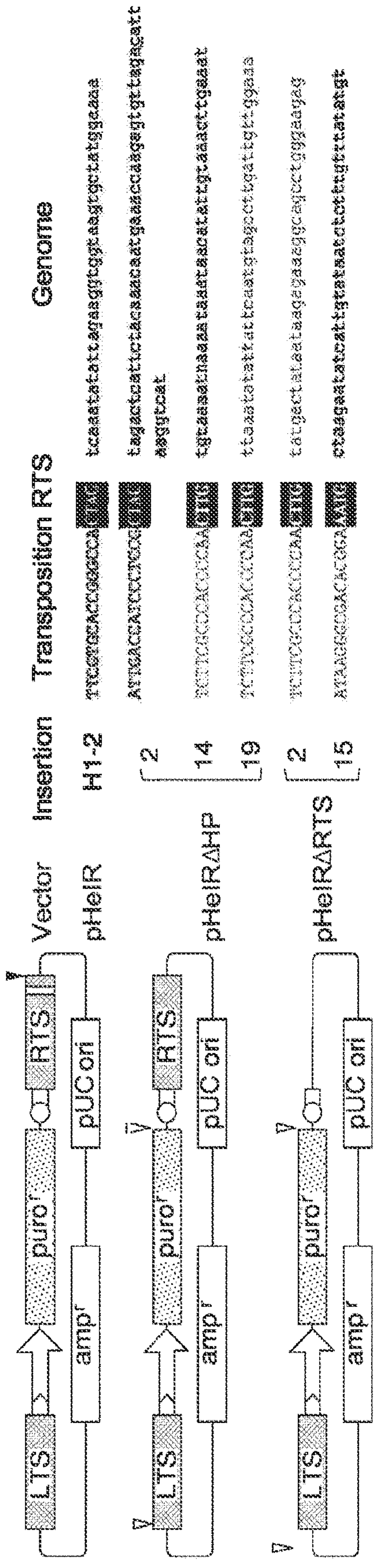

DNA sequencing of insertion sites generated by pHelR, pHelRΔHP and pHelRΔRTS revealed canonical junctions of the LTS 5'-TC sequence to A nucleotides at genomic target sites for all three transposons, indicating that these integrants were indeed Helraiser transposase-mediated products. Sequence analysis of the RTS-genome junction revealed the canonical CTAG-3' sequence flanked by a T nucleotide for pHelR (FIG. 6A; Insertion "H1-T"). In contrast, some insertions generated by the pHelRΔHP and pHelRΔRTS vectors ended with a CTTG-3' tetranucleotide (also seen with maize Helitrons (Dong et al. (2011)) inserted immediately adjacent to a T nucleotide at three different genomic target sites (FIG. 6A; shown in red). These transposon insertions represented truncation of the original transposon sequence, since the novel transposon end was situated internally, six bps downstream from the start of the SV40 poly-A sequence. In addition, two insertions generated by HelRΔHP and HelRΔRTS ended with CTAC-3' and AATG-3', respectively (FIG. 6A; shown in green). These events could be considered 3'-transduction events, in which a unique, external sequence representing an alternative transposon RTS has been utilized for transposition. In both cases, the last two nucleotides in the transposon RTS overlapped with the first two nucleotides at the genomic HeLa target site (also seen with one-ended transposition of the IS91 element (Mendiola et al. ((1994)) making precise identification of the actual RTSs impossible. None of the five sequences representing the novel RTSs contained an identifiable palindrome within the last 30 bps (data not shown), in line with previous observations (Han et al. (2013))

Figure 6B:
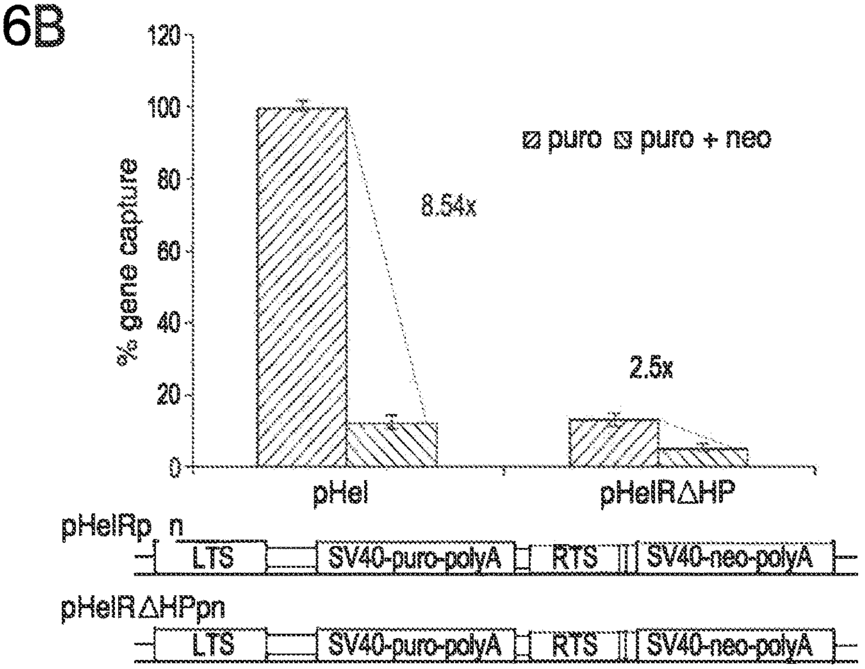

To further investigate the frequency and extent of 3'-transduction events generated during Helraiser transposition, we introduced an SV40-neo-polyA selection cassette immediately downstream of the transposon RTS into the pHelR and pHelRΔHP vectors (renamed "pHelRpn" and "pHelRΔHPpn" for puro and neo, respectively; FIG. 6B). In this way, read-through events that capture the entire neo cassette can be quantified. As shown in FIG. 6B, the intact Helraiser transposon is likely to capture flanking DNA sequence in ~11.7% of the transposition events. In contrast, although the overall frequency of transposition is lower, at least 36% of the transposition events generated with pHelRΔHPpn resulted in the transfer of the entire 1.6 kb neo cassette downstream of the transposon. This experimental set-up probably gave an underestimate of the frequency of 3'-transduction as it required the capture of the entire 1.6 kb neo cassette.

Diversification of Helitron 3'-Ends in *Myotis* Genomes

Figures 11A, 11B, 11C:
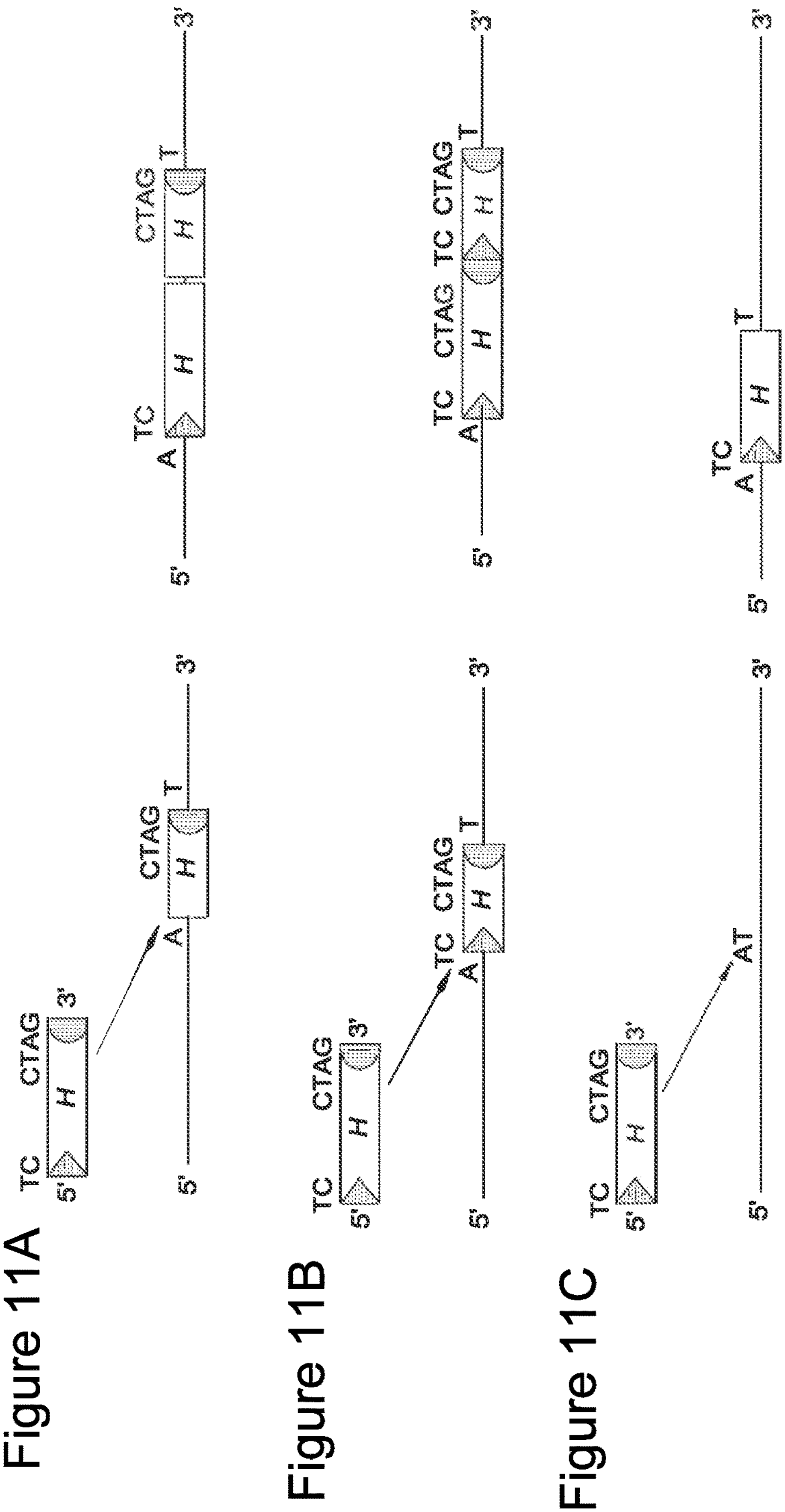

The above experiments demonstrated that premature truncation and read-through events generated through palindrome or RTS deletion leads to the generation of novel 3'-ends. To investigate if such events have also occurred in vivo, we analyzed 395 copies of the recently active HelibatN541, HelibatN542, and HelibatN580 subfamilies (26, 339 and 30 copies, respectively), and found 39 exemplars that have de novo 3'-ends (>20% diverged over the last 30 bps of the consensus) (Table 1). These exemplars were likely generated by 1) insertion adjacent to pre-existing 5'-truncated Helitrons (FIG. 11A), 2) insertion right next to another Helitron where the 5'-end of one Helitron abuts the 3'-end of the other (FIG. 11B), and 3) deletion or mutation within the last 30 bps of the 3'-end (FIG. 11C). Empty site evidence suggests that these are indeed bona fide insertion events (FIG. 11D). Most interestingly, similar to insertion #2 of the pHelRΔHP transposon (FIG. 6A), we identified one exemplar (FIG. 11E), where the de novo 3'-end was generated through bypass of the CTAG-3' sequence in the RTS lacking a palindrome. Thus, bypassing the 3'-end and resulting emergence of de novo transposon ends in Helraiser transposition (FIG. 6A,B) faithfully recapitulates a natural process.

Analysis of 3'-Ends of Recently Active Helitrons in *Myotis* Genomes

To understand the pattern of acquisition of de novo ends by Helitrons in sequenced genomes, we analyzed the copies of three Helibat exemplars (HelibatN541, HelibatN542 and HelibatN580) in the *Myotis* lineage. The copies were recently active (98-99% identical to the consensus), which minimizes the impact of selection on how the sequence signature is interpreted. The HelibatN541 copies are unique to the *M. lucifugus* lineage (Thomas et al. (2014)), the HelibatN580 copies unique to the M.)), the HelibatN580 copies unique to the *M. brandtii* lineage and the HelibatN542 copies are found in both lineages. Copies of Helibat exemplars (HelibatN541 and HelibatN580) that were 98-99% identical to the consensus were extracted from their respective genomes. The HelibatN542 copies that were >95% identical to the consensus and have intact 5'-ends were extracted from the *M. lucifugus* genome. Since the HelibatN542 copies are comparatively older, we used a different cut off. The last 30 bp of each copy were aligned to their respective consensus using MUSCLE (Edgar R C. MUSCLE: multiple sequence alignment with high accuracy and high throughput. *Nucleic Acids Res* 32, 1792-1797 (2004)). *Nucleic Acids Res* 32, 1792-1797 (2004)). The copies that have ends that are >20% diverged from the consensus or that do not align (de novo) were carefully analyzed using homology-based tools (BLAST tools (Altschul S F, Gish W, Miller W, Myers E W, Lipman D J. Basic local alignment search tool. *J Mol Biol* 215, 403-410 (1990)) to gain insights into the origin and evolution of the 3'-end. We also employed a comparative genomics approach using other bat whole genome sequences to exclude false positives. For example, if a copy in one bat genome has a de novo 3'-end and the orthologous copy has an end homologous to the consensus, then those changes were presumed to have occurred post insertion. In addition, empty sites (insertion-free sites) were used to confirm the boundaries of the element.

De Novo Generation of Novel, Chimeric Transcripts by HelibatN3 Transposition

In the *M. lucifugus* genome, promoter sequences from 15 different genes were captured and amplified to 4690 copies by Helitrons (Thomas et al. (2014)) For example, the HelibatN3 subfamily evolved out of a gene capture event, in which a transposing element picked up a fragment of the NUBPL (nucleotide binding protein-like) gene containing the promoter, coding sequence for six amino acids of the NUBPL N-terminus and a splice donor (SD) sequence [FIG. 6C (i)] (Pritham et al. (2007)) Thus, if a HelibatN3 element was to jump into an intron of a gene in the correct orientation, it would have the capacity to ectopically express an N-terminally truncated derivative of that gene by splicing between the SD sequence in the transposon and the nearest downstream splice acceptor (SA) (FIG. 6C).

Figure 6C:
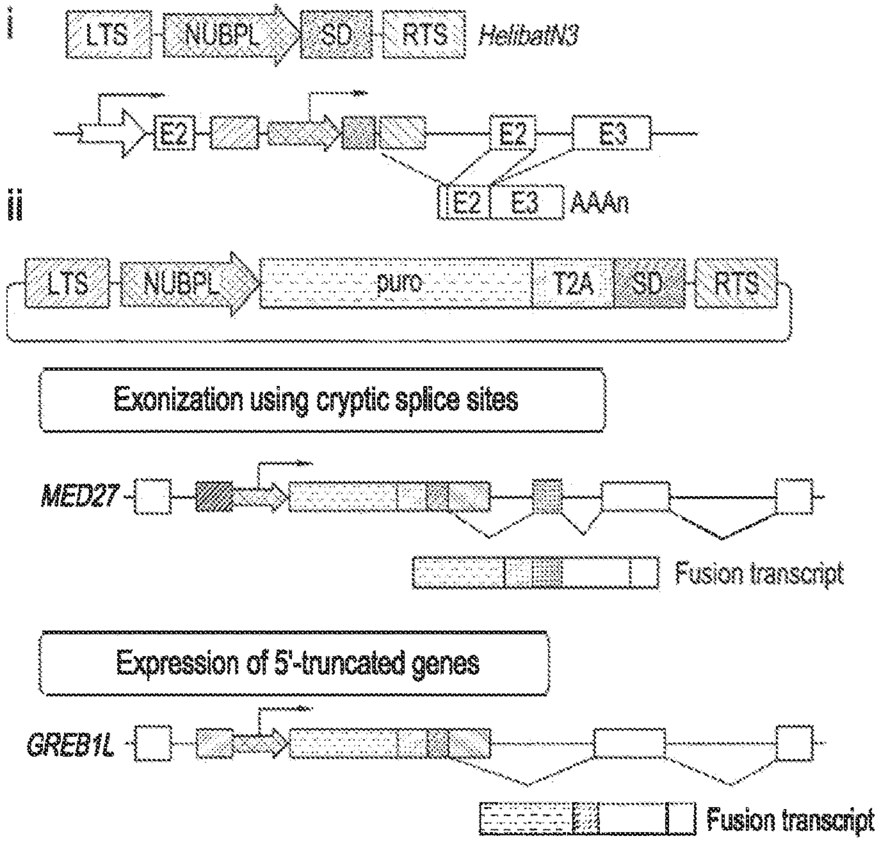

In order to demonstrate transcriptional exon trapping events, we inserted a selectable puro antibiotic resistance gene between the NUBPL promoter and the SD [FIG. 6C(ii)], and mobilized this transposon by the Helraiser transposase into the HeLa cell genome. Sequence analysis of cDNAs prepared from puro-resistant cells revealed splicing between the transposon-contained SD and SA sites present in human transcripts. These data indicated the capture of exonic sequence downstream of the transposon insertion (FIG. 6C). Furthermore, we also recovered chimeric transcripts, in which the SD was apparently spliced to cryptic splice sites in non-coding RNA, resulting in exonization of non-coding genetic information (FIG. 6C).

NUBPL-Driven Transcripts and their Genes in *M. brandtii*

The above data suggests that HelibatN3 elements act as potent exon traps when mobilized experimentally in HeLa cells. To document the capacity of endogenous Helitron transposition to generate novel transcripts in vivo, we annotated Helitron-captured NUBPL promoter-driven transcripts in the bat, *Myotis* brandtii. We found that a Helitron—captured NUBPL promoter insertion is present within 1 kb upstream of at least one annotated transcription start site (TSS) for 23 annotated genes; these insertions are predicted to drive a total of 46 transcripts [FPKM (fragments per kilobase of exon per million fragments mapped) >0.5], three of which have TSS supplied by the insertion (Table 2). Four of the 46 transcripts are predicted to be coding and, in contrast to their parent genes, 35 of the 46 transcripts show some tissue specificity in the tissues examined (FPKM>0.5 in only that tissue) (Table 2).

Figure 12C:
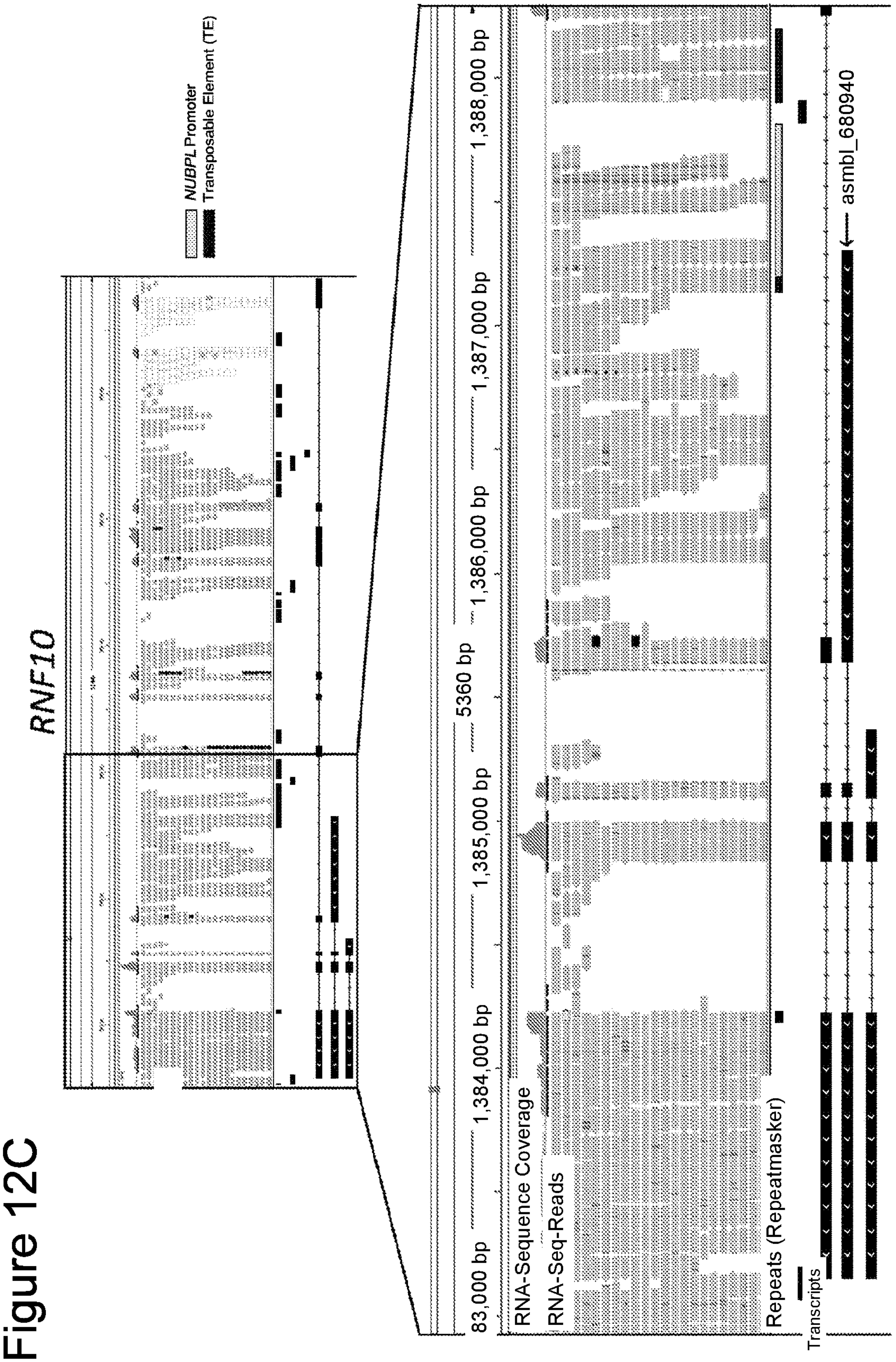

Those candidate NUBPL-driven transcripts, for which the predicted TSS overlapped with the Helitron insertion were considered to be bona fide NUBPL-driven transcripts. Three transcripts met this criterion, and implicated the genes RINT1 (FIG. 12A), ARMC9 (FIG. 12B), and RNF10 (FIG. 12C). Of these, the RINT1 (kidney) and RNF10 (constitutively expressed in the tissues examined) transcripts are predicted to be coding (an intact open reading frame is present), and ARMC9 (brain) noncoding (Table 2). In sum, Helitrons impact genetic novelty at the transcription level, and Helraiser can faithfully recapitulate this biological phenomenon.

Detection of NUBPL Promoter-Driven Fusion Transcripts 500 ng of total RNA purified from puro resistant HeLa colonies were reverse-transcribed using Maxima Reverse Transcriptase (Thermo Scientific) and oligo dT primers at 50° C. for 30 min. After heat-inactivation the reverse-transcription reaction was repeated. The RNA was hydrolyzed with one-fifth volume of 1 N NaOH and 0.5 M EDTA at 65° C. for 15 min. The cDNA was purified with DNA Clean & Concentrator Kit (Zymo Research) and 2 μl of the elute was used for 6 independent PCR amplifications with the following conditions: 95° C. 1 min, 40 cycles of (94° C. 30 s, 65° C. 30 s, 72° C. 30 s), 2 cycles of (94° C. 30 s, 25° C. 1 min, ramp to 72° C. at 0.2° C./s, 72° C. 1 min) with the primer Puro1 specific for the Helitron vector sequence and 4-mer hemi-specific primers computationally predicted for high representation on the entire human transcriptome. The first PCR reaction was supplemented with 25 μls of PCR master mix containing the vector specific oligo Puro2 to perform the subsequent asymmetric PCR reaction with the following condition: 10 super-cycles of [3 cycles of (94° C. 30 s, 65° C. 30 s, 72° C. 40 s) 1 cycle of (94° C. 30 s, 60° C. 30 s, 72° C. 40 s)]. The PCR products were column-purified and 2 μl of the 30 μl elute were used for the 1st exponential PCR, with the transposon-specific oligo T2a_SD_bc and PE_first specific for the overhang of the hemi-specific primers. The PCR products were purified and TA-cloned using the pGEM-T Vector System (Promega) and sequenced. Fusion transcripts were determined by aligning the sequences following the splice donor site within the Helitron transposon with the BLAT tool of the UCSC genome browser.

Annotation of Helitrons (Coordinates, Approximate Age, and Relative Orientation) in the *M. Brandtii* Genome Helitron insertions were identified in the *M. brandtii* genome assembly (KE161034-KE332376, 171343 scaffolds from GenBank at National Center for Biotechnology Information (NCBI) (Seim I, et al. Genome analysis reveals insights into physiology and longevity of the Brandt's bat *Myotis brandtii. Nature communications* 4, 2212 (2013))) using a *Myotis*-specific Helitron repeat library previously described[5]. Conservation of the Helitron insertions were determined by taking the Helitron DNA sequence plus 200 bp flanking sequence and performing a blastn query of the NCBI wgs database to determine if the insertion was present in other sequenced Vespertilionidae bats (*E. fuscus, M. lucifugus*, and *M. davidii*). If there was a hit to the entire length of the query sequence in a given species, it was considered present (conserved) in that species. If there was only a hit to the Helitron or no hit, it was considered absent. By combining this information with the known divergence times of the bats, we obtained an approximate age for each insertion. To determine if there was a bias in the orientation of Helitrons inserting into gene models, we used a pipeline previously described (Kapusta A, et al. Transposable elements are major contributors to the origin, diversification, and regulation of vertebrate long noncoding RNAs. *PLoS genetics* 9, e1003470 (2013)) to identify Helitrons either overlapping with introns, exons, or in regions 1 kb up or downstream of an annotated gene model. *PLoS genetics* 9, e1003470 (2013)) to identify Helitrons either overlapping with introns, exons, or in regions 1 kb up or downstream of an annotated gene model. Both Helitrons that inserted in the same orientation and opposite orientation as their target gene were quantified, and compared using a 2-tailed, 2-sample T-test, $\alpha=0.05$.

*M. brandtii* Transcriptome Assembly, Alternative Splicing Analysis, Abundance Estimation, and Gene Assignment

*M. brandtii* was used for these analyses, because numerous high quality directional RNA-seq with high coverage are publically available and the genome contains 2000 Helitron-captured NUBPL insertions. Ilumina RNA-seq reads (200 bp, paired) from the kidney, liver, and brain tissues of *M. brandtii* (SRA061140) (Seim et al. (2013)) were pooled, quality-trimmed using Trimmomatic (Lohse M, et al. RobiNA: a user-friendly, integrated software solution for RNA-Seq-based transcriptomics. *Nucleic Acids Res* 40, W622-627 (2012)), and assembled (de-novo and genome-guided) using Trinity (r20140413 (Grabherr M G, et al. Full-length transcriptome assembly from RNA-Seq data without a reference genome. *Nature biotechnology* 29, 644-652 (2011))), and assembled (de-novo and genome-guided) using Trinity (r20140413 (Grabherr M G, et al. and Haas B J, et al. De novo transcript sequence reconstruction from RNA-seq using the Trinity platform for reference generation and analysis. *Nature protocols* 8, 1494-1512 (2013)). The resulting assemblies from the two analyses were combined and alternative splicing analysis was performed using Program to Assemble Spliced Alignments (PASA_20140417) (Haas B J, et al. Improving the *Arabidopsis* genome annotation using maximal transcript alignment assemblies. *Nucleic Acids Res* 31, 5654-5666 (2003) and Campbell M A, Haas B J, Hamilton J P, Mount S M, Buell C R. Comprehensive analysis of alternative splicing in rice and comparative analyses with *Arabidopsis. BMC genomics* 7, 327 (2006)). *BMC genomics* 7, 327 (2006)). The relative abundance of each transcript (FPKM) was determined using RNA-Seq by Expectation-Maximization (RSEM; v.1.2.12) (Li B, Dewey C N. RSEM: accurate transcript quantification from RNA-Seq data with or without a reference genome. *BMC bioinformatics* 12, 323 (2011)). Transcripts lacking splicing information (and thus directionality information), abundance of FPKM<0.5, and total length <200 bp were removed from the assembly, resulting in the final *M. brandtii* transcriptome assembly. Transcripts lacking splicing information (and thus directionality information), abundance of FPKM<0.5, and total length <200 bp were removed from the assembly, resulting in the final *M. brandtii* transcriptome assembly. Transcripts were assigned to genes by intersecting genomic coordinates with the current genome annotation (Bedtools; v.2.22.1 (Quinlan A R, Hall I M. BEDTools: a flexible suite of utilities for comparing genomic features. *Bioinformatics* (*Oxford, England*) 26, 841-842 (2010)) and by verifying homology to known transcripts of that gene using BLAST.) and by verifying homology to known transcripts of that gene using BLAST. Coding potential for each transcript was determined as having a predicted ORF>100 amino acids (Haas et al. (2013)). Tissue specificity for each transcript was also determined, and a transcript was considered to be tissue specific if its FPKM value was >0.5 in only one or two of the three examined tissues.

Identifying Helitron-Captured NUBPL Promoter (NUBPL-HCP) Driven Transcripts in *M. brandtii*

The genomic coordinates of Helitrons containing the captured NUBPL promoter were intersected with the coordinates of the assembled transcripts. We used stringent criteria to ensure that the transcript was detectable (FPKM>0.5), that it had strand-specificity, and that the NUBPL promoter itself was within 1 kb upstream of the TSS (Andersson et al. (2014)). (2014)). Transcripts with an NUBPL promoter-containing Helitron located were classified as candidate NUBPL-HCP driven transcripts. Transcripts whose TSS was provided by the NUBPL promoter-containing Helitron were considered to be authenticated NUBPL-HCP driven transcripts. Those genes that had at least one transcript putatively driven by a Helitron were included in a GO Term Analysis Enrichment Analysis and terms were considered significant if their p-values were less than 0.05 (Mi H, Muruganujan A, Thomas P D. PANTHER in 2013: modeling the evolution of gene function, and other gene attributes, in the context of phylogenetic trees. *Nucleic Acids Res* 41, D377-386 (2013) and Ashburner M, et al. Gene ontology: tool for the unification of biology. The Gene Ontology Consortium. *Nature genetics* 25, 25-29 (2000)). *Nature genetics* 25, 25-29 (2000)). Each NUBPL promoter within 1 kb of the TSS of a transcript with FPKM>0.5 was analyzed for promoter motifs such as TATA, CAAT, and GC boxes, and predicted transcription factor (TF) binding sites using GPMiner (Lee T Y, Chang W C, Hsu J B, Chang T H, Shien D M. GPMiner: an integrated system for mining combinatorial cis-regulatory elements in mammalian gene group. *BMC genomics* 13 Suppl 1, S3 (2012)). *BMC genomics* 13 Suppl 1, S3 (2012)).

Determining Enrichment/Depletion of Helitrons in *M. brandtii* in Regions +/−1 kb to Transcription Start Sites (TSS)

To obtain coordinates corresponding to a 2-kb interval centered on the TSSs of *M. brandtii* genes, we extracted coordinates for −1 kb and +1 kb relative to the TSSs from our *M. brandtii* gene assemblies. We then intersected these coordinates with those of known Helitron insertions in *M. brandtii* (RepeatMasker, see above) using Bedtools, and determined enrichment or depletion via Fisher's Exact test ($\alpha$=0.05) (Quinlan et al. (2010)). Results were considered significant if the two-tailed p-value was <0.05, and the direction of the significance (enriched or depleted) was determined via the p-value of the appropriate one-tailed test. (2010)). Results were considered significant if the two-tailed p-value was <0.05, and the direction of the significance (enriched or depleted) was determined via the p-value of the appropriate one-tailed test.

Discussion

An active Helitron transposon from the genome of the bat *M. lucifugus* has been resurrected, and this novel transposon, Helraiser, has been used to explore the mechanism and genomic impact of Helitron transposition.

Consistent with the known properties of other HUH nuclease domains (Chandler et al. (2013)) nuclease activity was detected only on ssDNA fragments derived from Helraiser's LTS and RTS in vitro. This may indicate that Helraiser relies on some cellular process to make ssDNA available for cleavage. For instance, transposition of IS608, a well-characterized prokaryotic transposase that encodes an HUH nuclease, is dependent on lagging strand DNA replication to generate ssDNA (Ton-Hoang B, Guynet C, Ronning D R, Cointin-Marty B, Dyda F, Chandler M. Transposition of ISHp608, member of an unusual family of bacterial insertion sequences. *EMBO J* 24, 3325-3338 (2005) and Ton-Hoang B, et al. Single-stranded DNA transposition is coupled to host replication. *Cell* 142, 398-408 (2010)) Alternatively, the ssDNA necessary for the initial steps of Helraiser transposition could become available through negative supercoiling shown to induce local melting of dsDNA in AT-rich regions (Dayn A, Malkhosyan S, Mirkin S M. Transcriptionally driven cruciform formation in vivo. *Nucleic Acids Res* 20, 5991-5997 (1992); Krasilnikov A S, Podtelezhnikov A, Vologodskii A, Mirkin S M. Large-scale effects of transcriptional DNA supercoiling in vivo. *J Mol Biol* 292, 1149-1160 (1999) and Stick T R, Allemand J F, Bensimon D, Croquette V. Behavior of supercoiled DNA. *Biophysical journal* 74, 2016-2028 (1998)) In eukaryotic cells, negative supercoiling of DNA occurs upstream of the transcription complex (Liu L F, Wang J C. Supercoiling of the DNA template during transcription. *Proceedings of the National Academy of Sciences of the United States of America* 84, 7024-7027 (1987) and Rahmouni A R, Wells R D. Direct evidence for the effect of transcription on local DNA supercoiling in vivo. *J Mol Biol* 223, 131-144 (1992) and could generate single-stranded patches (Parsa J Y, et al. Negative supercoiling creates single-stranded patches of DNA that are substrates for AID-mediated mutagenesis. *PLoS genetics* 8, e1002518 (2012) required for Helraiser transposition. Furthermore, as AT-rich regions can facilitate local DNA melting, perhaps it is not a coincidence that the consensus LTS contains an AT-rich region close to the cleavage site (FIG. 8). Both the homology between the Helraiser helicase domain and PifI and the critical requirement of helicase function for transposition (FIG. 2) support a model, in which the role of the helicase domain is to unwind DNA at ssDNA-dsDNA junctions, once ssDNA has been generated at the transposon ends.

The data suggesting that Helraiser transposition proceeds through a circular intermediate defines a crucial distinction when compared to other known eukaryotic DNA transposons. It is possible that Helitron transposition is mechanistically related to some ssDNA-based prokaryotic transposition systems (del Pilar Garcillan-Barcia et al. (2001)) or to certain ssDNA virus replication processes (Faurez F, Dory D, Grasland B, Jestin A. Replication of porcine circoviruses. *Virology journal* 6, 60 (2009)) The lack of local hopping and random distribution of transposon insertions when transposition was initiated from genomic donor loci (FIG. 5) strongly support the idea of episomal transposition intermediates.

The following observations are consistent with a modified rolling circle model of Helitron transposition: 1) Helraiser transposition requires the LTS, while the RTS is not strictly necessary (FIG. 3), 2) the hairpin appears to be the most important component of the RTS as its deletion or of the whole RTS have similar effects on transposition (FIG. 3), and 3) both transposon truncations and transduction of sequences adjacent to the RTS occur ex vivo, and the frequency of these non-canonical transposition events is significantly increased when the hairpin is deleted (FIG. 6). Collectively, the data suggest that the hairpin structure in the RTS plays an important regulatory role in Helraiser transposition by serving as a transposition termination signal. Our observations support a "read-through" model of capturing DNA sequences flanking the transposon: when the hairpin is missing from the RTS or is not recognized by the transposition machinery, the transposase bypasses the 3'-end of the transposon and finds an alternative transposition terminator sequence further downstream, resulting in transduction of the flanking host sequence (Feschotte et al. (2001) (FIG. 7)).

The relatively loose functional definition of the RTS is most likely the core reason why Helitrons can efficiently transduce downstream host genomic sequences. Gene capture may contribute to the emergence and diversification of novel Helitron families and to the generation of novel cellular transcripts. For example, the captured NUBPL gene fragment, when mobilized by the Helraiser transposase into the genome of human cells, gives rise to novel coding and non-coding transcripts by imposed transcription and splicing (FIG. 6C). Several Helibat insertions were identified that drive transcription of cellular genes (Table 2), and identified transcripts that initiate within the NUBPL insertion. All of these bona fide NUBPL-driven transcripts were N-terminally truncated and had exonized non-coding sequence, most often resulting in a novel 5'-UTR (FIG. 12 and Table 2), as seen with some of the Helraiser-catalyzed insertions ex vivo (FIG. 6C).

TEs have been shaping genome structure and function for millions of years, and have exerted a strong influence on the evolutionary trajectory of their hosts (reviewed in Feschotte C. Transposable elements and the evolution of regulatory networks. *Nature reviews Genetics* 9, 397-405 (2008). The most prominent agents documented to provide alternative promoters, enhancer elements, polyadenylation signals and splice sites are retrotransposons. In addition, it has been shown that ~1000 cellular gene fragments had been captured by cut-and-paste Pack-MULE DNA transposons in the rice genome, suggesting that these transposons might have played an important role in the evolution of genes in plants (Jiang N, Bao Z, Zhang X, Eddy S R, Wessler S R. Pack-MULE transposable elements mediate gene evolution in plants. *Nature* 431, 569-573 (2004)). *Nature* 431, 569-573 (2004)). It appears that Helitrons also have a profound potential to generate genome variation. Indeed, about sixty percent of maize Helitrons were found to carry captured gene fragments, adding up to tens of thousands of gene fragments disseminated across the maize genome by Helitron transposition (Yang et al. *Proceedings of the National Academy of Sciences of the United States of*

*America* 106, 19922-19927 (2009)). Although most captured gene fragments are apparently undergoing random drift in maize, ~4% of them are estimated to be under purifying selection, suggesting beneficial effects for the host. Thus, the molecular mechanism of 3'-transduction and subsequent, genome-wide dissemination of captured gene fragments or entire genes by copy-and-paste transposition uniquely positions Helitrons as powerful genome shuffling agents with wide-reaching biological consequences.

Example 2: Use of HelRaiser Transposase to Amplify Genomic Content

HelRaiser is the first transposon that uses a copy and paste mechanism for replication and that is operational in eukaryotic cells. One attractive application of this transposon as a molecular biology tool is the amplification of genomic content, such that cell lines are created that contain multiple copies of a gene or genomic region of interest. To exemplify this, a cell line bearing a defined single-copy integration of a "model gene" (TurboGFP), flanked by HelRaiser terminal sequences (LTS and RTS) was used as a starting point. Then, these cells were transduced with the HelRaiser transposase and assessed as to whether the TurboGFP had been replicated by a copy and paste mechanism.

Figure 13A:
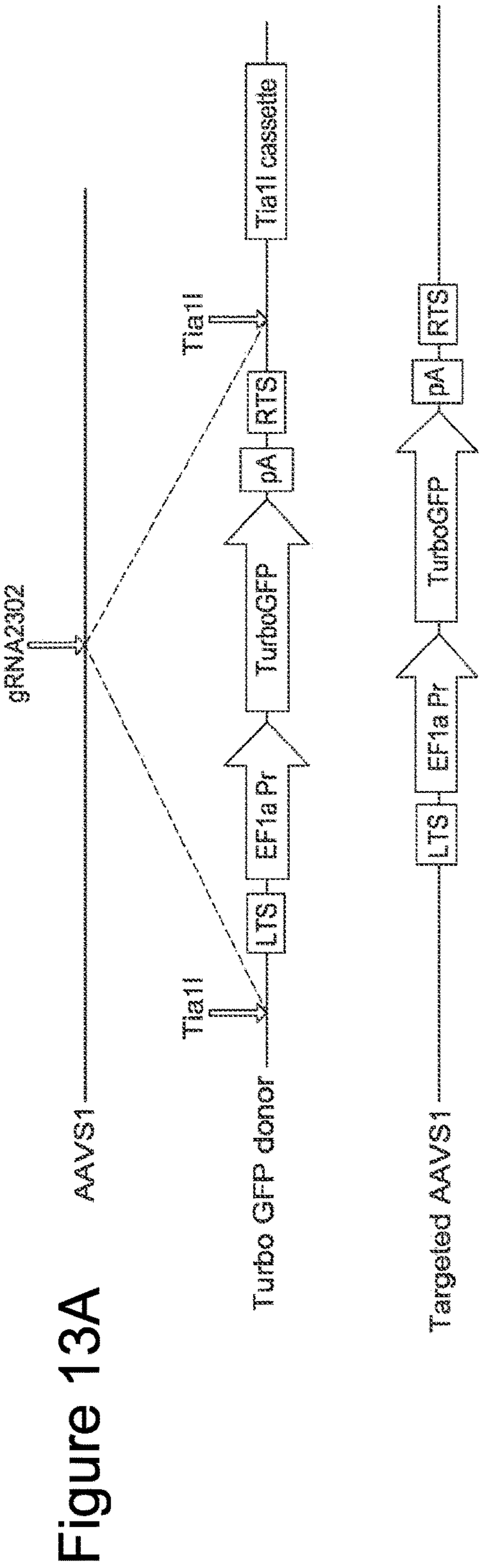
Figure 14A:
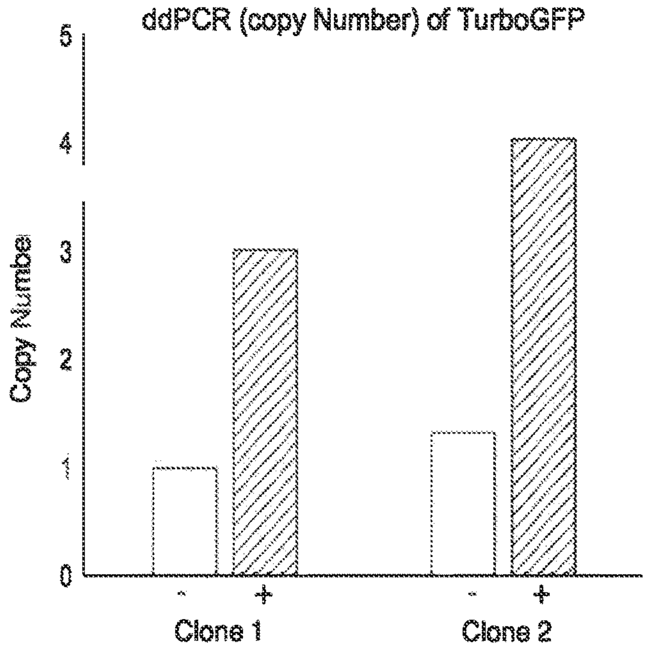

To generate a cell line bearing a defined copy number of LTS-EF1A-TurboGFP-RTS, an in situ ligation approach was used in which the donor (here LTS-TurboGFP-RTS) is flanked by a generic gRNA recognition site called TialL (gRNA sequence: GGTATGTCGGGAACCTCTCC (SEQ ID NO:9); gRNA recognition site: GGTATGTCGGGAACCTCTCCAGG (SEQ ID NO:10) with PAM sequence underlined). A detailed description of this approach has been published recently (Lackner, D. H. et al. A generic strategy for CRISPR-Cas9-mediated gene tagging. *Nat. Commun* 6:10237 doi: 10.1038/ncomms10237 (2015)). The tagging cassette contains TialL sites encompassing terminal sequences from the HelRaiser transposon (LTS and RTS). TurboGFP is expressed from an EF1A promoter and is followed by a polyadenylation cassette (FIG. 13A).

HEK293 cells were transfected by electroporation with Cas9, a gRNA targeting the AAVS1 safe harbor locus (gRNA sequence: GTCACCAATCCTGTCCCTAG (SEQ ID NO:10)) and the tagging cassette described above. Note that this cassette also expresses the TialL gRNA from a U6 promoter. Cleavage of the AAVS1 locus will trigger insertion of the tagging cassette liberated by TialL cleavage of the tagging plasmid. Next, single cell clones expressing TurboGFP were obtained by FACS sorting. Clones were genotyped by a dual strategy, amplifying either the 5' or the 3' junction of the cassette with the genome:

```
Primer pair for 5' Junction PCR AAVS1-EF1A
Fwd:
                                  (SEQ ID NO: 12)
TATATTCCCAGGGCCGGTTA,

Rev:
                                  (SEQ ID NO: 13)
TCTCCACCTCAGTGATGACG

Primer pair for 3' Junction PCR TurboGFP-AAVS1
Fwd:
                                  (SEQ ID NO: 14)
AGGAGGATCACAGCAACACC,

Rev:
                                  (SEQ ID NO: 15)
ACAGGAGGTGGGGGTTAGAC
```

Figure 13B:
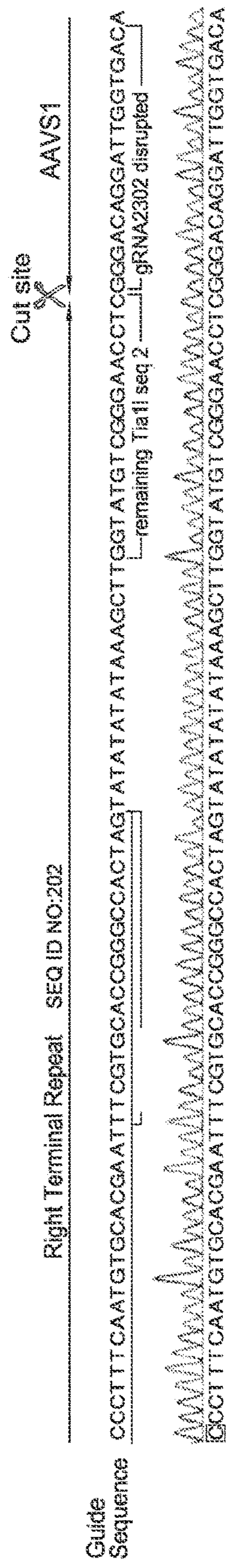

A number of clonal cell lines were obtained for which both of the genotyping PCRs described above were positive. A selection of these was also analyzed by Sanger sequencing to unequivocally confirm integration of the tagging cassette at the AAVS1 locus (FIG. 13B).

Next, single cell clones bearing the tagging cassette were analyzed by digital droplet PCR (ddPCR). ddPCR is a powerful method to determine the copy number of a given locus in the cells. To this end, 50 ng of genomic DNA from each clone was added to the Bio-Rad 2XddPCR Mastermix (20 µl total reaction volume), along with TaqMan primers (at 900 nM final concentration) and probe (at 250 nM final concentration) specific to the locus of interest:

| TurboGFP primer/probe sequences | |
|---|---|
| Fwd primer | 5'-CTGCACGTGAGCTTCAGCTA-3' (SEQ ID NO: 16) |
| Rev primer | 5'-AAGCCGGTGCCCATCA-3' (SEQ ID NO: 17) |
| Probe | FAM-CCGCGTGATCGGCGACTT-MGB (SEQ ID NO: 18) |
| Amplicon length | 74 bp |

To be able to relate the TurboGFP copy number to a reference locus, a probe set for the human RnaseP gene was included (Catalog number 4403326 from ThermoFisher). This assay detects the Ribonuclease P RNA component H1 (H1RNA) on chromosome 14:
Assay location: chr.14:20811565
Build: NCBI build37
Gene Symbol: RPPH1
Probe modification: VIC dye (5'), TAMRA Quencher (3')
Amplicon length: 87 bp Droplets were generated using the DG8 cartridges and 70 µl oil and transferred to a 96 well PCR plate. Next, a PCR was performed on the droplets using the following conditions:

| Temperature | Time | Cycles |
|---|---|---|
| 96° C. | 10 min | 1 |
| 96° C. | 30 sec | 40 |
| 61° C. | 60 s | |
| 98° C. | 10 min | 1 |
| 4° C. | ∞ | |

Following the PCR reaction, the PCR plate was then transferred to QX100 droplet reader which automatically measures the droplets and categorises them into four distinct populations. The data were then analysed using the Quantasoft software.

Figure 14B:
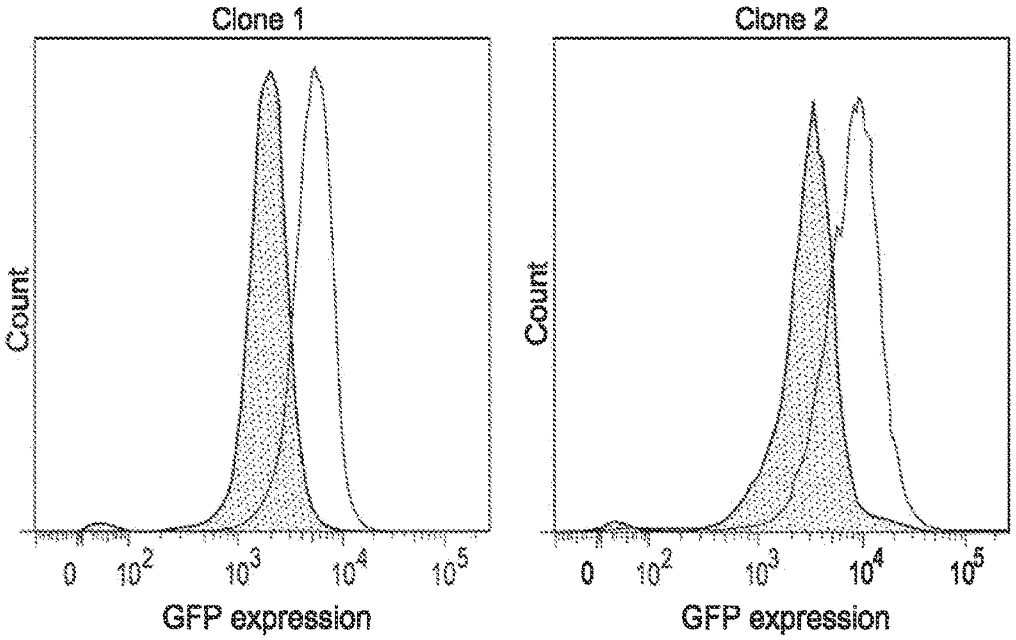

For future experiments, two clones bearing a single copy of the TurboGFP cassette (FIG. 14A) were selected that express TurboGFP to detectable levels as indicated by FACS (FIG. 14B). To mobilize and amplify the TurboGFP cassette, HEK293 cells were transfected with the HelRaiser transposase gene (SEQ ID NO: 6), expressed from a CMV promoter (from pcDNA3.1(−) (Invitrogen)). Following transfection, single cell clones were isolated and the copy number of TurboGFP was quantified using the ddPCR assay described above. The assay clearly showed an increase in copy number in both clones shown here (clones 1 and 2 in FIG. 14A). In clone 2, the copy number rose from 1n to 4n, which is remarkable and suggests a very high activity of HelRaiser transposase. In other clones, no increase was observed (data not shown).

Next, it was assessed whether the increase in copy number translated into an increase of TurboGFP expression. To this end, clones were analyzed before and after transposase transduction by FACS analysis. Of note, a significant increase in TurboGFP expression was observed following transposase transduction (FIG. 14B). This suggests that HelRaiser transposase activity is sufficient to copy the TurboGFP cassette and paste it at another genomic locus. From previous literature (Grabundzija et al. Nat Commun. 2016 Mar. 2; 7:10716. doi: 10.1038/ncomms10716.), it is assumed that insertion will occur randomly throughout the genome (with preference for an AT dinucleotide at the target site).

In summary, this experiment shows that a gene or genomic region which is flanked by the HelRaiser terminal sequences can be amplified following addition of HelRaiser transposase. While this has only been exemplified with a model gene here (TurboGFP, inserted into the AAVS1 locus at a single copy), it is easy to anticipate that a similar amplification could be observed if an endogenous gene had been tagged with LTS and RTS. Hence, this approach is geared to generate cell lines bearing genomic amplifications. Such cell lines could be of particular interest in oncology where certain treatments are stratified based on the degree of amplification of a target gene (e.g. Her2 in breast cancer) and where appropriate reference standards are missing.

Example 3: Genomic Amplification of the Two Endogenous Human Loci: CDK4 and CD81

In order to measure the efficiency of the Helraiser transposon when used for gene amplification in cells, Hap1 cells are engineered to contain the transposase recognition sites (LTS and RTS) flanking an endogenous gene of interest. Once these cell lines are engineered, the transposase is expressed in these cells and it is observed if the gene locus increases in copy number due to the copy-paste activity of the transposase. Two genes are selected for this proof of concept experiment: Cyclin-dependent kinase 4 (CDK4) and Cluster of Differentiation 81 (CD81).

To insert the Left Terminal Sequence (LTS) and Right Terminal Sequence (RTS) required for transposition into the genome, an established Non-Homologous End joining tagging method is used. Plasmids which contained the LTS or RTS sequence flanked by zebrafish tia1L gRNA recognition sites and a U6 promoter driving expression of this zebrafish tia1L gRNA are constructed. The LTS and RTS cassette would be liberated from the plasmid upon Cas9 cleavage at the tia1L gRNA sites. If a gRNA specifying the genomic locus of interest is also provided, the LTS or RTS cassette would be inserted at this site following cleavage of Cas9/gRNA. LTS is specified in SEQ ID3 and RTS is specified in SEQ ID4.

Ideally, the LTS is flanked by an upstream A and RTS is flanked by a downstream T to reflect the fact that natural Helraiser transposition events occur at AT dinucleotides, where the LTS-donor-RTS sequence is inserted between A and T.

To engineer the cell lines (one for CDK4 and one for CD81), gRNAs are designed upstream and downstream of the CDK4 and CD81 genomic loci. The LTS cassette must be inserted upstream (5') of the genes and the RTS cassette downstream (3'). Since each cell line needs to have a cassette integrated at 2 different loci (LTS upstream and RTS downstream) two sequential engineering steps are performed. The gRNAs designed are shown in the table below:

gRNAs Used for Engineering:

| SEQ ID NO: | Name | ID | Sequence | Genomic location |
|---|---|---|---|---|
| 19 | CDK4 upstream LTS | 4890 | GTGGCTCTAAGGGTAAATCA | Chr12: 57747617-57747636 |
| 20 | CDK4 downstream RTS | 4891 | TAATCATAGAACCTTCCTAC | Chr12: 57753231-57753250 |
| 21 | CD81 upstream LTS | 5350 | GGCCTGACATCTGATTGCGG | Chr11: 2375107-2375126 |
| 22 | CD81 downstream RTS | 5353 | CAGGGGAATCTGACATCGGT | Chr11: 2397458-2397477 |

Hap1 cells are transfected by lipofection with a plasmid expressing Cas9, the tagging plasmid (either LTS or RTS), the corresponding gene-specific gRNA plasmid and a plasmid conferring blasticidin resistance. After transfection the cells are briefly selected with blasticidin to enrich for transfected cells. After three days of recovery, cells are single cell diluted to isolate clonal lines. The clones are analyzed by PCR and Sanger sequencing to identify clones that have integrated the LTS or RTS cassette. The primers used for PCR and Sanger sequencing are shown in the table below:

Primers Used for Genotyping:

| SEQ ID NO: | Name | ID | Sequence | Genomic location |
|---|---|---|---|---|
| 23 | CDK4_LTS_fwd | HG25161 | GGTTGTTTTCTCCTTGGCCC | Chr12: 57747643-57747662 |
| 24 | CDK4_LTS_rev | HG25162 | ATCCTAGAGCCAACCCCAGT | Chr12: 57747259-57747278 |

-continued

| SEQ ID NO: | Name | ID | Sequence | Genomic location |
|---|---|---|---|---|
| 25 | CDK4_RTS_fwd | HG25159 | AAGTGCTAAGAAAGCGGCAC | Chr12: 57753478-57753497 |
| 26 | CDK4_RTS_rev | HG25160 | TCCAACAGGCTCAGTGACAAG | Chr12: 57753075-57753095 |
| 27 | CD81_LTS_fwd | HG26676 | CACTTCTGGGTGCGTACTGT | Chr11: 2374860-2374879 |
| 28 | CD81_LTS_rev | HG26677 | GCTTGCTAGAGGGTCACAGG | Chr11: 2375434-2375453 |
| 29 | CD81_RTS_fwd | HG26722 | TAACACGTCGCCTTCAACTG | Chr11: 2397323-2397342 |
| 30 | CD81_RTS_rev | HG26723 | TTACAATCTGGCGGCTTCAT | Chr11: 2397889-2397908 |

After clonal cell lines containing either the LTS or the RTS at the correct locus are identified, these cells are re-targeted to insert the other sequence (either LTS or RTS). The same procedure described for the first targeting experiment is repeated, but ensuring that the LTS containing cell lines are engineered to contain the RTS and vice-versa. Correctly edited clonal cell lines from the second targeting experiment with both the LTS and RTS sequences at the desired locations are now used to test the activity of the transposase.

CDK4 LTS/RTS and CD81 LTS/RTS cell lines are electroporated with a plasmid expressing the Helraiser transposase. This expression plasmid contains the transposase coding sequence under the CMV promoter, which ensures high expression levels of the transposase. The coding sequence of the transposase is depicted in SEQ ID NO: 6. Engineered CDK4 LTS/RTS and CD81 LTS/RTS Hap1 cells are electroporated with the transposase plasmid using the Lonza Nucleofection system with SE Buffer and the program DS120. In order to allow many transposition events to occur, cells undergo five rounds of electroporation with four days of recovery between each round. After the fifth and last round of electroporation, the cell lines are single cell diluted to isolate clonal cell lines. The clones are analyzed by droplet digital PCR (ddPCR) to assess the copy number of the CDK4 and CD81 genes using commercially available assays (e.g. PrimePCR™ ddPCR™ Copy Number Assay: CDK4, Human; Assay ID dHsaCP2500374 from Bio-Rad). For those clonal cell lines where an increase in copy number is detected, the cell lines are analyzed by qPCR and Western Blot to confirm the presence of increased mRNA and protein expression levels.

Example 4: Use of HelRaiser to Deliver DNA Cargo and Establish Cell Lines Bearing Multiple Copies of a Target Gene One potential application of transposons is the delivery of DNA cargo to target cells where the transposase mediates random high-copy number integration. This is of particular interest where transposons may be applied to deliver DNA cargo in a therapeutic context. In addition, this is relevant for CHO cell engineering, where CHO cells are used as bioreactors to produce antibodies and other biologicals.

Figure 1D:
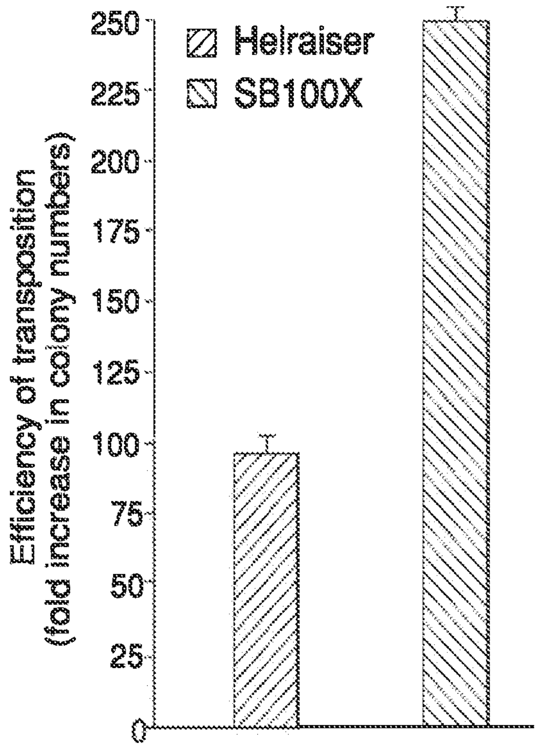
Figure 1E:
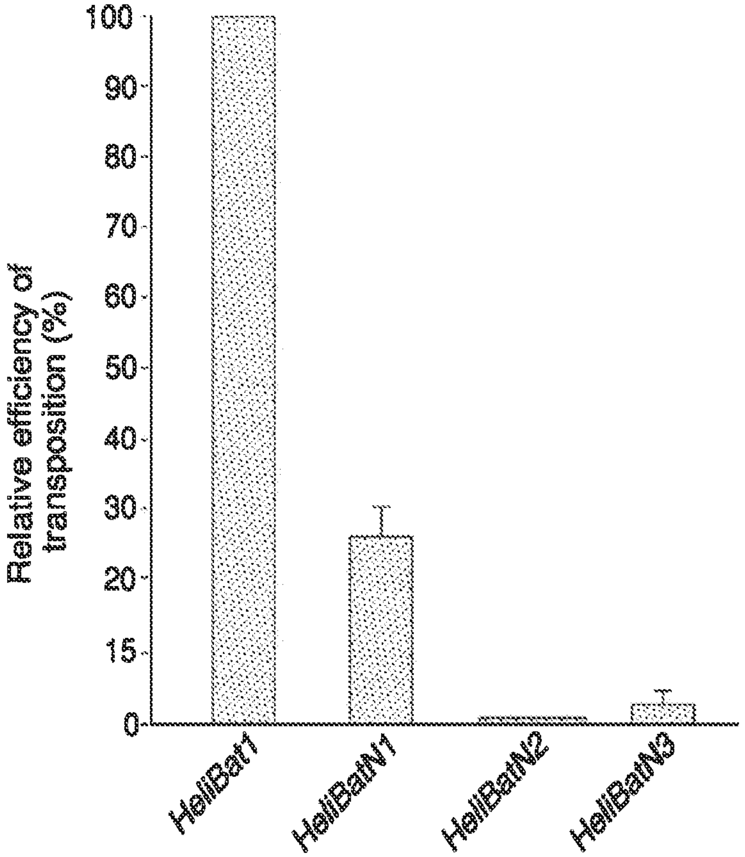

Our experiments suggest that HelRaiser is very efficient at establishing cell lines that stably contain the transgene of interest (as shown in FIG. 1D). In fact, as described above, HelRaiser is almost as active as an engineered version of Sleeping Beauty that is 100 times more active than the naturally occurring system (hence, it is called SB100). However, from these experiments, it was not entirely clear how many copies of the transgene one could expect per cell as this had only been quantified by splinkerette PCR (FIG. 3) and not by digital droplet PCR.

To address this question, HEK293 cells were transfected with a HelRaiser donor in which a Puromycin resistance gene is expressed from an SV40 promoter and flanked by HelRaiser terminal sequences to allow transposition from the plasmid into the genome of HEK293 cells. Transposition was catalysed by co-transfecting a plasmid encoding the HelRaiser transposase, expressed from a CMV promoter. Following transfection, cells were selected by applying 1 μg/ml Puromycin to enrich for cells bearing stable integration of the target gene (PuroR). Next, single cell clones were isolated by limiting dilution and these clones were expanded to extract genomic DNA.

Selected single cell clones were then analysed by a ddPCR assay in which the copy number of the PuroR gene was determined by the following assay:

| PuroR primer/probe sequences | |
|---|---|
| Fwd primer | 5'-CACCAGGGCAAGGGTCTG-3' (SEQ ID NO: 31) |
| Rev primer | 5'-GCTCGTAGAAGGGGAGGTTG-3' (SEQ ID NO: 32) |
| Probe | VIC-GCCTTCCTGGAGACCT-MGB (SEQ ID NO: 33) |
| Amplicon length | 118 bp |

To be able to relate the PuroR copy number to a reference locus, a probe set for the human EGFR gene (Catalog number 4400291 from ThermoFisher) was included. This assay detects the EGF receptor on chromosome 7.

ddPCR was essentially performed as described in Example 2. FIG. 15 shows ddPCR results from a selection of clones bearing stable PuroR integrations. Of note, several clones contained high copy numbers of the transgene (e.g. clone 5E11 with a copy number of 12; clone 5F10 with a copy number of 15; clone 10B1 with a copy number 14). As these experiments were run post antibiotic selection and post limiting dilution, they are likely to represent true genomic integration events (rather than plasmid carry-over).

In summary, this experiment suggests HelRaiser is a powerful tool to deliver cargo to recipient cells and establish cell lines bearing high copy numbers of the transgene. Of interest, copy numbers obtained here exceed the copy numbers reported for an engineered version of Sleeping Beauty (compare FIG. 6 of PMID 22402491; Kacherovsky N et al., Combination of Sleeping Beauty transposition and chemically induced dimerization selection for robust production of engineered cells. *Nucleic Acids Research,* 2012, Vol. 40, No. 11 e85 doi:10.1093/nar/gks213). This highlights the utility of HelRaiser as a gene delivery vehicle and strongly suggests that its applicability for the purposes outlined above.

Example 5—Application of Helraiser for Bioprocess Applications

In order to assess the suitability of the Helitron transposase described herein for bioprocess applications, the following experimental validation is conducted.

Donor vectors with appropriate selection cassettes are constructed, containing cassettes encoding industrially relevant recombinant proteins, for example anti-HER2 antibodies. Suitable vectors for validating the technology include those encoding:

Control GFP vector—eGFP with puromycin$^R$ selection cassette flanked by RTS and LTS (Vector (1)).

IgG1 HC donor—anti-HER2 IgG1 heavy chain with glutamine synthase selection cassette flanked by RTS and LTS (Vector (2)).

IgG1 LC donor—anti-HER2 IgG1 light chain with glutamine synthase selection cassette flanked by RTS and LTS (Vector (3)).

Multi gene IgG1 donor—anti-HER2 IgG1 heavy chain, anti-HER2 IgG1 light chain with glutamine synthetase selection cassette flanked by RTS and LTS (Vector (4)).

Incorporation of a Recombinant Protein Such as GFP Using Helraiser.

The Helraiser transposase protein and donor control GFP vector (Vector (1) above) are delivered into cells via electroporation using a Lonza Nucleofector standardised CHO procedure. After 72 hours, the cells are analysed by flow cytometry for the number of positive GFP cells, to determine the efficiency of the transfection. The cells are seeded into two E125 Erlenmeyer flasks ($0.5\times10^6$ cells/mL). The cells in the first flask (a) are put under puromycin selection for two weeks, whereas the cells in the second flask (b) are passaged for two weeks with shaking (maximum cell density $4.0\times10^6$ cells/mL). After two weeks, the selection pressure is removed from flask (a) and the cells in both flasks are analysed by flow cytometry to determine the percentage of cells that have a stable integration of GFP. 100% of cells expressing GFP in flask (a) indicates integration of the GFP gene into 100% of cells under selection. Flask (b) provides a measure of the efficiency of Helraiser transposase to integrate a cassette without selection. The puromycin selected cells in flask (a) are harvested for Targeted Locus Amplification (TLA) assessment by Cergentis to determine the number of integrations and their locations.

The GFP-positive cells are seeded into 384-well plates at 1 cell/well using FACS. A distribution of the population is selected to capture cells with a range of integration frequencies, ranging from single integrations to cells harbouring multiple integrations. The cells are grown on for two weeks, and the intensity of the GFP fluorescence is determined. Low-, medium- and high-fluorescence cells are picked and cultured for further analysis. These clones are assessed for numbers of integrations using ddPCR. A clone with a single integration is used to assess amplification protocols. The locations of the integrations are determined by TLA in the clones showing the highest signals. The clones are sequenced by NGS to determine any unwanted modifications to the genome caused by the use of Helraiser transposase. This information is important for regulatory approval as certain genomic Helraiser integration events may be avoided as they affect cell growth, proliferation or stability.

The clone with a single GFP integration is exposed to Helraiser transposase protein to determine the efficiency of amplification. The cells are analysed by flow cytometry to determine a change in the fluorescent signal. Cells are cloned and integration number is determined by ddPCR. The clones are categorised into low (<5 copies), medium (10-20 copies) and high (20-100 copies) fluorescence. Assessment of the integrity of the transposable element is made using TLA. The protocol is optimised to increase the production of clones harbouring 10-20 copies of the GFP cassette.

Incorporation of a Large Multigene Cassette (Monoclonal Antibody Heavy Chain and Light Chain) Using Helraiser.

Two transfections are setup to compare the efficiency of delivering a multigene cargo by single gene donors (separate IgG1 HC and IgG1 LC donors) versus double gene donors (multigene IgG1 donors combined in one cassette). The Helraiser transposase and donors are delivered into cells via electroporation using a Lonza Nucleofector standardised CHO procedure. Three pools are generated: Pool (a) is transfected with single gene donors Vectors (2) and (3) as above, Pool (b) is transfected with double gene donor Vector (4) as above and Pool (c) is mock control, no donor. After 72 hours, the cells are selected under minus L-Glutamine conditions in a T flask according to Horizon's standard procedure. After 10 days selection, the cells from pools (a) and (b) are assessed for productivity in a 10-day fed-batch culture. This determines the efficiency of the transposase in generating a highly expressing pool which can be used to generate gram quantities of product. At the same time, the cells from pools (a) and (b) are seeded into 384-well plates to generate 1000 clones. The 1000 clones are seeded into 96-well plates and supernatant is harvested from them after 5 days culture to determine IgG1 productivity. The clones are selected based on growth and production of IgG1 (low, medium and high). The pools and clones are assessed for stability by culturing the cells for 60 generations. At the end of this period, the cells are assessed for productivity by a 10 day fed-batch culture. This information is important for regulatory approval.

For assessment of the transposase for use in bioprocess applications the following metrics should be considered:

1) The selected pool yields recombinant protein at greater than 2 g/L
2) The product titre does not differ by +/−30% between generation 1 and generation 60 of a stable cell line.

Example 6: Use of HelRaiser to Deliver DNA Cargo into Human Cells Ex Vivo for Therapeutic Purposes Ex Vivo Gene Therapy Accomplished Using the Helraiser Transposon.

A type and number of cells appropriate to the targeted pathology are isolated from a patient, a donor or a population derived from an iPSC cell appropriately engineered to limit graft vs host disease and prevent/reduce rejection by the host. A DNA vector is assembled that contains an LTS sequence, an appropriate promoter and/or enhancer that operates in the cells of interest, optionally insulation sequences that restrain the ability of the promoter/enhancer to also activate adjacent genes, a cDNA encoding the protein (or RNA) of interest, appropriate transcription termination sequences and an RTS sequence. The cells are cultured (and expanded if required) in appropriate cell culture media until the desired number of cells has been obtained. The vector described above (LTS-cDNA of interest-RTS) is introduced into the recipient cells by electroporation or transfection. Alternatively, the vector may be introduced via a viral particle derived from a packaging system designed to eliminate the risk that active virus is generated. In a further alternative, the vector is introduced in non-viral particles with properties suitable for fusing with the host cells, for example liposomes.

In all cases, it is necessary for the host cells to also express the Helitron transposase (at least transiently) at/around the time that the vector is introduced into the cells. The Helitron transposase can be introduced as DNA (either as a free plasmid via transfection/electroporation or via transduction with viral on non-viral particles), as mRNA encoding the transposase, or as transposase protein.

The transduced cell population is cultured until the source of transposase has been removed from the system. The presence/absence of the transposase can be determined by PCR using primers directed to the nucleotide sequence of the transposon.

A sample of the engineered cells are examined to see how efficiently they were transduced, the number of desired gene sequences that have been integrated, and also how much the copy number varies between cells. Where the engineering event creates a phenotype that can be observed by flow cytometry in a manner that preserves cell integrity, then a population with the desired behaviour can be enriched by FACS sorting. The cells are then expanded in cell culture until an appropriate number for therapy has been achieved. Cryopreservation can be used to store populations for follow-on treatments or to create an off-the-shelf therapeutic product.

The transfected cells are introduced into the patient by injection into an appropriate tissue of the body, or into the peripheral blood circulation. In some cases, increased therapeutic benefit will be achieved if host tissues (e.g. bone marrow) have been ablated thereby increasing the ratio of engineered, introduced cells to those wild-type cells existent in the body. The pathological phenotype of the patient is assessed to measure the therapeutic benefit arising from introduction of the engineered cells. In some cases, a one-time treatment may be optimal, in other cases, further introductions of engineered cells will be beneficial.

Example 7: Use of HelRaiser to Deliver DNA Cargo into Human Cells In Vivo for Therapeutic Purposes In vivo gene therapy is another approach for restoring pathological situations to normal function. It is apparent to those skilled in the art that the Helitron transposon could be used for in vivo gene therapy by taking the following steps.

First, a DNA vector is assembled that contains a LTS sequence, an appropriate promoter and/or enhancer that operates in the cell line of interest, potentially insulation sequences that restrain the ability of the promoter/enhancer to activate adjacent genes, a cDNA encoding the protein (or RNA) of interest, appropriate transcription termination sequences and an RTS sequence.

Second, a therapeutic dose of LTS-cDNA of interest-RTS vector is prepared along with a system that can introduce the Helitron transposon into cells in vivo. The DNA vectors may be prepared as plasmids, with sufficient care taken to ensure they are free of endotoxins, or they may be packaged in an appropriate viral particle generated in a packaging system that prevents the generation of live virus that can sustain an infection, or they may be packaged in a non-viral delivery system build around an appropriate lipid or polymer particle. In some cases, the Helitron transposase might be delivered in the form of an encoding mRNA or alternatively, a recombinant protein of appropriate purity.

Third, the transduction system of LTS-cDNA of interest-RTS vector and transposase above is introduced into the patient's body via injection into the desired tissue or organ. The doses and methods employed will have been selected (and appropriately scaled to account for difference in size and physiology) from those that yielded therapeutic benefit with acceptable safety when used in pre-clinical models that may include, but are not limited to, mice, rats and/or non-human primates.

Example 8: Use of Helitrons to Generate a Library of Mutants

Gene traps are synthetic genetic elements that are frequently used across various species to disrupt the expression of a gene of interest (cite PMID 18370072; Floss T and Schniitgen F; Chapter 9 in *Chromosomal Mutagenesis*, Humana Press, Eds. Davis G D and Kayser K J (2008)). They containing a strong splice acceptor fused to a reporter gene, such as GFP, RFP, mCherry, PuroR or BlaR, followed by a strong transcriptional termination signal (cite PMID 19965467; Carette J E et al. (2009) Science Vol. 326, Issue 5957, pp. 1231-1235 DOI: 10.1126/science.1178955). If such a gene trap cassette gets inserted within the expressed portion of a gene, it will capture the transcript by the means of its splice acceptor and create a fusion transcript that will abrogate transcription of this gene specifically. This has been exploited to create loss-of-function (LOF) models in various organisms (e.g. mice, zebrafish; cite PMID 15167922; International Gene Trap Consortium, Skarnes W C et al. (2004). Nature Genetics, 36(6), 543-544.).

Massive parallel delivery of gene traps can be used as an approach to create a library of mutants that can be subjected to genetic screening. This has been nicely exemplified in yeast and haploid human cells (Carette et al. (2009)) which contain a single set of chromosomes/genes and hence, it is straightforward to obtain "homozygous" LOF mutations. It is also possible in other cells and organisms (cite PMID 25961939; Moriarity B S et al. (2015). Nature Genetics, 47(6), 615-624. http://doi.org/10.1038/ng.3293), albeit at lower frequencies and possibly at lower "conversion rates" (where heterozygous LOF mutants may be most predominant).

Such screens require the transduction of cells at high efficiency and the simultaneous inactivation of many thousands genes in a massive parallel approach. Historically, this has been achieved using retroviruses, lentiviruses or transposons (mostly PiggyBac, Tol2 and Sleeping Beauty). While all of these approaches are feasible, retroviruses have particular shortcomings as their integration pattern is biased towards genes and transcriptional start sites (cite PMID 16175173; Bushman F et al. (2005) Nat Rev Microbiol. November; 3(11):848-58.) and retroviral integration sites are silenced by epigenetic mechanisms (cite PMID 26022416; Tchasovnikarova I A et al. (2015) GENE SILENCING. Science. 2015 Jun. 26; 348(6242):1481-5. Epub 2015 May 28). Lentiviruses are less biased, yet still subject to silencing. Transposons represent attractive alternatives and are much easier to produce, but at least some of them seem to favour "local hopping" as opposed to an unbiased distribution over the entire genome (cite PMID 19391106; Liang Q et al. (2009) Genesis. 2009 June; 47(6): 404-8.).

The Helraiser transposon system is an attractive means to create libraries of cells containing many tens of thousands (up to a million) independent Helraiser integration events. Cells are transduced with a donor in which a gene trap cassette consisting of a splice acceptor driving the expression of a Puromycin-resistance gene is flanked by Helraiser terminal sequences LTS and RTS. Co-application (e.g. by transfection) of a transposase expression plasmid mobilizes the gene trap from the plasmid to create a library of cell lines containing many different insertion mutants. The size of those libraries is proportional to the number of cells used and transpositional activity, such that libraries in which every single human gene is inactivated by a transposon insertion are created. Following transduction, cells containing Helraiser integration events are, optionally, enriched by Puromycin selection.

Next, those libraries are subjected to genetic screening using methods known to those skilled in the art. To determine surviving transposon mutants in a population of cells, transposon integration sites are mapped by a splinkerette PCR as outlined below:

Five μg of genomic DNA from cells containing Helraiser transposon insertions is digested with FspBI for four hours followed by ethanol precipitation. In the next step, samples are ligated (300 ng) to BfaI splinkerette adapters (100 pmol) in 20 μl reactions. Three microliters of the ligation reaction are used for the first PCR with primers Linker primer and Hell (see Table 4). The temperature profile for the first PCR round is: one cycle of 94° C. for 3 min, followed by 15 cycles of 94° C. for 30 s, 70° C. for 30 s and 72° C. for 30 s; 5 cycles of 94° C. for 30 s, 63° C. for 30 s and 72° C. for 2 s with an increase of 2 s per cycle; 5 cycles of 94° C. for 30 s, 62° C. for 30 s and 72° C. for 12 s with an increase of 2 s per cycle; 5 cycles of 94° C. for 30 s, 61° C. for 30 s and 72° C. for 22 s with an increase of 2 s per cycle and 5 cycles of 94° C. for 30 s, 60° C. for 30 s and 72° C. for 30 s. Nested PCR is performed with primers Nested and Hel2 (see Table 4), and 1 μl of a 1:100 dilution of the first PCR is used per 50 μl reaction. The temperature profile for the nested PCR started with a cycle of 3 min at 94° C. followed by 10 cycles of 94° C. for 30 s, 65° C. for 30 s and 72° C. for 30 s and 20 cycles of 94° C. for 30 s, 55° C. for 30 s and 72° C. for 2 min. The final elongation is performed for 5 min at 72° C.

In order to analyze transposon-genome junction sites at the 3'-terminus of the Helraiser insertions generated with the pHelR, pHelRΔHP and pHelRΔRTS transposons, first left-end splinkerette PCR is performed with the genomic DNA isolated from cells to determine genomic locations of the transposon insertions. In the next step, specific primers complementary to the genomic sequence located between 50 and 100 bp downstream from each transposon insertion (WT6a, WT6b, WT6c, WT6d, DelH2, DelH14, DelH19, DelRTS2, DelRTS15a; see Table 4) are used in genomic PCR together with the HelCD1 primer complementary to the sequence at the 5'-terminus of the Helraiser transposon. The temperature profile for PCR is: 95° C. 2 min, followed by 40 cycles of 95° C. 20 s, 57° C. 20 s, 72° C. 90 s. The final elongation step is performed at 72° C. 5 min. PCR products obtained in the genomic PCR are sequenced and analyzed.

TABLE 1

| | | In +/−1 kb TSS | Outside +/−1 kb TSS | p-value (Fisher's exact)° |
|---|---|---|---|---|
| All Helitrons # insertions: 497811 # genes: 8829 | In Helitrons | 2455* | 495356ˣ | Left: p = 0 |
| | Outside Helitrons | 6374† | 444254⁺ | Right: p = 1 Two-tailed: p = 0 |
| Helitrons w/ gene captures # insertions: 96521 # genes: 8829 | In Helitrons | 643* | 95878ˣ | Left: p = 3.16e−19 |
| | Outside Helitrons | 8186† | 861384⁺ | Right: p = 1 Two-tailed: p = 6.017e−19 |

TABLE 2

| | | | # copies with de novo end (different from the consensus end, >20% divergence over the last 30 bps/or do not align) | | | | | |
|---|---|---|---|---|---|---|---|---|
| Name of the Helitron | # copies analyzed | # copies with ends similar to consensus | with CTAG termini | End-bypass | Novel Helitron end (insertion next to a 5' truncated Helitron) | Most likely by deletion | With empty site evidence | No empty site evidence |
| HelibatN541 | 26 | 26 | — | — | — | — | — | — |
| HelibatN542 | 339 | 316 | 4 | 1 | 3 | 5 | 1 | 9 |
| HelibatN580 | 30 | 13 | 2 | — | 2 | 6 | 1 | 6 |

TABLE 3

| | | | | | | Promoter | | |
|---|---|---|---|---|---|---|---|---|
| Transcript | Gene | Coordinates | Scaffold | Expression | FPKM | Origin | Distance from TSS | Approximate Age |
| asmbl_702530[1] | RINT1 | 1319873 · 1322604 | KE161857.1 | Kidney | 0.51 (K) | HelibatN3 | −1069 to +12 | 25-12 mya |
| asmbl_111852[2] | ARMC9 | 1586631 · 1591216 | KE164457.1 | Brain | 0.65 (B) | HelibatN3 | −1020 to +65 | 40-25 mya |
| asmbl_680940[1] | RNF10 | 983155 · 987306 | KE161970.1 | Constitutive | 1.25(B); 1.23 (K); 0.97 (L) | HelibatN3 | −894 to +168 | 40-75 mya |
| asmbl_43689[2] | RBBP5 | 1998130 · 2025813 | KE164706.1 | Constitutive | 2.26 (B); 3.47 (K); 0.94 (L) | HelibatN3 | −1779 to −764 | 40-25 mya |

TABLE 3-continued

| | | | | | | Promoter | | |
|---|---|---|---|---|---|---|---|---|
| Transcript | Gene | Coordinates | Scaffold | Expression | FPKM | Origin | Distance from TSS | Approximate Age |
| asmbl_43690[2] | RBBP5 | 1998130 · 2025813 | KE164706.1 | Constitutive | 5.22 (B); 2.42 (K); 1.69 (L) | HelibatN3 | −1779 to −764 | 40-25 mya |
| asmbl_89539[2] | ATG5 | 9804872 · 9922472 | KE164550.1 | Constitutive | 1.6 (B); 2.3 (K); 4.7 (L) | HelibatN3 | −1415 to −614 | 12-10 mya |
| asmbl_89540[2] | ATG5 | 9804872 · 9984397 | KE164550.1 | Brain/Kidney | 1.01 (B); 1.77 (K) | HelibatN3 | −1415 to −614 | 12-10 mya |
| asmbl_89542[2] | ATG5 | 9804872 · 9922472 | KE164550.1 | Brain/Kidney | 1.32 (B); 1.45 (K) | HelibatN3 | −1415 to −614 | 12-10 mya |
| asmbl_89543[2] | ATG5 | 9804872 · 9964407 | KE164550.1 | Constitutive | 0.91 (B); 0.82 (K); 1.36 (L) | HelibatN3 | −1415 to −614 | 12-10 mya |
| asmbl_122965[2] | NUP88 | 599827 · 609108 | KE164426.1 | Brain | 2.34 (B) | HelibatN3 | −1527 to −801 | 40-25 mya |
| asmbl_133658[1] | PSMB5 | 513728 · 521120 | KE164377.1 | Constitutive | 19.71 (B); 14.73 (K); 18.87 (L) | HelibatN3 | −1467 to −807 | 40-25 mya |
| asmbl_406297[1] | ACAP2 | 5280571 · 5292804 | KE163428.1 | Kidney/Liver | 1.06 (K); 0.91 (L) | HelibatN3 | −1390 to −796 | 12-10 mya |
| asmbl_406298[1] | ACAP2 | 5280571 · 5286727 | KE163428.1 | Brain | 2.64 (B) | HelibatN3 | −1390 to −796 | 12-10 mya |
| asmbl_409885[2] | KIF13A | 2335940 · 2346111 | KE163411.1 | Brain/Kidney | 0.64 (B); 0.66 (K) | HelibaN3 | −1453 to −796 | 25-12 mya |
| asmbl_519813[2] | IL15RA | 401446 · 437510 | KE162829.1 | Liver | 0.87 (L) | HelibatN3 | −1374 to −668 | 25-12 mya |
| asmbl_519842[2] | IL15RA | 401446 · 431544 | KE162829.1 | Liver | 0.57 (L) | HelibatN3 | −1374 to −668 | 25-12 mya |
| asmbl_519905[2] | IL15RA | 401446 · 434643 | KE162829.1 | Liver | 0.59 (L) | HelibatN3 | −1374 to −668 | 25-12 mya |
| asmbl_519907[2] | IL15RA | 401446 · 441051 | KE162829.1 | Liver | 0.66 (L) | HelibatN3 | −1374 to −668 | 25-12 mya |
| asmbl_519908[2] | IL15RA | 401446 · 441051 | KE162629.1 | Kidney | 0.53 (K) | HelibatN3 | −1374 to −668 | 25-12 mya |
| asmbl_519910[2] | IL15RA | 401446 · 434643 | KE162829.1 | Liver | 0.86 (L) | HelibatN3 | −1374 to −668 | 25-12 mya |
| asmbl_519912[2] | IL15RA | 401446 · 441051 | KE162829.1 | Liver | 1.93 (L) | HelibatN3 | −1374 to −668 | 25-12 mya |
| asmbl_519913[2] | IL15RA | 401446 · 441051 | KE162829.1 | Liver | 2.96 (L) | HelibatN3 | −1374 to −668 | 25-12 mya |
| asmbl_519914[2] | IL15RA | 401446 · 434643 | KE162829.1 | Liver | 0.64 (L) | HelibatN3 | −1374 to −668 | 25-12 mya |
| asmbl_541112[1] | ZMYM4 | 1291579 · 1314976 | KE162671.1 | Kidney | 0.65 (K) | HelibatN3 | −1661 to −923 | 25-12 mya |
| asmbl_592789[1] | EP58 | 3447651 · 3533166 | KE162407.1 | Kidney/Liver | 9.81 (K); 0.75 (L) | HelibatN3 | −2025 to −1171 | 40-25 mya |
| asmbl_602260[1] | PJA2 | 5546545 · 5584009 | KE162363.1 | Brain | 2.11 (B) | HelibatN3 | −908 to −144 | 40-25 mya |
| asmbl_502361[1] | PJA2 | 5570209 · 5584009 | KE162363.1 | Liver | 0.68 (K) | HelibatN3 | −908 to −144 | 40-25 mya |
| asmbl_610360[2] | RNF114 | 3183763 · 3193548 | KE162314.1 | Brain/Kidney | 1.21 (B); 1.06 (K) | HelibatN3 | −1718 to −701 | 40-25 mya |
| asmbl_244933[2] | ELOVL2 | 3937750 · 3961655 | KE164122.1 | Constitutive | 7.12 (B); 0.77 (K); 17.52 (L) | HelibatN3 | −542 to −135 | 25-12 mya |
| asmbl_711145[1] | PROSER1 | 794021 · 862504 | KE161809.1 | Brain/Kidney | 4.59 (B); 2.1 (K) | HelibatN3 | −1456 to −477 | 25-12 mya |
| asmbl_710521[1] | FOXJ2 | 95891 · 114448 | KE161817.1 | Brain | 1.42 (B) | HelibatN264 | −888 to −373 | <10 mya |
| asmbl_710522[1] | FOXJ2 | 95991-114448 | KE161817.1 | Constitutive | 8.01 (B); 5.15 (K); 1.68 (L) | HelibatN264 | −888 to −373 | <10 mya |
| asmbl_547482[2] | CCDC66 | 1750516-1776865 | KE162632.1 | Constitutive | 1.18 (B); 0.84 (K); 0.59 (L) | HelibatN3 | −1097 to −95 | 40-25 mya |
| asmbl_562141[1] | VPS52 | 451415 · 452557 | KE162539.1 | Constitutive | 7.53 (B); 5.51 (K); 2.38 (L) | HelibatN3 | −1967 to −954 | 40-25 mya |
| asmbl_458633[1] | PCKS1 | 7667370 · 7665976 | KE163134.1 | Brain | 0.61 (B) | HelibatN3 | −1982 to −996 | 40-25 mya |
| asmbl_280594[2] | HSPH1 | 3557538 · 3572255 | KE163986.l | Constitutive | 6.02 (B); 4.97 (K); 1.25 (L) | HelibatN3 | −1567 to −530 | 12-10 mya |
| asmbl_225943[2] | R3HDM2 | 275902 · 403344 | KE164166.1 | Brain/Kidney | 3.48 (B); 6.38 (K) | HelibatN3 | −2429 to −809 | 25-12 mya |
| asmbl_225947[2] | R3HDM2 | 275902 · 403344 | KE164166.1 | Brain | 0.69 (B) | HelibatN3 | −2429 to −809 | 25-12 mya |
| asmbl_225950[2] | R3HDM2 | 275902 · 403344 | KE164166.1 | Kidney/Liver | 1.18 (K); 1.23 (L) | HelibatN3 | −2429 to −809 | 25-12 mya |
| asmbl_225952[2] | R3HDM2 | 275902 · 403344 | KE164166.1 | Brain | 5.61 (B) | HelibatN3 | −2429 to −809 | 25-12 mya |
| asmbl_225955[2] | R3HDM2 | 275902 · 403344 | KE164166.1 | Kidney/Liver | 1.9 (K); 1.64 (L) | HelibatN3 | −2429 to −809 | 25-12 mya |
| asmbl_225956[2] | R3HDM2 | 275902 · 403344 | KE164166.1 | Brain | 1.16 (B) | HelibatN3 | −2429 to −809 | 25-12 mya |
| asmbl_225958[2] | R3HDM2 | 275902 · 403344 | KE164166.1 | Kidney/Liver | 1.15 (K); 0.82 (L) | HelibatN3 | −2429 to −809 | 25-12 mya |
| asmbl_225959[2] | R3HDM2 | 275902 · 403344 | KE164166.1 | Kidney/Liver | 1.97 (K); 2.48 (L) | HelibatN3 | −2429 to −809 | 25-12 mya |
| asmbl_226010[1] | R3HDM2 | 311551 · 403344 | KE164166.1 | Brain | 0.69 (B) | HelibatN3 | −2429 to −809 | 25-12 mya |
| asmbl_150342[1] | STX10 | 475164 · 482635 | KE164342.1 | Brain | 0.63 (B) | HelibatN3 | −1388 to −357 | <10 mya |

TABLE 4

| SEQ ID NO: | Primer name | Primer sequence 5'-3' |
|---|---|---|
| 34 | Hel_Lft1 | GGCGCTTGACACCTGCGTAT |
| 35 | Hel_Lft2 | GTGGCTTGAGCGTAGCGGAG |
| 36 and 37 | Hel_L_bc | ACACTCTTTCCCTACACGACGCTCTTCCGATCT_ILLUMINA_ TRUSEQ_BARCODE_TTTGCATGTTTCTCTTTTATTATATAG |
| 38 | Hel_3P_1 | ATTAATTCCCTTTCAATGTGCACGAA |
| 39 | Hel_3P_2 | TTCCCTTTCAATGTGCACGAATTT |
| 40 and 41 | Hel_3P_3BC | ACACTCTTTCCCTACACGACGCTCTTCCGATCT_ILLUMINA_ TRUSEQ_BARCODE_AATTTCGTGCACCGGGCCACT |
| 42 | Puro1 | CCTTCTATGAACGGCTGGGCTT |

TABLE 4-continued

| SEQ ID NO: | Primer name | Primer sequence 5'-3' |
|---|---|---|
| 43 | Puro2 | GGGCTTTACTGTGACCGCAGAT |
| 44 and 45 | T2a_SD_bc | ACACTCTTTCCCTACACGACGCTCTTCCGATCT_ILLUMINA_TRUSEQ_BARCODE_GAAAACCCTGGACCAATGGTTTGT |
| 46 | PE first | gtgactggagttcagacgtg |
| 47 and 48 | PE nest | CAAGCAGAAGACGGCATACGAGAT_REVERSE_COMPLEMEN-T_OF_ILLUMINA_TRUSEQ_BARCODE_GTGACTGGAGTTCAGACGTGTGCTCTTCCGATCT |
| 49 | Illumina 1 (Oligonucleotide sequences ©2006-2010 Illumina, Inc. All rights reserved. | AATGATACGGCGACCACCGAGATCTACACTCTTTCCCTACACGACGCTCTTCCGATCT |
| 50 | Hemispecific prim-ers for 3' end | GTGACTGGAGTTCAGACGTGTGCTCTTCCGATCTDDDNNNAACG |
| 51 | | GTGACTGGAGTTCAGACGTGTGCTCTTCCGATCTHHHNNNCTAC |
| 52 | | GTGACTGGAGTTCAGACGTGTGCTCTTCCGATCTHHHNNNGGAC |
| 53 | | GTGACTGGAGTTCAGACGTGTGCTCTTCCGATCTNBNNBHCGTT |
| 54 | | GTGACTGGAGTTCAGACGTGTGCTCTTCCGATCTVNVNVNGCAA |
| 55 | | GTGACTGGAGTTCAGACGTGTGCTCTTCCGATCTHNHNNNGTCC |
| 56 | Hemispecific prim-ers for 5' end | GTGACTGGAGTTCAGACGTGTGCTCTTCCGATCTHHHNHNATTC |
| 57 | | GTGACTGGAGTTCAGACGTGTGCTCTTCCGATCTBBBNNNGAAT |
| 58 | | GTGACTGGAGTTCAGACGTGTGCTCTTCCGATCTHHHNNNGAAC |
| 59 | | GTGACTGGAGTTCAGACGTGTGCTCTTCCGATCTVNVNNNGTAA |
| 60 | | GTGACTGGAGTTCAGACGTGTGCTCTTCCGATCTHNHNNNGTCC |
| 61 | | GTGACTGGAGTTCAGACGTGTGCTCTTCCGATCTHHHNNNTTAC |
| 62 | Hemispecific primers for | GTGACTGGAGTTCAGACGTGTGCTCTTCCGATCTNDDNNNAGTG |
| 63 | fusion transcript detec-tion | GTGACTGGAGTTCAGACGTGTGCTCTTCCGATCTBBBNNNCACT |
| 64 | | GTGACTGGAGTTCAGACGTGTGCTCTTCCGATCTVNVNNNTCAA |
| 65 | | GTGACTGGAGTTCAGACGTGTGCTCTTCCGATCTDVVNNNTTGA |
| 66 | | GTGACTGGAGTTCAGACGTGTGCTCTTCCGATCTHVVNVNTACA |
| 67 | | GTGACTGGAGTTCAGACGTGTGCTCTTCCGATCTSVVNNNTGTA |
| 68 | First Y to Phe* | GCCTCCATCAAATCCGTGAAGTTCCTGTTCAAATACATCTACAAAGGC |
| 69 | Second Y to Phe* | GTGAAGTACCTGTTCAAATTTATCTACAAAGGCCACGACTGC |
| 70 | Double H to Ala* | CAGAAACGGGGCCTGCCAGCAGCCGCAATCCTGCTGATCCTGG |
| 71 | Double H to Gln* | CAGAAACGGGGCCTGCCACAAGCCCAAATCCTGCTGATCCTGG |
| 72 | Double Y to Phe* | GCCTCCATCAAATCCGTGAAGTTCCTGTTCAAATTTATCTACAAAGGC |
| 73 | Helicase K1068Q* | GGACCCGGAGGGTCTGGCCAAACCTACCTGTATAAAGTG |
| 74 | Helicase R1457Q* | CTGTATGTGGCCTTTAGCCAAGTGCGCCGGGCCTGCGAT |
| 75 | HUH NcoI site* | GATAATGTGCCGATTGGCACCATGGTTATTCTGCCGAGCAGTTTTG |
| 76 | HUH stop one* | CAGATTAGCGAAAAAAACTGAATCAACCACGATGAGGTG |
| 77 | First Y to Phe-insect* | GCCAGCATTAAAAGCGTGAAATTCCTGTTCAAATATATCTATAAAGGC |
| 78 | Second Y to Phe-insect* | GTGAAATACCTGTTCAAATTTATCTATAAAGGCCACGATTGC |
| 79 | Double H to Ala-insect* | CAGAAACGGGGCCTGCCAGCAGCCGCAATCCTGCTGATCCTGG |
| 80 | Double H to Gln-insect* | CAGAAACGTGGTCTGCCGCAAGCCCAAATTCTGCTGATTCTGG |
| 81 | Double Y to Phe-insect* | GCCAGCATTAAAAGCGTGAAATTCCTGTTCAAATTTATCTATAAAGGC |
| 82 | Helicase K1068Q-insect* | GGTCCGGGTGGCAGCGGTAACACCTATCTGTATAAAGTG |
| 83 | Helicase R1457Q-insect* | CTGTACGTTGCCTTTAGCAACGTTCGTCGTGCATGTGAT |

TABLE 4-continued

| SEQ ID NO: | Primer name | Primer sequence 5'-3' |
|---|---|---|
| 84 | Helraiser LTS substrate (+)* | CACCATATGATCCTATATAATAAAAGAGAAACATGCAAATTGACCA TCCC |
| 85 | Helraiser RTS substrate (+)* | CCCTTTCAATGTGCACGAATTTCGTGCACCGGGCCACTAGTATATA TATA |
| 86 | HelMut fwd* | CCCTTTCAATGTGCACGAA CGGGCCACTAGTATATATATAAAGC |
| 87 | HelRDelH* | CTAATTAATTCCCTTTCAAT CGGGCCACTAGTATATATATAAAGC |
| 88 | ATH1 | TTATATATATACTAGTGGCCCGACCTGCGGTACACCGCAGGTATTG |
| 89 | ATH2 | GCTATTTGCCCTTTCTCTATAATAGAAGTGTGAGAGATGAAAGGAA ATGAGTAAAATGTATATGAAAATAATAC |
| 90 | ATH3 | GAGAAAGGGCAAATAGCAATATTAAAATATTTCCTCTAATTAATTC CCTTTCAATACCTGCGGTGTACCGC |
| 91 | ATH4 | TATCATGTCTGGATCCAAATTTATGTATTATTTTCATATAC |
| 92 | ATH5 | TTATATATATACTAGTGG |
| 93 | ATH6 | TATCATGTCTGGATCC |
| 94 | LX1 | TTATATATATACTAGTGGCCCGGTGCACGACGGACGTGCACATTG |
| 95 | LX2 | GCTATTTGCCCTTTCTCTATAATAGAAGTGTGAGAGATGAAAGGAA ATGAGTAAAATGTATATGAAAATAATAC |
| 96 | LX3 | GAGAAAGGGCAAATAGCAATATTAAAATATTTCCTCTAATTAATTC CCTTTCAATGTGCACGACGGACGTGCACCGGGCC |
| 97 | LX4 | TATCATGTCTGGATCCAAATTTATGTATTATTTTCATATAC |
| 98 | LX5 | TTATATATATACTAGTGG |
| 99 | LX6 | TATCATGTCTGGATCC |
| 100 | SX fwd | AATTTCCGCAGGTCGGGCCAC |
| 101 | SX rev | CCGCAGGTATTGAAAGGG |
| 102 | Hel1 | CCTCCTGGGGCGCTTGACACCTGCG |
| 103 | Hel2 | TGGCTGGTGGGCGTGGCTTG |
| 104 | Hel5 | TCATCTCTCACACTTCTATTATAGAG |
| 105 | Linker primer | GTAATACGACTCACTATAGGGC |
| 106 | Nested primer | AGGGCTCCGCTTAAGGGAC |
| 107 | HelCD1 | GGCAGTTAAATTTGCATACGCAG |
| 108 | WT6a | CAGTTACCTAGAAGGAAACAGAG |
| 109 | WT6b | GTCACAGCCCATGATATGCCC |
| 110 | WT6c | CTTGCTGTTTGAATATGAAATTATGTTATTC |
| 111 | WT6d | CATTATGCCAATTTCACAGATGAGG |
| 112 | DelH2 | GAAGGTAATTTAGAAGTGAAAGAACAC |
| 113 | DelH14 | GTATCTATCACCTCACCTAGTTAAC |
| 114 | DelH19 | GCTGGAACGTTAATTATGATGCG |
| 115 | DelRTS2 | GTTGATATGGAAGATGAGAATGAAAC |
| 116 | DelRTS15a | CTGACAGGATTTTGGAGAATACG |
| 117 | HA tag top | gactctactagtgccaccATGTACCCTTACGACGTACCGGATTACG CC TACCCTTACGACGTACCGGATTACGCCactagtgactct |
| 118 | HA tag bottom | agagtcactagtGGCGTAATCCGGTACGTCGTAAGGGTAGGCGTAA TC CGGTACGTCGTAAGGGTACATggtggcactagtagagtc |

TABLE 4-continued

| SEQ ID NO: | Primer name | Primer sequence 5'-3' |
|---|---|---|
| 119 | Universal primer for the ssDNA LM-PCR | CGCTGGAAGCTTAAG |
| 120 | 5+ primer for the ssDNA LM-PCR | GCGCGGGAATTCCACCATATG |
| 121 | 5- primer for the ssDNA LM-PCR | GCGCGGGAATTCGGGATGGTCAATTTGC |
| 122 | 3+ primer for the ssDNA LM-PCR | GCGCGGGAATTCCCCTTTCAATGTGCACG |
| 123 | 3- primer for the ssDNA LM-PCR | GCGCGGGAATTCTATATATATA |

TABLE 5

| SEQ ID NO: | | |
|---|---|---|
| 124 | Tagging Cassette bearing TialL-LTS-EF1A-TurboGFP-RTS-TialL | **CCTGGAGAGGTTCCCGACATACC**TCCTATATAATAAAAGAGAAACATG<br>CAAATTGACCATCCCTCCGCTACGCTCAAGCCACGCCCACCAGCCAAT<br>CAGAAGTGACTATGCAAATTAACCCAACAAAGATGGCAGTTAAATTTG<br>CATACGCAGGTGTCAAGCGCCCCAGGAGGatcgatgagtaattcatac<br>aaaaggactcgcccctgccttggggaatcccagggaccgtcgttaaac<br>tcccactaacgtagaacccagagatcgctgcgttcccgccccctcacc<br>cgcccgctctcgtcatcactgaggtggagaagagcatgcgtgaggctc<br>cggtgcccgtcagtgggcagagcgcacatcgcccacagtccccgagaa<br>gttggggggaggggtcggcaattgaaccggtgcctagagaaggtggcg<br>cggggtaaactgggaaagtgatgtcgtgtactggctccgcctttttcc<br>cgagggtgggggagaaccgtatataagtgcagtagtcgccgtgaacgt<br>tctttttcgcaacgggtttgccgccagaacacaggtaagtgccgtgtg<br>tggttcccgcgggcctggcctctttacgggttatggcccttgcgtgcc<br>ttgaattacttccacgcccctggctgcagtacgtgattcttgatcccg<br>agcttcgggttggaagtgggtgggagagttcgaggccttgcgcttaag<br>gagccccttcgcctcgtgcttgagttgaggcctggcttgggcgctggg<br>gccgccgcgtgcgaatctggtggcaccttcgcgcctgtctcgctgctt<br>tcgataagtctctagccatttaaaatttttgatgacctgctgcgacgc<br>tttttttctggcaagatagtcttgtaaatgcgggccaagatctgcaca<br>ctggtatttcggtttttggggccgcgggcggcgacggggcccgtgcgt<br>cccagcgcacatgttcggcgaggcggggcctgcgagcgcggccaccga<br>gaatcggacgggggtagtctcaagctggccggcctgctctggtgcctg<br>gcctcgcgccgccgtgtatcgccccgccctgggcggcaaggctggccc<br>ggtcggcaccagttgcgtgagcggaaagatggccgcttcccggccctg<br>ctgcagggagctcaaaatggaggacgcggcgctcgggagagcgggcgg<br>gtgagtcacccacacaaaggaaaagggcctttccgtcctcagccgtcg<br>cttcatgtgactccacggagtaccgggcgccgtccaggcacctcgatt<br>agttctcgagcttttggagtacgtcgtctttaggttggggggaggggt<br>tttatgcgatggagtttccccacactgagtgggtggagactgaagtta<br>ggccagcttggcacttgatgtaattctccttggaatttgccctttttg<br>agtttggatcttggttcattctcaagcctcagacagtggttcaaagtt<br>tttttcttccatttcaggtgtcgtgagccaccATGGGATCCGAGAGCG<br>ACGAGAGCGGCCTGCCCGCCATGGAGATCGAGTGCCGCATCACCGGCA<br>CCCTGAACGGCGTGGAGTTCGAGCTGGTGGGCGGCGGAGAGGGCACCC<br>CCGAGCAGGGCCGCATGACCAACAAGATGAAGAGCACCAAAGGCGCCC<br>TGACCTTCAGCCCCTACCTGCTGAGCCACGTGATGGGCTACGGCTTCT<br>ACCACTTCGGCACCTACCCCAGCGGCTACGAGAACCCCTTCCTGCACG<br>CCATCAACAACGGCGGCTACACCAACACCCGCATCGAGAAGTACGAGG<br>ACGGCGGCGTGCTGCACGTGAGCTTCAGCTACCGCTACGAGGCCGGCC<br>GCGTGATCGGCGACTTCAAGGTGATGGGCACCGGCTTCCCCGAGGACA<br>GCGTGATCTTCACCGACAAGATCATCCGCAGCAACGCCACCGTGGAGC<br>ACCTGCACCCCATGGGCGATAACGATCTGGATGGCAGCTTCACCCGCA<br>CCTTCAGCCTGCGCGACGGCGGCTACTACAGCTCCGTGGTGGACAGCC<br>ACATGCACTTCAAGAGCGCCATCCACCCCAGCATCCTGCAGAACGGGG<br>GCCCCATGTTCGCCTTCCGCCGCGTGGAGGAGGATCACAGCAACACCG<br>AGCTGGGCATCGTGGAGTACCAGCACGCCTTCAAGACCCCGGATGCAG<br>ATGCCGGTGAAGAAGGATCCTAGacgcgtggatcc*AATAAAAGATCCT*<br>*TATTTTCATTGGATCTGTGTGTTGGTTTTTTGTGTG*gctagcAAATTT<br>ATGTATTATTTTCATATACATTTTACTCATTTCCTTTCATCTCTCACA<br>CTTCTATTATAGAGAAAGGGCAAATAGCAATATTAAAATATTTCCTCT<br>AATTAATTCCCTTTCAATGTGCACGAATTTCGTGCACCGGGCCACTAG<br>tatatatataaagctt**GGTATGTCGGGAACCTCTCCAGG**cagcggccg<br>cccaaggtcgggcaggaagagggcctatttcccatgattccttcatat |

TABLE 5-continued

| SEQ ID NO: | | |
|---|---|---|
| | | ttgcatatacgatacaaggctgttagagagataattagaattaatttg<br>actgtaaacacaaagatattagtacaaaatacgtgacgtagaaagtaa<br>taatttcttgggtagtttgcagttttaaaattatgttttaaaatggac<br>tatcatatgcttaccgtaacttgaaagtatttcgatttcttggcttta<br>tatatcttgtggaaaggacgaaacaccGGTATGTCGGGAACCTCTCC***G***<br>***GTTTTAGAGCTAGAAATAGCAAGTTAAAATAAGGCTAGTCCGTTATCA***<br>***ACTTGAAAAAGTGGCAACCGAGTCGGTGCTTTTTTTATCGGATC***<br>***CCGGGCCCGTCGACTGCAGAGGCCTGCATGCAAGCTTGGCGTA***<br>***ATCATGGTCAT***<br>TialL recognition sites (**BOLD**)<br>Left Terminal sequence (LTS) (UNDERLINED)<br>Efla promoter (lower case underlined)<br>Turbo GFP (CAPITALS)<br>PolyA (*ITALICIZED*)<br>Right Terminal sequences (RTS) (DOUBLE UNDERLINED)<br>U6 promoter (lower case boxed)<br>TialL gRNA (DOTTED UNDERLINED)<br>guideRNA scaffold (***ITALICIZED BOLD TEXT***) |
| 125 | TialL recognition site 5' | CCTGGAGAGGTTCCCGACATACC |
| 126 | TialL recognition site 3' | GGTATGTCGGGAACCTCTCCAGG |
| 127 | Left Terminal sequence (LTS) | TCCTATATAATAAAAGAGAAACATGCAAATTGACCATCCCTCCGCTAC<br>GCTCAAGCCACGCCCACCAGCCAATCAGAAGTGACTATGCAAATTAAC<br>CCAACAAAGATGGCAGTTAAATTTGCATACGCAGGTGTCAAGCGCCCC<br>AGGAGG |
| 128 | Efla promoter | GAGTAATTCATACAAAAGGACTCGCCCCTGCCTTGGGGAATCCCAGGG<br>ACCGTCGTTAAACTCCCACTAACGTAGAACCCAGAGATCGCTGCGTTC<br>CCGCCCCCTCACCCGCCCGCTCTCGTCATCACTGAGGTGGAGAAGAGC<br>ATGCGTGAGGCTCCGGTGCCCGTCAGTGGGCAGAGCGCACATCGCCCA<br>CAGTCCCCGAGAAGTTGGGGGGAGGGGTCGGCAATTGAACCGGTGCCT<br>AGAGAAGGTGGCGCGGGGTAAACTGGGAAAGTGATGTCGTGTACTGGC<br>TCCGCCTTTTTCCCGAGGGTGGGGGAGAACCGTATATAAGTGCAGTAG<br>TCGCCGTGAACGTTCTTTTTCGCAACGGGTTTGCCGCCAGAACACAGG<br>TAAGTGCCGTGTGTGGTTCCCGCGGGCCTGGCCTCTTTACGGGTTATG<br>GCCCTTGCGTGCCTTGAATTACTTCCACGCCCCTGGCTGCAGTACGTG<br>ATTCTTGATCCCGAGCTTCGGGTTGGAAGTGGGTGGGAGAGTTCGAGG<br>CCTTGCGCTTAAGGAGCCCCTTCGCCTCGTGCTTGAGTTGAGGCCTGG<br>CTTGGGCGCTGGGGCCGCCGCGTGCGAATCTGGTGGCACCTTCGCGCC<br>TGTCTCGCTGCTTTCGATAAGTCTCTAGCCATTTAAAATTTTTGATGA<br>CCTGCTGCGACGCTTTTTTTCTGGCAAGATAGTCTTGTAAATGCGGGC<br>CAAGATCTGCACACTGGTATTTCGGTTTTTGGGGCCGCGGGCGGCGAC<br>GGGGCCCGTGCGTCCCAGCGCACATGTTCGGCGAGGCGGGGCCTGCGA<br>GCGCGGCCACCGAGAATCGGACGGGGGTAGTCTCAAGCTGGCCGGCCT<br>GCTCTGGTGCCTGGCCTCGCGCCGCCGTGTATCGCCCCGCCCTGGGCG<br>GCAAGGCTGGCCCGGTCGGCACCAGTTGCGTGAGCGGAAAGATGGCCG<br>CTTCCCGGCCCTGCTGCAGGGAGCTCAAAATGGAGGACGCGGCGCTCG<br>GGAGAGCGGGCGGGTGAGTCACCCACACAAAGGAAAAGGGCCTTTCCG<br>TCCTCAGCCGTCGCTTCATGTGACTCCACGGAGTACCGGGCGCCGTCC<br>AGGCACCTCGATTAGTTCTCGAGCTTTTGGAGTACGTCGTCTTTAGGT<br>TGGGGGGAGGGGTTTTATGCGATGGAGTTTCCCCACACTGAGTGGGTG<br>GAGACTGAAGTTAGGCCAGCTTGGCACTTGATGTAATTCTCCTTGGAA<br>TTTGCCCTTTTTGAGTTTGGATCTTGGTTCATTCTCAAGCCTCAGACA<br>GTGGTTCAAAGTTTTTTTCTTCCATTTCAGGTGTCGTGA |
| 129 | Turbo GFP | ATGGGATCCGAGAGCGACGAGAGCGGCCTGCCCGCCATGGAGATCGAG<br>TGCCGCATCACCGGCACCCTGAACGGCGTGGAGTTCGAGCTGGTGGGC<br>GGCGGAGAGGGCACCCCCGAGCAGGGCCGCATGACCAACAAGATGAAG<br>AGCACCAAAGGCGCCCTGACCTTCAGCCCCTACCTGCTGAGCCACGTG<br>ATGGGCTACGGCTTCTACCACTTCGGCACCTACCCCAGCGGCTACGAG<br>AACCCCTTCCTGCACGCCATCAACAACGGCGGCTACACCAACACCCGC<br>ATCGAGAAGTACGAGGACGGCGGCGTGCTGCACGTGAGCTTCAGCTAC<br>CGCTACGAGGCCGGCCGCGTGATCGGCGACTTCAAGGTGATGGGCACC<br>GGCTTCCCCGAGGACAGCGTGATCTTCACCGACAAGATCATCCGCAGC<br>AACGCCACCGTGGAGCACCTGCACCCCATGGGCGATAACGATCTGGAT |

TABLE 5-continued

| SEQ ID NO: | | |
|---|---|---|
| | | GGCAGCTTCACCCGCACCTTCAGCCTGCGCGACGGCGGCTACTACAGC TCCGTGGTGGACAGCCACATGCACTTCAAGAGCGCCATCCACCCCAGC ATCCTGCAGAACGGGGGCCCCATGTTCGCCTTCCGCCGCGTGGAGGAG GATCACAGCAACACCGAGCTGGGCATCGTGGAGTACCAGCACGCCTTC AAGACCCCGGATGCAGATGCCGGTGAAGAAGGATCCTAG |
| 130 | PolyA | AATAAAAGATCCTTATTTTCATTGGATCTGTGTGTTGGTTTTTTGTGT G |
| 131 | Right Terminal sequences (RTS) | AAATTTATGTATTATTTTCATATACATTTTACTCATTTCCTTTCATCT CTCACACTTCTATTATAGAGAAAGGGCAAATAGCAATATTAAAATATT TCCTCTAATTAATTCCCTTTCAATGTGCACGAATTTCGTGCACCGGGC CACTAG |
| 132 | U6 promoter | CCAAGGTCGGGCAGGAAGAGGGCCTATTTCCCATGATTCCTTCATATT TGCATATACGATACAAGGCTGTTAGAGAGATAATTAGAATTAATTTGA CTGTAAACACAAAGATATTAGTACAAAATACGTGACGTAGAAAGTAAT AATTTCTTGGGTAGTTTGCAGTTTTAAAATTATGTTTTAAAATGGACT ATCATATGCTTACCGTAACTTGAAAGTATTTCGATTTCTTGGCTTTAT ATATCTTGTGGAAAGGACGAAACACC |
| 133 | TialL gRNA sequence | GGTATGTCGGGAACCTCTCC |
| 134 | guideRNA scaffold | GTTTTAGAGCTAGAAATAGCAAGTTAAAATAAGGCTAGTCCGTTATCA ACTTGAAAAAGTGGCACCGAGTCGGTGCTTTTTTTATCGGATCCCGGG CCCGTCGACTGCAGAGGCCTGCATGCAAGCTTGGCGTAATCATGGTCA T |

TABLE 6

| TABLE OF SEQ ID NOS: | |
|---|---|
| Description | SEQ ID NO: |
| Helraiser transposase amino acid sequence: MSKEQLLIQRSSAAERCRRYRQKMSAEQRASDLERRRRLQQNVSEEQLLEKRRSE AEKQRRHRQKMSKDQRAFEVERRRWRRQNMSREQSSTSTINTGRNCLLSKNGVHE DAILEHSCGGMTVRCEFCLSLNFSDEKPSDGKFTRCCSKGKVCPNDIHFPDYPAY LKRLMTNEDSDSKNFMENIRSINSSFAFASMGANIASPSGYGPYCFRIHGQVYHR TGTLHPSDGVSRKFAQLYILDTAEATSKRLAMPENQGCSERLMININNLMHEINE LIKSYKMLHEVEKEAQSEAAAKGIAPTEVTMAIKYDRNSDPGRYNSPRVIEVAVI FRNEDGEPPFERDLLIHCKPDPNNPNATKMKQISILFPTLDAMTYPILFPHGEKG WGTDIALRLRDNSVIDNNTRQNVRTRVTQMQYYGFHLSVRDTFNPILNAGKLTQQ FIVDSYSKMEANRINFIKANQSKLRVEKYSGLMDYLKSRSENDNVPIGKMIILPS SFEGSPRNMQQRYQDAMAIVTKYGKPDLFITMTCNPKWADITNNLQRWQKVENRP DLVARVFNIKLNALLNDICKFHLFGKVIAKIHVIEFQKRGLPHAHILLILDSESK LRSEDDIDRIVKAEIPDEDQCPRLFQIVKSNMVHGPCGIQNPNSPCMENGKCSKG YPKEFQNATIGNIDGYPKYKRRSGSTMSIGNKVVDNTWIVPYNPYLCLKYNCHIN VEVCASIKSVKYLFKYIYKGHDCANIQISEKNIINHDEVQDFIDSRYVSAPEAVW RLFAMRMHDQSHAITRLAIHLPNDQNLYFHTDDFAEVLDRAKRHNSTLMAWFLLN REDSDARNYYYWEIPQHYVFNNSLWTKRKKGGNKVLGRLFTVSFREPERYYLRLL LLHVKGAISFEDLRTVGGVTYDTFHEAAKHRGLLDDTIWKDTIDDAIILNMPKQ LRQLFAYICVFGCPSAADKLWDENKSHFIEDFCWKLHRREGACVNCEMHALNEIQ EVFTLHGMKCSHFKLPDYPLLMNANTCDQLYEQQQAEVLINSLNDEQLAAFQTIT SAIEDQTVHPKCFFLDGPGGSGKTYLYKVLTHYIRGRGGTVLPTASTGIAANLLL GGRTFHSQYKLPIPLNETSISRLDIKSEVAKTIKKAQLLIIDECTMASSHAINAI DRLLREIMNLNVAFGGKVLLLGGDFRQCLSIVPHAMRSAIVQTSLKYCNVWGCFR KLSLKTNMRSEDSAYSEWLVKLGDGKLDSSFHLGMDIIEIPHEMICNGSIIEATF GNSISIDNIKNISKRAILCPKNEHVQKLNEEILDILDGDFHTYLSDDSIDSTDDA EKENFPIEFLNSITPSGMPCHKLKLKVGAIIMLLRNLNSKWGLCNGTRFIIKRLR PNIIEAEVLTGSAEGEVVLIPRIDLSPSDTGLPFKLIRRQFPVMPAFAMTINKSQ GQTLDRVGIFLPEPVFAHGQLYVAFSRVRRACDVKVKVVNTSSQGKLVKHSESVF TLNVVYREILE* | 1 |
| Helitron transposase nucleic acid sequence as shown in FIG. 8 (Transposase coding sequence) 5' ATGTCTAAAGAACAACTGTTGATACAACGTAGCTCTGCAGCCGAAAGATGCCGGC GTTATCGACAGAAAATGTCTGCAGAGCAACGTGCGTCTGATCTTGAAAGAAGGCG GCGCCTGCAACAGAATGTATCTGAAGAGCAGCTACTGGAAAAACGTCGCTCTGAA GCCGAAAAACAGCGGCGTCATCGACAGAAAATGTCTAAAGACCAACGTGCCTTTG | 2 |

TABLE 6-continued

TABLE OF SEQ ID NOS:

| Description | SEQ ID NO: |
|---|---|

AAGTTGAAAGAAGGCGGTGGCGACGACAGAATATGTCTAGAGAACAGTCATCAAC
AAGTACTACCAATACCGGTAGGAACTGCCTTCTCAGCAAAAATGGAGTACATGAG
GATGCAATTCTCGAACATAGTTGTGGTGGAATGACTGTTCGATGTGAATTTTGCC
TATCACTAAATTTCTCTGATGAAAAACCATCCGATGGGAAATTTACTCGATGTTG
TAGCAAAGGGAAAGTCTGTCCAAATGATATACATTTTCCAGATTACCCGGCATAT
TTAAAAAGATTAATGACAAACGAAGATTCTGACAGTAAAAATTTCATGGAAAATA
TTCGTTCCATAAATAGTTCTTTTGCTTTTGCTTCCATGGGTGCAAATATTGCATC
GCCATCAGGATATGGGCCATACTGTTTTAGAATACACGGACAAGTTTATCACCGT
ACTGGAACTTTACATCCTTCGGATGGTGTTTCTCGGAAGTTTGCTCAACTCTATA
TTTTGGATACAGCCGAAGCTACAAGTAAAAGATTAGCAATGCCAGAAAACCAGGG
CTGCTCAGAAAGACTCATGATCAACATCAACAACCTCATGCATGAAATAAATGAA
TTAACAAAATCGTACAAGATGCTACATGAGGTAGAAAAGGAAGCCCAATCTGAAG
CAGCAGCAAAAGGTATTGCTCCCACAGAAGTAACAATGGCGATTAAATACGATCG
TAACAGTGACCCAGGTAGATATAATTCTCCCCGTGTAACCGAGGTTGCTGTCATA
TTCAGAAACGAAGATGGAGAACCTCCTTTTGAAAGGGACTTGCTCATTCATTGTA
AACCAGATCCCAATAATCCAAATGCCACTAAAATGAAACAAATCAGTATCCTGTT
TCCTACATTAGATGCAATGACATATCCTATTCTTTTTCCACATGGTGAAAAAGGC
TGGGGAACAGATATTGCATTAAGACTCAGAGACAACAGTGTAATCGACAATAATA
CTAGACAAAATGTAAGGACACGAGTCACACAAATGCAGTATTATGGATTTCATCT
CTCTGTGCGGGACACGTTCAATCCTATTTTAAATGCAGGAAAATTAACTCAACAG
TTTATTGTGGATTCATATTCAAAAATGGAGGCCAATCGGATAAATTTCATCAAAG
CAAACCAATCTAAGTTGAGAGTTGAAAAATATAGTGGTTTGATGGATTATCTCAA
ATCTAGATCTGAAAATGACAATGTGCCGATTGGTAAAATGATAATACTTCCATCA
TCTTTTGAGGGTAGTCCCAGAAATATGCAGCAGCGATATCAGGATGCTATGGCAA
TTGTAACGAAGTATGGCAAGCCCGATTTATTCATAACCATGACATGCAACCCCAA
ATGGGCAGATATTACAAACAATTTACAACGCTGGCAAAAAGTTGAAAACAGACCT
GACTTGGTAGCCAGAGTTTTTAATATTAAGCTGAATGCTCTTTTAAATGATATAT
GTAAATTCCATTTATTTGGCAAAGTAATAGCTAAAATTCATGTCATTGAATTTCA
GAAACGCGGACTGCCTCACGCTCACATATTATTGATATTAGATAGTGAGTCCAAA
TTACGTTCAGAAGATGACATTGACCGTATAGTTAAGGCAGAAATTCCAGATGAAG
ACCAGTGTCCTCGACTTTTTCAAATTGTAAAATCAAATATGGTACATGGACCATG
TGGAATACAAAATCCAAATAGTCCATGTATGGAAAATGGAAAATGTTCAAAGGGA
TATCCAAAAGAATTTCAAAATGCGACCATTGGAAATATTGATGGATATCCCAAAT
ACAAACGAAGATCTGGTAGCACCATGTCTATTGGAAATAAAGTTGTCGATAACAC
TTGGATTGTCCCTTATAACCCGTATTTGTGCCTTAAATATAACTGTCATATAAAT
GTTGAAGTCTGTGCATCAATTAAAAGTGTCAAATATTTATTTAAATACATCTATA
AAGGGCACGATTGTGCAAATATTCAAATTTCTGAAAAAAATATTATCAATCATGA
CGAAGTACAGGACTTCATTGACTCCAGGTATGTGAGCGCTCCTGAGGCTGTTTGG
AGACTTTTTGCAATGCGAATGCATGACCAATCTCATGCAATCACAAGATTAGCTA
TTCATTTGCCAAATGATCAGAATTTGTATTTTCATACCGATGATTTTGCTGAAGT
TTTAGATAGGGCTAAAAGGCATAACTCGACTTTGATGGCTTGGTTCTTATTGAAT
AGAGAAGATTCTGATGCACGTAATTATTATTATTGGGAGATTCCACAGCATTATG
TGTTTAATAATTCTTTGTGGACAAAACGCCGAAAGGGTGGGAATAAAGTATTAGG
TAGACTGTTCACTGTGAGCTTTAGAGAACCAGAACGATATTACCTTAGACTTTTG
CTTCTGCATGTAAAAGGTGCGATAAGTTTTGAGGATCTGCGAACTGTAGGAGGTG
TAACTTATGATACATTTCATGAAGCTGCTAAACACCGAGGATTATTACTTGATGA
CACTATCTGGAAAGATACGATTGACGATGCAATCATCCTTAATATGCCCAAACAA
CTACGGCAACTTTTTGCATATATATGTGTGTTTGGATGTCCTTCTGCTGCAGACA
AATTATGGGATGAGAATAAATCTCATTTTATTGAAGATTTCTGTTGGAAATTACA
CCGAAGAGAAGGTGCCTGTGTGAACTGTGAAATGCATGCCCTTAACGAAATTCAG
GAGGTATTCACATTGCATGGAATGAAATGTTCACATTTCAAACTTCCGGACTATC
CTTTATTAATGAATGCAAATACATGTGATCAATTGTACGAGCAACAACAGGCAGA
GGTTTTGATAAATTCTCTGAATGATGAACAGTTGGCAGCCTTTCAGACTATAACT
TCAGCCATCGAAGATCAAACTGTACACCCCAAATGCTTTTTCTTGGATGGTCCAG
GTGGTAGTGGAAAAACATATCTGTATAAAGTTTTAACACATTATATTAGAGGTCG
TGGTGGTACTGTTTTACCCACAGCATCTACAGGAATTGCTGCAAATTTACTTCTT
GGTGGAAGAACCTTTCATTCCCAATATAAATTACCAATTCCATTAAATGAAACTT
CAATTTCTAGACTCGATATAAAGAGTGAAGTTGCTAAAACCATTAAAAAGGCCCA
ACTTCTCATTATTGATGAATGCACCATGGCATCCAGTCATGCTATAAACGCCATA
GATAGATTACTAAGAGAAATTATGAATTTGAATGTTGCATTTGGTGGGAAAGTTC
TCCTTCTCGGAGGGGATTTTCGACAATGTCTCAGTATTGTACCACATGCTATGCG
ATCGGCCATAGTACAAACGAGTTTAAAGTACTGTAATGTTTGGGGATGTTTCAGA
AAGTTGTCTCTTAAAACAAATATGAGATCAGAGGATTCTGCTTATAGTGAATGGT
TAGTAAAACTTGGAGATGGCAAACTTGATAGCAGTTTTCATTTAGGAATGGATAT
TATTGAAATCCCCCATGAAATGATTTGTAACGGATCTATTATTGAAGCTACCTTT
GGAAATAGTATATCTATAGATAATATTAAAAATATATCTAAACGTGCAATTCTTT
GTCCAAAAAATGAGCATGTTCAAAAATTAAATGAAGAAATTTTGGATATACTTGA
TGGAGATTTTCACACATATTTGAGTGATGATTCCATTGATTCAACAGATGATGCT
GAAAAGGAAAATTTTCCCATCGAATTTCTTAATAGTATTACTCCTTCGGGAATGC
CGTGTCATAAATTAAAATTGAAAGTGGGTGCAATCATCATGCTATTGAGAAATCT
TAATAGTAAATGGGGTCTTTGTAATGGTACTAGATTTATTATCAAAAGATTACGA
CCTAACATTATCGAAGCTGAAGTATTAACAGGATCTGCAGAGGGAGAGGTTGTTC
TGATTCCAAGAATTGATTTGTCCCCATCTGACACTGGCCTCCCATTTAAATTAAT
TCGAAGACAGTTTCCCGTGATGCCAGCATTTGCGATGACTATTAATAAATCACAA
GGACAAACTCTAGACAGAGTAGGAATATTCCTACCTGAACCCGTTTTCGCACATG

TABLE 6-continued

| TABLE OF SEQ ID NOS: | |
|---|---|
| Description | SEQ ID NO: |
| GTCAGTTATATGTTGCTTTCTCTCGAGTTCGAAGAGCATGTGACGTTAAAGTTAA AGTTGTAAATACTTCATCACAAGGGAAATTAGTCAAGCACTCTGAAAGTGTTTTT ACTCTTAATGTGGTATACAGGGAGATATTAGAATAA 3' | |
| LTS nucleotide sequence: 5'-TCCTATATAATAAAAGAGAAACATGCAAATTGACCATCCCTCCGCT ACGCTCAAGCCACGCCCACCAGCCAATCAGAAGTGACTATGCAAATTA ACCCAACAAAGATGGCAGTTAAATTTGCATACGCAGGTGTCAAGCGCC CCAGGAGG-3' | 3 |
| RTS nucleotide sequence: 5'-AAATTTATGTATTATTTTCATATACATTTTACTCATTTCCTTTCATCT CTCACACTTCTATTATAGAGAAAGGGCAAATAGCAATATTAAAATATT TCCTCTAATTAATTCCCTTTCAATGTGCACGAATTTCGTGCACCGGGCC ACTAG-3' | 4 |
| Complete consensus sequence for Helraiser transposon (as shown in FIG. 8) 5'-TCCTATATAATAAAAGAGAAACATGCAAATTGACCATCCCTCCGCT ACGCTCAAGCCACGCCCACCAGCCAATCAGAAGTGACTATGCAAATTA ACCCAACAAAGATGGCAGTTAAATTTGCATACGCAGGTGTCAAGCGCC CCAGGAGGCAACGGCGGCCGCGGGCTCCCAGGACCTTCGCTGGCCCC GGGAGGCGAGGCCGGCCGCGCCTAGCCACACCCGCGGGCTCCCGGGA CCTTCGCCAGCAGAGAGCAGAGCGGGAGAGCGGGCGGAGAGCGGGA GGTTTGGAGGACTTGGCAGAGCAGGAGGCCGCTGGACATAGAGCAGA GCGAGAGAGAGGGTGGCTTGGAGGGCGTGGCTCCCTCTGTCACCCCA GCTTCCTCATCACAGCTGTGGAAACTGACAGCAGGGAGGAGGAAGTC CCACCCCCACAGAATCAGCCAGAATCAGCCGTTGGTCAGACAGCTCTC AGCGGCCTGACAGCCAGGACTCTCATTCACCTGCATCTCAGACCGTGA CAGTAGAGAGGTGGGACTATGTCTAAAGAACAACTGTTGATACAACG TAGCTCTGCAGCCGAAAGATGCCGGCGTTATCGACAGAAAATGTCTGC AGAGCAACGTGCGTCTGATCTTGAAAGAAGGCGGCGCCTGCAACAGA ATGTATCTGAAGAGCAGCTACTGGAAAAACGTCGCTCTGAAGCCGAA AAACAGCGGCGTCATCGACAGAAAATGTCTAAAGACCAACGTGCCTTT GAAGTTGAAAGAAGGCGGTGGCGACGACAGAATATGTCTAGAGAACA GTCATCAACAAGTACTACCAATACCGGTAGGAACTGCCTTCTCAGCAA AAATGGAGTACATGAGGATGCAATTCTCGAACATAGTTGTGGTGGAAT GACTGTTCGATGTGAATTTTGCCTATCACTAAATTTCTCTGATGAAAAA CCATCCGATGGGAAATTTACTCGATGTTGTAGCAAAGGGAAAGTCTGT CCAAATGATATACATTTTCCAGATTACCCGGCATATTTAAAAAGATTA ATGACAAACGAAGATTCTGACAGTAAAAATTTCATGGAAAATATTCGT TCCATAAATAGTTCTTTTGCTTTTGCTTCCATGGGTGCAAATATTGCAT CGCCATCAGGATATGGGCCATACTGTTTTAGAATACACGGACAAGTTT ATCACCGTACTGGAACTTTACATCCTTCGGATGGTGTTTCTCGGAAGTT TGCTCAACTCTATATTTTGGATACAGCCGAAGCTACAAGTAAAAGATT AGCAATGCCAGAAAACCAGGGCTGCTCAGAAAGACTCATGATCAACA TCAACAACCTCATGCATGAAATAAATGAATTAACAAAATCGTACAAG ATGCTACATGAGGTAGAAAAGGAAGCCCAATCTGAAGCAGCAGCAAA AGGTATTGCTCCCACAGAAGTAACAATGGCGATTAAATACGATCGTAA CAGTGACCCAGGTAGATATAATTCTCCCCGTGTAACCGAGGTTGCTGT CATATTCAGAAACGAAGATGGAGAACCTCCTTTTGAAAGGGACTTGCT CATTCATTGTAAACCAGATCCCAATAATCCAAATGCCACTAAAATGAA ACAAATCAGTATCCTGTTTCCTACATTAGATGCAATGACATATCCTATT CTTTTTCCACATGGTGAAAAAGGCTGGGGAACAGATATTGCATTAAGA CTCAGAGACAACAGTGTAATCGACAATAATACTAGACAAAATGTAAG GACACGAGTCACACAAATGCAGTATTATGGATTTCATCTCTCTGTGCG GGACACGTTCAATCCTATTTTAAATGCAGGAAAATTAACTCAACAGTT TATTGTGGATTCATATTCAAAAATGGAGGCCAATCGGATAAATTTCAT CAAAGCAAACCAATCTAAGTTGAGAGTTGAAAAATATAGTGGTTTGAT GGATTATCTCAAATCTAGATCTGAAAATGACAATGTGCCGATTGGTAA AATGATAATACTTCCATCATCTTTTGAGGGTAGTCCCAGAAATATGCA GCAGCGATATCAGGATGCTATGGCAATTGTAACGAAGTATGGCAAGC CCGATTTATTCATAACCATGACATGCAACCCCAAATGGGCAGATATTA CAAACAATTTACAACGCTGGCAAAAAGTTGAAAACAGACCTGACTTG GTAGCCAGAGTTTTTAATATTAAGCTGAATGCTCTTTTAAATGATATAT GTAAATTCCATTTATTTGGCAAAGTAATAGCTAAAATTCATGTCATTG AATTTCAGAAACGCGGACTGCCTCACGCTCACATATTATTGATATTAG ATAGTGAGTCCAAATTACGTTCAGAAGATGACATTGACCGTATAGTTA AGGCAGAAATTCCAGATGAAGACCAGTGTCCTCGACTTTTTCAAATTG TAAAATCAAATATGGTACATGGACCATGTGGAATACAAAATCCAAAT AGTCCATGTATGGAAAATGGAAAATGTTCAAAGGGATATCCAAAAGA ATTTCAAAATGCGACCATTGGAAATATTGATGGATATCCCAAATACAA ACGAAGATCTGGTAGCACCATGTCTATTGGAAATAAAGTTGTCGATAA CACTTGGATTGTCCCTTATAACCCGTATTTGTGCCTTAAATATAACTGT CATATAAATGTTGAAGTCTGTGCATCAATTAAAAGTGTCAAATATTTA | 5 |

TABLE 6-continued

TABLE OF SEQ ID NOS:

| Description | SEQ ID NO: |
|---|---|
| TTTAAATACATCTATAAAGGGCACGATTGTGCAAATATTCAAATTTCT<br>GAAAAAAATATTATCAATCATGACGAAGTACAGGACTTCATTGACTCC<br>AGGTATGTGAGCGCTCCTGAGGCTGTTTGGAGACTTTTTGCAATGCGA<br>ATGCATGACCAATCTCATGCAATCACAAGATTAGCTATTCATTTGCCA<br>AATGATCAGAATTTGTATTTTCATACCGATGATTTTGCTGAAGTTTTAG<br>ATAGGGCTAAAAGGCATAACTCGACTTTGATGGCTTGGTTCTTATTGA<br>ATAGAGAAGATTCTGATGCACGTAATTATTATTATTGGGAGATTCCAC<br>AGCATTATGTGTTTAATAATTCTTTGTGGACAAAACGCCGAAAGGGTG<br>GGAATAAAGTATTAGGTAGACTGTTCACTGTGAGCTTTAGAGAACCAG<br>AACGATATTACCTTAGACTTTTGCTTCTGCATGTAAAAGGTGCGATAA<br>GTTTTGAGGATCTGCGAACTGTAGGAGGTGTAACTTATGATACATTTC<br>ATGAAGCTGCTAAACACCGAGGATTATTACTTGATGACACTATCTGGA<br>AAGATACGATTGACGATGCAATCATCCTTAATATGCCCAAACAACTAC<br>GGCAACTTTTTGCATATATATGTGTGTTTGGATGTCCTTCTGCTGCAGA<br>CAAATTATGGGATGAGAATAAATCTCATTTTATTGAAGATTTCTGTTG<br>GAAATTACACCGAAGAGAAGGTGCCTGTGTGAACTGTGAAATGCATG<br>CCCTTAACGAAATTCAGGAGGTATTCACATTGCATGGAATGAAATGTT<br>CACATTTCAAACTTCCGGACTATCCTTTATTAATGAATGCAAATACATG<br>TGATCAATTGTACGAGCAACAACAGGCAGAGGTTTTGATAAATTCTCT<br>GAATGATGAACAGTTGGCAGCCTTTCAGACTATAACTTCAGCCATCGA<br>AGATCAAACTGTACACCCCAAATGCTTTTTCTTGGATGGTCCAGGTGG<br>TAGTGGAAAAACATATCTGTATAAAGTTTTAACACATTATATTAGAGG<br>TCGTGGTGGTACTGTTTTACCCACAGCATCTACAGGAATTGCTGCAAA<br>TTTACTTCTTGGTGGAAGAACCTTTCATTCCCAATATAAATTACCAATT<br>CCATTAAATGAAACTTCAATTTCTAGACTCGATATAAAGAGTGAAGTT<br>GCTAAAACCATTAAAAAGGCCCAACTTCTCATTATTGATGAATGCACC<br>ATGGCATCCAGTCATGCTATAAACGCCATAGATAGATTACTAAGAGAA<br>ATTATGAATTTGAATGTTGCATTTGGTGGGAAAGTTCTCCTTCTCGGAG<br>GGGATTTTCGACAATGTCTCAGTATTGTACCACATGCTATGCGATCGG<br>CCATAGTACAAACGAGTTTAAAGTACTGTAATGTTTGGGGATGTTTCA<br>GAAAGTTGTCTCTTAAAACAAATATGAGATCAGAGGATTCTGCTTATA<br>GTGAATGGTTAGTAAAACTTGGAGATGGCAAACTTGATAGCAGTTTTC<br>ATTTAGGAATGGATATTATTGAAATCCCCCATGAAATGATTTGTAACG<br>GATCTATTATTGAAGCTACCTTTGGAAATAGTATATCTATAGATAATAT<br>TAAAAATATATCTAAACGTGCAATTCTTTGTCCAAAAAATGAGCATGT<br>TCAAAAATTAAATGAAGAAATTTTGGATATACTTGATGGAGATTTTCA<br>CACATATTTGAGTGATGATTCCATTGATTCAACAGATGATGCTGAAAA<br>GGAAAATTTTCCCATCGAATTTCTTAATAGTATTACTCCTTCGGGAATG<br>CCGTGTCATAAATTAAAATTGAAAGTGGGTGCAATCATCATGCTATTG<br>AGAAATCTTAATAGTAAATGGGGTCTTTGTAATGGTACTAGATTTATT<br>ATCAAAAGATTACGACCTAACATTATCGAAGCTGAAGTATTAACAGGA<br>TCTGCAGAGGGAGAGGTTGTTCTGATTCCAAGAATTGATTTGTCCCCA<br>TCTGACACTGGCCTCCCATTTAAATTAATTCGAAGACAGTTTCCCGTGA<br>TGCCAGCATTTGCGATGACTATTAATAAATCACAAGGACAAACTCTAG<br>ACAGAGTAGGAATATTCCTACCTGAACCCGTTTTCGCACATGGTCAGT<br>TATATGTTGCTTTCTCTCGAGTTCGAAGAGCATGTGACGTTAAAGTTAA<br>AGTTGTAAATACTTCATCACAAGGGAAATTAGTCAAGCACTCTGAAAG<br>TGTTTTTACTCTTAATGTGGTATACAGGGAGATATTAGAATAAGTTTAA<br>TCACTTTATCAGTCATTGTTTGCATCAATGTTGTTTTTATATCATGTTTT<br>TGTTGTTTTTATATCATGTCTTTGTTGTTGTTATATCATGTTGTTATTGT<br>TTATTTATTAATAAATTTATGTATTATTTTCATATACATTTTACTCATTT<br>CCTTTCATCTCTCACACTTCTATTATAGAGAAAGGGCAAATAGCAATA<br>TTAAAATATTTCCTCTAATTAATTCCCTTTCAATGTGCACGAATTTCGT<br>GCACCGGGCCACTAG-3' | |
| Codon-optimized sequence encoding Helraiser transposase (for use in human cells)<br>5'-<br>ATGTCCAAGGAACAGCTGCTGATTCAGCGGAGCTCCGCCGCCGAGAGATGCCGCC<br>GCTATCGCCAGAAAATGTCTGCCGAGCAGAGGGCCTCCGATCTGGAGCGCCGGCG<br>GAGACTGCAGCAGAACGTGAGCGAAGAGCAGCTGCTGGAGAAGCGGCGGTCTGAA<br>GCCGAGAAGCAGAGAAGACACCGGCAGAAAATGTCCAAAGATCAGAGGGCCTTCG<br>AGGTGGAGCGGCGGAGGTGGAGAAGACAGAATATGAGCAGAGAACAGTCTTCTAC<br>CAGCACAACCAATACCGGGAGAAACTGTCTGCTGTCCAAGAACGGCGTGCACGAA<br>GATGCCATCCTGGAGCACAGCTGTGGCGGCATGACCGTGAGATGCGAGTTTTGTC<br>TGAGCCTGAATTTTTCCGACGAGAAGCCATCTGATGGCAAGTTTACCAGATGTTG<br>TTCCAAAGGGAAAGTGTGCCCAAATGATATCCACTTCCCCGACTACCCAGCCTAT<br>CTGAAGAGGCTGATGACCAACGAGGATAGCGATTCCAAGAACTTCATGGAAAATA<br>TCAGGAGCATCAACTCCTCTTTCGCCTTTGCCTCTATGGGCGCCAACATTGCCTC<br>CCCCTCTGGGTACGGCCCTTACTGTTTCCGGATTCACGGACAGGTGTACCACCGC<br>ACCGGCACCCTGCACCCCTCTGACGGCGTGTCTCGGAAGTTCGCCCAGCTGTATA<br>TCCTGGACACCGCCGAGGCCACCTCCAAGAGGCTGGCCATGCCTGAGAATCAGGG<br>CTGCAGCGAAAGGCTGATGATCAACATTAACAACCTGATGCACGAGATCAACGAG<br>CTGACCAAGAGCTACAAGATGCTGCACGAGGTGGAGAAAGAAGCCCAGTCTGAGG<br>CCGCCGCCAAGGGGATCGCCCCCACCGAGGTGACCATGGCCATCAAATATGATCG | 6 |

TABLE 6-continued

TABLE OF SEQ ID NOS:

| Description | SEQ ID NO: |
|---|---|
| GAATTCCGATCCTGGCCGGTACAATAGCCCAAGAGTGACAGAGGTGGCCGTGATT<br>TTCAGGAACGAGGACGGAGAGCCCCCCTTCGAGAGGGATCTGCTGATTCACTGTA<br>AGCCTGACCCTAATAACCCTAATGCCACCAAGATGAAGCAGATTTCTATCCTGTT<br>CCCAACCCTGGACGCCATGACCTATCCTATTCTGTTCCCCCACGGCGAAAAGGGA<br>TGGGGGACAGATATCGCCCTGCGGCTGAGGGACAATTCCGTGATTGACAATAATA<br>CCAGACAGAACGTGCGGACAAGGGTGACACAGATGCAGTATTACGGCTTCCACCT<br>GTCTGTGAGAGACACCTTTAATCCAATCCTGAATGCCGGAAAGCTGACCCAGCAG<br>TTTATCGTGGACTCCTACTCCAAGATGGAAGCCAACAGAATTAATTTCATCAAGG<br>CCAATCAGTCTAAGCTGCGGGTGGAGAAATACTCTGGGCTGATGGATTACCTGAA<br>GTCTAGGTCTGAGAATGACAACGTGCCTATTGGAAAGATGATCATTCTGCCCAGC<br>TCTTTTGAAGGGAGCCCACGGAATATGCAGCAGCGGTACCAGGATGCCATGGCCA<br>TTGTGACAAAGTATGGGAAGCCTGATCTGTTCATCACAATGACATGTAACCCCAA<br>GTGGGCCGATATTACCAACAACCTGCAGAGGTGGCAGAAGGTGGAGAACAGACCC<br>GACCTGGTGGCCAGGGTGTTCAACATCAAGCTGAACGCCCTGCTGAACGACATTT<br>GCAAGTTTCACCTGTTTGGGAAGGTGATTGCCAAAATTCACGTGATTGAGTTTCA<br>GAAACGGGGCCTGCCACACGCCCACATCCTGCTGATCCTGGACTCCGAAAGCAAG<br>CTGAGATCTGAGGACGATATCGACAGGATTGTGAAGGCCGAGATCCCCGACGAGG<br>ATCAGTGTCCACGCCTGTTCCAGATTGTGAAATCCAACATGGTGCACGGCCCCTTG<br>TGGGATCCAGAATCCCAACTCCCCATGCATGGAAAACGGGAAGTGCAGCAAGGGC<br>TATCCCAAGGAGTTCCAGAACGCCACCATCGGCAACATCGACGGCTATCCAAAAT<br>ATAAGAGGAGGTCCGGCTCTACCATGAGCATTGGCAATAAGGTGGTGGATAACAC<br>CTGGATCGTGCCTTATAACCCCTATCTGTGCCTGAAGTACAACTGTCACATCAAT<br>GTGGAGGTGTGCGCCTCCATCAAATCCGTGAAGTACCTGTTCAAATACATCTACA<br>AAGGCCACGACTGCGCCAATATCCAGATCTCTGAGAAGAACATTATTAACCACGA<br>TGAGGTGCAGGACTTTATTGATTCTAGATACGTGAGCGCCCCCGAGGCCGTGTGG<br>AGACTGTTCGCCATGAGGATGCACGACCAGAGCCACGCCATCACCCGGCTGGCCA<br>TCCACCTGCCCAATGATCAGAATCTGTACTTTCACACCGATGATTTCGCCGAGGT<br>GCTGGATAGGGCCAAGAGACACAACAGCACCCTGATGGCCTGGTTCCTGCTGAAC<br>AGGGAGGATTCCGACGCCAGGAACTATTATTATTGGGAAATCCCACAGCACTACG<br>TGTTTAACAACAGCCTGTGGACCAAGAGAAGAAAAGGGGGCAACAAGGTGCTGGG<br>CCGCCTGTTCACCGTGTCTTTTAGAGAGCCTGAAAGGTACTACCTGAGGCTGCTG<br>CTGCTGCACGTGAAGGGGGCCATCTCTTTCGAAGACCTGCGCACCGTGGGGGGAG<br>TGACCTACGATACCTTCCACGAAGCCGCCAAACACAGGGGCCTGCTGCTGGACGA<br>CACAATCTGGAAAGACACCATCGATGATGCCATTATTCTGAACATGCCAAAGCAG<br>CTGAGACAGCTGTTCGCCTACATCTGCGTGTTTGGATGCCCCTCCGCCGCCGACA<br>AGCTGTGGGATGAGAATAAGTCCCACTTTATTGAGGATTTCTGTTGGAAGCTGCA<br>CAGAAGGGAGGGGGCCTGTGTGAACTGCGAAATGCACGCCCTGAATGAGATCCAG<br>GAAGTGTTTACACTGCACGGCATGAAGTGTTCTCACTTCAAACTGCCTGACTATC<br>CTCTGCTGATGAATGCCAACACCTGTGATCAGCTGTACGAGCAGCAGCAGGCCGA<br>GGTGCTGATCAATTCCCTGAATGACGAGCAGCTGGCCGCCTTCCAGACCATTACA<br>TCTGCCATTGAGGACCAGACCGTGCACCCCAAGTGCTTCTTCCTGGACGGACCCG<br>GAGGGTCTGGCAAGACCTACCTGTATAAAGTGCTGACACACTATATCAGAGGAAG<br>GGGGGGGACCGTGCTGCCTACCGCCAGCACAGGCATTGCCGCCAACCTGCTGCTG<br>GGGGGCAGGACCTTCCACTCTCAGTACAAGCTGCCCATCCCTCTGAACGAGACAT<br>CTATCTCTAGACTGGACATCAAATCCGAGGTGGCCAAGACCATTAAAAAGGCCCA<br>GCTGCTGATTATCGACGAGTGTACCATGGCCAGCTCCCACGCCATCAACGCCATC<br>GACAGACTGCTGAGGGAAATCATGAACCTGAACGTGGCCTTCGGAGGCAAGGTGC<br>TGCTGCTGGGCGGCGATTTTAGGCAGTGCCTGAGCATTGTGCCCCACGCCATGCG<br>GTCCGCCATCGTGCAGACCTCCCTGAAGTATTGTAATGTGTGGGGCTGCTTCCGG<br>AAGCTGAGCCTGAAAACCAATATGAGGAGCGAGGACAGCGCCTACAGCGAGTGGC<br>TGGTGAAGCTGGGCGATGGAAAACTGGATTCCTCTCCTTCCACCTGGGGATGGACAT<br>TATCGAGATCCCCCACGAGATGATTTGTAACGGGAGCATTATCGAGGCCACCTTC<br>GGGAACTCCATCAGCATCGATAACATCAAGAATATTTCTAAGAGAGCCATTCTGT<br>GCCCAAAGAACGAACACGTGCAGAAGCTGAATGAGGAGATCCTGGATATTCTGGA<br>CGGAGATTTCCACACCTACCTGTCTGACGATAGCATCGATTCCACCGACGACGCC<br>GAGAAGGAAAACTTCCCAATTGAATTCCTGAATAGCATCACCCCCAGCGGCATGC<br>CCTGTCACAAGCTGAAGCTGAAGGTGGGCGCCATCATCATGCTGCTGCGGAACCT<br>GAACTCTAAGTGGGGCCTGTGTAACGGCACCCGCTTTATCATTAAAAGGCTGAGG<br>CCAAACATCATTGAAGCCGAGGTGCTGACCGGCAGCGCCGAAGGCGAAGTGGTGC<br>TGATCCCACGCATTGACCTGTCTCCAAGCGACACCGGCCTGCCCTTCAAACTGAT<br>CCGCCGCCAGTTTCCTGTGATGCCCGCCTTCGCCATGACAATTAACAAGTCCCAG<br>GGCCAGACACTGGACCGCGTGGGCATTTTTCTGCCCGAACCAGTGTTCGCCCACG<br>GGCAGCTGTATGTGGCCTTTAGCAGAGTGCGCCGGGCCTGCGATGTGAAGGTGAA<br>AGTGGTGAACACCTCTTCCCAGGGCAAGCTGGTGAAGCACAGCGAATCTGTGTTC<br>ACACTGAACGTGGTGTATAGAGAGATCCTGGAATAA | |

The invention claimed is:

1. An in vitro or ex vivo method for introducing a single copy or multiple copies of a gene of interest into a mammalian cell, comprising:

a) providing a Helitron transposase, wherein the Helitron transposase is a Helraiser transposase comprising an amino acid sequence set forth in SEQ ID NO:1, or a sequence having at least 95% identity thereto;

b) providing a construct comprising a gene of interest flanked by Helitron transposase LTS sequences, wherein the LTS sequences comprise a nucleic acid sequence set forth in SEQ ID NO:3, or a sequence having at least 95% identity thereto; and c) introducing the Helitron transposase and the construct into a mammalian cell in vitro or ex vivo, wherein the Helitron transposase and the construct are provided as two separate entities, and wherein introducing the Helitron transposase and the construct into the mammalian cell results in the introduction of a single copy or multiple copies of the gene of interest into the genome of the mammalian cell.

2. The method as claimed in claim 1, wherein the cell is a human cell, a rat cell, a hamster cell, or a mouse cell.

3. The method as claimed in claim 1, wherein the gene of interest is also flanked by a RTS sequence.

4. The method as claimed in claim 3 wherein the RTS sequence comprises a nucleic acid sequence as set out in SEQ ID NO: 4 or a sequence having at least 95% identity thereto.

5. The method as claimed in claim 1, where the gene of interest is an endogenous gene or a cDNA thereof and multiple copies of the endogenous gene or the cDNA thereof are introduced into the genome of the mammalian cell.

6. The method as claimed in claim 1, wherein the gene of interest is a non-endogenous gene or a cDNA thereof.

7. The method as claimed in claim 1, further comprising detecting and selecting clones of the mammalian cell comprising multiple copies of said gene of interest, thereby generating a cell line, wherein said providing a Helitron transposase in step a) comprises introducing a construct comprising a nucleic acid encoding the Helitron transposase into the mammalian cell.

8. The method as claimed in claim 7, wherein the gene of interest is also flanked by RTS sequences.

9. The method as claimed in claim 7, wherein said selecting clones comprises selecting clones with known copy numbers of the gene of interest.

10. The method as claimed in claim 1, wherein the gene of interest encodes a therapeutic protein.

11. A cell line produced by a method as claimed in claim 1.

12. The method as claimed in claim 1, wherein the cell is a Chinese hamster ovary (CHO) cell, a 293T cell, a HEK293 cell, a human induced pluripotent stem cell, a human stem cell, a murine embryonic stem cell, a hematopoietic stem cell, a T cell, or a B cell.

* * * * *

UNITED STATES PATENT AND TRADEMARK OFFICE

CERTIFICATE OF CORRECTION

PATENT NO. : 11,396,664 B2
APPLICATION NO. : 16/077328
DATED : July 26, 2022
INVENTOR(S) : Tilmann Buerckstuemmer et al.

It is certified that error appears in the above-identified patent and that said Letters Patent is hereby corrected as shown below:

In the Claims

Claim 3, Column 177, Line 35, delete "a RTS sequence" and insert --RTS sequences--.

Signed and Sealed this
Eighth Day of November, 2022

Katherine Kelly Vidal

Katherine Kelly Vidal
*Director of the United States Patent and Trademark Office*